(12) United States Patent
Allan et al.

(10) Patent No.: US 12,043,612 B2
(45) Date of Patent: Jul. 23, 2024

(54) METHODS OF MANUFACTURING A BIFUNCTIONAL COMPOUND, ULTRAPURE FORMS OF THE BIFUNCTIONAL COMPOUND, AND DOSAGE FORMS COMPRISING THE SAME

(71) Applicant: Arvinas Operations, Inc., New Haven, CT (US)

(72) Inventors: Laura E. N. Allan, Dalkeith (GB); Chungpin Herman Chen, Madison, CT (US); Hanqing Dong, Madison, CT (US); John A. Grosso, Princeton Jct., NJ (US); Royal J. Haskell, III, Durham, CT (US); Rhys LLoyd, North Lanarkshire (GB); Hayley Reece, Dalkeith (GB)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 17/313,679

(22) Filed: May 6, 2021

(65) Prior Publication Data
US 2023/0012321 A1    Jan. 12, 2023

Related U.S. Application Data

(60) Provisional application No. 63/177,378, filed on Apr. 20, 2021, provisional application No. 63/149,143, filed on Feb. 12, 2021, provisional application No. 63/022,475, filed on May 9, 2020.

(51) Int. Cl.
| | |
|---|---|
| *C07D 401/14* | (2006.01) |
| *A61K 9/00* | (2006.01) |
| *A61K 9/20* | (2006.01) |
| *A61K 45/06* | (2006.01) |

(52) U.S. Cl.
CPC .......... *C07D 401/14* (2013.01); *A61K 9/0053* (2013.01); *A61K 9/2009* (2013.01); *A61K 9/2018* (2013.01); *A61K 9/2054* (2013.01); *A61K 45/06* (2013.01); *C07B 2200/13* (2013.01)

(58) Field of Classification Search
CPC ................ C07D 401/14; A61K 9/0053; A61K 9/2009; A61K 9/2018; A61K 9/2054; A61K 45/06; C07B 2200/13
See application file for complete search history.

(56) References Cited

U.S. PATENT DOCUMENTS

| | | | |
|---|---|---|---|
| 6,306,663 B1 | 10/2001 | Kenton et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |
| 7,109,219 B2 | 9/2006 | Tsuruoka et al. | |
| 7,153,867 B2 | 12/2006 | Shah et al. | |
| 7,208,157 B2 | 4/2007 | Sakamoto et al. | |
| 7,468,380 B2 | 12/2008 | Tsuruoka et al. | |
| 8,012,997 B2 | 9/2011 | Robarge et al. | |
| 8,481,568 B2 | 7/2013 | Muller et al. | |
| 8,765,176 B2 | 7/2014 | Yamamoto et al. | |

(Continued)

FOREIGN PATENT DOCUMENTS

| | | |
|---|---|---|
| CA | 2945975 A1 | 10/2015 |
| CN | 1844118 A | 10/2006 |

(Continued)

OTHER PUBLICATIONS

Prabu, SL; Suriyaprakash, TNK, Impurities and its importance in pharmacy, International Journal of Pharmaceutical Sciences Review and Research, 2010, vol. 3, Issue 2, p. 66-71. (Year: 2010).*

Prakash Khadka, et. al. Pharmaceutical particle technologies: An approach to improve drug solubility, dissolution and bioavailability, Asian Journal of Pharmaceutical Sciences, vol. 9, Issue 6, 2014, pp. 304-316, ISSN 1818-0876, https://doi.org/10.1016/j.ajps.2014.05.005. (Year: 2014).*

(Continued)

*Primary Examiner* — Bahar Craigo
*Assistant Examiner* — Manahil Mirghani Ali Abdalhameed
(74) *Attorney, Agent, or Firm* — COOLEY LLP

(57) ABSTRACT

The present disclosure relates to ultra-pure forms, polymorphs, amorphous forms, and formulations of N-[(1r,4r)-4-(3-chloro-4-cyanophenoxy)cyclohexyl]-6-[4-({4-[2-(2,6-dioxopiperidin-3-yl)-6-fluoro-1,3-dioxo-2,3-dihydro-1H-isoindol-5-yl]piperazin-1-yl}methyl)piperidin-1-yl]pyridazine-3-carboxamide, referred to herein as Compound A:

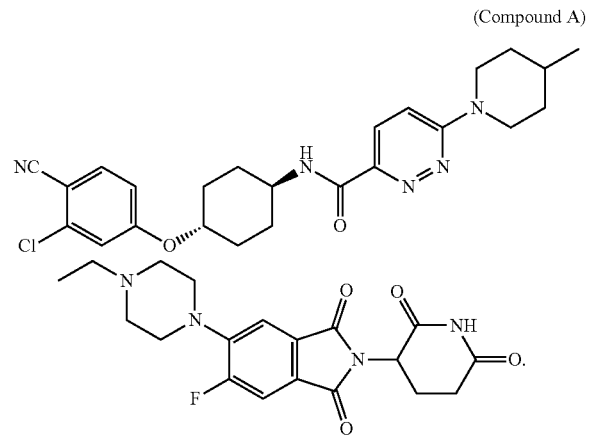

(Compound A)

The present disclosure also relates methods of manufacturing and purifying the same, as well as intermediates useful in the synthesis of Compound A. The ultra-pure forms, polymorphs, amorphous forms, and formulations of Compound A can be used as therapeutic agents for the treatment of various diseases and conditions such as cancer.

12 Claims, 44 Drawing Sheets

(56) References Cited

U.S. PATENT DOCUMENTS

| | | | |
|---|---|---|---|
| 8,921,378 | B2 | 12/2014 | Törmäkangas et al. |
| 9,500,653 | B2 | 11/2016 | Crews et al. |
| 9,632,089 | B2 | 4/2017 | Crews et al. |
| 9,796,698 | B2 | 10/2017 | Muller et al. |
| 9,801,868 | B2 | 10/2017 | Muller et al. |
| 10,047,151 | B2 | 8/2018 | Lopez-Girona et al. |
| 10,118,933 | B2 | 11/2018 | Wohlfahrt et al. |
| 10,584,101 | B2 * | 3/2020 | Crew .................. A61K 31/506 |
| 10,844,021 | B2 | 11/2020 | Crew et al. |
| 11,149,007 | B2 | 10/2021 | Ammirante et al. |
| 11,236,051 | B2 | 2/2022 | Crew et al. |
| 11,312,702 | B2 | 4/2022 | Fan et al. |
| 11,325,889 | B2 | 5/2022 | Ammirante et al. |
| 11,420,956 | B2 | 8/2022 | Fan et al. |
| 11,535,606 | B2 | 12/2022 | Fan et al. |
| 11,560,371 | B2 | 1/2023 | Alexander et al. |
| 11,634,407 | B2 | 4/2023 | Alexander et al. |
| 11,660,267 | B2 | 5/2023 | Coric et al. |
| 11,739,075 | B2 | 8/2023 | Alexander et al. |
| 2007/0254933 | A1 | 11/2007 | Jung et al. |
| 2008/0051432 | A1 | 2/2008 | Zhang |
| 2008/0214501 | A1 | 9/2008 | Zhengying et al. |
| 2009/0035362 | A1 | 2/2009 | Shih et al. |
| 2009/0142297 | A1 | 6/2009 | Muller et al. |
| 2010/0048517 | A1 | 2/2010 | Hu et al. |
| 2011/0196150 | A1 | 8/2011 | Man et al. |
| 2012/0270800 | A1 | 10/2012 | Verdine et al. |
| 2014/0079636 | A1 | 3/2014 | Chimmanamada et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0304450 | A1 | 10/2016 | Liang et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0134684 | A1 | 5/2018 | Bradner et al. |
| 2018/0228907 | A1 | 8/2018 | Crew et al. |
| 2020/0095205 | A1 | 3/2020 | Crew et al. |
| 2020/0155689 | A1 | 5/2020 | Crew et al. |
| 2020/0155690 | A1 | 5/2020 | Crew et al. |
| 2021/0009528 | A1 | 1/2021 | Crew et al. |
| 2021/0040044 | A1 | 2/2021 | Crew et al. |
| 2021/0087170 | A1 | 3/2021 | Fan et al. |
| 2021/0113557 | A1 | 4/2021 | Crew et al. |
| 2021/0171470 | A1 | 6/2021 | Crew et al. |
| 2021/0353621 | A1 | 11/2021 | Peck et al. |
| 2022/0089570 | A1 | 3/2022 | Crew et al. |
| 2022/0144809 | A1 | 5/2022 | Dong et al. |
| 2022/0184078 | A1 | 6/2022 | Chirnomas et al. |
| 2022/0220124 | A1 | 7/2022 | Fan et al. |
| 2022/0227771 | A1 | 7/2022 | Fu et al. |
| 2022/0257774 | A1 | 8/2022 | Du et al. |
| 2022/0259154 | A1 | 8/2022 | Berlin et al. |
| 2022/0313826 | A1 | 10/2022 | Phillips et al. |
| 2022/0372016 | A1 | 11/2022 | Phillips et al. |
| 2022/0380368 | A1 | 12/2022 | Wang et al. |
| 2023/0002321 | A1 | 1/2023 | Ammirante et al. |
| 2023/0082997 | A1 | 3/2023 | Berlin et al. |
| 2023/0084249 | A1 | 3/2023 | Berlin et al. |
| 2023/0111119 | A1 | 4/2023 | Lu et al. |
| 2023/0128132 | A1 | 4/2023 | Crew et al. |
| 2023/0241227 | A1 | 8/2023 | Desantis et al. |
| 2023/0242509 | A1 | 8/2023 | Alexander et al. |
| 2023/0331681 | A1 | 10/2023 | Berlin et al. |
| 2024/0002360 | A1 | 1/2024 | Desantis et al. |
| 2024/0066032 | A1 | 2/2024 | Chirnomas |

FOREIGN PATENT DOCUMENTS

| | | |
|---|---|---|
| CN | 103688176 A | 3/2014 |
| CN | 110746399 A | 2/2020 |
| CN | 113582974 A | 11/2021 |
| CN | 113912589 A | 1/2022 |
| CN | 114133379 A | 3/2022 |
| CN | 114163444 A | 3/2022 |
| CN | 114853846 A | 8/2022 |
| CN | 116891457 A | 10/2023 |
| CN | 117024390 A | 11/2023 |
| EP | 2985285 A1 | 2/2016 |
| EP | 3971176 A1 | 3/2022 |
| EP | 4023649 A1 | 7/2022 |
| JP | 2004-525889 A | 8/2004 |
| JP | 2010-502627 A | 1/2010 |
| JP | 2013-508447 A | 3/2013 |
| JP | 2014-511895 A | 5/2014 |
| JP | 7061135 B2 | 4/2022 |
| KR | 101859074 B1 | 5/2018 |
| KR | 102119465 B1 | 6/2020 |
| RU | 2298554 C2 | 5/2007 |
| RU | 2310651 C2 | 11/2007 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 A1 | 1/1998 |
| WO | WO-9931061 A1 | 6/1999 |
| WO | WO 2000/066119 A1 | 11/2000 |
| WO | WO 2002/000617 A2 | 1/2002 |
| WO | WO 2002/066512 A1 | 8/2002 |
| WO | WO 2002/100845 A1 | 12/2002 |
| WO | WO 2006/113942 A2 | 10/2006 |
| WO | WO 2007/106670 A2 | 9/2007 |
| WO | WO 2008/011392 A2 | 1/2008 |
| WO | WO 2009/015254 A1 | 1/2009 |
| WO | WO 2010/053732 A1 | 5/2010 |
| WO | WO 2010/141805 A1 | 12/2010 |
| WO | WO 2011/008260 A2 | 1/2011 |
| WO | WO 2012/003281 A2 | 1/2012 |
| WO | WO 2012/040527 A2 | 3/2012 |
| WO | WO 2012/078559 A2 | 6/2012 |
| WO | WO 2012/090104 A1 | 7/2012 |
| WO | WO 2013/106643 A2 | 7/2013 |
| WO | WO 2013/106646 A2 | 7/2013 |
| WO | WO 2013/170147 A1 | 11/2013 |
| WO | WO-2014015157 A2 | 1/2014 |
| WO | WO 2014/108452 A1 | 7/2014 |
| WO | WO 2014/123418 A1 | 8/2014 |
| WO | WO 2015/000868 A1 | 1/2015 |
| WO | WO 2015/038649 A1 | 3/2015 |
| WO | WO-2015114314 A1 | 8/2015 |
| WO | WO 2015/134464 A1 | 9/2015 |
| WO | WO 2015/160845 A2 | 10/2015 |
| WO | WO 2016/105518 A1 | 6/2016 |
| WO | WO 2016/118666 A1 | 7/2016 |
| WO | WO 2016/146985 A1 | 9/2016 |
| WO | WO 2016/169989 A1 | 10/2016 |
| WO | WO 2016/172134 A2 | 10/2016 |
| WO | WO 2016/197032 A1 | 12/2016 |
| WO | WO 2016/197114 A1 | 12/2016 |
| WO | WO 2017/011590 A1 | 1/2017 |
| WO | WO 2017/030814 A1 | 2/2017 |
| WO | WO 2017/079267 A1 | 5/2017 |
| WO | WO 2017/185031 A1 | 10/2017 |
| WO | WO 2017/185034 A1 | 10/2017 |
| WO | WO-2017184995 A1 | 10/2017 |
| WO | WO 2017/197051 A1 | 11/2017 |
| WO | WO 2017/197056 A1 | 11/2017 |

(56) References Cited

FOREIGN PATENT DOCUMENTS

| WO | WO 2018/071606 A1 | 4/2018 |
|---|---|---|
| WO | WO-2018098280 A1 | 5/2018 |
| WO | WO-2018177989 A1 | 10/2018 |
| WO | WO-2020047487 A1 | 3/2020 |
| WO | WO-2020132014 A1 | 6/2020 |
| WO | WO-2020132016 A1 | 6/2020 |
| WO | WO 2020/211822 A1 | 10/2020 |
| WO | WO-2020198711 A1 | 10/2020 |
| WO | WO-2020198712 A1 | 10/2020 |
| WO | WO 2021/081108 A1 | 4/2021 |
| WO | WO 2021/231431 A1 | 11/2021 |
| WO | WO-2021249534 A1 | 12/2021 |
| WO | WO-2022048605 A1 | 3/2022 |
| WO | WO-2022111526 A1 | 6/2022 |
| WO | WO-2022187419 A1 | 9/2022 |
| WO | WO-2022192481 A1 | 9/2022 |
| WO | WO-2023205481 A1 | 10/2023 |
| WO | WO-2023222011 A1 | 11/2023 |

OTHER PUBLICATIONS

Handbook of Pharmaceutical Excipients, 5th edition 2006 (http://www.gmpua.com/RD/RD/HandbookPharmaceutical%20Excipients.pdf). (Year: 2006).*
Brittain, H.G. (Ed.). (2009). Polymorphism in Pharmaceutical Solids (2nd ed.). CRC Press. https://doi.org/10.3109/9781420073225 (Year: 2009).*
Ahn, et al., "HIF-1α peptide derivatives with modifications at the hydroxyproline residue as activators of HIF-1α", Bioorg Med Chem Lett, 2009, 19(15), 4403-4405.
Allan, G.F., et. al., "Therapeutic androgen receptor ligands", Nuclear Receptor Signaling, 2003, 1, e009 DOI:10.621.01009 9, 1-4.
Asangani, I.A. et al., "Therapeutic Targeting of BET Bromodomain Proteins in Castration-Resistant Prostate Cancer", Nature, 2014, 510, 278-282.
Bargagna-Mohan, et al., "Use of PROTACS as molecular probes of angiogenesis", Bioorg Med Chem Left, 2005, 15(11), 2724-2727.
Bondeson, et al., "Targeted Protein Degradation by Small Molecules." Annu Rev Pharmacol Toxicol, 2017, 57, 107-123.
Bondeson, et al., "Catalytic in Vivo protein knockdown by small-molecule PROTACS", National Chem Biol., Aug. 2015, 11(8), 611-617.
Bradbury, R.H., et al, "Small-molecule androgen receptor downregulators as an approach to treatment of advanced prostate cancer", Bioorganic & Medicinal Chemistry Letters, 2011, 21, 5442-5445.
Buckley, et al., "HaloPROTACS: use of small molecule PROTACS to induce degradation of HaloTag fusion proteins", ACS Chem Biol., 2015, 10(8), 1831-1837.
Buckley, et al., "Small-molecule inhibitors of the interaction between the E3 ligase VHL and HIF1α", Angew Chem Int Ed Engl, 2012, 51(46), 11463-11467.
Buckley, et al., "Targeting the von Hippel-Lindau E3 ubiquitin ligase using small molecules to disrupt the VHL/HIF-1α interaction", Journal of the American Chemical Society, 2012, 134(10), 4465-4468.
Burslem, et al., "Small-Molecule Modulation of Protein Homeostasis." Chem Rev., 2017, 117(17), 11269-11301.
Caira, "Crystalline Polymorphism of Organic Compounds," Topics in Current Chemistry, Jan. 1, 1998, 198, 163-208.
Capitosti, S., et al., "Thalidomide analogues demonstrate dual inhibition of both angiogenesis and prostate cancer", Bioorganic & Medicinal Chemistry, 2004, 12, 327-336.
Carmony, K.C, et al., "PROTAC-Induced Proteolytic Targeting", Methods Mol. Biol, 2012, 832, 627-638.
CAS 155180-53-3 published 1994.
CAS 155255-73-5 published 1995.
CAS 186040-53-9 published 1997.
CAS 186798-71-0 published 1997.
CAS 186798-85-6 published 1997.
CAS 534612-78-7 published 2003.

CAS Registry No. 1004933-70-3, which entered STN on Feb. 21, 2008.
CAS Registry No. 871986-52-6 entered STN Jan. 16, 2006.
CAS Registry No. 1323488-78-3; STN Entry Date Aug. 26, 2011; 2,6-Piperidinedione, 3-[4-[[4-[[4-(2,4-difluorophenyl)-1-piperidinyl]methyl]phenyl]methoxy]-1,3-dihydro-1-oxo-2H-isoindol-2-yl]-, (3S)-[1], entered STN: Aug. 26, 2011.
CAS Registry No. 1323488-76-1; STN Entry Date Aug. 26, 2011; 2,6-Piperidinedione, 3-[4-[[4- [[4-(3,5-difluorophenyl)-1-piperidinyl]methyl]phenyl]methoxy]-1,3-dihydro-1-oxo-2H-isoindol-2-yl]-[1], entered STN: Aug. 26, 2011.
CAS Registry No. 1323403-74-2; STN Entry Date Aug. 26, 2011; 2,4'-Bipyridinium, 1'-[[4-[[[2-(2,6-dioxo-3-piperidinyl)-2,3-dihydro-1-oxo-1H-isoindol-4-yl]oxy]methyl]phenyl]methyl]-[1], entered STN: Aug. 26, 2011.
Chemical Abstracts Registry No. 1226974-40-8, indexed in the Registry file on STN CAS Online Jun. 4, 2010. (Year: 2010).
Chemical Abstracts Registry No. 1818885-25-4, indexed in the Registry file on STN CAS Online Nov. 10, 2015. (Year: 2015).
Contino-Pepin, Christiane, et al., "Preliminary biological evaluations of new thalidomide analogues for multiple sclerosis application", Bioorganic & Medicinal Chemistry Letter 19, 2009, 878-881.
Corson, et al., "Design and applications of bifunctional small molecules: why two heads are better than one", ACS Chemical Biology, Nov. 21, 2008, 3(11), 677-692.
Crews, C. M., "Targeting the undruggable proteome: the small molecules of my dreams", Chem Biol, 2010, 17, 551-555, doi:S1074-5521g10200196-1 [pii] 10.1016/j.chembiol.2010.05.011.
Cromm, et al., "Targeted Protein Degradation: from Chemical Biology to Drug Discovery." Cell Chem Biol, 2017, 24(9), 1181-1190.
Cyrus, et al., "Jostling for position: optimizing linker location in the design of estrogen receptortargeting PROTACs", Chem Med Chem, Jul. 5, 2010, 5(7), 979-985.
Cyrus, K. et al, "Impact of Linker Length on the Activity of PROTACs," Mol. Biosyst., 2011, 7(2), 359-364.
Cyrus, K. et al, "Two-Headed PROTAC: An Effective New Tool for Targeted Protein De gradation," Chembiochem., 2010, 11, 1531-1534.
Fischer, et al., "Structure of the DDB1-CRBN E3 Ubiquitin ligase in complex with thalidomide," Nature, 2014, 512, 49-53.
Gadd, M.S., et al., "Structural basis of PROTAC cooperative recognition for selective protein degadation", Nat Chem Biol, 2017, 13, 514-521.
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, 57, 8657-8663.
Golub, et al., "Molecular classification of cancer: class discovery and class prediction by gene expression monitoring", Science, 1991 286, 531-537.
Gosink, M et al., "Redirecting the specificity of ubiquitination by modifying ubiquitin-conjugating enzymes", Pro. Natl. Acad Sci, 1995, 92, 9117-9121.
Guidelines for conducting preclinical studies of drugs, Part one.—M.: Grif and K, 2012.—944 p., under the editorship of A. N. Mironov, Chapter 39, 640-654, p. 640.
Guo, C., et. al, "Design of oxobenzimidazoles and oxindoles as novel androgen receptor antagonists", Bioorganic & Medicinal Chemistry Letters, 2012, 22, 2572-2578.
Guo, C. et al "Discovery of Aryloxy Tetramethylcyclobutanes as Novel Androgen Receptor Antagonists", J. Med. Chem. 2011, 54, 7693-7704.
Gustafson, et al., "Small-Molecule-Mediated Degradation of the Androgen Receptor through Hydrophobic Tagging", Agnew Chem Int Ed., 2015, 54, 9659-9662.
Han, X. et al., "Discovery of ARD-69 as a Highly Potent Proteolysis Targeting Chimera (PROTAC) Degrader of Androgen Receptor (AR) for the Treatment of Prostate Cancer," J. Med. Chem., 2019, 62, 941-964.

(56) References Cited

OTHER PUBLICATIONS

Hines, J., et al., "Posttranslational protein knockdown coupled to receptor tyrosine kinase activation with phosphoPROTACs", Proc Natl Acad Sci USA, 2013, 110, 8942-8947.

Hon, et al., "Structural basis for the recognition of hydroxyproline in HIF-1α by pVHL", Nature, Jun. 27, 2002, 417, 975-978.

Huang, et al., "Drugging the undruggables: exploring the ubiquitin system for drug development." Cell Res, 2016, 26(4), 484-498.

Hughes, et al., "Molecular recognition of ternary complexes: a new dimension in the structure-guided design of chemical degraders." Essays Biochem, 2017, 61(5), 505-516.

International Search Report and Written Opinion issued in PCT/US2021/031091, dated Aug. 5, 2021, 1-23.

Ivan, M., et al., "HIFalpha Targeted for VHL-Mediated Destruction by Proline Hydroxylation: Implications for $O_2$ Sensing", Science, 2001, 292(5516), 464-468.

Jang, E.R. et al., "Targeted Degradation of Proteins by PROTACs," Curr. Protoc. Chem. Biol., 2010, 2(2), 71-87.

Jung, M. E. et al "Structure-Activity Relationship for Thioydantoin Androgen Receptor Antagonists for Castration-Resistant Prostate Cancer (CRPC)", J. Med. Chem., 2010, 53, 2779-2796.

Kharkevich D.A. Pharmacology / Textbook, 2010, 10th edition, 72-82.

Knott, E. "Compounds containing sulphur chromophores. Part I. The action of bases on heterocyclic sulphide quartemary salts", Journal of The Chemical Society (resumed), 1955, 10.1039/jr9550000916. 949-954.

Kronke, et al, "Lenalidomide Causes Selective Degradation of IKZF1 and IKZF3 in Multiple Myeloma Cells", Science, 2014, 343, 301-305.

Lai, A.C., et al., "Modular PROTAC Design for the Degradation of Oncogenic BCR-ABL", Angew Chem Int Ed Engl, 2016, 55, 807-810.

Lai, et al., "Induced protein degradation: an emerging drug discovery paradigm." Nat Rev Drug Discov, 2017, 16(2), 101-114.

Lala, et al., "Role of nitric oxide in tumor progression: Lessons from experimental tumors", Cancer and Metastasis Reviews, 1998, 17, 91-106.

Lebraud, H., et al., "Protein Degradation by In-Cell Self-Assembly of Proteolysis Targeting Chimeras", ACS Central Science, 2016, 2, 927-934.

Lee, B. Y., "FAK signaling in human cancer as a target for therapeutics", Pharmacol. Ther., 2015, 146, 132-149.

Lee, et al., "Targeted Degradation of the Aryl Hydrocarbon Receptor by the PROTAC Approach: A Useful Chemical Genetic Tool", ChemBioChem, Nov. 23, 2007, 8(17), 2058-2062.

Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistent (T790M) EGFR mutants for the treatment of EGFR mutant non-small-cell lung cancers", Journal of Medicinal Chemistry, 2016, 59(14), 6671-6689.

Lemmon, M.A., et al., "Cell Signaling by Receptor Tyrosine Kinases", Cell, 2010, 141, 1117-1134.

Levine, et al., "Targeting the androgen receptor with steroid conjugates," J. Med. Chem., 2014, 57(20), 8224-8237.

Li, Yan, et al., "Single polymer-drug conjugate carrying two drugs for fixed-dose co-delivery", Medicinal Chemistry, 2014, 4(10), 676-683.

Liu, K., et al., "Design and biological characterization of hybrid compounds of curcumin and thalidomide for multiple myeloma", Org. Biomol. Chem., 2013, 11, 4757-4763.

Lopez-Girona, A. et al., "Cereblon is a direct protein target for immunomodulatory and antiproliferative activities of lenalidomide and pomalidomide", Leukemia, 2012, 26, 2326-2335.

Lu, et al., "Hijacking the E3 ubiquitin ligase cereblon to efficiently target BRD4", Chem Biol, 2015, 22(6), 755-763.

Lu, et al., "The myeloma drug lenalidomide promotes the cereblon-dependent destruction of ikaros proteins", Science, 2014, 343, 305-309.

Lu, N.Z., et al., "International Union of Pharmacology. LXV. The pharmacology and classification of the nuclear receptor superfamily: glucocorticoid, mineralocorticoid, progesterone, and androgen receptors", Pharmacol Rev., Dec. 2006, 58(4), 782-797. Review. PubMed PMID: 17132855.

Maniaci, C., et al. "Homo-PROTACs: bivalent small-molecule dimerizers of the VHL E3 ubiquitin ligase to induce self-deradation." Nat Commun, 2017, 8(1):830, 1-13.

M.D. Mashkovsky, Medicines, 14th edition, vol. 1. Moscow., 2001, pp. 11 (5 pages total).

M.D. Mashkovsky, Medicinal Drugs, Moscow, Medicine, 1993, Part I, p. 8.

Medline Plus Trusted Health Information for You, www.nlm.nih.gov/medlineplus/cancer.html pp. 1-10, (2007).

Min, J., et al., "Structure of an HIF-1α-pVHL complex: hydroxyproline recognition in signaling", Science, 2002, 296, 1886-1889.

Mohler, M.L., et al., Androgen receptor antagonists: a patent review, Expert Opinion on Therapeutic Patents, 2008-2011, 2012, 22(5), 541-565.

Muller, G., et al., "Amino-Substituted Thalodomide Analogs: Potent Inhibitors of TNF-α Production", Biooranic & Medicinal Chemist Letters, 1999, 9, 1625-1630.

Neklesa, T.K., et al., "Chemical biology: Greasy tags for protein removal", Nature, 2012, 487, 308-309.

Neklesa, T.K. et al., "ARV-110: An oral androgen receptor PROTAC degrader for prostate cancer." Journal of Clinical Oncology, 37(7), Mar. 2019, p. 259, retrieved from internet: https://s3.us-east-1.amazonaws.com/arvinas-assets.investeddigital.com/scientific-publications/AR-GUASCO-2-11-2019.pdf.

Neklesa, "Targeted protein degradation by PROTACs", Pharmacology & Therapeutics, 2017, 174, 138-144.

Office Action and Prior Art Search Report for RU Application No. 2020106066, filing date of Oct. 11, 2017, dated Jul 30, 2020, Enlish Translation, 7 paaes.

Office Action issued in Russian Application No. 2020106066/04(009395), dated Jun. 22, 2021, 1-26.

Ohoka, N. et al. "SNIPER(TACC3) induces cytoplasmic vacuolization and sensitizes cancer cells to Bortezomib." Cancer Sci., 2017, 108, 1032-1041.

Ottis, P, et al. "Assessing Different E3 Ligases for Small Molecule Induced Protein Ubiquitination and Deradation." ACS Chem Biol, 2017, 12(10), 2570-2578.

Ottis, et al., "Proteolysis-Targeting Chimeras: Induced Protein Degradation as a Therapeutic Strate." ACS Chem Biol, 2017, 12(4), 892-898.

Pepe, A. et. al., "Synthesis and structure-activity relationship studies of novel dihydropyridones as androgen receptor modulators", J. Med. Chem., 2013, 56, 8280-8297.

Poutiainen, P.K., et. al., "Design, synthesis, and biological evaluation of nonsteroidal cycloalkane [d] isoxazole-containing androgen receptor modulators", J. Med. Chem., 2012, 55, 6316-6327.

Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, 73(4), 1064-1071.

Raina, et al., "Targeted protein knockdown using small molecule degraders." Curr Opin Chem Biol, 2017, 39, 46-53.

Raina, K., et al., "PROTAC-induced BET protein degradation as a therapy for castration-resistant prostate cancer", Proc Natl Acad Sci USA, 2016, 113, 7124-7129.

Remillard, D., et al. "Degradation of the BAF Complex Factor BRD9 by Heterobifunctional Liands." Anew Chem Int Ed Enl, 2017, 56(21), 5738-5743.

Rodriguez-Gonzalez, et al., "Targeting steroid hormone receptors for ubiquitination and degradation in breast and rostate cancer", Oncogene. Dec. 4, 2008, 27 57, 7201-7211.

Rotili, D., et al., "Photoactivable peptides for identifying enzyme-substrate and protein-protein interactions", Chem Commun (Carob), Feb. 2011, 47(5), 1488-1490.

(56) References Cited

OTHER PUBLICATIONS

Ruchelman, A., et al., "Isosteric analogs of lenalidominde and pomalidomide: Synthesis and biological activity", Bioorganic & Medicinal Chemistry Letters, 2013, 23, 360-365.
Sakamoto, et al., "Development of Protacs to target cancer-promoting proteins for ubiquitination and degradation", Mol Cell Proteomics., Dec. 2003, 2(12), 1350-1358.
Sakamoto, et al., "Protacs: chimeric molecules that target proteins to the Skp1-Cullin-F box complex for ubiquitination and degradation", Proc Natl Acad Sci U S A, Jul. 17, 2001, 98(15), 8554-8559.
Salami, J. & Crews, C. M. "Waste disposal—An attractive strategy for cancer therapy.", Science, 2017, 355, 1163-1167.
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem., 2017, 61, 482-491.
Schneekloth, et al., "Chemical Genetic Control of Protein Levels: Selective in Vivo Targeted Degradation", J Am Chem Soc., March 31, 2004, 126(12), 3748-3754.
Schneekloth, et al., Targeted intracellular protein degradation induced by a small molecule: Enroute to chemical proteomics, Bioorg. Med. Chem. Lett., 2008, 18, 5904-5908.
Smirnova et al, "Optical Isomerism and Biological Activity of Medicines", Moscow University Gazette, Series 2, Chemistry, 2012, 53(3), 147-156.
Smith, et al., "Targeted Intracellular Protein Degradation Induced by a Small Molecule: En Route to Chemical Proteomics", Bioorg Med Chem Lett., Nov. 15, 2008, 18(22), 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017 .
Toure, et al., (2016) "Small-MoleculePROTACS: New Approaches toProtein Degradation." Angew Chem Int Ed Engl, 2016, 55(6), 1966-1973.
Trewartha, D. & Carter, K. "Advances in prostate cancer treatment", Nat Rev Drug Discov. Nov. 2013; 12(11):823-824. doi: 10.1038/nrd4068.PubMedPMID: 24172327.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
V.G. Belikov, "Pharmaceutical Chemistry", textbook, 2007, Moscow, "MEDpress-inform," 27-29.
Van Molle, et al., "Dissecting fragment-based lead discovery at the von Hippel-Lindau protein: hypoxia inducible factor 1α: protein-protein interface", Chem Biol., Oct. 26, 2012, 19(10), 1300-1312.
Winter, et al., "Phthalimide Conjugation as a strategy for in vivo target protein degradation", Science, 2015 vol. 348 (6241), 1376-1381 [Pub online: May 21, 2015].
Zengerle, et al., "Selective Small Molecule Induced Degradation of the BET Bromodomain Protein BRD4" ACS Chemical Biology, Jun. 2, 2015, 10, 1770-1777.
Zhang, D. et al., "Targeted Degradation of Proteins by Small Molecules: A Novel Tool for Functional Proteomics," Comb. Chem. High Throughput Screen., 2004, 7(7), 689-697.
U.S. Appl. No. 18/085,869, filed Dec. 21, 2022, Crew et al.
Chevalier-Larsen, E. et al. "Castration Restores Function and Neurofilament Alterations of Aged Symptomatic Males in a Transgenic Mouse Model of Spinal and Bulbar Muscular Atrophy," The Journal of Neuroscience, May 19, 2004, 24(20):4778-4786.
Fizazi, K., et al., "Activity and safety of ODM-201 in patients with progressive metastatic castration-resistant prostate cancer (ARADES): an open-label phase 1 dose-escalation and randomised phase 2 dose expansion trial," Lancet Oncol, Aug. 2014, 15(9):975-985.

Inacio, P. et al. "FDA Clears Phase 1 Trial of ARV-110 for Advanced Prostate Cancer," Prostate Cancer News Today, Jan. 30, 2019, retrieved from internet at https://prostatecancernewstoday.com/2019/01/30/fda-clears-phase-1-trial-arv-110-advanced-prostate-cancer/, 5 pages.
Kümmerer, K. "Pharmaceuticals in the Environment," Annu. Rev. Environ. Resour., 2010, 35:57-75.
Lallous, N. et al., "Functional analysis of androgen receptor mutations that confer anti-androgen resistance identified in circulating cell-free DNA from prostate cancer patients," Genome Biology, 2016, 17(10):1-15.
Li, S. et al. "IMiD immunomodulatory compounds block C/EBPβ translation through eIF4E down-regulation resulting in inhibition of MM," Blood, May 12, 2011, 117(19):5157-5165.
Office Action for RU Application No. 2019113229/04(025529), filing date of Oct. 11, 2017, dated May 25, 2022, English Translation, 30 pages.
Percy and Dyson, The Chemistry of Synthetic Drugsquot, USSR, Moscow, quot; Mirquot; Publishing House, 1964, pp. 12-19.
PubChem CID 11835243, National Center for Biotechnology Information. "PubChem Compound Summary for CID 118435243" PubChem, https://pubchem.ncbi.nlm.nih.gov/compound/11835243. Accessed Sep. 15, 2022, create date Feb. 23, 2016, 11 pages.
PubChem CID No. 134414307, "Bavdegalutamide," Created Jun. 23, 2018, modified Jan. 7, 2023, retrieved from the internet at https://pubchem.ncbi.nlm.nih.gov/compound/134414307, 15 pages.
Szajewska, H. "Evidence-Based Medicine and Clinical Research: Both Are Needed, Neither Is Perfect," Ann Nutr Metab, 2018, 72(suppl 3):13-23.
Trial of ARV-110 in Patients with Metastatic Castration Resistant Prostate Cancer (MCRPC). (first posted on Mar. 25, 2019). Retrieved from https://clinicaltrials.gov/ct2/show/NCT03888612, 10 pages.
Wesserling and Drewa, Will In Vitro Tests Replace Animal Models in Experimental Oncology? J. Tissue Sci. Eng., 2011, 2(1):1-4.
Arvinas, Inc., "Arvinas Announces Poster Presentation at ASCO 2019 Genitourinary Cancers Symposium", Press Release (Feb. 7, 2019); 2 pages.
Arvinas, Inc., "Arvinas Announces Updated Phase 1 Data Demonstrating Clinical Activity of PROTAC® Protein Degrader ARV-110 in Patients with Refractory Prostate Cancer", Press Release (May 13, 2020); 2 pages.
Arvinas, Inc., "Arvinas Nominates Oral Clinical Candidate for Androgen Receptor Degrader Program", Press Release (Nov. 2, 2017); 1 page.
Arvinas, Inc., "Arvinas Presents a Platform Update, Including Initial Data from the First Two Clinical Trials of PROTAC® Targeted Protein Degraders", Press Release (Oct. 23, 2019); 2 pages.
Arvinas, Inc., "Arvinas Presents New Preclinical Data on Oral Androgen Receptor PROTAC at ASCO 2017 Genitourinary Cancers Symposium", Press Release (Feb. 17, 2017); 1 page.
Arvinas, Inc., "Arvinas Presents New Preclinical Data on Oral Androgen Receptor Protac® ARV-110 at ASCO 2018 Genitourinary Cancers Symposium", Press Release (Feb. 9, 2018); 1 page.
Arvinas, Inc., "Arvinas Provides Update on Business Continuity Related to the Impact of the COVID-19 Pandemic", Press Release (Apr. 13, 2020); 2 pages.
Arvinas, Inc., "Arvinas Receives Authorization to Proceed for its IND Application for PROTAC™ Therapy to Treat Patients with Metastatic Castration-Resistant Prostate Cancer", Press Release (Jan. 4, 2019); 2 pages.
Arvinas, Inc., "Arvinas Receives Fast Track Designation for its Targeted Protein Degrader ARV-110 as a Treatment for Men with Metastatic Castration-Resistant Prostate Cancer", Press Release (May 29, 2019); 2 pages.
Arvinas, Inc., "Arvinas Releases Interim Clinical Data Further Demonstrating the Powerful Potential of PROTAC® Protein Degraders ARV-471 and ARV-110", Press Release (Dec. 14, 2020); 3 pages.
Arvinas, Inc., "Arvinas Releases Updated Dose Escalation Data from Clinical Trial of PROTAC® Protein Degrader ARV-110 in Patients with Metastatic Castration-Resistant Prostate Cancer", Press Release (May 29, 2020); 2 pages.

(56) References Cited

OTHER PUBLICATIONS

Arvinas, Inc., "Arvinas Reports First Quarter 2020 Financial Results and Provides a Corporate Update", Press Release (Apr. 28, 2020); 3 pages.

Arvinas, Inc., "Arvinas Reports First Quarter 2021 Financial Results and Provides Corporate Update", Press Release (May 4, 2021); 3 pages.

Arvinas, Inc., "Arvinas Reports First Quarter Financial Results and Provides Corporate Update", Press Release (May 8, 2019); 4 pages.

Arvinas, Inc., "Arvinas Reports Fourth Quarter and Full Year 2018 Financial Results and Provides Corporate Update", Press Release (Mar. 26, 2019); 4 pages.

Arvinas, Inc., "Arvinas Reports Fourth Quarter and Full Year 2019 Financial Results and Provides Corporate Update", Press Release (Mar. 16, 2020); 4 pages.

Arvinas, Inc., "Arvinas Reports Fourth Quarter and Full Year 2020 Financial Results and Provides Corporate Update", Press Release (Mar. 1, 2021); 4 pages.

Arvinas, Inc., "Arvinas Reports Second Quarter 2019 Financial Results and Provides Corporate Update", Press Release (Aug. 5, 2019); 4 pages.

Arvinas, Inc., "Arvinas Reports Second Quarter 2020 Financial Results and Provides Corporate Update", Press Release (Aug. 4, 2020); 3 pages.

Arvinas, Inc., "Arvinas Reports Third Quarter 2019 Financial Results and Provides Corporate Update", Press Release (Nov. 4, 2019); 4 pages.

Arvinas, Inc., "Arvinas Reports Third Quarter 2020 Financial Results and Provides Corporate Update", Press Release (Nov. 5, 2020); 4 pages.

Arvinas, Inc., "Arvinas to Present at the American Society of Clinical Oncology Annual Meeting", Press Release (Mar. 31, 2020); 1 page.

Arvinas, Inc., "Arvinas to Present Initial Data from Ongoing Clinical Trials and a Pipeline Update at the 2nd Targeted Protein Degradation Summit", Press Release (Oct. 17, 2019); 2 pages.

"ARV-110 Phase 1/2 Dose Escalation: Interim Update", Arvinas, Inc. [online] https://ir.arvinas.com/events-and-presentations?page=0%2C0%2C0 (May 29, 2020); 30 pages.

"Clinical Program Update: ARV-471 & ARV-110", Arvinas, Inc. [online] https://ir.arvinas.com/events-and-presentations?page=0%2C0%2C0 (Dec. 14, 2020); 43 pages.

[Author Unknown] "VCaP" ATCC [Online] https://www.atcc.org/products/crl-2876 (May 19, 2021); 7 pages.

Berge, S. M., et al., "Pharmaceutical salts", Journal of Pharmaceutical Sciences (1977); 66(1): 1-19.

Berlin, M., "Targeted Protein Degradation as a Clinical-stage Modality: Insights From ARV-110 and Other PROTAC® Protein Degraders", North American Protein Degradation Congress [online] https://ir.arvinas.com/events-and- presentations?page=0%2C0%2C0 (Feb. 5-6, 2020); 35 pages.

Fleisher, D. et al., "Improved oral drug delivery: solubility limitations overcome by the use of prodrugs," Advanced Drug Delivery Reviews (1996); 19: 115-130.

Heinlein, C. A., et al., "Androgen receptor in prostate cancer", Endocrine Reviews (2004); 25(2): 276-308.

Houston, J. G., "The Promise of PROTAC® Protein Degraders: What's Next for Arvinas' Pipeline & Platform" [online] https://ir.arvinas.com/events-and-presentations?page=0%2C0%2C0 (Oct. 14, 2020); 23 pages.

Jernberg, E., et al., "Clinical relevance of androgen receptor alterations in prostate cancer," Endocrine Connections (2017); 6: R146-R161.

Jung, J., "Human tumor xenograft models for preclinical assessment of anticancer drug development", Toxicological Research (2014); 30: 1-5.

Knuuttila, M., et al., "Castration induces up-regulation of intratumoral androgen biosynthesis and androgen receptor expression in an orthotopic VCaP human prostate cancer xenograft model", The American Journal of Pathology (2014); 184(8): 2163-2173.

Morissette, S. L., et al., "High-throughput crystallization: polymorphs, salts, cocrystals and solvates of pharmaceutical solids", Advanced Drug Delivery Reviews (2004); 56(3): 275-300.

Mullard, A., "First targeted protein degrader hits the clinic", Nature Reviews, Drug Discovery (Apr. 2019); 18: 237-239.

Neklesa, T. K. et al., "An oral androgen receptor PROTAC® degrader for prostate cancer", ASCO Genitourinary Cancers Symposium (2018) [online] https://s3.us-east-1.amazonaws.com/arvinas-assets.investeddigital.com/scientific-publications/AR-GUASCO2018-final.pdf; 1 page.

Office Action for RU Application No. 2020106066/04(009395), filing date of Oct. 11, 2017, dated Jul. 7, 2022, 20 pages; with English translation.

PubChem CID 118435243, "4-{[5-(3-{[2-(2,6-dioxopiperidin-3-yl)-1,3-dioxo-2,3-dihydro-1H-isoindol-4-yl]amino}propoxy)pentyl]oxy}-N-[trans-3-(3-chloro-4-cyanophenoxy)-2,2,4,4-tetramethylcyclobutyl]benzamide", National Center for Biotechnology Information [online] https://pubchem.ncbi.nlm.nih.gov/compound/118435243; Create date Feb. 23, 2016; 11 pages.

Robinson, R. P., et al., "Discovery of the Hemifumarate and (a-L-Alanyloxy) methyl Ether as Prodrugs of an Antirheumatic Oxindole: Prodrugs for the Enolic OH Group", Journal of Medicinal Chemistry (1996); 39(1): 10-18.

Scudellari, M., "The protein slayers", Nature (Mar. 21, 2019); 567: 298-300.

Zhulenko, V. N., et al., "Pharmacology", Moscow, KoloS (2008); pp. 34-35; 3 pages. (Not in English).

[Author Unknown] "Abiraterone Mylan (abiraterone acetate)", European Medicines Agency Science Medicines Health (Aug. 1, 2021) [online] https://www.ema.europa.eu/en/documents/overview/abiraterone-mylan-epar-medicine-overview_en.pdf (Access Date: Aug. 21, 2023); 2 pages.

Gao, X., et al. "Phase 1/2 study of ARV-110, an androgen receptor (AR) Protac degrader, in metastatic castration-resistant prostate cancer (mCRPC)", Journal Of Clinical Oncology 2022 American Society Of Clinical Oncology Nld (2022); (40)6; 1 page.

Romanel, A., et al., "Plasma AR and abiraterone-resistant prostate cancer", Science Translational Medicine (2015); 7(312): 312re10; 9 pages.

Wyatt, A. W., et al., "Genomic alterations in cell-free DNA and enzalutamide resistance in castration-resistant prostate cancer", JAMA Oncology (2016); 2(12): 1598-1606.

Caro-Maldonado, A., et al., "Low-dose statin treatment increases prostate cancer aggressiveness", Oncotarget (2018); 9(2): 1494-1504.

Co-pending U.S. Appl. No. 18/489,262, inventor Chirnomas; Sarah Deborah, filed on Oct. 18, 2023.

\* cited by examiner

| | |
|---|---|
| Start Position [°2Th.] | 3.0100 |
| End Position [°Th.] | 45.0100 |
| Step Size [°Th.] | 0.0200 |
| Scan Step Time [s] | 10.1600 |
| Scan Type | Continuous |
| Divergence Slit Type | Fixed |
| Divergence Slit Size [°] | 1.0000 |
| Anode Material | Cu |
| Generator Settings | 40 mA, 45 kV |
| Spinning | Yes |

Powder Pattern:

Counts

FIG. 3B

| Pos. [°2Th.] | Height. [cts] | FWHM [°2Th.] | d-spacing [A] | Pos. [°2Th.] | Tip width [°2Th.] |
|---|---|---|---|---|---|
| 3.1709 | 1201.95 | 0.0787 | 27.86388 | 30.15 | 0.0945 |
| 4.5720 | 213.33 | 0.0394 | 19.32751 | 5.35 | 0.0472 |
| 4.6735 | 278.69 | 0.0590 | 18.90811 | 6.99 | 0.0708 |
| 4.8843 | 169.69 | 0.0787 | 18.09245 | 4.26 | 0.0945 |
| 5.3055 | 358.60 | 0.0787 | 16.65717 | 9.00 | 0.0945 |
| 5.6096 | 313.04 | 0.0394 | 15.75483 | 7.85 | 0.0472 |
| 5.9629 | 252.25 | 0.0590 | 14.82218 | 6.33 | 0.0708 |
| 6.1718 | 235.43 | 0.0787 | 14.32084 | 5.91 | 0.0945 |
| 7.0636 | 313.43 | 0.0984 | 12.51461 | 7.86 | 0.1181 |
| 7.6348 | 1411.40 | 0.0984 | 11.57965 | 35.41 | 0.1181 |
| 8.0591 | 419.77 | 0.0590 | 10.97093 | 10.53 | 0.0708 |
| 8.5949 | 452.14 | 0.0590 | 10.28813 | 11.34 | 0.0708 |
| 9.1518 | 327.87 | 0.0590 | 9.66329 | 8.22 | 0.0708 |
| 9.8125 | 260.50 | 0.1574 | 9.01415 | 6.53 | 0.1889 |
| 10.1874 | 348.01 | 0.0590 | 8.68325 | 8.73 | 0.0708 |
| 10.3886 | 415.88 | 0.1181 | 8.51553 | 10.43 | 0.1417 |
| 10.8136 | 375.06 | 0.1181 | 8.18172 | 9.41 | 0.1417 |
| 11.3769 | 829.34 | 0.0590 | 7.77791 | 20.80 | 0.0708 |
| 11.5017 | 855.56 | 0.0590 | 7.69375 | 21.46 | 0.0708 |
| 12.9499 | 260.60 | 0.0590 | 6.83645 | 6.54 | 0.0708 |
| 13.0784 | 294.85 | 0.0590 | 6.76956 | 7.40 | 0.0708 |
| 13.2726 | 271.04 | 0.0787 | 6.67095 | 6.80 | 0.0945 |
| 13.7106 | 493.55 | 0.1181 | 6.45879 | 12.38 | 0.1417 |
| 14.6517 | 537.42 | 0.0394 | 6.04600 | 13.48 | 0.0472 |
| 15.3808 | 690.61 | 0.1968 | 5.76101 | 17.32 | 0.2362 |
| 16.2277 | 794.79 | 0.2362 | 5.46221 | 19.94 | 0.2834 |
| 17.0484 | 1284.10 | 0.1181 | 5.20106 | 32.21 | 0.1417 |
| 17.5612 | 3986.33 | 0.1574 | 5.05031 | 100.00 | 0.1889 |
| 18.5067 | 919.60 | 0.0590 | 4.79437 | 23.07 | 0.0708 |
| 19.4654 | 638.66 | 0.1181 | 4.56035 | 16.02 | 0.1417 |
| 21.2230 | 779.38 | 0.0590 | 4.19649 | 19.55 | 0.0708 |
| 21.4057 | 816.51 | 0.1181 | 4.15118 | 20.48 | 0.1417 |
| 22.3660 | 536.91 | 0.0787 | 3.97507 | 13.47 | 0.0945 |
| 22.7613 | 608.02 | 0.1181 | 3.90692 | 15.25 | 0.1417 |
| 23.3553 | 466.07 | 0.2362 | 3.80887 | 11.69 | 0.2834 |
| 24.5115 | 559.92 | 0.1968 | 3.63177 | 14.05 | 0.2362 |
| 25.1231 | 489.43 | 0.0590 | 3.54473 | 12.28 | 0.0708 |
| 27.8586 | 305.95 | 0.1181 | 3.20257 | 7.67 | 0.1417 |
| 28.6722 | 222.62 | 0.4723 | 3.11352 | 5.58 | 0.5668 |
| 30.1276 | 131.85 | 0.3149 | 2.96635 | 3.31 | 0.3779 |
| 31.5251 | 111.50 | 0.0787 | 2.83796 | 2.80 | 0.0945 |
| 32.8617 | 84.31 | 0.2362 | 2.72553 | 2.11 | 0.2834 |
| 34.8079 | 49.99 | 0.2362 | 2.57747 | 1.25 | 0.2834 |
| 35.6919 | 44.90 | 0.4723 | 2.51563 | 1.13 | 0.5668 |
| 36.8486 | 59.84 | 0.0590 | 2.43928 | 1.50 | 0.0708 |
| 41.0595 | 34.71 | 0.1440 | 2.19650 | 0.87 | 0.1728 |

Start Position [°2Th.]      3.0100
End Position [°Th.]         45.0100
Step Size [°Th.]            0.0200
Scan Step Time [s]          10.1600
Scan Type                   Continuous
Divergence Slit Type        Fixed
Divergence Slit Size [°]    1.0000
Anode Material              Cu
Generator Settings          40 mA, 45 kV
Spinning                    Yes

Powder Pattern:

FIG. 3D

| Pos. [°2Th.] | Height. [cts] | FWHM [°2Th.] | d-spacing [A] | Rel. Inc [%] | Tip width [°2Th.] |
|---|---|---|---|---|---|
| 3.1895 | 308.19 | 0.1181 | 27.70194 | 6.24 | 0.1417 |
| 3.6257 | 448.01 | 0.0394 | 24.36997 | 9.08 | 0.0472 |
| 3.9923 | 103.33 | 0.0990 | 22.13301 | 2.09 | 0.0708 |
| 4.1312 | 199.88 | 0.0394 | 21.38872 | 4.05 | 0.0472 |
| 5.5347 | 556.31 | 0.0787 | 15.96771 | 11.27 | 0.0945 |
| 6.4732 | 239.15 | 0.0394 | 13.65483 | 4.85 | 0.0472 |
| 6.7036 | 186.26 | 0.0394 | 13.18590 | 3.77 | 0.0472 |
| 6.8438 | 266.16 | 0.0787 | 12.91519 | 5.39 | 0.0945 |
| 7.5383 | 213.23 | 0.0590 | 11.72772 | 4.32 | 0.0708 |
| 7.8671 | 1467.38 | 0.0984 | 11.23828 | 29.73 | 0.1181 |
| 8.2671 | 547.55 | 0.1281 | 10.77790 | 11.09 | 0.1417 |
| 8.9707 | 380.59 | 0.0550 | 9.85804 | 7.71 | 0.0708 |
| 9.7063 | 665.48 | 0.1181 | 9.11250 | 13.48 | 0.1417 |
| 11.0077 | 1882.92 | 0.0984 | 8.03793 | 38.15 | 0.1183 |
| 11.3491 | 1489.30 | 0.0984 | 7.79690 | 30.18 | 0.1181 |
| 12.5308 | 136.66 | 0.0950 | 7.06411 | 2.77 | 0.0708 |
| 12.8614 | 586.94 | 0.0984 | 6.88326 | 12.10 | 0.1181 |
| 13.5914 | 912.72 | 0.0984 | 6.51517 | 18.49 | 0.1181 |
| 14.6013 | 348.93 | 0.1378 | 6.06675 | 7.07 | 0.1653 |
| 14.9112 | 143.14 | 0.0590 | 5.94134 | 2.90 | 0.0708 |
| 15.3686 | 269.61 | 0.1181 | 5.76555 | 5.46 | 0.1417 |
| 15.6211 | 446.17 | 0.0787 | 5.67289 | 9.04 | 0.0945 |
| 16.0925 | 4935.27 | 0.1771 | 5.50778 | 100.00 | 0.2125 |
| 16.8720 | 561.88 | 0.1574 | 5.25504 | 11.38 | 0.1889 |
| 17.2061 | 1505.38 | 0.1771 | 5.15374 | 30.50 | 0.2125 |
| 17.8863 | 3136.80 | 0.1574 | 4.99925 | 63.56 | 0.1889 |
| 18.3192 | 392.64 | 0.1574 | 4.86301 | 7.96 | 0.1889 |
| 18.8905 | 213.30 | 0.1181 | 4.70770 | 4.32 | 0.1417 |
| 19.4066 | 368.20 | 0.2362 | 4.57404 | 7.06 | 0.2834 |
| 19.6969 | 231.15 | 0.0787 | 4.50729 | 4.68 | 0.0945 |
| 20.0963 | 1521.67 | 0.1378 | 4.41858 | 30.83 | 0.1653 |
| 20.7669 | 326.32 | 0.0584 | 4.37739 | 6.61 | 0.1181 |
| 21.0700 | 480.91 | 0.1378 | 4.21654 | 9.74 | 0.1653 |
| 22.0929 | 1257.63 | 0.1378 | 4.02359 | 25.48 | 0.1653 |
| 22.6727 | 1525.81 | 0.0787 | 3.92199 | 30.92 | 0.0945 |
| 24.3672 | 1818.75 | 0.1771 | 3.65294 | 36.85 | 0.2125 |
| 24.9493 | 653.74 | 0.0584 | 3.56902 | 13.25 | 0.1181 |
| 25.4106 | 1069.72 | 0.1378 | 3.50528 | 21.68 | 0.1653 |
| 25.8665 | 846.60 | 0.0787 | 3.44451 | 17.15 | 0.0945 |
| 26.5896 | 533.88 | 0.1378 | 3.35247 | 10.82 | 0.1653 |
| 27.2137 | 299.12 | 0.1574 | 3.27698 | 5.25 | 0.1889 |
| 27.4773 | 241.71 | 0.0787 | 3.24614 | 4.90 | 0.0945 |
| 28.0911 | 786.83 | 0.1968 | 3.17659 | 15.94 | 0.2362 |
| 28.4834 | 5128.21 | 0.0550 | 3.13373 | 10.70 | 0.0708 |
| 28.9767 | 317.43 | 0.0984 | 3.08149 | 6.43 | 0.1181 |
| 30.2102 | 173.54 | 0.1968 | 2.95843 | 3.52 | 0.2362 |
| 30.9687 | 182.10 | 0.1574 | 2.88767 | 3.69 | 0.1889 |
| 31.2954 | 182.96 | 0.1574 | 2.85827 | 3.71 | 0.1889 |
| 31.9854 | 123.57 | 0.0984 | 2.79817 | 2.50 | 0.1181 |
| 33.0727 | 96.56 | 0.1968 | 2.70862 | 1.56 | 0.2362 |
| 33.4905 | 115.86 | 0.2755 | 2.67578 | 2.35 | 0.3306 |
| 34.1836 | 57.16 | 0.1181 | 2.62310 | 1.16 | 0.1417 |
| 34.4866 | 63.68 | 0.1181 | 2.60074 | 1.29 | 0.1417 |
| 35.6470 | 82.19 | 0.3149 | 2.51869 | 1.67 | 0.3779 |
| 38.3558 | 56.57 | 0.3149 | 2.34683 | 1.15 | 0.3779 |
| 39.9862 | 83.39 | 0.2362 | 2.25681 | 1.69 | 0.2834 |
| 40.6172 | 155.94 | 0.1974 | 2.22123 | 3.16 | 0.1889 |
| 42.0418 | 72.19 | 0.1968 | 2.14920 | 1.46 | 0.2362 |
| 43.1832 | 46.35 | 0.3840 | 2.09327 | 0.94 | 0.4608 |
| 43.9535 | 40.08 | 0.1920 | 2.06347 | 0.81 | 0.2304 |

| Ion (positively charge ions) | Molecular Formula | Exact mass | Experimental mass | mass error (ppm) |
|---|---|---|---|---|
| Compound A MS$^1$ Parent mass) | $C_{41}H_{44}ClFN_9O_6^+$ | 812.3082 | 812.3079 | -0.4 |
| MS$^2$ Product 1 | $C_{28}H_{29}FN_7O_5^+$ | 562.2209 | 562.2193 | -2.8 |
| MS$^2$ Product 2 | $C_{28}H_{32}FN_8O_5^+$ | 579.2474 | 579.2459 | -2.6 |
| MS$^2$ Product 3 | $C_{34}H_{40}FN_8O_5^+$ | 659.3100 | 659.3081 | -2.8 |
| MS$^2$ Product 4 | $C_{24}H_{27}ClN_5O_2^+$ | 452.1848 | 452.1834 | -3.2 |
| MS$^3$ Product 1 | $C_{27}H_{29}FN_7O_4^+$ | 534.2260 | 534.2245 | -2.7 |
| MS$^3$ Product 2 | $C_{23}H_{24}FN_6O_3^+$ | 451.1888 | 451.1882 | -1.4 |
| MS$^3$ Product 3 | $C_{17}H_{23}N_4O^+$ | 299.1866 | 299.1866 | 0.1 |
| MS$^3$ Product 4 | $C_{19}H_{19}ClN_5O_2^+$ | 384.1222 | 384.1221 | -0.2 |

<<LC Time Program>>

| Time | Module | Command | Value |
|---|---|---|---|
| 0.01 | Pumps | Pump B Conc. | 5 |
| 1.10 | Pumps | Pump B Conc. | 100 |
| 1.70 | Pumps | Pump B Conc. | 100 |
| 1.75 | Pumps | Pump B Conc. | 5 |
| 2.00 | Controller | Stop | |

FIG.17A
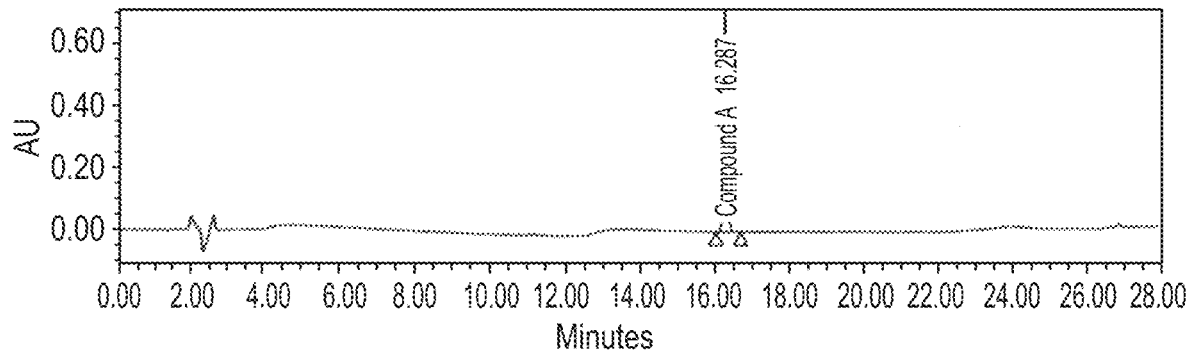
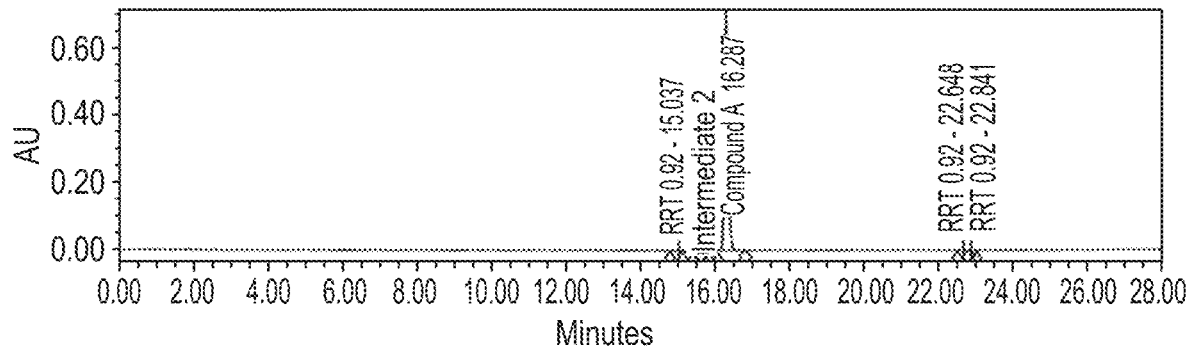
Component Results
| | Name | Int Type | RT | Height | Area | % Area |
|---|---|---|---|---|---|---|
| 1 | RRT 0.92 | bb | 15.037 | 258 | 2688 | 0.06 |
| 2 | Intermediate 2 | BV | 15.547 | 797 | 4834 | 0.10 |
| 3 | RRT 0.96 | VB | 15.682 | 654 | 4178 | 0.09 |
| 4 | Compound A | BB | 16.287 | 679240 | 4859094 | 100.00 |
| 5 | Compound A | Bv | 16.287 | 676579 | 4838227 | 99.60 |
| 6 | RRT 1.39 | BV | 22.648 | 975 | 6120 | 0.13 |
| 7 | RRT 1.40 | Vb | 22.841 | 262 | 1657 | 0.03 |

FIG.17B

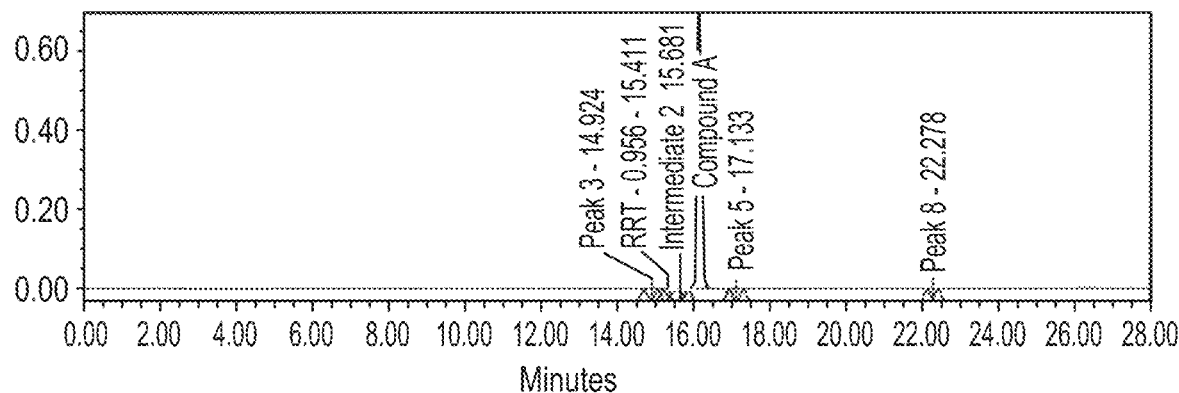

Vial 5; Injection 1; Injection Volume 10.00; Run Time 28.00; Channel Description PDA 200.0 to 350.0 nm at 1.2 nm; Processed Channel Descr. PDA 260.0 nm; Integration Algorithm ApexTrack; Peak Width 10.00; Threshold 25.000; Manual No; Result Id 7390; Sample Set Id 7003; Processing Method Id 7198

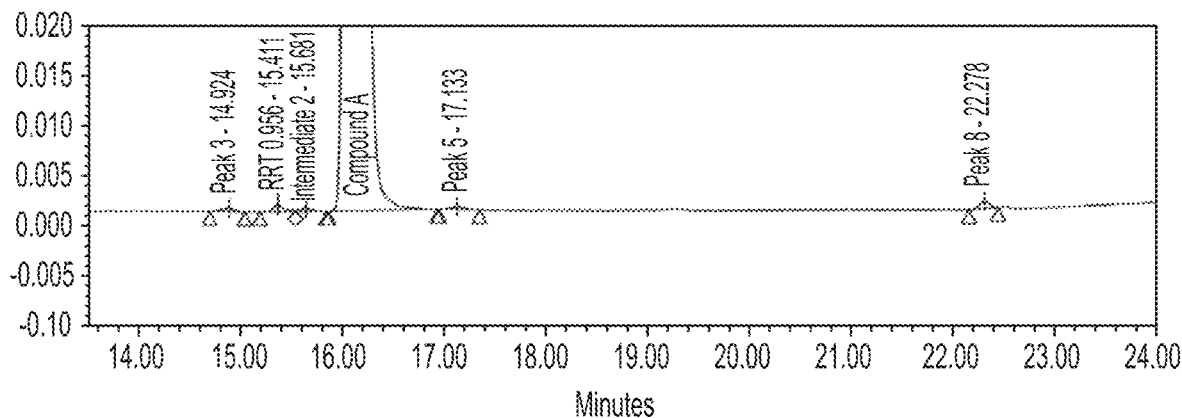

Component Results

| | Name | RT | Height | Area | % Area | Processed Channel Descr. | Result Id |
|---|---|---|---|---|---|---|---|
| 1 | Peak 3 | 14.924 | 379 | 3389 | 0.067 | PDA 260.0 nm | 7390 |
| 2 | RRT 0.956 | 15.411 | 724 | 5523 | 0.110 | PDA 260.0 nm | 7390 |
| 3 | Intermediate 2 | 15.681 | 419 | 3061 | 0.061 | PDA 260.0 nm | 7390 |
| 4 | Compound A | 16.121 | 660612 | 5007172 | 99.621 | PDA 260.0 nm | 7390 |
| 5 | Peak 5 | 17.133 | 280 | 2457 | 0.049 | PDA 260.0 nm | 7390 |
| 6 | Peak 8 | 22.278 | 673 | 4612 | 0.092 | PDA 260.0 nm | 7390 |

FIG.17C

| Time (min) | % A | % A |
|---|---|---|
| 0:00 | 95 | 5 |
| 1:00 | 95 | 5 |
| 10:00 | 55 | 45 |
| 20:00 | 45 | 55 |
| 24:00 | 5 | 95 |
| 28:00 | 5 | 95 |
| 28:01 | 95 | 5 |
| 36:00 | 95 | 5 |

FIG.18A

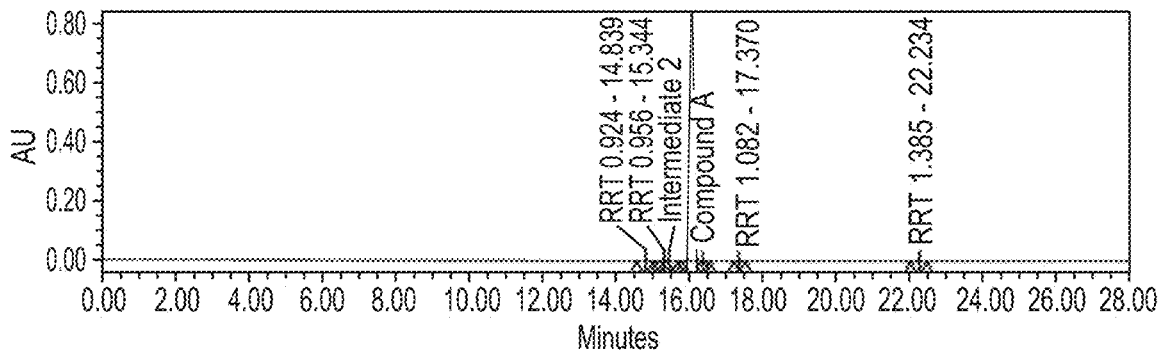

Vial 5; Injection 1; Injection Volume 10.00; Run Time 28.00; Channel Description W2489 ChA 260nm; Processed Channel Descr. W2489 ChA 260nm; Integration Algorithm ApexTrack; Peak Width 10.00; Threshold 10.000; Manual No; Result Id 2177; Sample Set Id 2104; Processing Method Id 2138

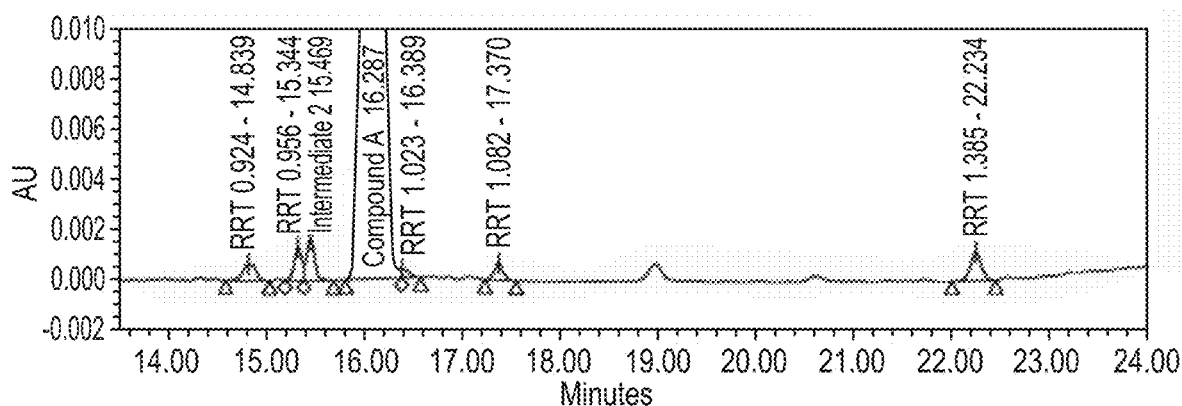

Component Results

| | Name | Int Type | RT | Area | % Area | RT Ratio |
|---|---|---|---|---|---|---|
| 1 | Intermediate 10 | Missing | 4.988 | | | |
| 2 | Intermediate 5 | Missing | 8.042 | | | |
| 3 | RRT 0.531 | Missing | 8.502 | | | |
| 4 | RRT 0.686 | Missing | 10.976 | | | |
| 5 | Intermediate 7 | Missing | 11.569 | | | |
| 6 | RRT 0.894 | Missing | 14.282 | | | |
| 7 | RRT 0.903 | Missing | 14.426 | | | |

| | Name | Int Type | RT | Area | % Area | RT Ratio |
|---|---|---|---|---|---|---|
| 8 | RRT 0.924 | BB | 14.839 | 6179 | 0.13 | 0.924 |
| 9 | RRT 0.956 | VV | 15.344 | 7021 | 0.14 | 0.955 |
| 10 | Intermediate 2 | VB | 15.469 | 9520 | 0.20 | 0.963 |
| 11 | /Compound A | BV | 16.061 | 4814283 | 99.23 | 1.000 |
| 12 | RRT 1.023 | VB | 16.389 | 1846 | 0.04 | 1.020 |
| 13 | Intermediate 3 | Missing | 16.644 | | | |
| 14 | Impurity 1 | Missing | 16.816 | | | |

FIG. 18B

| Time (min) | % A | % B |
|---|---|---|
| 0:00 | 95.0 | 5.0 |
| 1:00 | 95.0 | 5.0 |
| 10:00 | 55.0 | 45.0 |
| 20:00 | 45.0 | 55.0 |
| 24:00 | 5.0 | 95.0 |
| 28:00 | 5.0 | 95.0 |
| 28:01 | 95.0 | 5.0 |
| 36:00 | 95.0 | 5.0 |

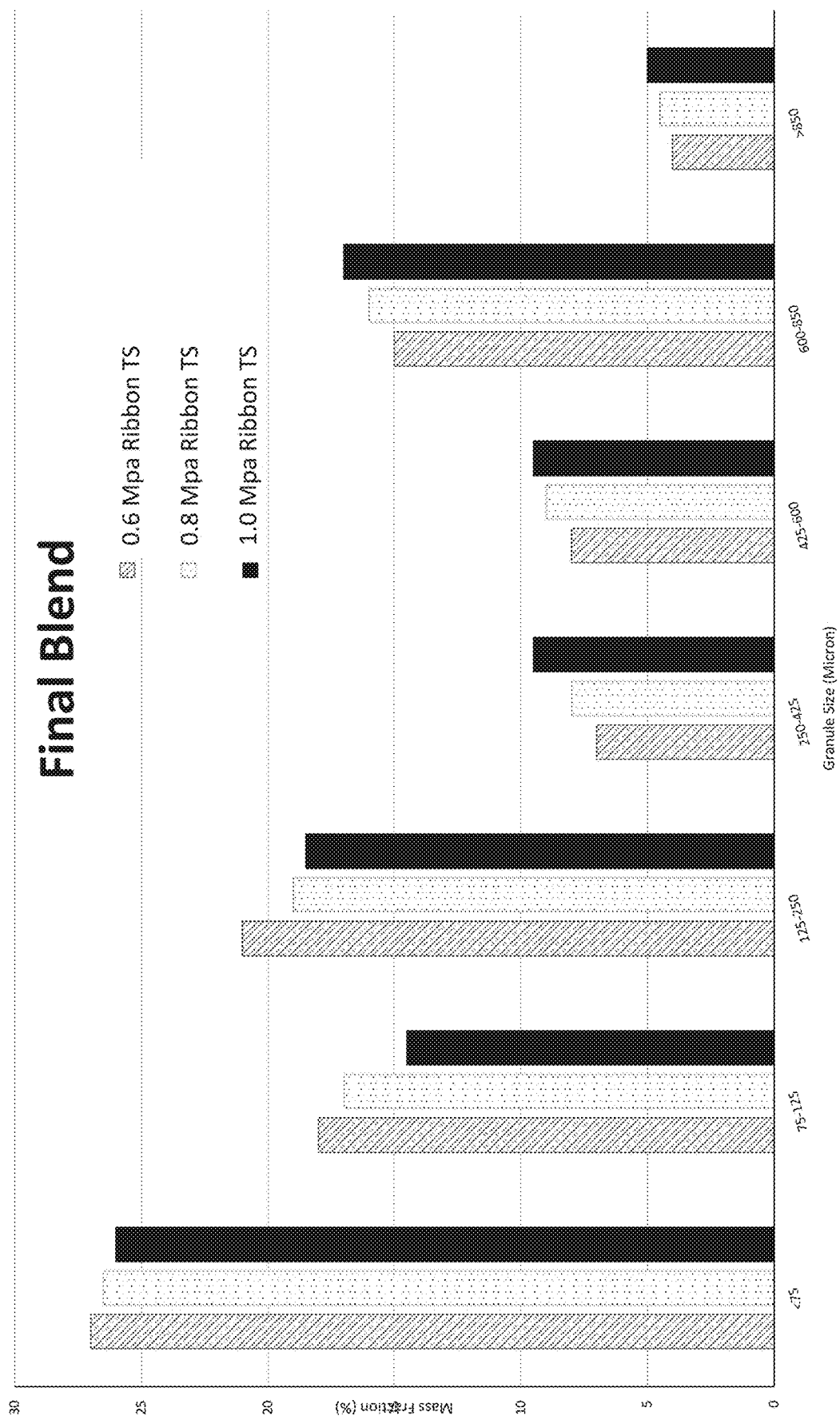

METHODS OF MANUFACTURING A BIFUNCTIONAL COMPOUND, ULTRAPURE FORMS OF THE BIFUNCTIONAL COMPOUND, AND DOSAGE FORMS COMPRISING THE SAME

RELATED APPLICATIONS

This application claims priority to, and the benefit of, U.S. Provisional Application No. 63/022,475, filed May 9, 2020, U.S. Provisional Application No. 63/149,143, filed Feb. 12, 2021, and U.S. Provisional Application No. 63/177,378, filed Apr. 20, 2021. These applications are incorporated herein by reference in their entireties for all purposes.

STATEMENT REGARDING FEDERALLY FUNDED RESEARCH

This invention was made with government support under grant number 1R44CA203199-01 by the National Cancer Institute. The government has certain rights in the invention.

TECHNICAL FIELD

This application relates to a bifunctional compound that has been shown to be a useful modulator of targeted protein ubiquitination and degradation via the ubiquitin-proteasome system. In particular, the application relates to a process for manufacturing the bifunctional compound. The application further relates to crystalline forms, amorphous forms, ultrapure forms, and stable forms of the bifunctional compound. The application also relates to oral dosage forms (e.g., tablets) comprising the bifunctional compound and methods of making the same, along with methods of treating cancer (e.g., prostate cancer) comprising administering a therapeutically effective amount of a dosage form of the invention to a subject in need of such treatment.

BACKGROUND

Most small molecule drugs bind to enzymes or receptors in tight and well-defined pockets. In contrast, protein-protein interactions are notoriously difficult to target using small molecules due to their large contact surfaces and the shallow grooves or flat interfaces typically involved. E3 ubiquitin ligases (of which hundreds are known in humans) confer substrate specificity for ubiquitination, and therefore are attractive therapeutic targets due to their specificity for certain protein substrates. The development of ligands of E3 ligases has proven challenging, in part because they must disrupt protein-protein interactions. However, recent developments have provided specific ligands which bind to these ligases. For example, since the discovery of nutlins, the first small molecule E3 ligase inhibitors, additional compounds have been reported that target E3 ligases, though the field remains underdeveloped.

One E3 ligase with particular therapeutic potential is cereblon, a protein that in humans is encoded by the CRBN gene. CRBN orthologs are highly conserved from plants to humans, indicating its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates several other proteins. Through a mechanism not yet been completely elucidated, cereblon ubiquitination of target proteins results in increased levels of fibroblast growth factor 8 (FGF8) and fibroblast growth factor 10 (FGF10). FGF8, in turn, regulates several developmental processes, such as limb and auditory vesicle formation. The net result is that this ubiquitin ligase complex is important for limb outgrowth in embryos. In the absence of cereblon, DDB1 forms a complex with DDB2, which functions as a DNA damage-binding protein.

Thalidomide, which has been approved for the treatment of a number of immunological indications, has also been approved for the treatment of certain neoplastic diseases, including multiple myeloma. In addition, thalidomide and several of its analogs are currently under investigation for use in treating a variety of other types of cancer. While the precise mechanism of thalidomide's anti-tumor activity is still emerging, it is known to inhibit angiogenesis. Recent literature discussing the biology of the imides includes Lu et al. Science 343, 305 (2014) and Kronke et al. Science 343, 301 (2014).

Significantly, thalidomide and its analogs, e.g. pomalidomide and lenalidomide, are known to bind cereblon, and to alter the specificity of the complex to induce the ubiquitination and degradation of Ikaros (IKZF1) and Aiolos (IKZF3), which are transcription factors essential for multiple myeloma growth. Indeed, higher expression of cereblon has been linked to an increase in efficacy of imide drugs in the treatment of multiple myeloma.

Androgen receptor (AR) belongs to a nuclear hormone receptor family that is activated by androgens, such as testosterone and dihydrotestosterone (Pharmacol. Rev. 2006, 58(4), 782-97; Vitam. Horm. 1999, 55:309-52). In the absence of androgens, AR is bound by Heat Shock Protein 90 (Hsp90) in the cytosol. When an androgen binds AR, its conformation changes to release AR from Hsp90 and to expose the Nuclear Localization Signal (NLS). The NLS enables AR to translocate into the nucleus where AR acts as a transcription factor to promote gene expression responsible for male sexual characteristics (Endocr. Rev. 1987, 8(1):1-28; Mol. Endocrinol. 2002, 16(10), 2181-7). AR deficiency leads to Androgen Insensitivity Syndrome, formerly termed testicular feminization.

While AR is responsible for development of male sexual characteristics, it is also a well-documented oncogene in certain cancers including prostate cancer (Endocr. Rev. 2004, 25(2), 276-308). A commonly measured target of AR activity is the secreted Prostate Specific Antigen (PSA) protein. The current treatment regimen for prostate cancer involves inhibiting the androgen-AR axis by either of two methods. The first approach relies on reduction of androgens, while the second aims to inhibit AR function (Nat. Rev. Drug Discovery, 2013, 12, 823-824). Despite the development of effective targeted therapies, most patients develop resistance and the disease progresses. An alternative approach for the treatment of prostate cancer may involve eliminating the AR protein. Because AR is a critical driver of tumorigenesis in many forms of prostate cancer, its elimination could lead to a therapeutically beneficial response.

The bifunctional compound made and used according to the present invention is Compound A having the molecular formula of $C_{41}H_{43}ClFN_9O_6$, and with the following structural formula:

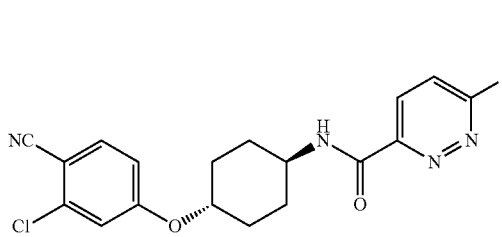

Compound A is under development as a PROTAC® protein degrader that targets AR for the potential treatment of men having metastatic, castration-resistant prostate cancer (mCRPC).

SUMMARY

The present disclosure provides ultra-pure forms, crystalline forms, amorphous forms, and formulations of N-[(1r,4r)-4-(3-chloro-4-cyanophenoxy)cyclohexyl]-6-[4-({4-[2-(2,6-dioxopiperidin-3-yl)-6-fluoro-1,3-dioxo-2,3-dihydro-1H-isoindol-5-yl]piperazin-1-yl}methyl)piperidin-1-yl]pyridazine-3-carboxamide, referred to herein as Compound A, and processes for manufacturing Compound A:

(Compoud A)

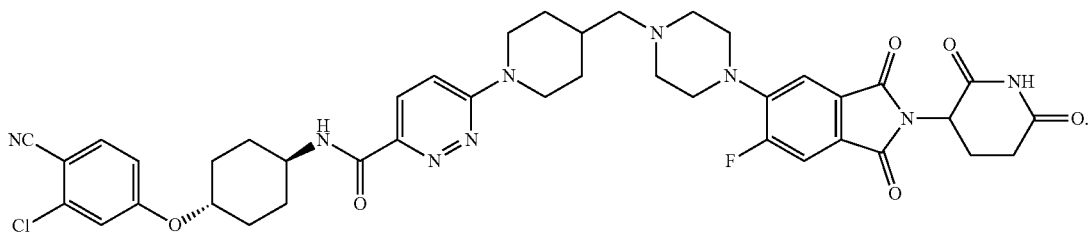 [SMILES: N#Cc1ccc(O[C@H]2CC[C@H](NC(=O)c3ccc(N4CCC(CN5CCN(c6cc7c(cc6F)C(=O)N(C6CCC(=O)NC6=O)C7=O)CC5)CC4)nn3)CC2)cc1Cl]

In one aspect, this application pertains to a method of treating prostate cancer in a subject in need thereof, comprising administering to the subject a therapeutically effective amount of a compound of Compound A. In one embodiment, the method further comprises the administration of an additional anti-cancer agent.

In one aspect, this disclosure provides a crystalline form of Compound A having a powder x-ray diffraction pattern comprising peaks at 7.6°±0.2° 2θ, 11.5°±0.2° 2θ, and 17.6°±0.2° 2θ, wherein said powder x-ray diffraction pattern is obtained using Cu Kα radiation at an x-ray wavelength of 1.5406 Å. This crystalline form is designated as "Form 2."

In another aspect, this disclosure provides a crystalline form of Compound A having a powder x-ray diffraction pattern comprising peaks at 11.00°±0.2° 2θ, 16.10°±0.2° 2θ, and 17.9°±0.2° 2θ, wherein said powder x-ray diffraction pattern is obtained using Cu Kα radiation at an x-ray wavelength of 1.5406 Å. This crystalline form is designated as "Form 4."

In another aspect, this disclosure provides processes for manufacturing Compound A, wherein the process comprises the reductive amination of N-((1r,4r)-4-(3-chloro-4-cyanophenoxy)cyclohexyl)-6-(4-formylpiperidin-1-yl)pyridazine-3-carboxamide (Intermediate 3) with 2-(2,6-dioxopiperidin-3-yl)-5-fluoro-6-(piperazin-1-yl)isoindoline-1,3-dione hydrochloride (Intermediate 5) and a reducing agent to provide Compound A:

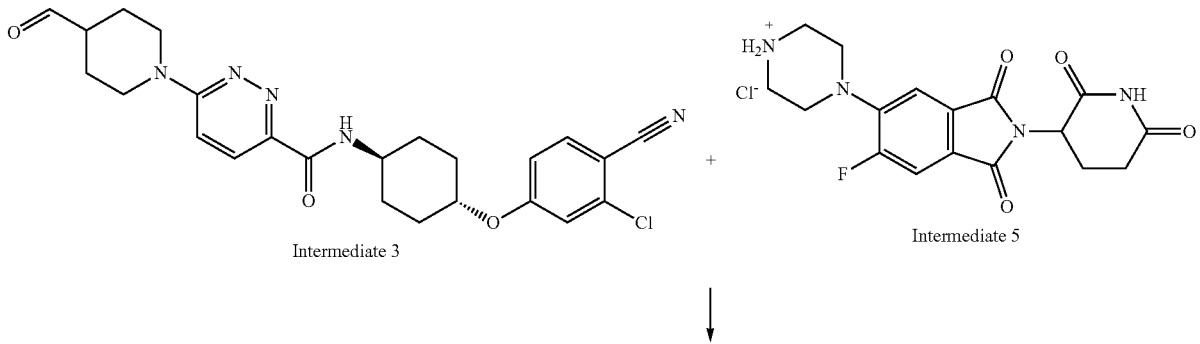

Intermediate 3 + Intermediate 5

↓

-continued

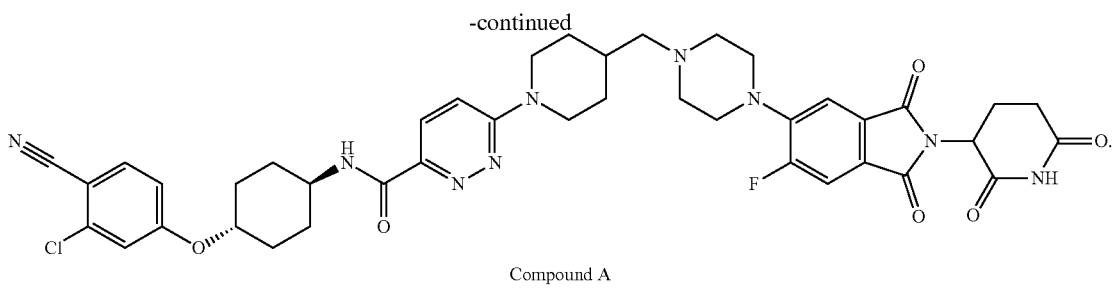

Compound A

In another aspect, this disclosure provides an intermediate useful for the synthesis of Compound A which is 6-chloro-N-((1r,4r)-4-(3-chloro-4-cyanophenoxy)cyclohexyl)pyridazine-3-carboxamide (Intermediate 4), Intermediate 4

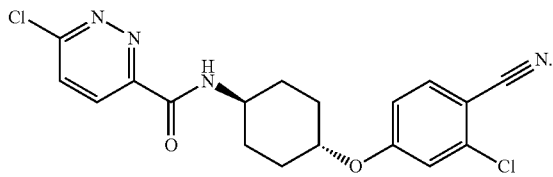

In another aspect, this disclosure provides an ultrapure form of Compound A having a purity greater than about 95 wt %.

In another aspect, this disclosure provides processes for manufacturing an amorphous form of Compound A wherein the process comprises the following steps:
(1) dissolving crystalline Compound A in a solvent to afford a solution of Compound A;
(2) introducing the solution of Compound A from step (1) into a spray dryer to create the amorphous form of Compound A; and
(3) Drying the amorphous form of Compound A to remove residual solvent.

Alternative methods of preparing amorphous forms of Compound A may include lyophilization, hot-melt extrusion, milling, or high-shear mixing.

In another aspect, this disclosure provides an oral dosage form comprising one or more pharmaceutically acceptable excipients and Compound A, wherein the oral dosage form is selected from the group consisting of a tablet, a sachet, or a capsule.

In a preferred aspect, the oral dosage form comprises one or more pharmaceutically acceptable excipients and an ultrapure form of Compound A.

In another aspect, this disclosure provides processes of manufacturing a tablet Compound A comprising the following steps:
(1) blending a form of Compound A with at least one pharmaceutically acceptable excipient to create a powder;
(2) delumping the powder from step (1), adding at least one pharmaceutically acceptable excipient, and blending to create a first blend;
(3) granulating the blend from step (2) and passing the resultant powder through a screen to produce a plurality of granules;
(4) adding at least one pharmaceutical excipient to the at least one granule from step (3) and blending to produce a second blend; and (5) compressing the second blend from step (4) into one or more tablets.

In another aspect, this disclosure provides methods of treating cancer in a subject comprising administering to a subject in need of such treatment one or more unit dosage forms (e.g., tablets) of the present disclosure. In one embodiment, the method further comprises the administration of an additional anti-cancer agent.

The preceding general areas of utility are given by way of example only and are not intended to limit the scope of the present disclosure or appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages, objects, and embodiments are expressly included within the scope of the present disclosure. The publications and other materials used herein to illuminate the background of the invention, and in particular cases, to provide additional details respecting the practice, are incorporated by reference.

Where applicable or not specifically disclaimed, any one of the embodiments described herein are contemplated to be able to combine with any other one or more embodiments, even though the embodiments are described under different aspects of the disclosure.

BRIEF DESCRIPTION OF THE DRAWINGS

FIG. 3A is a powder X-ray diffraction pattern of Form 2 of Compound A and FIG. 3B is a table that includes the peak listings of the diffraction pattern in FIG. 3A.

FIG. 3C is a powder X-ray diffraction pattern of Form 4 of Compound A and FIG. 3D is a table that includes the peak listings of the diffraction pattern in FIG. 3C.

FIG. 8A and FIG. 8B are an ion map and corresponding table showing the further fragmentation of the observed MS/MS ions (MS$^3$).

FIG. 16B is the solvent gradient used to obtain the chromatogram in FIG. 16A. FIG. 17A is a chromatogram of crude Compound A, as produced by the Second-Generation synthesis. Column: Atlantis T3, 3 μm, 4.6×150 mm. Mobile Phase A: 0.1% TFA in Water. Mobile Phase B: 0.05% TFA in 75:25 ACN/MeOH. Flow Rate: 1.0 mL/min. Column temperature 45° C. Detector: 260 nm. FIG. 17B is a chromatogram of purified Compound A, as produced by the second-generation synthesis. Column: Atlantis T3, 3 μm, 4.6×150 mm. Mobile Phase A: 0.1% TFA in Water. Mobile Phase B: 0.05% TFA in 75:25 ACN/MeOH. Flow Rate: 1.0 mL/min. Column temperature 45° C. Detector: 260 nm. FIG. 17C is the solvent gradient used to obtain the chromatogram in FIG. 17A and FIG. 17B.

FIG. 18A is a chromatogram of crude Compound A, as produced by the third-generation synthesis. Column: Atlantis T3, 3 μm, 4.6×150 mm. Mobile Phase A: Water with 0.1% TFA. Mobile Phase B: 75:25 Acetonitrile/MeOH with 0.05% TFA. Column Temperature: 45° C. Detection: 260 nm. FIG. 18B is the solvent gradient used to obtain the chromatogram in FIG. 18A.

FIG. 30A and FIG. 30B show a comparison of granule size between the granules (A) and the final blend (B)

DETAILED DESCRIPTION

Figure 1:
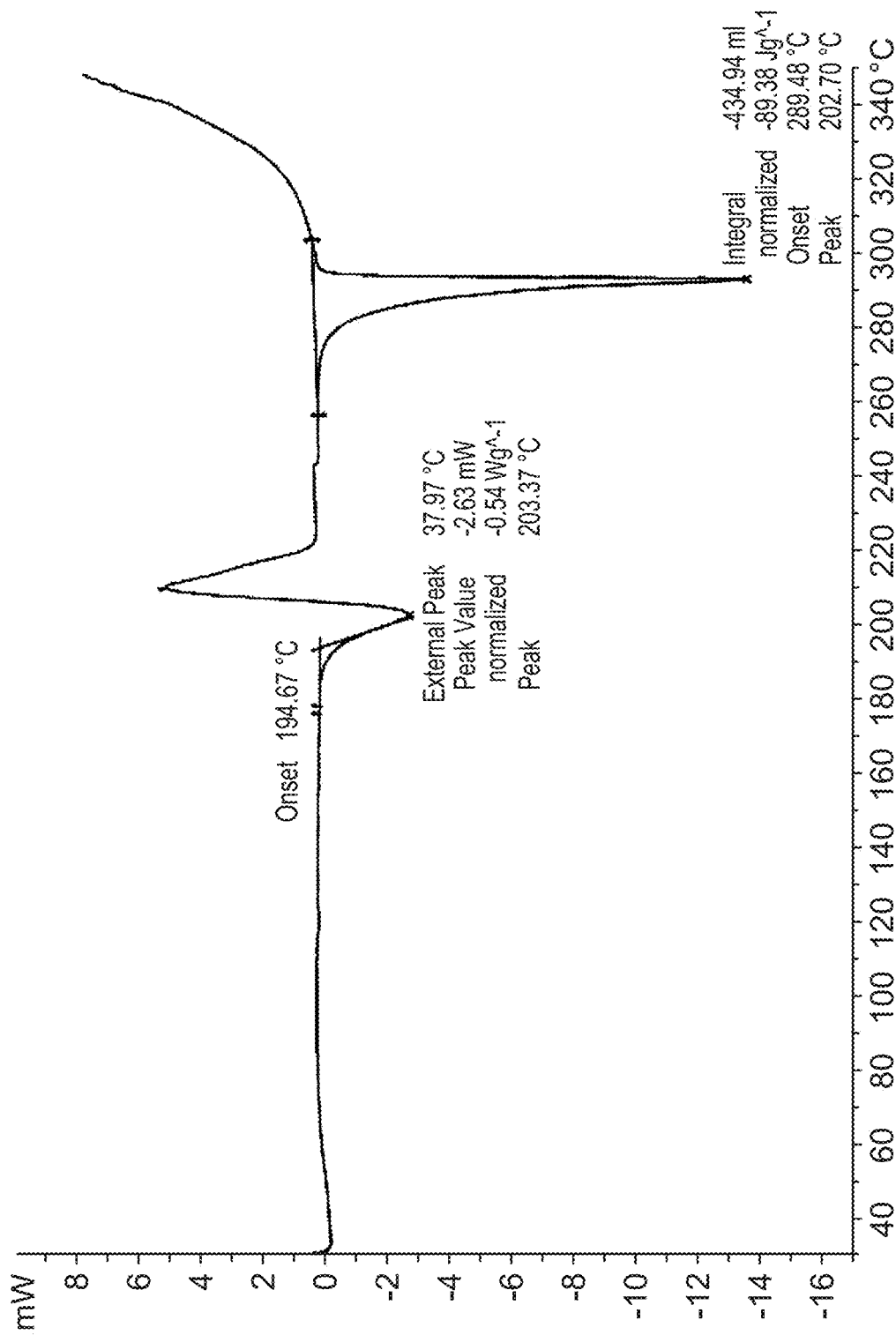
FIG. 1 is a Differential Scanning Calorimetry plot for Compound A.

The present disclosure is related in certain aspects to U.S. patent application Ser. No. 15/730,728, issued as U.S. Pat. No. 10,584,101; U.S. patent application Ser. No. 16/577,901, issued as U.S. Pat. No. 10,844,021; and U.S. Provisional Patent Application Ser. Nos. 62/528,385 and 62/406,888. The present disclosure is related in certain aspects to U.S. patent application Ser. No. 17/075,808, now published as US 2021/0113557, and Provisional Patent Application Ser. Nos. 62/924,655, 62/945,418, 63/028,843, and 63/032, 453. Each of these applications are incorporated herein by reference in their entireties for all purposes.

Definitions

Unless otherwise defined, all technical and scientific terms used herein have the same meaning as commonly understood by one of ordinary skill in the art to which this disclosure belongs. The terminology used in the description is intended to describe particular embodiments only, and is not intended to limit the scope of the invention.

Where a range of values is provided, it is understood that the range includes both of the endpoints with that range, as well as all intervening values.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an ultrapure form" means one ultrapure form or more than one ultrapure form.

The phrase "and/or," as used herein in the specification and in the claims, should be understood to mean "either or both". Other elements may optionally be present other than the elements specifically identified by the "and/or" clause. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, means at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time-varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anti-cancer agent. In particularly preferred aspects, the co-administration of compounds results in synergistic activity and/or therapy, such as, e.g., anti-cancer activity.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a condition, disorder or disease state in a subject in need of such treatment or receiving such treatment. The term "effective" subsumes all other effective amount or effective concentration terms, e.g., "effective amount/dose," "pharmaceutically effective amount/dose" or "therapeutically effective amount/dose," which are otherwise described or used in the present application.

The effective amount depends on the age, weight, gender, previous patient history or family history, type and severity of disease, the composition used, the route of administration, the stage of treatment, the type of mammal being treated, the physical characteristics of the specific mammal under consideration, concurrent medication, and other factors which those skilled in the medical arts will recognize. The exact amount can be ascertainable by one skilled in the art using known techniques in view of clinical data and medical experience (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The terms "pharmacological composition," "pharmaceutical composition," "therapeutic composition," "therapeutic formulation," and "pharmaceutically acceptable formulation" are known in the art.

The terms "pharmaceutically acceptable" and "pharmacologically acceptable" are known in the art.

The terms "pharmaceutically acceptable carrier" and "pharmacologically acceptable carrier" mean, but are not limited to, any and all solvents, excipients, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solution, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and leads to systemic absorption or accumulation of drugs in the blood stream followed by distribution throughout the entire body. Suitable forms, in part, depend upon the use or the route of entry, for example oral, transdermal, or by injection. For example, pharmacological compositions injected into the blood stream should be soluble. Other factors to avoid include toxicity, and any forms which prevent the composition or formulation from exerting its effect.

In one embodiment, Compound A may be solubilized in a vehicle suitable for parenteral administration by using a cyclodextrin. Exemplary cyclodextrins suitable for this process include, without limitation, sulfobetylether-β-cyclodextrin and (2-hydroxypropyl)-β-cyclodextrin.

Administration routes which lead to systemic absorption are known and include, without limitations: intravenous, subcutaneous, intra-peritoneal, inhalation, oral, buccal, sublingual, transdermal, intra-ocular, intra-nasal, intra-pulmonary, rectal, vaginal, and intra-muscular. The rate of entry of a drug into the circulation is a function of molecular weight or size. The use of a liposome or other drug carrier comprising Compound A may potentially localize the drug, for example, in certain tissue types, such as the tissues of the reticular endothelial system (RES). A liposome formulation which can facilitate the association of drug with the surface of cells, such as, lymphocytes and macrophages, may also be useful.

The term "local administration" refers to a route of administration in which the agent is delivered to a site that is proximal, e.g., within about 10 cm, to the site of the lesion or disease.

The formulation of the present invention preferably provides "oral administration" as used herein refers to enteral, buccal, sublabial, or sublingual medications in the form of tablets, capsules, syrups, powders, granules, pastilles, solutions, tinctures, elixirs, emulsions, hydrogels, teas, films, disintegrating tablets, mouthwashes, and others.

Suitable forms for oral administration may include one or more pharmaceutically acceptable excipients, including, for example, carriers, fillers, surfactants, diluents, sweeteners, disintegrants, binders, lubricants, glidants, colorants, flavors, stabilizing agents, coatings, or any mixtures thereof.

Carriers include, pharmaceutically acceptable excipients and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject. Examples include, but are not limited to, calcium carbonate, calcium phosphate, various sugars, starches, cellulose derivatives, gelatin, and polymers such as polyethylene glycols.

Fillers include, but are not limited to, mannitol, sucrose, sorbitol, xylitol, microcrystalline cellulose, lactose, silicic acid, silicified microcrystalline cellulose, hydroxypropyl methylcellulose, hydroxypropyl cellulose, starch, pullulan and fast dissolving carbohydrates such as Pharmaburst™ fast disintegrating tablets, mixtures thereof, and the like. For examples of fast-dissolving carbohydrates see, e.g., U.S. Pat. No. 8,617,588, which is incorporated herein by reference.

Surfactants include, but are not limited to, non-ionic, anionic, cationic, amphoteric or zwitterionic surfactants. Examples of suitable non-ionic surfactants include ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; Pluronics™; alkyl polyglucosides; stearol ethoxylates; alkyl polyglycosides. Examples of suitable anionic surfactants include alkylether sulfates; alkylether carboxylates; alkyl benzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates. Examples of suitable cationic surfactants include fatty amine salts; fatty diamine salts; quaternary ammonium compounds; phosphonium surfactants; sulfonium surfactants; sulfoxonium surfactants. Examples of suitable zwitterionic surfactants include N-alkyl derivatives of amino acids (such as glycine, betaine, aminopropionic acid); imidazoline surfactants; amine oxides; amidobetaines. Non-limiting examples of a surfactant that can be used in the ospemifene solid dispersions, include, for example. Tween 20, Tween 80, Span 20, Span 80, sodium docusate (e.g., AOT), sodium lauryl sulfate, and poloxamers (e.g., poloxamer 407, Kolliphor® EL, Pluronic F68). Poloxamers are also known by the trade names Synperonics®, Pluronics®, and Kolliphor®/Cremophor®.

Diluents include, but are not limited to, carbohydrates such as monosaccharides like glucose, oligosaccharides like sucrose and lactose (including anhydrous lactose and lactose monohydrate), starch such as maize starch, potato starch, rice starch and wheat starch, pregelatinized starch, calcium hydrogen phosphate, and sugar alcohols like sorbitol, mannitol, erythritol, and xylitol.

Sweeteners include, but are not limited to, sucrose, high fructose corn syrup, fructose, glucose, aspartame, acesulfame K, sucralose, cyclamate, sodium saccharin, neotame, rebaudioside A, and other stevia-based sweeteners.

Disintegrants include, but are not limited to, sodium starch glycolate, sodium carboxymethyl cellulose, calcium carboxymethyl cellulose, croscarmellose sodium, crospovidone, chitosan, agar, alginic acid, calcium alginate, methyl cellulose, microcrystalline cellulose, powdered cellulose, lower alkyl substituted hydroxypropyl cellulose, hydroxylpropyl starch, low-substituted hydroxypropylcellulose, polacrilin potassium, starch, pregelatinized starch, sodium alginate, magnesium aluminum silicate, polacrilin potassium, povidone, sodium starch glycolate, mixtures thereof, and the like.

Binders include, but are not limited to, hydroxypropylmethylcellulose (HPMC), hydroxypropyl cellulose (HPC), povidone, copovidone (copolymers of vinylpyrrolidone with other vinyl derivatives), methylcellulose, powdered acacia, gelatin, gum arabicum, guar gum, carbomer such as carbopol, and polymethacrylates.

Lubricants include, but are not limited to, calcium stearate, glyceryl monostearate, glyceryl behenate, glyceryl palmitostearate, hexagonal boron nitride, hydrogenated vegetable oil, light mineral oil, magnesium stearate, mineral oil, polyethylene glycol, poloxamer, sodium benzoate, sodium lauryl sulfate, sodium stearyl fumarate, stearic acid, talc, zinc stearate, mixtures thereof, and the like.

Glidants include, but are not limited to, silicon dioxide, colloidal silicon dioxide, calcium silicate, magnesium silicate, magnesium trisilicate, talc, starch, mixtures thereof, and the like.

Flavors include, but are not limited to, menthol, peppermint oil, peppermint spirit, vanillin, and almond oil.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the covalent attachment of several ubiquitin molecules to an available lysine residue on a target protein, thereby targeting the protein for degradation by the proteasome. Thus, E3 ubiquitin ligase, alone or in complex with an E2 ubiquitin conjugating enzyme, causes the transfer of ubiquitin to targeted proteins. In general, the ubiquitin ligase is involved in polyubiquitination such that a second ubiquitin is attached to the first; a third is attached to the second; and a fourth is attached to the third. Such polyubiquitination marks the protein for degradation by the proteasome.

The terms "patient" and "subject" are used throughout this specification to refer to an animal, preferably a mammal, more preferably a human or a domesticated or companion animal, to whom treatment, including prophylactic treatment, with a composition according to the present disclosure, is provided. For treatment of those conditions or disease states specific for a specific type of animal, such as a human patient, the term "patient" refers to that specific type of animal, including a domesticated or companion animal such as a dog or cat, or a farm animal such as a horse, cow, sheep, etc. In general, in the present disclosure, the term "patient" refers to a human patient unless otherwise stated or implied from the context of the use of the term.

"Pharmaceutically acceptable salt", as used herein with respect to a compound of the disclosure, means a salt form of that compound where the counterion is generally regarded as safe for therapeutic administration to a patient or subject, or otherwise presents an acceptable risk/benefit profile permitting therapeutic administration to a patient or subject. The term "pharmaceutically acceptable salt", as used herein with respect to a compound may also include solvates (e.g., hydrates) of such a salt, as well as cocrystals thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Solvate" means a solvent addition form of Compound A that contains either a stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with Compound A in which the water retains its molecular state as $H_2O$, such combination being able to form one or more hydrates. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of the pharmaceutically acceptable salts of Compound A.

Cocrystals represent novel forms of drug substances that would be suitable for incorporation in pharmaceutical solid dosage forms, and should enable formulation scientists to overcome a variety of problems that are encountered during development of traditional formulations. Cocrystals may be viewed as being an alternative to polymorphs, solvatomorphs, and salts, as cocrystals represent a different approach to solve problems related to dissolution, crystallinity, and hygroscopicity, among others. For further discussions of cocrystals, see: Aitipaumula et al. "Polymorphs, Salts, and Cocrystals: What's in a Name?" Crystal Growth Des. 2012, 12, 5, 2147-2152; and Brittain "Pharmaceutical Cocrystals: The Coming Wave of New Drug Substances" J. Pharm. Sci. 2013, 102, 2, 311-317; both of which are incorporated by reference herein in their entireties.

The term "powder X-ray diffraction pattern", "PXRD pattern", "PXRD", "powder X-ray diffraction diagram", "X-ray diffraction pattern", or "XRPD" refers to the experimentally observed diffractogram or parameters derived therefrom. Powder X-ray diffraction patterns are characterized by peak position (abscissa) and peak intensities (ordinate).

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). The reference herein to specific 2θ values for a specific solid form is intended to mean the 2θ values (in degrees) as measured using the X-ray diffraction experimental conditions as described herein.

"Isotopic derivative", as referred to herein, relates to Compound A that is isotopically enriched or labelled (with respect to one or more atoms of the compound) with one or more stable isotopes. Thus, in one embodiment, Compound A is isotopically enriched or labelled with one or more atoms such as deuterium in place of one or more hydrogens.

Metastatic prostate cancer, or metastases, refer to prostate cancer that has spread beyond the prostate to other parts or organs in the body, e.g., bones, lymph nodes, liver, lungs, brain.

Castrate-resistant prostate cancer, or castration-resistant prostate cancer, (or prostate cancer that is castrate- or castration-resistant), is a type of prostate cancer that continues to grow even when the amount of testosterone in the body is reduced to very low levels.

Metastatic, castrate-resistant prostate cancer is a type of prostate cancer that has metastasized and continues to grow even when the amount of testosterone in the body is reduced to very low levels.

As used herein, "treating", "treatment", and the like, describe the administration of a pharmaceutical composition of the invention to a subject or patient for the purpose of combating a disease, condition, or disorder, which includes decreasing, mitigating or eliminating one or more symptoms or complications of the disease, condition or disorder, or decreasing, mitigating, or eliminating the disease, condition or disorder.

As used herein, "prevent", "preventing" and the like describe stopping the onset of the disease, condition or disorder, or one or more symptoms or complications thereof.

"$C_{max}$", as used herein, refers to the observed maximum (peak) plasma concentration of a specified compound in the subject or patient after administration of a dose of that compound to the subject or patient.

"AUC", as used herein, refers to the total area under the plasma concentration-time curve, which is a measure of exposure to a compound of interest, and is the integral of the concentration-time curve after a single dose or at steady state. AUC is expressed in units of ng*H/mL (ng×H/mL), where "H" refers to hours.

"$AUC_{inf}$", as used herein, refers to the AUC from 0 hours to the end of a dosing interval.

"$AUC_{0-24}$" means the AUC from 0 hours to 24 hours after administration of a single dose.

"Controlled release" or "CR" as used herein with respect to an oral dosage form refers to a compound of the disclosure that is released from the dosage form, other than in an immediate release profile, according to a pre-determined profile that may include when and where release occurs after oral administration and/or a specified rate of release over a specified time period "Controlled release agent" as used herein with respect to an oral dosage form of the disclosure refers to one or more substances or materials that modify the release profile of a compound of the invention from the dosage form. Controlled release agents may be organic or inorganic, naturally occurring or synthetic, such as polymeric materials, triglycerides, derivatives of triglycerides, fatty acids and salts of fatty acids, talc, boric acid, colloidal silica, cellulosic derivatives, and combinations thereof.

"Enteric coating" as used herein with respect to a dosage form of the disclosure refers to a pH-dependent material that surrounds a core comprising a compound of the disclosure and which remains substantially intact in the acid environment of the stomach, but which subsequently dissolves in the pH environment of the intestines.

"Gastro-resistant" or "GR" as applied to a CR oral dosage form described herein means that release of a compound of the disclosure in the stomach of a subject shall not exceed 5%, 2.5%, 1% or 0.5% of the total amount of the compound of the disclosure in the dosage form.

"Loss on Drying" refers to the loss of weight expressed as percentage w/w/resulting from water and volatile matter of any kind that can be driven off under specified conditions. Loss on Drying can be determined by persons of skill in the art using standard methods, including, for example, USP <731>.

The "Residue on Ignition" test (also known as the sulfated ash test) uses a procedure to measure the amount of residual substance not volatilized from a sample when the sample is ignited in the presence of sulfuric acid according to the procedure described below. This test is usually used for determining the content of inorganic impurities in an organic substance. Residue on Ignition can be determined by persons of skill in the art using standard methods, including, for example, USP <281>.

"COA" stand for certificate of analysis.

"Oral dosage form" as used herein refers to a pharmaceutical drug product that contains a specified amount (dose) of a compound of the disclosure as the active ingredient, or a pharmaceutically acceptable salt and/or solvate thereof, and inactive components (excipients), formulated into a particular configuration that is suitable for oral administration, such as an oral tablet, liquid, or capsule. In one embodiment, the oral dosage form comprises a tablet. In one embodiment, the oral dosage form comprises a tablet that can be scored. In one embodiment, the oral dosage form comprises a sublingual tablet. In one embodiment, the oral dosage form comprises a capsule, which can be taken intact or used as a sprinkle onto food (e.g., applesauce or yogurt). In one embodiment, the oral dosage form comprises a sachet.

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. Thus, the term "about" is normally used to encompass values within standard error. In one embodiment, the term "about" as part of a quantitative expression such as "about X", includes any value that is up to 10% higher or lower than X, and also includes any numerical value that falls between X−10% and X+10% (e.g., X−5% and X+5%, or X−3% and X+3%). Thus, for example, a weight of about 40 g may include a weight of between 36 to 44 g, inclusive of the endpoints; a temperature of about 100° C. may include a temperature of 90° C. to 110° C., inclusive of endpoints; and a temperature range of about 90-100° C., may include a range of 81-110° C., inclusive of the endpoints. Thus, for example, a percent composition of about 50% may include a percent composition of between 45% to 55%, inclusive of the endpoints.

As used herein, "about 0° C." includes a temperature of −2° C. to 2° C., inclusive of endpoints.

As used herein, the term "CDK inhibitor" refers to a compound that inhibits the enzymes in humans referred to as cyclin-dependent kinases (CDK). In one embodiment, the CDK inhibitor is a CDK4/6 inhibitor. As used herein, the term "CDK4/6 inhibitor" refers to a compound that inhibits CDK 4 and/or 6. Examples of a CDK inhibitor include, without limitation, SHR6390, trilaciclib, lerociclib, AT7519M, dinaciclib, ribociclib, abemaciclib, palbociclib, or any pharmaceutically acceptable salt thereof. In one embodiment, the CDK inhibitor is palbociclib or a pharmaceutically acceptable salt thereof.

As used herein, the term "PARP inhibitor" refers to a compound that inhibits the enzymes in humans referred to as poly ADP ribose polymerase (PARP). Examples of a PARP inhibitor include, without limitation, olaparib, rucaparib, talazoparib, niraparib, veliparib, pamiparib, CEP 9722, E7016, 3-aminobenzamide, mefuparib, and AZD2281.

"Comprising" or "comprises" as applied to a particular dosage form, composition, use, method or process described or claimed herein means that the dosage form, composition, use, method, or process includes all of the recited elements in a specific description or claim, but does not exclude other elements. "Consists essentially of" and "consisting essentially of" means that the described or claimed composition, dosage form, method, use, or process does not exclude other materials or steps that do not materially affect the recited physical, pharmacological, pharmacokinetic properties or therapeutic effects of the composition, dosage form, method, use, or process. "Consists of" and "consisting of" means the exclusion of more than trace elements of other ingredients and substantial method or process steps.

"Fasted condition" or "fasted state" as used to describe a subject means the subject has not eaten for at least 4 hours before a time point of interest, such as the time of administering Compound A. In an embodiment, a subject in the fasted state has not eaten for at least any of 6, 8, 10 or 12 hours prior to administration of a compound of the disclosure.

"Fed condition" or "fed state" as used to describe a subject herein means the subject has eaten less than 4 hours before a time point of interest, such as the time of administering a compound of the disclosure. In an embodiment, a subject in the fed state has eaten within at least any of 3, 2, 1 or 0.5 hours prior to administration of a compound of the disclosure.

"Antacid medication", as used herein, refers to a substance that neutralizes stomach acidity in the subject. Antacids include, without limitation, bismuth subsalicylate, famotidine, and flavored liquids containing aluminum hydroxide and magnesium hydroxide (Maalox®). In one aspect, this application pertains to a subject who is administered Compound A, or a composition comprising Compound A, who is also taking, or being administered, an antacid medication.

All percentages provided herein are percentages by weight, and may be abbreviated wt % or (w/w), unless indicated otherwise.

In one embodiment, the term "ultrapure", as used herein with reference to Compound A, refers to any of crystalline or amorphous forms of Compound A described herein that have a purity equal to or greater than about 95%, 96%, 97%, 98%, 99%, 99.5, or 99.9 wt %.

In one embodiment, the term "ultrapure", as used herein with reference to Compound A, refers to any of crystalline or amorphous forms of Compound A described herein that contains less than about 5%, 4%, 3%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of one or more impurities.

In one embodiment, the term "ultrapure", as used herein with reference to Compound A, refers to any of crystalline or amorphous forms of Compound A described herein that have a purity equal to or greater than about 95%, 96%, 97%, 98%, 99%, 99.5, or 99.9 wt %, and also contains less than about 5%, 4%, 3%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of one or more impurities.

As used herein, the term "impurity" refers to an unwanted compound, trace metal, or solvent that contaminates Compound A. In one embodiment, the impurity is a compound selected from the group consisting of Intermediate 2, Intermediate 3, Intermediate 5, Impurity 1, Impurity 2, Impurity 3, and Impurity 4. In one embodiment, the impurity is a solvent that is selected from the group consisting of dichloromethane, methanol, and acetonitrile.

"Stable," as used herein with reference to Compound A, refers to forms of Compound A, including ultrapure forms, crystalline forms, ultrapure crystalline forms, amorphous forms, and ultrapure amorphous forms, that stably retain purity equal to, or greater than, 95%, 96%, 97%, 98%, 99%, 99.5, or 99.9% over a period of time (such as 6 months, 12 months, or 24 months) and under specified conditions (e.g., temperature and humidity) (such as 4° C., 25° C., or 40° C.).

Compound A refers to the compound: N-[(1r,4r)-4-(3-chloro-4-cyanophenoxy)cyclohexyl]-6-[4-({4-[2-(2,6-dioxopiperidin-3-yl)-6-fluoro-1,3-dioxo-2,3-dihydro-1H-isoindol-5-yl]piperazin-1-yl}methyl)piperidin-1-yl]pyridazine-3-carboxamide, that has a molecular formula of $C_{41}H_{43}ClFN_9O_6$, and has the following structural formula:

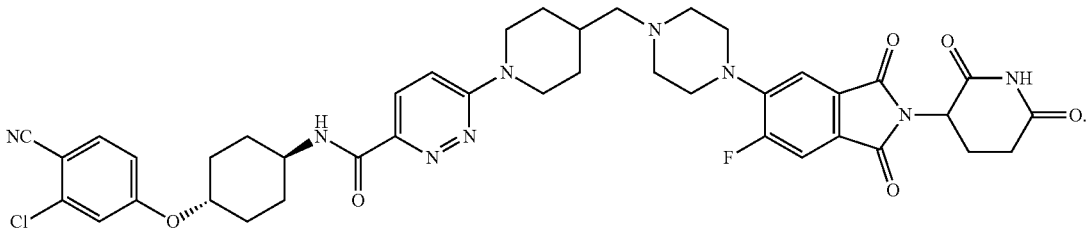

(Compoud A)

Intermediate 1, as used herein, refers to the compound with the following structural formula:

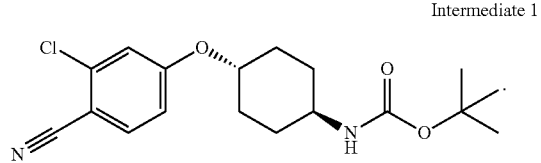 [SMILES: CC(C)(C)OC(=O)N[C@H]1CC[C@H](Oc2ccc(C#N)c(Cl)c2)CC1]

Intermediate 1

Intermediate 2, as used herein, refers to the compound with the following structural formula:

Intermediate 2

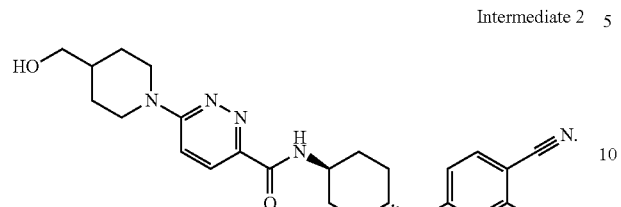

Intermediate 3, as used herein, refers to the compound with the following structural formula:

Intermediate 3

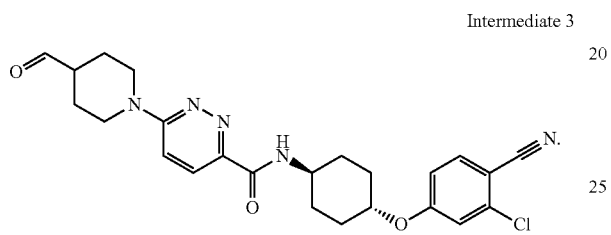

Intermediate 4, as used herein, refers to the compound with the following structural formula:

Intermediate 4

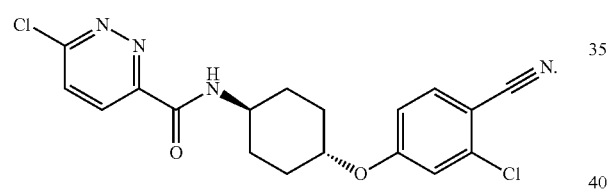

Intermediate 5, as used herein, refers to the compound with the following structural formula:

Intermediate 5

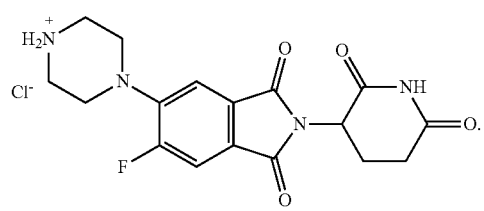

Intermediate 6, as used herein, refers to the compound with the following structural formula:

Intermediate 6

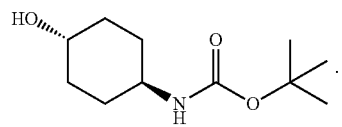

Intermediate 7, as used herein, refers to the compound with the following structural formula:

Intermediate 7

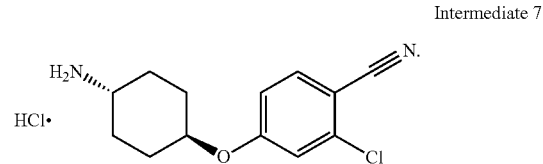 [SMILES: N#Cc1ccc(O[C@H]2CC[C@H](N)CC2)cc1Cl]

Intermediate 8, as used herein, refers to the compound with the following structural formula:

Intermediate 8

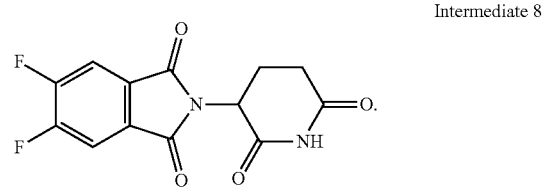 [SMILES: O=C1CCC(N2C(=O)c3cc(F)c(F)cc3C2=O)C(=O)N1]

Intermediate 9, as used herein, refers to the compound with the following structural formula:

Intermediate 9

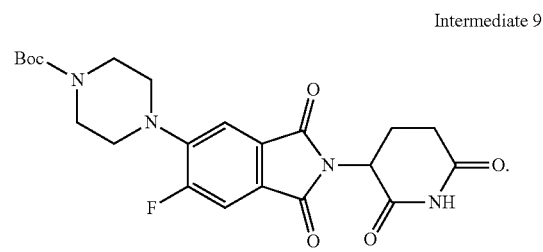 [SMILES: CC(C)(C)OC(=O)N1CCN(c2cc3c(cc2F)C(=O)N(C2CCC(=O)NC2=O)C3=O)CC1]

Intermediate 10, as used herein, refers to the compound with the following structural formula:

Intermediate 10

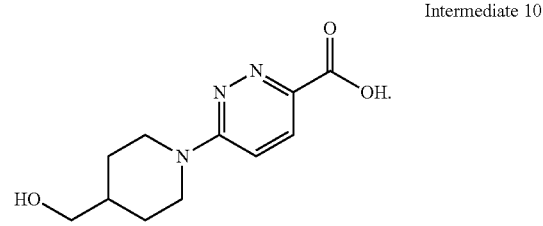 [SMILES: O=C(O)c1ccc(N2CCC(CO)CC2)nn1]

Impurity 1, as used herein, refers to the compound with the following structural formula:

Impurity 1

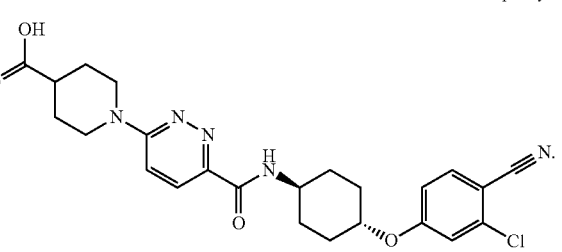

Impurity 2, as used herein, refers to the compound with the following structural formula:
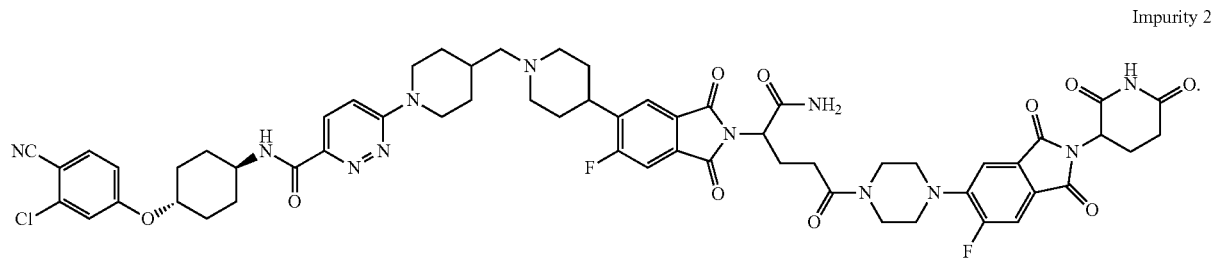 [SMILES: N#Cc1ccc(O[C@H]2CC[C@H](NC(=O)c3ccc(N4CCC(CN5CCC(c6cc7c(cc6F)C(=O)N(C(CCC(=O)N6CCN(c8cc9c(cc8F)C(=O)N(C8CCC(=O)NC8=O)C9=O)CC6)C(N)=O)C7=O)CC5)CC4)nn3)CC2)cc1Cl]
Impurity 2
Impurity 3, as used herein, refers to the compound with the following structural formula:
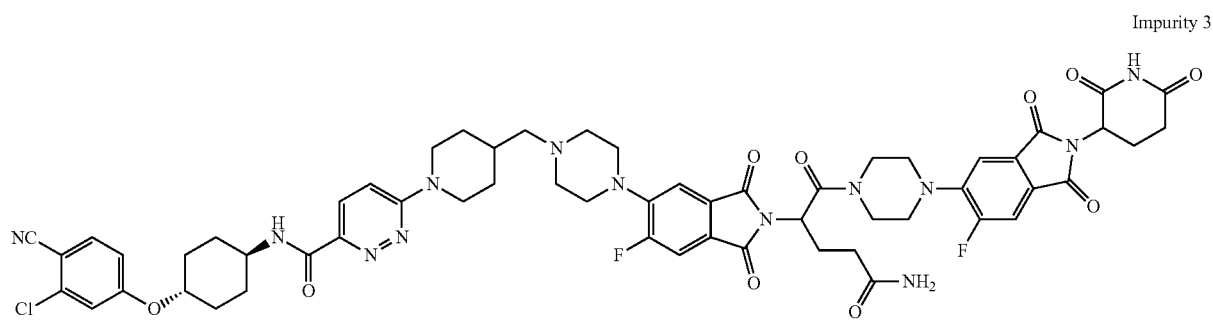 [SMILES: N#Cc1ccc(O[C@H]2CC[C@H](NC(=O)c3ccc(N4CCC(CN5CCN(c6cc7c(cc6F)C(=O)N(C(CCC(N)=O)C(=O)N6CCN(c8cc9c(cc8F)C(=O)N(C8CCC(=O)NC8=O)C9=O)CC6)C7=O)CC5)CC4)nn3)CC2)cc1Cl]
Impurity 3
Impurity 4, as used herein, refers to the compound with the following structural formula:
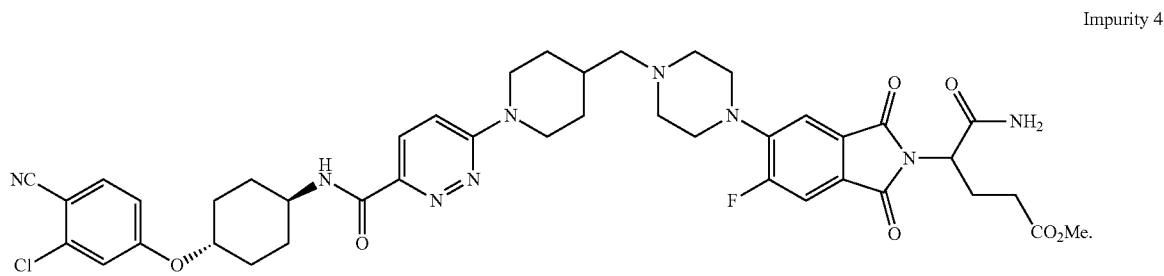 [SMILES: COC(=O)CCC(C(N)=O)N1C(=O)c2cc(F)c(N3CCN(CC4CCN(c5ccc(C(=O)N[C@H]6CC[C@H](Oc7ccc(C#N)c(Cl)c7)CC6)nn5)CC4)CC3)cc2C1=O]
Impurity 4
Compound A
The atoms in Compound A may be numbered as follows
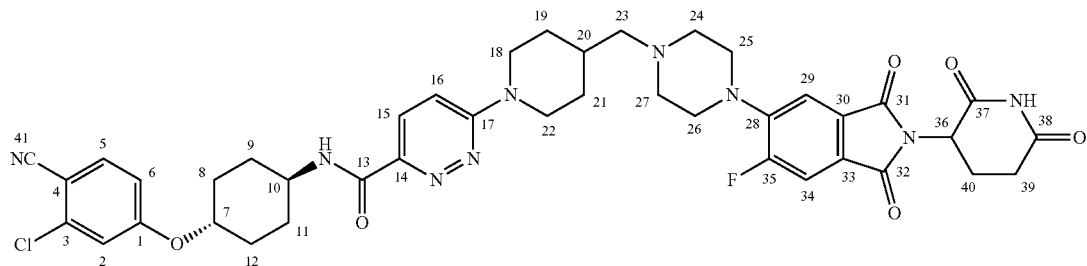 [SMILES: N#Cc1ccc(O[C@H]2CC[C@H](NC(=O)c3ccc(N4CCC(CN5CCN(c6cc7c(cc6F)C(=O)N(C6CCC(=O)NC6=O)C7=O)CC5)CC4)nn3)CC2)cc1Cl]

The centers carbon 10 and 7 are meso and by definition have no chirality and by definition are not stereogenic. The 1,4-trans relationship of the amide and ether on carbons 10 and 7, respectively, is supported by ¹H nuclear magnetic resonance (NMR) in conjunction with 2-D nOe NMR.

Compound A has a stereogenic center at carbon 36 (denoted by an * below). The starting materials for Compound A are sourced from racemic precursors, hence the molecule is racemic. Thus, Compound A, in one embodiment, refers to a 50/50 mixture of enantiomers—ent-1 and ent-2—which have the following structures:

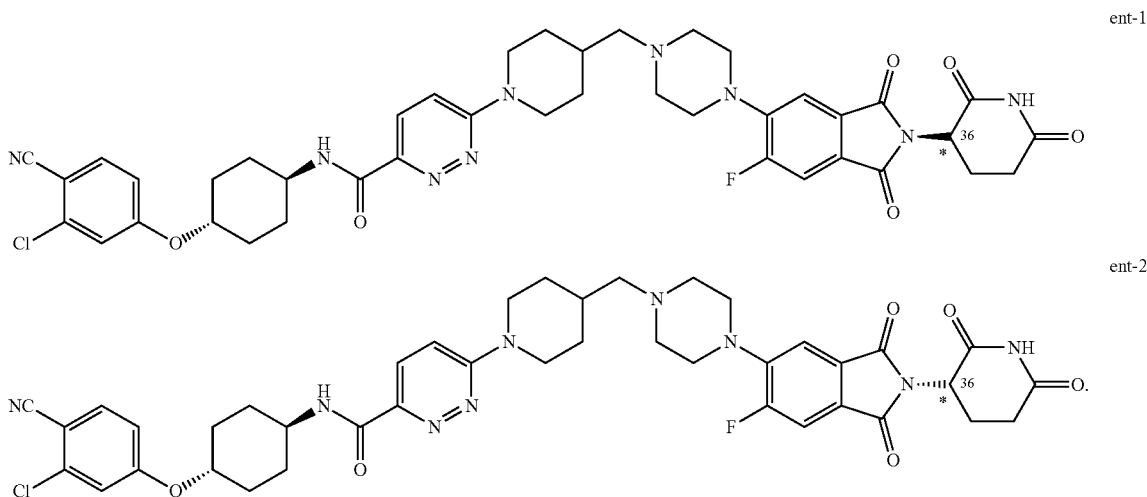

As used herein, Compound A refers to a compound that is entirely ent-1, entirely ent-2, or any mixture of ent-1 and ent-2, including, for example a 50/50 (racemic) mixture of ent-1 and ent-2.

Compound A was originally disclosed in U.S. patent application Ser. No. 15/730,728, which granted as U.S. Pat. No. 10,584,101 and which is incorporated by reference herein in its entirety.

Manufacturing Processes of Compound A

First Generation Process

The first generation manufacturing process for Compound A was described in U.S. Pat. No. 10,584,101, which is incorporated herein by reference. The process is summarized below in Scheme 1 and in the Examples section herein.

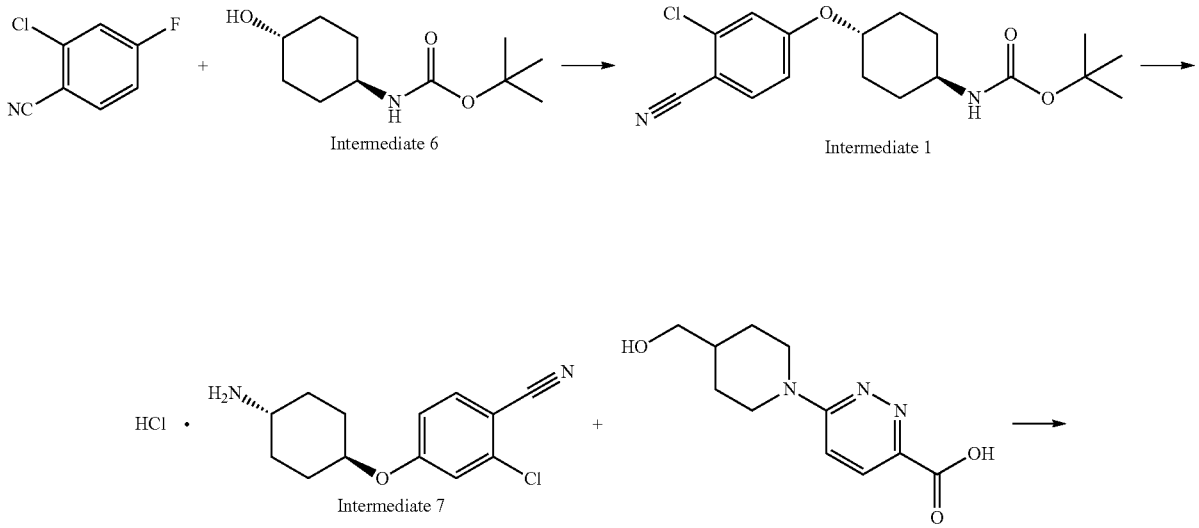

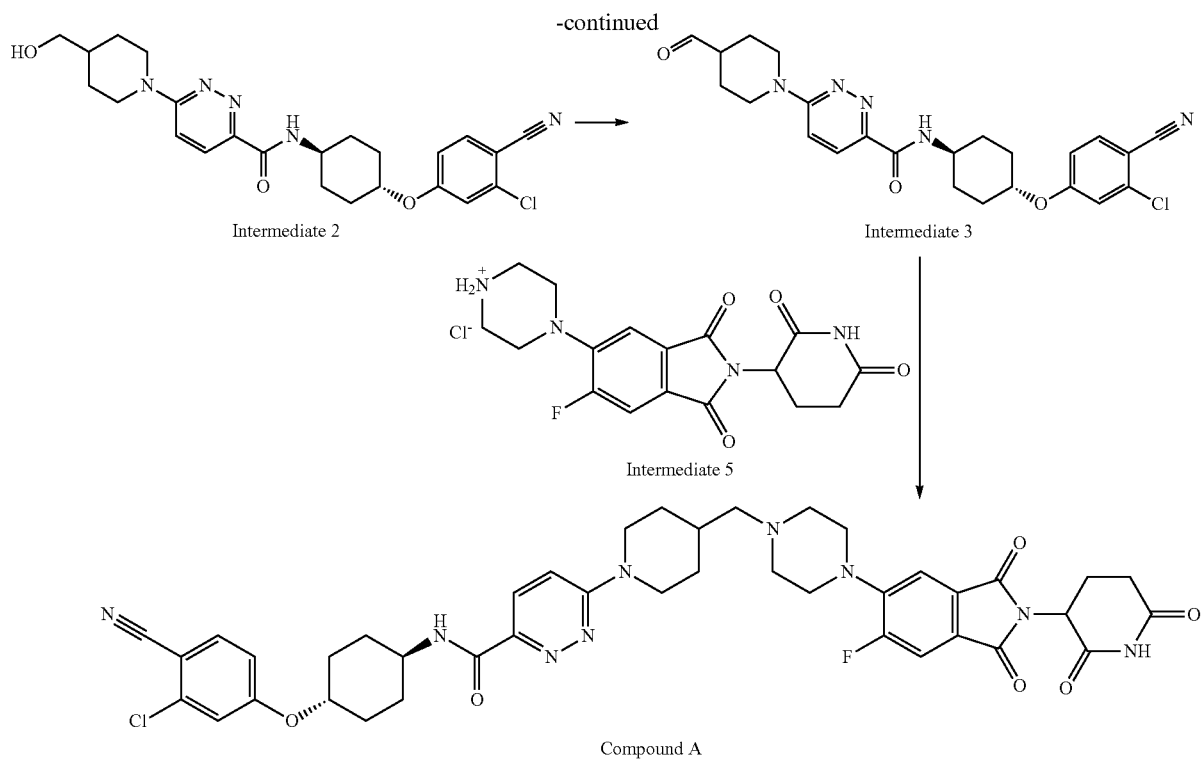

Second, Third, Fourth, and Fifth Generation Processes.

The second, third, fourth, and fifth generation processes are disclosed below and in the examples herein. These processes possess advantageous properties compared to the first generation synthesis. For example, the first generation process yielded Compound A with a purity of about 98%. In contrast, later-generation processes yield Compound A with higher purity, e.g. greater than 98%, greater than 99%, greater than 99.5%, etc.

Second Generation Process

The second generation manufacturing process for Compound A is described below in Schemes 2-4 and in the Examples herein.

The synthesis used for the manufacture of Intermediate 4 is shown below in Scheme 2.

Scheme 2. Synthetic Process for the Manufacturer of Intermediate 4.

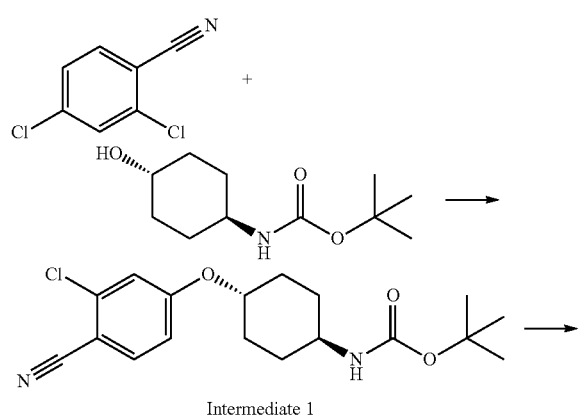

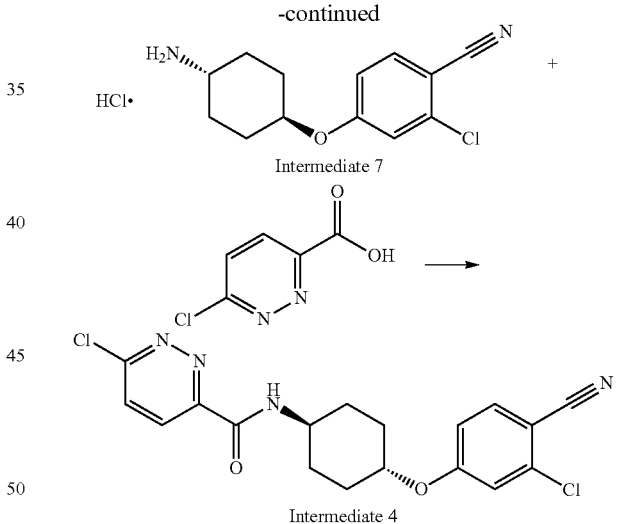

Step 1 involves an SnAr reaction between commercially-available 2,4-dichlorobenzonitrile and tert-butyl ((1r,4r)-4-hydroxycyclohexyl)carbamate in dimethylacetamide (DMA) with sodium hydride at 45o to afford Intermediate 1. The reaction is worked up with water and the precipitate dried to afford Intermediate 1. In the second step, the Boc protecting group is removed from Intermediate 1 by adding acetyl chloride in methanol at rt and the product is recrystallized in methyl tert-butyl ether to afford Intermediate 7. The third step involves amide coupling of Intermediate 7 and 6-chloropyridazine-3-carboxylic acid in ethyl acetate with triethylamine and propanephosphonic acid anhydride (T3P) to provide Intermediate 4. The reaction is quenched with 1 N aqueous HCl, and the crude Intermediate 4 is rinsed with ethyl acetate, filtered and dried. Intermediate 4 is added to isopropyl acetate and dimethylacetamide, filtered, and rinsed with IPAc.

The synthesis used for the manufacture of Intermediate 5 is shown below in Scheme 3.

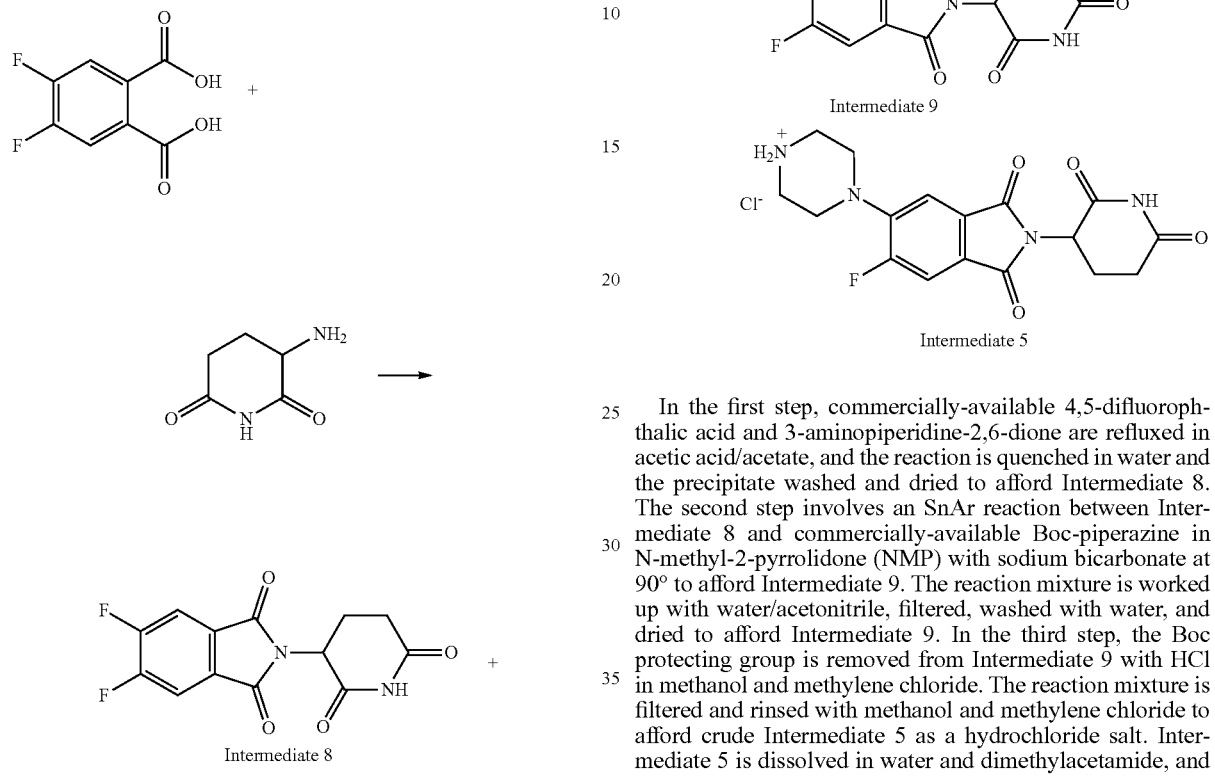

In the first step, commercially-available 4,5-difluorophthalic acid and 3-aminopiperidine-2,6-dione are refluxed in acetic acid/acetate, and the reaction is quenched in water and the precipitate washed and dried to afford Intermediate 8. The second step involves an SnAr reaction between Intermediate 8 and commercially-available Boc-piperazine in N-methyl-2-pyrrolidone (NMP) with sodium bicarbonate at 90° to afford Intermediate 9. The reaction mixture is worked up with water/acetonitrile, filtered, washed with water, and dried to afford Intermediate 9. In the third step, the Boc protecting group is removed from Intermediate 9 with HCl in methanol and methylene chloride. The reaction mixture is filtered and rinsed with methanol and methylene chloride to afford crude Intermediate 5 as a hydrochloride salt. Intermediate 5 is dissolved in water and dimethylacetamide, and recrystallized in isopropanol.

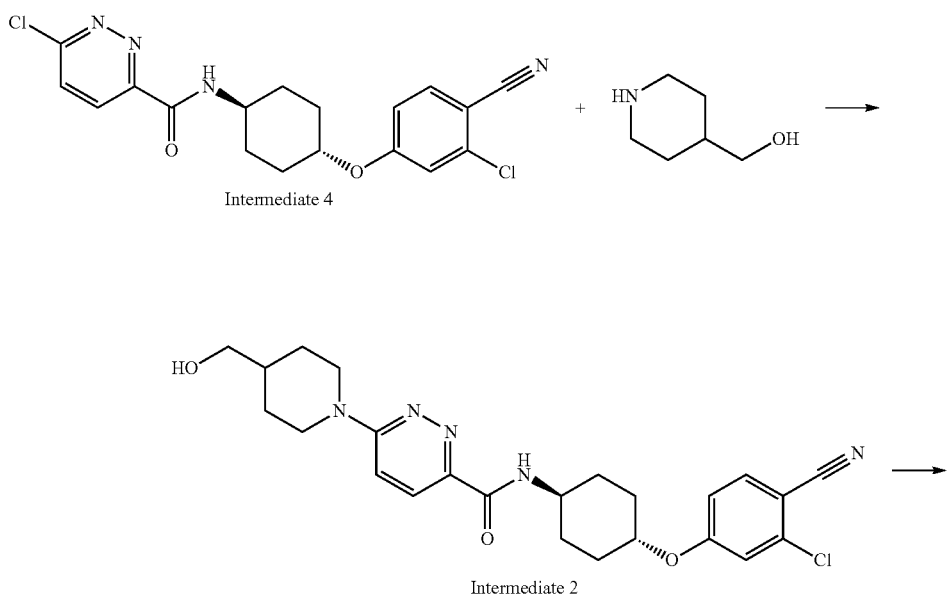

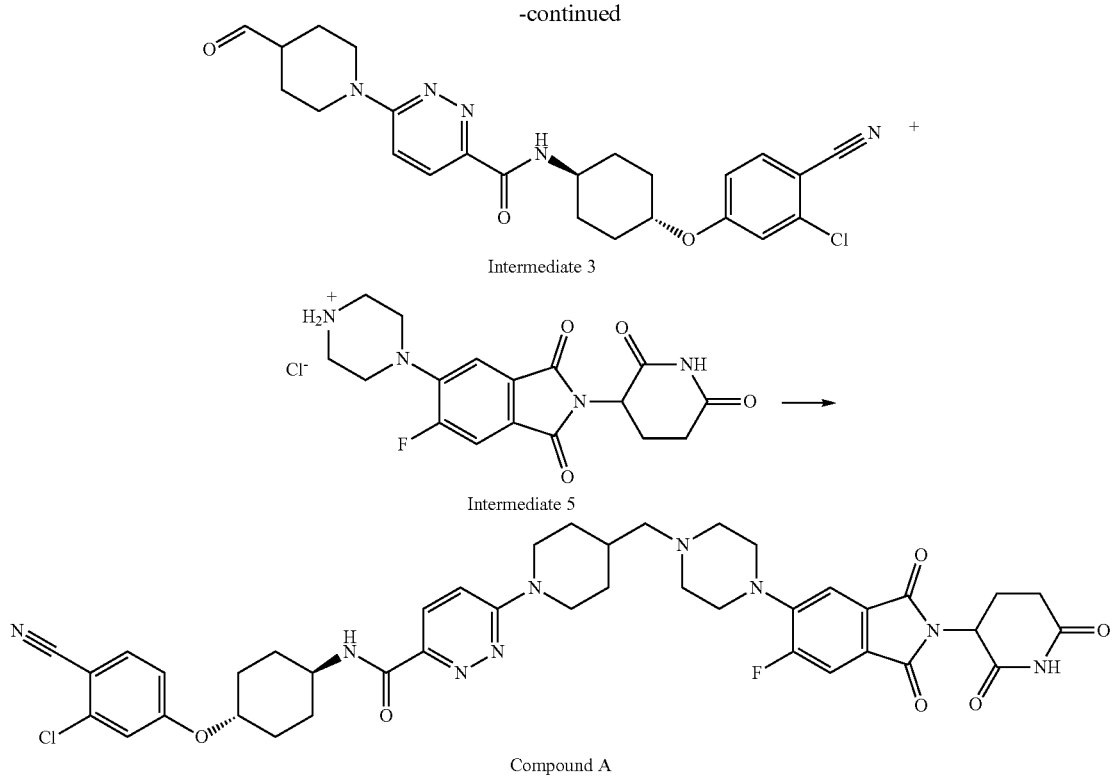

Intermediate 3

Intermediate 5

Compound A

Step 1 in the process includes a SnAr reaction between Intermediate 4 and commercially available piperidin-4-yl methanol in dimethylacetamide (DMA) with N,N-diisopropylethylamine at 90-100° C. to afford Intermediate 2. The reaction mixture is worked up with water and extracted with isopropylacetate (IPAc). The isopropylacetate layer is washed with water and concentrated to afford Intermediate 2 as an off white crystalline solid.

In some embodiments, Step 1 further comprises the step of purifying Intermediate 2 by recrystallization in an organic solvent. In some embodiments, the recrystallization further comprises the following steps:
 i) combining crude Intermediate 2 in an organic solvent with an agent that promotes crystallization;
 ii) reducing the volume of organic solvent;
 iii) adding additional amounts of the organic solvent;
 iv) stirring the mixture from part iii) at a temperature above 30° C. for about 30 to about 60 minutes or longer;
 v) cooling the mixture from part iii) to a temperature below 25° C. over about 30 to about 60 minutes or longer;
 vi) reducing the volume of organic solvent;
 vii) stirring the mixture from part vi) at a temperature below 25° C., for about 30 minutes, about 45 minutes, about 60 minutes, about 75 minutes, about 90 minutes, about 105 minutes, or about 120 minutes, or longer; and
 vii) filtering the mixture to obtain purified Intermediate 2.

In some embodiments, the organic solvent is isopropyl acetate. In some embodiments, the agent that promotes crystallization is a seed crystal of Intermediate 2. In some embodiments, the reducing of the volume of organic solvent in step ii) is performed by vacuum distillation. In some embodiments, the temperature of step iv) is about 50° C. In some embodiments, the temperature of step v) is about 20° C. In some embodiments, the temperature of step vii) is about 10° C.

Step 2 is an oxidation of Intermediate 2 with 0.01 equivalents of TEMPO (2,2,6,6-tetramethylpiperidin-1-yl)oxyl and 1 equivalent of sodium hypochlorite (4.5% aqueous solution) solution in dichloromethane at <10° C. to provide Intermediate 3. The reaction is quenched with 5% aqueous Na$_2$SO$_3$ solution and the crude aldehyde product is extracted into dichloromethane. The dichloromethane layer is distillatively exchanged with acetonitrile.

In some embodiments, Step 2 further comprises the step of purifying Intermediate 3 by recrystallization. For example, in one embodiment, addition of water to the acetonitrile solution afforded Intermediate 3 as a white crystalline solid. In some embodiments, the recrystallization occurs in the presence of a solvent and an anti-solvent. In some embodiments, the recrystallization comprises the following steps:
 i) combining crude Intermediate 3 with a mixture of solvent and anti-solvent;
 ii) stirring the mixture of crude Intermediate 3, solvent, and anti-solvent; and
 iii) filtering the mixture to obtain purified Intermediate 3.

In some embodiments, the solvent in i) is a polar aprotic organic solvent and the anti-solvent in i) is an aqueous solvent. In some embodiments, the solvent comprises acetonitrile. In some embodiments, the anti-solvent is water. In some embodiments, the ratio of solvent to anti-solvent is about 1:1 (v/v). In some embodiments, the ratio of solvent to anti-solvent is about 1.04:1 (v/v). In some embodiments, step ii) is performed at a temperature between 15° C. and 20° C. In some embodiments, step ii) is performed at a temperature of about 18° C. In some embodiments, step ii) is performed at a temperature of about 20° C. In some embodiments, the stirring of step ii) is performed for at least 12 hours, at least 14 hours, at least 16 hours, or at least 18 hours. In some embodiments, the stirring of step ii) is performed for about 18 hours.

Step 3 is a reductive amination of Intermediate 3 with Intermediate 5 in dimethylacetamide with sodium triacetoxyborohydride (STAB) and triethylamine at 5-10° C. to afford Compound A. In some embodiments, the molar ratio of Intermediate 3 to Intermediate 5 is about 1.1:1. In some embodiments, the molar ratio of Intermediate 3 to Intermediate 5 is about 1.05:1. In some embodiments, the molar ratio of Intermediate 3 to Intermediate 5 is between about 1:1 and about 1.1:1. A mixture of ethanol and water is added to the crude reaction mixture and Compound A is precipitated as a yellow solid. Crude Compound A is dissolved in a mixture of dichloromethane:methanol (9:1). The product-rich solution is filtered and distillatively exchanged with ethanol. Crystallization from ethanol solution affords Compound A as a light yellow crystalline solid which is dried in vacuo at 35-45° C.

Third Generation Process

The third generation manufacturing process for Compound A is described below in Scheme 5 and in the Examples that follow.

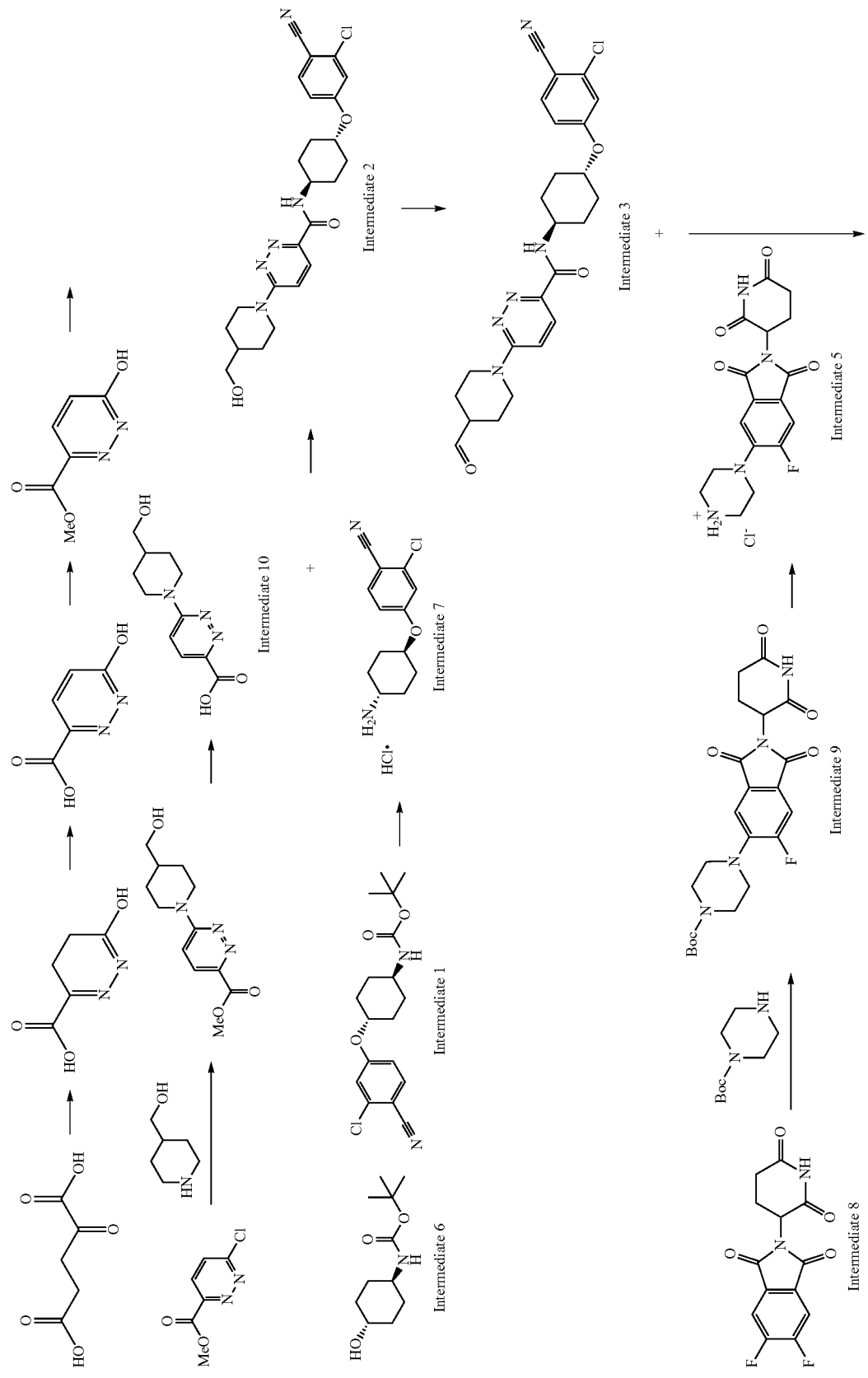

-continued
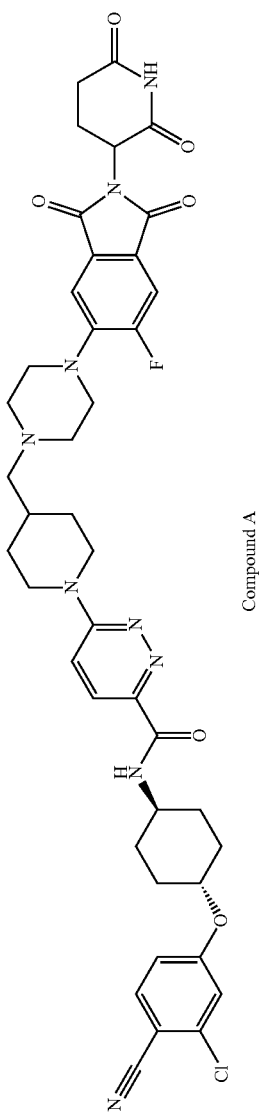
Compound A
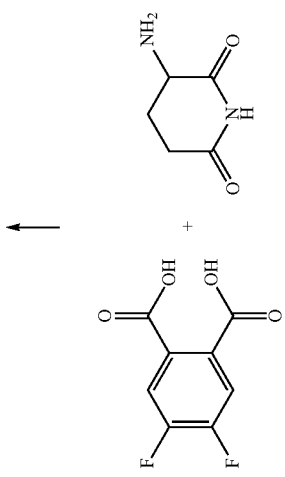

In the first step, the coupling of Intermediate 10 and Intermediate 7 in DMAc with DIPEA, ethyl cyanohydroxyiminoacetate, and 1-Ethyl-3-(3-dimethylaminopropyl)carbodiimide (EDCI) at about 40°, followed by extraction with IPAc and water, and then rinsing the organic layer with IPAc and drying affords Intermediate 2.

In some embodiments, the first step further comprises the step of purifying Intermediate 2 by recrystallization in an organic solvent. In some embodiments, the organic solvent is isopropyl acetate. In some embodiments, the recrystallization is performed by reduction of the volume of the organic solvent. In some embodiments, the reduction of the volume of the organic solvent is performed by vacuum distillation.

Oxidation of Intermediate 2 with about 0.003 equivalents of TEMPO and about 1 equivalent of sodium hypochlorite (3.12% aqueous solution) with sodium bicarbonate, sodium bromide, in dichloromethane and water at <5° C. affords Intermediate 3. The crude Intermediate 3 is extracted with dichloromethane and distillatively exchanged with acetonitrile. Addition of water to the acetonitrile solution afforded Intermediate 3 as a white crystalline solid. Reductive amination of Intermediate 3 with Intermediate 5 in dimethylacetamide with sodium triacetoxyborohydride (STAB) at 5-10° C. affords Compound A. In some embodiments, the molar ratio of Intermediate 3 to Intermediate 5 is about 1.1:1. A mixture of ethanol and water is added to the crude reaction mixture and crude Compound A is precipitated. Crude Compound A is dissolved in a mixture of dichloromethane:methanol (9:1). The product-rich solution is filtered and distillatively exchanged with ethanol. Crystallization from ethanol solution affords Compound A as a light yellow crystalline solid which is dried in vacuo at 25° C.

In some embodiments, the oxidation of Intermediate 2 to afford Intermediate 3 occurs in the presence of an alcohol. In some embodiments, the oxidation of Intermediate 2 to afford Intermediate 3 occurs in the presence of a secondary alcohol. In some embodiments, the oxidation of Intermediate 2 to afford Intermediate 3 occurs in the presence of isopropanol. In some embodiments, the oxidation of Intermediate 2 to afford Intermediate 3 occurs in the presence of 2-butanol. In some embodiments, the oxidation of Intermediate 2 to afford Intermediate 3 occurs in the presence of 2-pentanol. In some embodiments, the oxidation of Intermediate 2 to afford Intermediate 3 occurs in the presence of 3-methyl 2 butanol.

In one embodiment, the second generation synthesis provides an ultrapure form of Compound A that has a purity of greater than about 95%. In certain embodiments, the ultrapure form of Compound A has a purity greater than about 96%, 97%, 98%, 99%, 99.5, or 99.9%.

In one embodiment, the third generation synthesis provides an ultrapure form of Compound A that has a purity of greater than about 95%. In certain embodiments, the ultrapure form of Compound A has a purity greater than about 96%, 97%, 98%, 99%, 99.5, or 99.9%.

Fourth Generation Process

The fourth generation manufacturing process for Compound A is described below in Scheme 6 and in the Examples that follow.

Scheme 6. Fourth Generation Manufacturing Process of Compound A

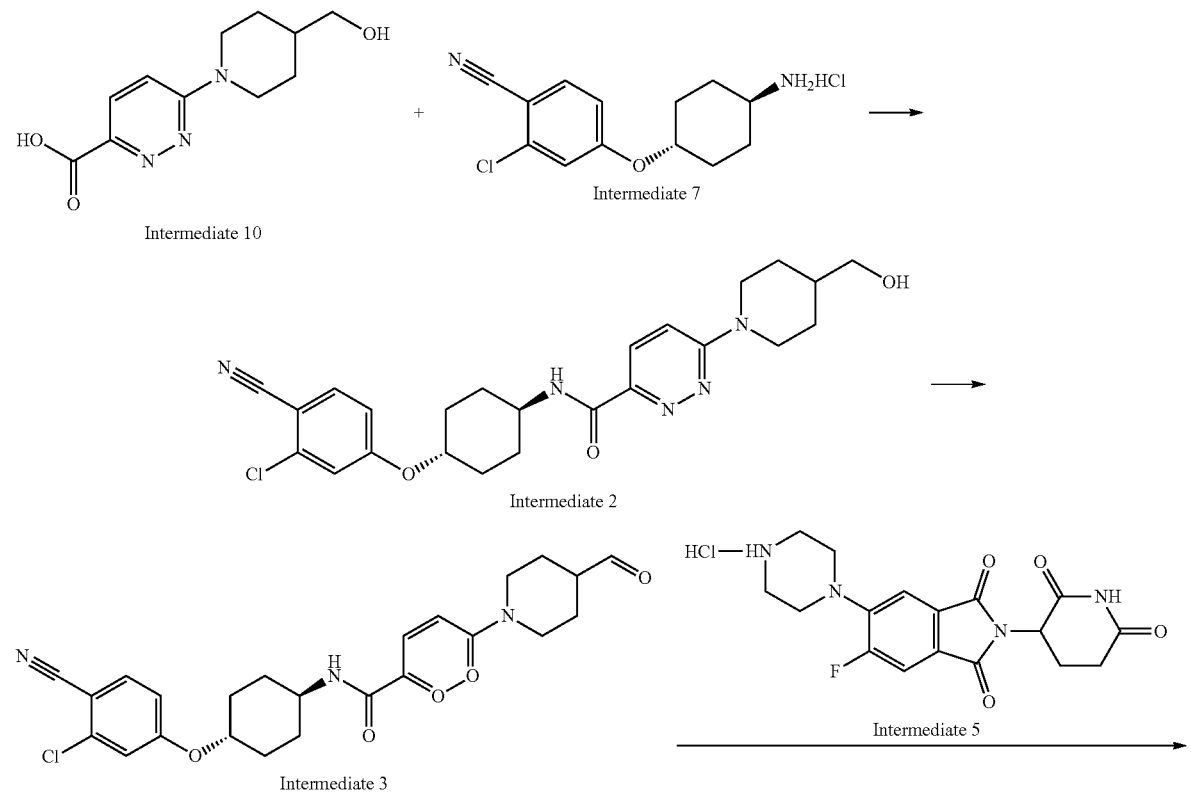

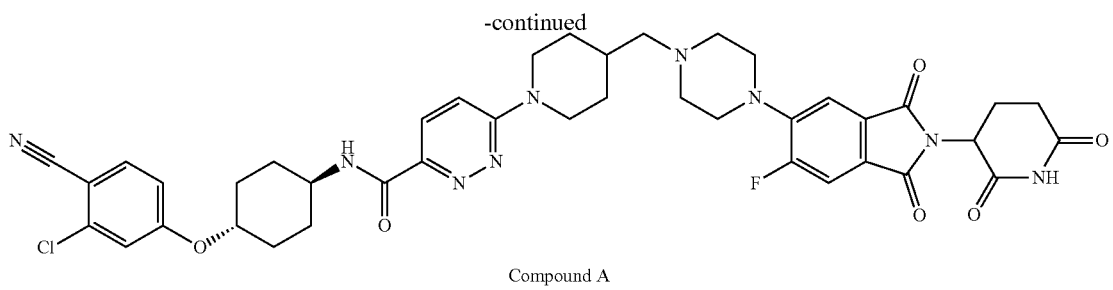

Compound A

In the first step, the coupling of Intermediate 10 with excess Intermediate 7 in DMAc with DIPEA, catalyzed by 2-pyridinol 1-oxide (HOPO) and 1-Ethyl-3-(3-dimethylaminopropyl)carbodiimide (EDCI) at about 20° C. affords Intermediate 2. In some embodiments, the molar ratio of Intermediate 10 to Intermediate 7 is about 1.00:1.05.

In some embodiments, the first step further comprises the step of purifying Intermediate 2 by recrystallization in an organic solvent. In some embodiments, the organic solvent is isopropyl acetate. In some embodiments, the recrystallization is performed by cooling the organic solvent. In some embodiments, the organic solvent is cooled to a temperature between about 15° C. and about 25° C. In some embodiments, the organic solvent is cooled to a temperature of about 20° C.

Oxidation of Intermediate 2 with about 0.01 equivalents of TEMPO and about 1 equivalent of sodium hypochlorite with sodium bicarbonate, sodium bromide, in dichloromethane and water at 0° C. affords crude Intermediate 3. The crude Intermediate 3 was extracted with dichloromethane and distillatively exchanged with tetrahydrofuran. Addition of n-heptane to the tetrahydrofuran solution affords Intermediate 3 as a white crystalline solid.

In some embodiments, the oxidation of Intermediate 2 to afford Intermediate 3 occurs in the presence of an alcohol. In some embodiments, the oxidation of Intermediate 2 to afford Intermediate 3 occurs in the presence of a secondary alcohol. In some embodiments, the oxidation of Intermediate 2 to afford Intermediate 3 occurs in the presence of isopropanol. In some embodiments, the oxidation of Intermediate 2 to afford Intermediate 3 occurs in the presence of 2-butanol. In some embodiments, the oxidation of Intermediate 2 to afford Intermediate 3 occurs in the presence of 2-pentanol. In some embodiments, the oxidation of Intermediate 2 to afford Intermediate 3 occurs in the presence of 3-methyl 2 butanol.

Reductive amination of Intermediate 3 with Intermediate 5 in dimethylacetamide with sodium triacetoxyborohydride (STAB) and N-methylmorpholine at 0° C. affords Compound A. In some embodiments, the molar ratio of Intermediate 3 to Intermediate 5 is about 1.1:1. In some embodiments, the ratio of Intermediate 5 to N-methyl morpholine is between about 1.5:1 and about 2:1 (w/w). In some embodiments, the ratio of Intermediate 5 to N-methyl morpholine is about 1.7:1 (w/w). A mixture of ethanol and water is added to the crude reaction mixture and Compound A is precipitated. Crude Compound A is dissolved in a mixture of dichloromethane:methanol (17:1 w/w). The product-rich solution is filtered and distillatively exchanged with ethanol. Crystallization from ethanol solution affords Compound A as a light yellow crystalline solid which is dried in vacuo at 65° C.

In one embodiment, the fourth generation synthesis provides an ultrapure form of Compound A that has a purity of greater than about 95%. In certain embodiments, the ultra-pure form of Compound A has a purity greater than about 96%, 97%, 98%, 99%, 99.5, or 99.9%.

Fifth Generation Process

The fifth generation manufacturing process for Compound A follows the same general scheme as the fourth generation process described above.

In the first step, the coupling of Intermediate 10 with excess Intermediate 7 in DMAc with DIPEA, catalyzed by 2-pyridinol 1-oxide (HOPO) and EDCI at about 20° C. affords Intermediate 2. In some embodiments, the molar ratio of Intermediate 10 to Intermediate 7 is about 1.00:1.02. In some embodiments, the precise amount of Intermediate 7 is adjusted based on the purity and potency of the Intermediate 7 used. In some embodiments, the precise amount of Intermediate 10 is adjusted based on the purity and potency of the Intermediate 10 used.

In some embodiments, the first step further comprises the step of purifying Intermediate 2 by recrystallization in an organic solvent. In some embodiments, the organic solvent comprises tetrahydrofuran and n-heptane. In some embodiments, the organic solvent for the recrystallization of Intermediate 2 is seeded with crystals of pure Intermediate 2. In some embodiments, the recrystallization is performed by cooling the organic solvent. In some embodiments, the organic solvent is cooled to a temperature between about 15° C. and about 25° C. In some embodiments, the organic solvent is cooled to a temperature of about 20° C.

Oxidation of Intermediate 2 with about 0.01 equivalents of TEMPO and about 1.15 equivalents of sodium hypochlorite with sodium bicarbonate, sodium chloride, and sodium bromide, in dichloromethane and water at 20° C. affords Intermediate 3. Addition of n-heptane and tetrahydrofuran to the solution affords Intermediate 3 as a white crystalline solid.

In some embodiments, the sodium hypochlorite is added to the reaction mixture rapidly. In some embodiments, the sodium hypochlorite is added over the course of less than 60 minutes, less than 45 minutes less than 30 minutes, or less than 20 minutes. In some embodiments, the sodium hypochlorite is added over the course of between about 15 and about 45 minutes. In some embodiments, the sodium hypochlorite is added over the course of about 30 minutes. In some embodiments, the oxidation of Intermediate 2 to afford Intermediate 3 occurs in the presence of an alcohol. In some embodiments, the oxidation of Intermediate 2 to afford Intermediate 3 occurs in the presence of a secondary alcohol. In some embodiments, the oxidation of Intermediate 2 to afford Intermediate 3 occurs in the presence of isopropanol. In some embodiments, the oxidation of Intermediate 2 to afford Intermediate 3 occurs in the presence of 2-butanol. In some embodiments, the oxidation of Intermediate 2 to afford Intermediate 3 occurs in the presence of 2-pentanol. In some embodiments, the oxidation of Intermediate 2 to afford Intermediate 3 occurs in the presence of 3-methyl 2 butanol.

Reductive amination of Intermediate 3 with Intermediate 5 in dimethylacetamide with sodium triacetoxyborohydride (STAB) and N-methylmorpholine at 0° C. affords Compound A. In some embodiments, the molar ratio of Intermediate 3 to Intermediate 5 is about 1.1:1. In some embodiments, the ratio of Intermediate 5 to N-methyl morpholine is between about 1.5:1 and 2:1 (w/w). In some embodiments, the ratio of Intermediate 5 to N-methyl morpholine is about 1.7:1 (w/w). A mixture of ethanol and water is added to the crude reaction mixture and Compound A precipitated. Crude Compound A was dissolved in a mixture of dichloromethane:methanol (17:1 w/w). The product-rich solution is filtered and distillatively exchanged with ethanol. Crystallization from ethanol solution affords Compound A as a light yellow crystalline solid which is dried in vacuo at 65° C.

In the solvent swap from DCM into EtOH, auto-crystallization (self-seeding) occurs around a 1:1 ratio of DCM/EtOH content, which occurs shortly after 14 vol of EtOH have been dispensed (end of atmospheric distillation; solvent swap 1). To have a more uniform and consistent filtration of mother liquors and washes, it is proposed to control the crystallization with seeding. Experiments showed that at reflux conditions, the product solution is supersaturated at/around 67% DCM content. In some embodiments, the seeding protocol comprises the following steps:

Distill to supersaturation point (7 vol EtOH added)
Remove sample for DCM content to ensure DCM≤67% (supersaturated)
Cool solution down to below reflux (~42° C.) to 35° C.
Charge 0.5 wt % seed (based on Intermediate 3 input) at 35° C.
Heat slurry back up to reflux and continue with remainder of solvent swap In one embodiment, the fifth generation synthesis provides an ultrapure form of Compound A that has a purity of greater than about 95%. In one embodiment, the ultrapure form of Compound A has a purity greater than about 96%, 97%, 98%, 99%, 99.5, or 99.9%.

Purification of Compound A

In one embodiment, the purification of Compound A comprises the following steps:
(1) dissolving Compound A in about a mixture of dichloromethane and methanol;
(2) filtering the solution comprising Compound A;
(3) distillatively exchanging the solvent of the solution comprising Compound A with ethanol;
(4) crystallizing Compound A from the ethanol solution; and
(5) drying the purified crystalline solid form of Compound A.

In one embodiment, the ratio of dichloromethane to methanol in (1) is about 9:1 (w/w). In one embodiment, the ratio of dichloromethane to methanol in (1) is about 10:1 (w/w)

In one embodiment, the purification of Compound A comprises dissolving compound A in a solvent of between about 95:5 (w/w) and about 80:20 (w/w) mixture of dichloromethane and methanol.

In one embodiment, the purification of Compound A comprises dissolving compound A in about an 80:20 (w/w) mixture of dichloromethane and methanol. In one embodiment, the purification of Compound A comprises dissolving compound A in about a 90:10 (w/w) mixture of dichloromethane and methanol. In one embodiment, the purification of Compound A comprises dissolving compound A in about a 95:5 (w/w) mixture of dichloromethane and methanol. In one embodiment, the purification of Compound A comprises dissolving compound A in about a 10:1 (v/v) mixture of dichloromethane and methanol.

In one embodiment, the volume of ethanol in step (3) is between approximately 5 volumes and approximately 9 volumes relative to the amount of Intermediate 3 provided in the reductive amination step. In one embodiment, the volume of ethanol in step (3) is between approximately 6 volumes and approximately 8 volumes relative to the amount of Intermediate 3 provided in the reductive amination step. In one embodiment, the volume of ethanol in step (3) is approximately 7 volumes relative to the amount of Intermediate 3 provided in the reductive amination step.

In some embodiments, the amount of ethanol in step (A3) is corrected for the ethanol content in the crude Compound A.

In one embodiment, drying of the purified crystalline solid form of Compound A is performed in vacuo. In some embodiments, the drying occurs at about 15° C. to about 30° C., about 20° C. to about 30° C., about 30° C. to about 40° C., or about 35° C. to about 45° C. In some embodiments, the drying occurs at greater than about 50° C., greater than about 60° C., greater than about 70° C., or greater than about 80° C. In some embodiments, the drying occurs at between about 60° C. and about 70° C. In some embodiments, the drying occurs at about 65° C. In some embodiments, the drying occurs at between about 75° C. and about 85° C.

In some embodiments, the drying occurs at about 80° C.

Purification of Compound A

In the following embodiments, the percent purity of Compound A, and the percent composition of one or more impurities, reflects the purity on a w/w basis.

In some embodiments, the percent purity of Compound A, and the percent composition of one or more impurities, represents the purity as determined by HPLC (area %).

In one embodiment, the ultrapure form of Compound A has a purity greater than about 95%, and further comprises less than about 1% of an impurity that is Intermediate 2.

In one embodiment, the ultrapure form of Compound A has a purity greater than about 96%, and further comprises less than about 1% of an impurity that is Intermediate 2. In one embodiment, the ultrapure form of Compound A has a purity greater than about 97%, and further comprises less than about 1% of an impurity that is Intermediate 2. In one embodiment, the ultrapure form of Compound A has a purity greater than about 98%, and further comprises less than about 1% of an impurity that is Intermediate 2. In one embodiment, the ultrapure form of Compound A has a purity greater than about 99%, and further comprises less than about 1% of an impurity that is Intermediate 2. In one embodiment, the ultrapure form of Compound A has a purity greater than about 99.5%, and further comprises less than about 0.5% of an impurity that is Intermediate 2. In one embodiment, the ultrapure form of Compound A has a purity of greater than about 99.9%, and further comprises less than about 0.1% of an impurity that is Intermediate 2. In one embodiment, the ultrapure form of Compound A has a purity of about 99.9%, and further comprises less than about 0.1% of an impurity that is Intermediate 2.

In one embodiment, the ultrapure form of Compound A has a purity greater than about 95%, and further comprises less than about 0.5% of an impurity that is Intermediate 2.

In one embodiment, the ultrapure form of Compound A has a purity greater than about 96%, and further comprises less than about 0.5% of an impurity that is Intermediate 2.

In one embodiment, the ultrapure form of Compound A has a purity greater than about 97%, and further comprises less than about 0.5% of an impurity that is Intermediate 2. In one embodiment, the ultrapure form of Compound A has a purity greater than about 98%, and further comprises less than about 0.5% of an impurity that is Intermediate 2. In one embodiment, the ultrapure form of Compound A has a purity greater than about 99%, and further comprises less than about 0.5% of an impurity that is Intermediate 2. In one embodiment, the ultrapure form of Compound A has a purity greater than about 99.5%, and further comprises less than about 0.5% of an impurity that is Intermediate 2. In one embodiment, the ultrapure form of Compound A has a purity of greater than about 99.9%, and further comprises less than about 0.1% of an impurity that is Intermediate 2. In one embodiment, the ultrapure form of Compound A has a purity of about 99.9%, and further comprises less than about 0.1% of an impurity that is Intermediate 2.

In one embodiment, the ultrapure form of Compound A has a purity greater than about 95%, and further comprises less than about 0.2% of an impurity that is Intermediate 2.

In one embodiment, the ultrapure form of Compound A has a purity greater than about 96%, and further comprises less than about 0.2% of an impurity that is Intermediate 2. In one embodiment, the ultrapure form of Compound A has a purity greater than about 97%, and further comprises less than about 0.2% of an impurity that is Intermediate 2. In one embodiment, the ultrapure form of Compound A has a purity greater than about 98%, and further comprises less than about 0.2% of an impurity that is Intermediate 2. In one embodiment, the ultrapure form of Compound A has a purity greater than about 99%, and further comprises less than about 0.2% of an impurity that is Intermediate 2. In one embodiment, the ultrapure form of Compound A has a purity greater than about 99.5%, and further comprises less than about 0.2% of an impurity that is Intermediate 2. In one embodiment, the ultrapure form of Compound A has a purity of greater than about 99.8%, and further comprises less than about 0.2% of an impurity that is Intermediate 2. In one embodiment, the ultrapure form of Compound A has a purity of about 99.8%, and further comprises less than about 0.2% of an impurity that is Intermediate 2.

In one embodiment, the ultrapure form of Compound A has a purity greater than about 95%, and further comprises less than about 0.1% of an impurity that is Intermediate 2.

In one embodiment, the ultrapure form of Compound A has a purity greater than about 96%, and further comprises less than about 0.1% of an impurity that is Intermediate 2. In one embodiment, the ultrapure form of Compound A has a purity greater than about 97%, and further comprises less than about 0.1% of an impurity that is Intermediate 2. In one embodiment, the ultrapure form of Compound A has a purity greater than about 98%, and further comprises less than about 0.1% of an impurity that is Intermediate 2. In one embodiment, the ultrapure form of Compound A has a purity greater than about 99%, and further comprises less than about 0.1% of an impurity that is Intermediate 2. In one embodiment, the ultrapure form of Compound A has a purity greater than about 99.5%, and further comprises less than about 0.1% of an impurity that is Intermediate 2. In one embodiment, the ultrapure form of Compound A has a purity greater than about 99.9%, and further comprises less than about 0.1% of an impurity that is Intermediate 2. In one embodiment, the ultrapure form of Compound A has a purity of about 99.9%, and further comprises less than about 0.1% of an impurity that is Intermediate 2.

In one embodiment, the ultrapure form of Compound A has a purity greater than about 95%, and further comprises less than about 0.05% of an impurity that is Intermediate 2.

In one embodiment, the ultrapure form of Compound A has a purity greater than about 96%, and further comprises less than about 0.05% of an impurity that is Intermediate 2. In one embodiment, the ultrapure form of Compound A has a purity greater than about 97%, and further comprises less than about 0.05% of an impurity that is Intermediate 2. In one embodiment, the ultrapure form of Compound A has a purity greater than about 98%, and further comprises less than about 0.05% of an impurity that is Intermediate 2. In one embodiment, the ultrapure form of Compound A has a purity greater than about 99%, and further comprises less than about 0.05% of an impurity that is Intermediate 2. In one embodiment, the ultrapure form of Compound A has a purity greater than about 99.5%, and further comprises less than about 0.05% of an impurity that is Intermediate 2. In one embodiment, the ultrapure form of Compound A has a purity of greater than about 99.9%, and further comprises less than about 0.05% of an impurity that is Intermediate 2. In one embodiment, the ultrapure form of Compound A has a purity of about 99.9%, and further comprises less than about 0.05% of an impurity that is Intermediate 2.

In one embodiment, the ultrapure form of Compound A has a purity greater than about 95%, and further comprises less than 1% of an impurity that is Intermediate 3.

In one embodiment, the ultrapure form of Compound A has a purity greater than about 96%, and further comprises less than about 1% of an impurity that is Intermediate 3. In one embodiment, the ultrapure form of Compound A has a purity greater than about 97%, and further comprises less than about 1% of an impurity that is Intermediate 3. In one embodiment, the ultrapure form of Compound A has a purity greater than about 98%, and further comprises less than about 1% of an impurity that is Intermediate 3. In one embodiment, the ultrapure form of Compound A has a purity greater than about 99%, and further comprises less than about 1% of an impurity that is Intermediate 3. In one embodiment, the ultrapure form of Compound A has a purity greater than about 99.5%, and further comprises less than about 0.5% of an impurity that is Intermediate 3. In one embodiment, the ultrapure form of Compound A has a purity of about 99.5%, and further comprises less than about 0.5% of an impurity that is Intermediate 3.

In one embodiment, the ultrapure form of Compound A has a purity greater than about 95%, and further comprises less than about 0.5% of an impurity that is Intermediate 3.

In one embodiment, the ultrapure form of Compound A has a purity greater than about 96%, and further comprises less than about 0.5% of an impurity that is Intermediate 3. In one embodiment, the ultrapure form of Compound A has a purity greater than about 97%, and further comprises less than about 0.5% of an impurity that is Intermediate 3. In one embodiment, the ultrapure form of Compound A has a purity greater than about 98%, and further comprises less than about 0.5% of an impurity that is Intermediate 3. In one embodiment, the ultrapure form of Compound A has a purity greater than about 99%, and further comprises less than about 0.5% of an impurity that is Intermediate 3. In one embodiment, the ultrapure form of Compound A has a purity greater than about 99.5%, and further comprises less than about 0.5% of an impurity that is Intermediate 3. In one embodiment, the ultrapure form of Compound A has a purity of greater than about 99.9%, and further comprises less than about 0.1% of an impurity that is Intermediate 3. In one embodiment, the ultrapure form of Compound A has a purity of about 99.9%, and further comprises less than about 0.1% of an impurity that is Intermediate 3.

In one embodiment, the ultrapure form of Compound A has a purity greater than about 95%, and further comprises less than about 0.2% of an impurity that is Intermediate 3. In one embodiment, the ultrapure form of Compound A has a purity greater than about 96%, and further comprises less than about 0.2% of an impurity that is Intermediate 3. In one embodiment, the ultrapure form of Compound A has a purity greater than about 97%, and further comprises less than about 0.2% of an impurity that is Intermediate 3. In one embodiment, the ultrapure form of Compound A has a purity greater than about 98%, and further comprises less than about 0.2% of an impurity that is Intermediate 3. In one embodiment, the ultrapure form of Compound A has a purity greater than about 99%, and further comprises less than about 0.2% of an impurity that is Intermediate 3. In one embodiment, the ultrapure form of Compound A has a purity greater than about 99.5%, and further comprises less than about 0.2% of an impurity that is Intermediate 3. In one embodiment, the ultrapure form of Compound A has a purity of greater than about 99.8%, and further comprises less than about 0.2% of an impurity that is Intermediate 3. In one embodiment, the ultrapure form of Compound A has a purity of about 99.8%, and further comprises less than about 0.2% of an impurity that is Intermediate 3.

In one embodiment, the ultrapure form of Compound A has a purity greater than about 95%, and further comprises less than about 0.1% of an impurity that is Intermediate 3. In one embodiment, the ultrapure form of Compound A has a purity greater than about 96%, and further comprises less than about 0.1% of an impurity that is Intermediate 3. In one embodiment, the ultrapure form of Compound A has a purity greater than about 97%, and further comprises less than about 0.1% of an impurity that is Intermediate 3. In one embodiment, the ultrapure form of Compound A has a purity greater than about 98%, and further comprises less than about 0.1% of an impurity that is Intermediate 3. In one embodiment, the ultrapure form of Compound A has a purity greater than about 99%, and further comprises less than about 0.1% of an impurity that is Intermediate 3. In one embodiment, the ultrapure form of Compound A has a purity greater than about 99.5%, and further comprises less than about 0.1% of an impurity that is Intermediate 3. In one embodiment, the ultrapure form of Compound A has a purity greater than about 99.9%, and further comprises less than about 0.1% of an impurity that is Intermediate 3. In one embodiment, the ultrapure form of Compound A has a purity of about 99.9%, and further comprises less than about 0.1% of an impurity that is Intermediate 3.

In one embodiment, the ultrapure form of Compound A has a purity greater than about 95%, and further comprises less than about 0.05% of an impurity that is Intermediate 3. In one embodiment, the ultrapure form of Compound A has a purity greater than about 96%, and further comprises less than about 0.05% of an impurity that is Intermediate 3. In one embodiment, the ultrapure form of Compound A has a purity greater than about 97%, and further comprises less than about 0.05% of an impurity that is Intermediate 3. In one embodiment, the ultrapure form of Compound A has a purity greater than about 98%, and further comprises less than about 0.05% of an impurity that is Intermediate 3. In one embodiment, the ultrapure form of Compound A has a purity greater than about 99%, and further comprises less than about 0.05% of an impurity that is Intermediate 3. In one embodiment, the ultrapure form of Compound A has a purity greater than about 99.5%, and further comprises less than about 0.05% of an impurity that is Intermediate 3. In one embodiment, the ultrapure form of Compound A has a purity of greater than about 99.9%, and further comprises less than about 0.05% of an impurity that is Intermediate 3. In one embodiment, the ultrapure form of Compound A has a purity of about 99.9%, and further comprises less than about 0.05% of an impurity that is Intermediate 3.

In one embodiment, the ultrapure form of Compound A has a purity greater than 95%, and further comprises less than about 1% of an impurity that is Intermediate 5.

In one embodiment, the ultrapure form of Compound A has a purity greater than about 96%, and further comprises less than about 1% of an impurity that is Intermediate 5. In one embodiment, the ultrapure form of Compound A has a purity greater than about 97%, and further comprises less than about 1% of an impurity that is Intermediate 5. In one embodiment, the ultrapure form of Compound A has a purity greater than about 98%, and further comprises less than about 1% of an impurity that is Intermediate 5. In one embodiment, the ultrapure form of Compound A has a purity greater than about 99%, and further comprises less than about 1% of an impurity that is Intermediate 5. In one embodiment, the ultrapure form of Compound A has a purity greater than about 99.5%, and further comprises less than about 0.5% of an impurity that is Intermediate 5. In one embodiment, the ultrapure form of Compound A has a purity of greater than about 99.9%, and further comprises less than about 0.1% of an impurity that is Intermediate 5. In one embodiment, the ultrapure form of Compound A has a purity of about 99.9%, and further comprises less than about 0.1% of an impurity that is Intermediate 5.

In one embodiment, the ultrapure form of Compound A has a purity greater than about 95%, and further comprises less than about 0.5% of an impurity that is Intermediate 5. In one embodiment, the ultrapure form of Compound A has a purity greater than about 96%, and further comprises less than about 0.5% of an impurity that is Intermediate 5. In one embodiment, the ultrapure form of Compound A has a purity greater than about 97%, and further comprises less than about 0.5% of an impurity that is Intermediate 5. In one embodiment, the ultrapure form of Compound A has a purity greater than about 98%, and further comprises less than about 0.5% of an impurity that is Intermediate 5. In one embodiment, the ultrapure form of Compound A has a purity greater than about 99%, and further comprises less than about 0.5% of an impurity that is Intermediate 5. In one embodiment, the ultrapure form of Compound A has a purity greater than about 99.5%, and further comprises less than about 0.5% of an impurity that is Intermediate 5. In one embodiment, the ultrapure form of Compound A has a purity of about 99.5%, and further comprises less than about 0.5% of an impurity that is Intermediate 5. In one embodiment, the ultrapure form of Compound A has a purity greater than about 95%, and further comprises less than about 0.2% of an impurity that is Intermediate 5.

In one embodiment, the ultrapure form of Compound A has a purity greater than about 96%, and further comprises less than about 0.2% of an impurity that is Intermediate 5. In one embodiment, the ultrapure form of Compound A has a purity greater than about 97%, and further comprises less than about 0.2% of an impurity that is Intermediate 5. In one embodiment, the ultrapure form of Compound A has a purity greater than about 98%, and further comprises less than about 0.2% of an impurity that is Intermediate 5. In one embodiment, the ultrapure form of Compound A has a purity greater than about 99%, and further comprises less than about 0.2% of an impurity that is Intermediate 5. In one embodiment, the ultrapure form of Compound A has a purity greater than about 99.5%, and further comprises less than about 0.2% of an impurity that is Intermediate 5. In one embodiment, the ultrapure form of Compound A has a purity of greater than about 99.8%, and further comprises less than about 0.2% of an impurity that is Intermediate 5. In one embodiment, the ultrapure form of Compound A has a purity of about 99.8%, and further comprises less than about 0.2% of an impurity that is Intermediate 5.

In one embodiment, the ultrapure form of Compound A has a purity greater than about 95%, and further comprises less than about 0.1% of an impurity that is Intermediate 5.

In one embodiment, the ultrapure form of Compound A has a purity greater than about 96%, and further comprises less than about 0.1% of an impurity that is Intermediate 5. In one embodiment, the ultrapure form of Compound A has a purity greater than about 97%, and further comprises less than about 0.1% of an impurity that is Intermediate 5. In one embodiment, the ultrapure form of Compound A has a purity greater than about 98%, and further comprises less than about 0.1% of an impurity that is Intermediate 5. In one embodiment, the ultrapure form of Compound A has a purity greater than about 99%, and further comprises less than about 0.1% of an impurity that is Intermediate 5. In one embodiment, the ultrapure form of Compound A has a purity greater than about 99.5%, and further comprises less than about 0.1% of an impurity that is Intermediate 5. In one embodiment, the ultrapure form of Compound A has a purity of greater than about 99.9%, and further comprises less than about 0.1% of an impurity that is Intermediate 5. In one embodiment, the ultrapure form of Compound A has a purity of about 99.9%, and further comprises less than about 0.1% of an impurity that is Intermediate 5.

In one embodiment, the ultrapure form of Compound A has a purity greater than about 95%, and further comprises less than about 0.05% of an impurity that is Intermediate 5.

In one embodiment, the ultrapure form of Compound A has a purity greater than about 96%, and further comprises less than about 0.05% of an impurity that is Intermediate 5. In one embodiment, the ultrapure form of Compound A has a purity greater than about 97%, and further comprises less than about 0.05% of an impurity that is Intermediate 5. In one embodiment, the ultrapure form of Compound A has a purity greater than about 98%, and further comprises less than about 0.05% of an impurity that is Intermediate 5. In one embodiment, the ultrapure form of Compound A has a purity greater than about 99%, and further comprises less than about 0.05% of an impurity that is Intermediate 5. In one embodiment, the ultrapure form of Compound A has a purity greater than about 99.5%, and further comprises less than about 0.05% of an impurity that is Intermediate 5. In one embodiment, the ultrapure form of Compound A has a purity of greater than about 99.9%, and further comprises less than about 0.05% of an impurity that is Intermediate 5. In one embodiment, the ultrapure form of Compound A has a purity of about 99.9%, and further comprises less than about 0.05% of an impurity that is Intermediate 5.

In one embodiment, the ultrapure form of Compound A has a purity greater than about 95%, and further comprises less than about 1% of an impurity that is Impurity 1.

In one embodiment, the ultrapure form of Compound A has a purity greater than about 96%, and further comprises less than about 1% of an impurity that is Impurity 1. In one embodiment, the ultrapure form of Compound A has a purity greater than about 97%, and further comprises less than about 1% of an impurity that is Impurity 1. In one embodiment, the ultrapure form of Compound A has a purity greater than about 98%, and further comprises less than about 1% of an impurity that is Impurity 1. In one embodiment, the ultrapure form of Compound A has a purity greater than about 99%, and further comprises less than about 1% of an impurity that is Impurity 1. In one embodiment, the ultrapure form of Compound A has a purity greater than about 99.5%, and further comprises less than about 0.5% of an impurity that is Impurity 1. In one embodiment, the ultrapure form of Compound A has a purity of greater than about 99.9%, and further comprises less than about 0.1% of an impurity that is Impurity 1. In one embodiment, the ultrapure form of Compound A has a purity of about 99.9%, and further comprises less than about 0.1% of an impurity that is Impurity 1.

In one embodiment, the ultrapure form of Compound A has a purity greater than about 95%, and further comprises less than about 0.5% of an impurity that is Impurity 1.

In one embodiment, the ultrapure form of Compound A has a purity greater than about 96%, and further comprises less than about 0.5% of an impurity that is Impurity 1. In one embodiment, the ultrapure form of Compound A has a purity greater than about 97%, and further comprises less than about 0.5% of an impurity that is Impurity 1. In one embodiment, the ultrapure form of Compound A has a purity greater than about 98%, and further comprises less than about 0.5% of an impurity that is Impurity 1. In one embodiment, the ultrapure form of Compound A has a purity greater than about 99%, and further comprises less than about 0.5% of an impurity that is Impurity 1. In one embodiment, the ultrapure form of Compound A has a purity greater than about 99.5%, and further comprises less than about 0.5% of an impurity that is Impurity 1. In one embodiment, the ultrapure form of Compound A has a purity of about 99.5%, and further comprises less than about 0.5% of an impurity that is Impurity 1. In one embodiment, the ultrapure form of Compound A has a purity greater than about 95%, and further comprises less than about 0.2% of an impurity that is Impurity 1.

In one embodiment, the ultrapure form of Compound A has a purity greater than about 96%, and further comprises less than about 0.2% of an impurity that is Impurity 1. In one embodiment, the ultrapure form of Compound A has a purity greater than about 97%, and further comprises less than about 0.2% of an impurity that is Impurity 1. In one embodiment, the ultrapure form of Compound A has a purity greater than about 98%, and further comprises less than about 0.2% of an impurity that is Impurity 1. In one embodiment, the ultrapure form of Compound A has a purity greater than about 99%, and further comprises less than about 0.2% of an impurity that is Impurity 1. In one embodiment, the ultrapure form of Compound A has a purity greater than about 99.5%, and further comprises less than about 0.2% of an impurity that is Impurity 1. In one embodiment, the ultrapure form of Compound A has a purity of greater than about 99.8%, and further comprises less than about 0.2% of an impurity that is Impurity 1. In one embodiment, the ultrapure form of Compound A has a purity of about 99.8%, and further comprises less than about 0.2% of an impurity that is Impurity 1.

In one embodiment, the ultrapure form of Compound A has a purity greater than about 95%, and further comprises less than about 0.1% of an impurity that is Impurity 1.

In one embodiment, the ultrapure form of Compound A has a purity greater than about 96%, and further comprises less than about 0.1% of an impurity that is Impurity 1. In one embodiment, the ultrapure form of Compound A has a purity greater than about 97%, and further comprises less than about 0.1% of an impurity that is Impurity 1. In one embodiment, the ultrapure form of Compound A has a purity greater than about 98%, and further comprises less than about 0.1% of an impurity that is Impurity 1. In one embodiment, the ultrapure form of Compound A has a purity greater than about 99%, and further comprises less than about 0.1% of an impurity that is Impurity 1. In one embodiment, the ultrapure form of Compound A has a purity greater than about 99.5%, and further comprises less than about 0.1% of an impurity that is Impurity 1. In one embodiment, the ultrapure form of Compound A has a purity of greater than about 99.9%, and further comprises less than about 0.1% of an impurity that is Impurity 1. In one embodiment, the ultrapure form of Compound A has a purity of about 99.9%, and further comprises less than about 0.1% of an impurity that is Impurity 1.

In one embodiment, the ultrapure form of Compound A has a purity greater than about 95%, and further comprises less than about 0.05% of an impurity that is Impurity 1.

In one embodiment, the ultrapure form of Compound A has a purity greater than about 96%, and further comprises less than about 0.05% of an impurity that is Impurity 1. In one embodiment, the ultrapure form of Compound A has a purity greater than about 97%, and further comprises less than about 0.05% of an impurity that is Impurity 1. In one embodiment, the ultrapure form of Compound A has a purity greater than about 98%, and further comprises less than about 0.05% of an impurity that is Impurity 1. In one embodiment, the ultrapure form of Compound A has a purity greater than about 99%, and further comprises less than about 0.05% of an impurity that is Impurity 1. In one embodiment, the ultrapure form of Compound A has a purity greater than about 99.5%, and further comprises less than about 0.05% of an impurity that is Impurity 1. In one embodiment, the ultrapure form of Compound A has a purity of greater than about 99.9%, and further comprises less than about 0.05% of an impurity that is Impurity 1. In one embodiment, the ultrapure form of Compound A has a purity of about 99.9%, and further comprises less than about 0.05% of an impurity that is Impurity 1.

In one embodiment, the ultrapure form of Compound A has a purity greater than about 95%, and further comprises less than about 1% of an impurity that is Impurity 2.

In one embodiment, the ultrapure form of Compound A has a purity greater than about 96%, and further comprises less than about 1% of an impurity that is Impurity 2. In one embodiment, the ultrapure form of Compound A has a purity greater than about 97%, and further comprises less than about 1% of an impurity that is Impurity 2. In one embodiment, the ultrapure form of Compound A has a purity greater than about 98%, and further comprises less than about 1% of an impurity that is Impurity 2. In one embodiment, the ultrapure form of Compound A has a purity greater than about 99%, and further comprises less than about 1% of an impurity that is Impurity 2. In one embodiment, the ultrapure form of Compound A has a purity greater than about 99.5%, and further comprises less than about 0.5% of an impurity that is Impurity 2. In one embodiment, the ultrapure form of Compound A has a purity of greater than about 99.9%, and further comprises less than about 0.1% of an impurity that is Impurity 2. In one embodiment, the ultrapure form of Compound A has a purity of about 99.9%, and further comprises less than about 0.1% of an impurity that is Impurity 2.

In one embodiment, the ultrapure form of Compound A has a purity greater than about 95%, and further comprises less than about 0.5% of an impurity that is Impurity 2.

In one embodiment, the ultrapure form of Compound A has a purity greater than about 96%, and further comprises less than about 0.5% of an impurity that is Impurity 2. In one embodiment, the ultrapure form of Compound A has a purity greater than about 97%, and further comprises less than about 0.5% of an impurity that is Impurity 2. In one embodiment, the ultrapure form of Compound A has a purity greater than about 98%, and further comprises less than about 0.5% of an impurity that is Impurity 2. In one embodiment, the ultrapure form of Compound A has a purity greater than about 99%, and further comprises less than about 0.5% of an impurity that is Impurity 2. In one embodiment, the ultrapure form of Compound A has a purity greater than about 99.5%, and further comprises less than about 0.5% of an impurity that is Impurity 2. In one embodiment, the ultrapure form of Compound A has a purity of about 99.5%, and further comprises less than about 0.5% of an impurity that is Impurity 2. In one embodiment, the ultrapure form of Compound A has a purity greater than about 95%, and further comprises less than about 0.2% of an impurity that is Impurity 2.

In one embodiment, the ultrapure form of Compound A has a purity greater than about 96%, and further comprises less than about 0.2% of an impurity that is Impurity 2. In one embodiment, the ultrapure form of Compound A has a purity greater than about 97%, and further comprises less than about 0.2% of an impurity that is Impurity 2. In one embodiment, the ultrapure form of Compound A has a purity greater than about 98%, and further comprises less than about 0.2% of an impurity that is Impurity 2. In one embodiment, the ultrapure form of Compound A has a purity greater than about 99%, and further comprises less than about 0.2% of an impurity that is Impurity 2. In one embodiment, the ultrapure form of Compound A has a purity greater than about 99.5%, and further comprises less than about 0.2% of an impurity that is Impurity 2. In one embodiment, the ultrapure form of Compound A has a purity of greater than about 99.8%, and further comprises less than about 0.2% of an impurity that is Impurity 2. In one embodiment, the ultrapure form of Compound A has a purity of about 99.8%, and further comprises less than about 0.2% of an impurity that is Impurity 2.

In one embodiment, the ultrapure form of Compound A has a purity greater than about 95%, and further comprises less than about 0.15% of an impurity that is Impurity 2.

In one embodiment, the ultrapure form of Compound A has a purity greater than about 96%, and further comprises less than about 0.15% of an impurity that is Impurity 2. In one embodiment, the ultrapure form of Compound A has a purity greater than about 97%, and further comprises less than about 0.15% of an impurity that is Impurity 2. In one embodiment, the ultrapure form of Compound A has a purity greater than about 98%, and further comprises less than about 0.15% of an impurity that is Impurity 2. In one embodiment, the ultrapure form of Compound A has a purity greater than about 99%, and further comprises less than about 0.15% of an impurity that is Impurity 2. In one embodiment, the ultrapure form of Compound A has a purity greater than about 99.5%, and further comprises less than about 0.15% of an impurity that is Impurity 2. In one embodiment, the ultrapure form of Compound A has a purity of greater than about 99.85%, and further comprises less than about 0.15% of an impurity that is Impurity 2. In one embodiment, the ultrapure form of Compound A has a purity of about 99.85%, and further comprises less than about 0.15% of an impurity that is Impurity 2.

In one embodiment, the ultrapure form of Compound A has a purity greater than about 95%, and further comprises less than about 1% of an impurity that is Impurity 3.

In one embodiment, the ultrapure form of Compound A has a purity greater than about 96%, and further comprises less than about 1% of an impurity that is Impurity 3. In one embodiment, the ultrapure form of Compound A has a purity greater than about 97%, and further comprises less than about 1% of an impurity that is Impurity 3. In one embodiment, the ultrapure form of Compound A has a purity greater than about 98%, and further comprises less than about 1% of an impurity that is Impurity 3. In one embodiment, the ultrapure form of Compound A has a purity greater than about 99%, and further comprises less than about 1% of an impurity that is Impurity 3. In one embodiment, the ultrapure form of Compound A has a purity greater than about 99.5%, and further comprises less than about 0.5% of an impurity that is Impurity 3. In one embodiment, the ultrapure form of Compound A has a purity of greater than about 99.9%, and further comprises less than about 0.1% of an impurity that is Impurity 3. In one embodiment, the ultrapure form of Compound A has a purity of about 99.9%, and further comprises less than about 0.1% of an impurity that is Impurity 3.

In one embodiment, the ultrapure form of Compound A has a purity greater than about 95%, and further comprises less than about 0.5% of an impurity that is Impurity 3.

In one embodiment, the ultrapure form of Compound A has a purity greater than about 96%, and further comprises less than about 0.5% of an impurity that is Impurity 3. In one embodiment, the ultrapure form of Compound A has a purity greater than about 97%, and further comprises less than about 0.5% of an impurity that is Impurity 3. In one embodiment, the ultrapure form of Compound A has a purity greater than about 98%, and further comprises less than about 0.5% of an impurity that is Impurity 3. In one embodiment, the ultrapure form of Compound A has a purity greater than about 99%, and further comprises less than about 0.5% of an impurity that is Impurity 3. In one embodiment, the ultrapure form of Compound A has a purity greater than about 99.5%, and further comprises less than about 0.5% of an impurity that is Impurity 3. In one embodiment, the ultrapure form of Compound A has a purity of about 99.5%, and further comprises less than about 0.5% of an impurity that is Impurity 3. In one embodiment, the ultrapure form of Compound A has a purity greater than about 95%, and further comprises less than about 0.2% of an impurity that is Impurity 3.

In one embodiment, the ultrapure form of Compound A has a purity greater than about 96%, and further comprises less than about 0.2% of an impurity that is Impurity 3. In one embodiment, the ultrapure form of Compound A has a purity greater than about 97%, and further comprises less than about 0.2% of an impurity that is Impurity 3. In one embodiment, the ultrapure form of Compound A has a purity greater than about 98%, and further comprises less than about 0.2% of an impurity that is Impurity 3. In one embodiment, the ultrapure form of Compound A has a purity greater than about 99%, and further comprises less than about 0.2% of an impurity that is Impurity 3. In one embodiment, the ultrapure form of Compound A has a purity greater than about 99.5%, and further comprises less than about 0.2% of an impurity that is Impurity 3. In one embodiment, the ultrapure form of Compound A has a purity of greater than about 99.8%, and further comprises less than about 0.2% of an impurity that is Impurity 3. In one embodiment, the ultrapure form of Compound A has a purity of about 99.8%, and further comprises less than about 0.2% of an impurity that is Impurity 3.

In one embodiment, the ultrapure form of Compound A has a purity greater than about 95%, and further comprises less than about 0.15% of an impurity that is Impurity 3.

In one embodiment, the ultrapure form of Compound A has a purity greater than about 96%, and further comprises less than about 0.15% of an impurity that is Impurity 3. In one embodiment, the ultrapure form of Compound A has a purity greater than about 97%, and further comprises less than about 0.15% of an impurity that is Impurity 3. In one embodiment, the ultrapure form of Compound A has a purity greater than about 98%, and further comprises less than about 0.15% of an impurity that is Impurity 3. In one embodiment, the ultrapure form of Compound A has a purity greater than about 99%, and further comprises less than about 0.15% of an impurity that is Impurity 3. In one embodiment, the ultrapure form of Compound A has a purity greater than about 99.5%, and further comprises less than about 0.15% of an impurity that is Impurity 3. In one embodiment, the ultrapure form of Compound A has a purity of greater than about 99.85%, and further comprises less than about 0.15% of an impurity that is Impurity 3. In one embodiment, the ultrapure form of Compound A has a purity of about 99.85%, and further comprises less than about 0.15% of an impurity that is Impurity 3.

In one embodiment, the ultrapure form of Compound A has a purity greater than about 95%, and further comprises less than about 1% of an impurity that is Impurity 4.

In one embodiment, the ultrapure form of Compound A has a purity greater than about 96%, and further comprises less than about 1% of an impurity that is Impurity 4. In one embodiment, the ultrapure form of Compound A has a purity greater than about 97%, and further comprises less than about 1% of an impurity that is Impurity 4. In one embodiment, the ultrapure form of Compound A has a purity greater than about 98%, and further comprises less than about 1% of an impurity that is Impurity 4. In one embodiment, the ultrapure form of Compound A has a purity greater than about 99%, and further comprises less than about 1% of an impurity that is Impurity 4. In one embodiment, the ultrapure form of Compound A has a purity greater than about 99.5%, and further comprises less than about 0.5% of an impurity that is Impurity 4. In one embodiment, the ultrapure form of Compound A has a purity of greater than about 99.9%, and further comprises less than about 0.1% of an impurity that is Impurity 4. In one embodiment, the ultrapure form of Compound A has a purity of about 99.9%, and further comprises less than about 0.1% of an impurity that is Impurity 4.

In one embodiment, the ultrapure form of Compound A has a purity greater than about 95%, and further comprises less than about 0.5% of an impurity that is Impurity 4.

In one embodiment, the ultrapure form of Compound A has a purity greater than about 96%, and further comprises less than about 0.5% of an impurity that is Impurity 4. In one embodiment, the ultrapure form of Compound A has a purity greater than about 97%, and further comprises less than about 0.5% of an impurity that is Impurity 4. In one embodiment, the ultrapure form of Compound A has a purity greater than about 98%, and further comprises less than about 0.5% of an impurity that is Impurity 4. In one embodiment, the ultrapure form of Compound A has a purity greater than about 99%, and further comprises less than about 0.5% of an impurity that is Impurity 4. In one embodiment, the ultrapure form of Compound A has a purity greater than about 99.5%, and further comprises less than about 0.5% of an impurity that is Impurity 4. In one embodiment, the ultrapure form of Compound A has a purity of about 99.5%, and further comprises less than about 0.5% of an impurity that is Impurity 4. In one embodiment, the ultrapure form of Compound A has a purity greater than about 95%, and further comprises less than about 0.2% of an impurity that is Impurity 4.

In one embodiment, the ultrapure form of Compound A has a purity greater than about 96%, and further comprises less than about 0.2% of an impurity that is Impurity 4. In one embodiment, the ultrapure form of Compound A has a purity greater than about 97%, and further comprises less than about 0.2% of an impurity that is Impurity 4. In one embodiment, the ultrapure form of Compound A has a purity greater than about 98%, and further comprises less than about 0.2% of an impurity that is Impurity 4. In one embodiment, the ultrapure form of Compound A has a purity greater than about 99%, and further comprises less than about 0.2% of an impurity that is Impurity 4. In one embodiment, the ultrapure form of Compound A has a purity greater than about 99.5%, and further comprises less than about 0.2% of an impurity that is Impurity 4. In one embodiment, the ultrapure form of Compound A has a purity of greater than about 99.8%, and further comprises less than about 0.2% of an impurity that is Impurity 4. In one embodiment, the ultrapure form of Compound A has a purity of about 99.8%, and further comprises less than about 0.2% of an impurity that is Impurity 4.

In one embodiment, the ultrapure form of Compound A has a purity greater than about 95%, and further comprises less than about 0.15% of an impurity that is Impurity 4.

In one embodiment, the ultrapure form of Compound A has a purity greater than about 96%, and further comprises less than about 0.15% of an impurity that is Impurity 4. In one embodiment, the ultrapure form of Compound A has a purity greater than about 97%, and further comprises less than about 0.15% of an impurity that is Impurity 4. In one embodiment, the ultrapure form of Compound A has a purity greater than about 98%, and further comprises less than about 0.15% of an impurity that is Impurity 4. In one embodiment, the ultrapure form of Compound A has a purity greater than about 99%, and further comprises less than about 0.15% of an impurity that is Impurity 4. In one embodiment, the ultrapure form of Compound A has a purity greater than about 99.5%, and further comprises less than about 0.15% of an impurity that is Impurity 4. In one embodiment, the ultrapure form of Compound A has a purity of greater than about 99.85%, and further comprises less than about 0.15% of an impurity that is Impurity 4. In one embodiment, the ultrapure form of Compound A has a purity of about 99.85%, and further comprises less than about 0.15% of an impurity that is Impurity 4.

In one embodiment, the ultrapure form of Compound A has a purity greater than about 95%, and further comprises less than about 1%, 0.9%, 0.8%, 0.7%, 0.6%, or 0.5% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 95%, and further comprises less than about 1%, 0.9%, 0.8%, 0.7%, 0.6%, or 0.5% of each of at least two of the following impurities. Intermediate 2, Intermediate 3, Intermediate 5, Impurity 1, Impurity 2, Impurity 3, and Impurity 4.

In one embodiment, the ultrapure form of Compound A has a purity greater than about 96%, and further comprises less than about 1%, 0.9%, 0.8%, 0.7%, 0.6%, or 0.5% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 96%, and further comprises less than about 1%, 0.9%, 0.8%, 0.7%, 0.6%, or 0.5% of each of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 97%, and further comprises less than about 1%, 0.9%, 0.8%, 0.7%, 0.6%, or 0.5% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 97%, and further comprises less than about 1%, 0.9%, 0.8%, 0.7%, 0.6%, or 0.5% of each of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 98%, and further comprises less than about 1%, 0.9%, 0.8%, 0.7%, 0.6%, or 0.5% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 98%, and further comprises less than about 1%, 0.9%, 0.8%, 0.7%, 0.6%, or 0.5% of each of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 99%, and further comprises less than about 1% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 99%, and further comprises less than about 1% of each of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 99.5%, and further comprises less than about 1%, 0.9%, 0.8%, 0.7%, 0.6%, or 0.5% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity greater than about 99.5%, and further comprises less than about 1%, 0.9%, 0.8%, 0.7%, 0.6%, or 0.5% of each of at least two of the following impurities. Intermediate 2, Intermediate 3, Intermediate 5, Impurity 1, Impurity 2, Impurity 3, and Impurity 4.

In one embodiment, the ultrapure form of Compound A has a purity of about 99.9%, and further comprises less than about 1%, 0.9%, 0.8%, 0.7%, 0.6%, or 0.5% in total of at least two of the following impurities: Intermediate 2, Intermediate 3, Intermediate 5, Impurity 1, Impurity 2, Impurity 3, and Impurity 4.

In one embodiment, the ultrapure form of Compound A has a purity of about 99.9%, and further comprises less than about 1%, 0.9%, 0.8%, 0.7%, 0.6%, or 0.5% of each of at least two of the following impurities: Intermediate 2, Intermediate 3, Intermediate 5, Impurity 1, Impurity 2, Impurity 3, and Impurity 4.

In one embodiment, the ultrapure forms of Compound A as described herein are crystalline.

In one embodiment, the ultrapure forms of Compound A as described herein are amorphous.

Crystalline Forms of Compound A

In one aspect, this application pertains to a crystalline form of Compound A wherein Compound A is an ethanolate (i.e., an ethanol solvate). The XRPD pattern corresponding to this crystalline form is referred to as Form 4, and is provided in FIG. 3C.

Figure 3A:
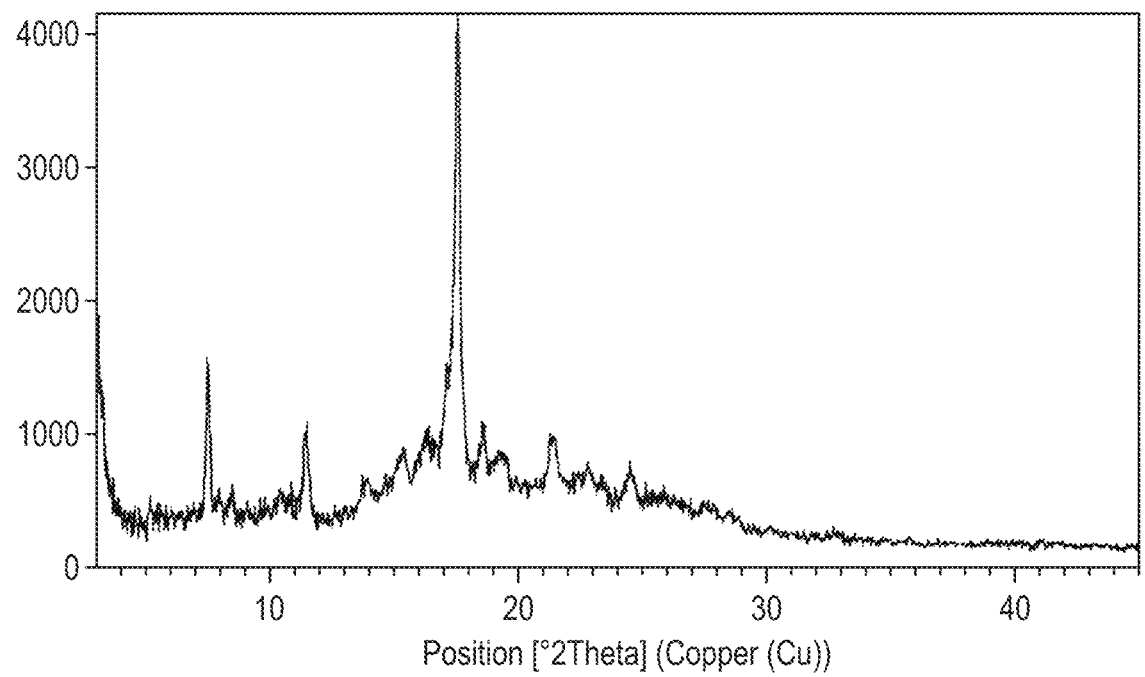
Figure 3C:
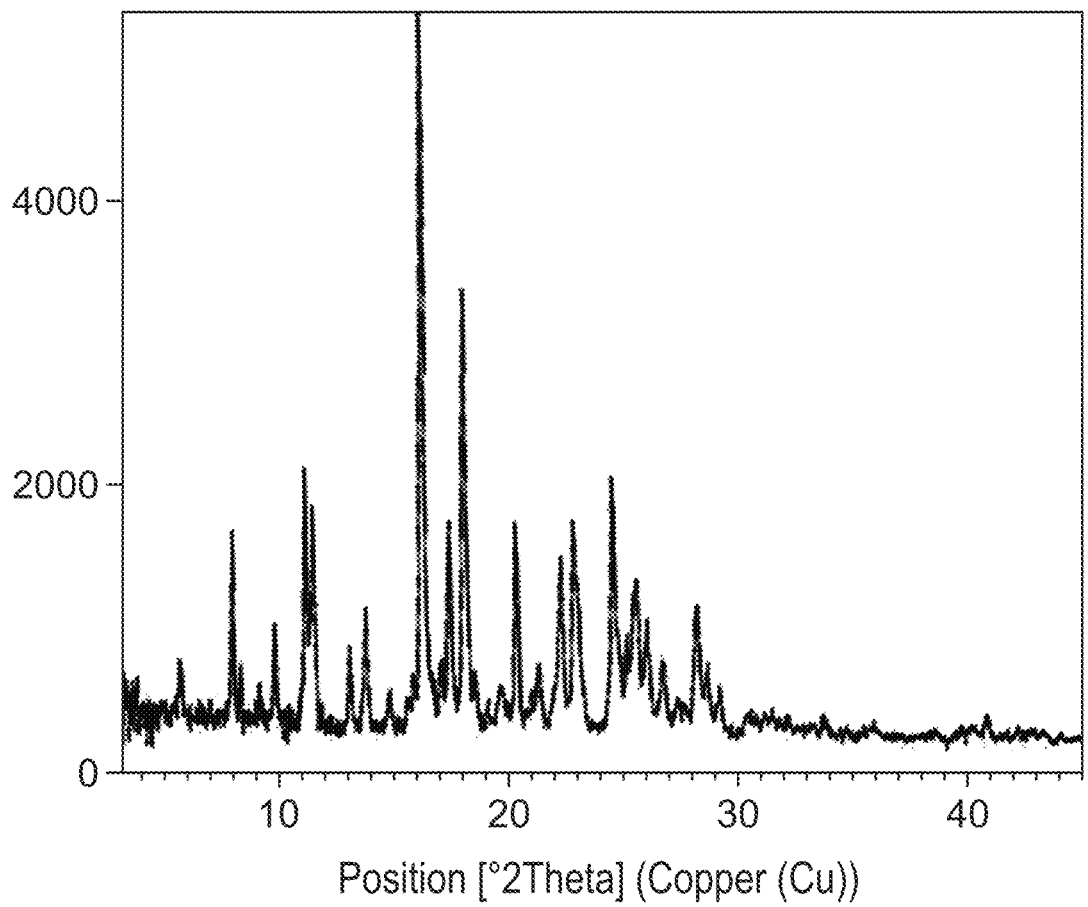

The crystalline form of Compound A ethanolate, referred to as Form 4 and characterized by the XRPD pattern in FIG. 3C, has a powder x-ray diffraction pattern comprising at least one peak selected from the group consisting of 7.9°±0.2° 2θ, 9.70±0.2° 2θ, 11.0°±0.2° 2θ, 11.3°±0.2° 2θ, 13.60°±0.2° 2θ, 16.10°±0.2° 2θ, 17.2°±0.2' 2θ, 17.9°±0.2° 2θ and 20.1°±0.2° 2θ, wherein said powder x-ray diffraction pattern is obtained using Cu Kα radiation at an x-ray wavelength of 1.5406 Å.

In one embodiment, this crystalline form of Compound A ethanolate, i.e. Form 4, has a powder x-ray diffraction pattern comprising peaks at 11.0±0.2° 2θ, 16.10°±0.2° 2θ, and 17.90±0.2° 2θ. In one embodiment, this crystalline form of Compound A ethanolate, i.e. Form 4, has a powder x-ray diffraction pattern further comprising a peak at 11.3±0.2° 2θ. In one embodiment, this crystalline form of Compound A ethanolate, i.e. Form 4, has a powder x-ray diffraction pattern further comprising a peak at 17.2°±0.2° 2θ. In one embodiment, this crystalline form of Compound A ethanolate, i.e. Form 4, has a powder x-ray diffraction pattern further comprising a peak at 7.9°±0.2° 2θ. In one embodiment, this crystalline form of Compound A ethanolate, i.e. Form 4, has a powder x-ray diffraction pattern further comprising a peak at 20.10°±0.2° 2θ. In one embodiment, this crystalline form of Compound A ethanolate, i.e. Form 4, has a powder x-ray diffraction pattern further comprising a peak at 13.60°±0.2° 2θ. In one embodiment, this crystalline form of Compound A ethanolate, i.e. Form 4, has a powder x-ray diffraction pattern further comprising a peak at 9.7°±0.2° 2θ.

In one embodiment, the crystalline form of Compound A ethanolate, i.e. Form 4, has a powder x-ray diffraction pattern comprising peaks at 11.0±0.2° 2θ, 1.3°±0.2° 2θ, 16.1°±0.2° 2θ, and 17.9°±0.2° 2θ. In one embodiment, the crystalline form of Compound A ethanolate, i.e. Form 4, has a powder x-ray diffraction pattern comprising peaks at 11.0°±0.2° 2θ, 11.3°±0.2° 2θ, 16.1°±0.2° 2θ, 17.2°±0.2° 2θ, and 17.9°±0.2° 2θ. In one embodiment, the crystalline form of Compound A ethanolate, i.e. Form 4, has a powder x-ray diffraction pattern comprising peaks at 7.9°±0.2° 2θ, 11.0°±0.2° 2θ, 11.3°±0.2° 2θ, 16.1°±0.2° 2θ, 17.2°±0.2° 2θ, and 17.9°±0.2° 2θ. In one embodiment, the crystalline form of Compound A ethanolate, i.e. Form 4, has a powder x-ray diffraction pattern comprising peaks at 7.9°±0.2° 2θ, 11.0°±0.2° 2θ, 11.3°±0.2° 2θ, 16.1°±0.2° 2θ, 17.2°±0.2° 2θ, 17.90°±0.2° 2θ and 20.1°±0.2° 2θ. In one embodiment, the crystalline form of Compound A ethanolate, i.e. Form 4, has a powder x-ray diffraction pattern comprising peaks at 7.9±0.2° 2θ, 11.00°±0.2° 2θ, 11.3°±0.2° 2θ, 13.6°±0.2° 2θ, 16.1°±0.2° 2θ, 17.2°±0.2° 2θ, 17.9°±0.2° 2θ and 20.1°±0.2° 2θ.

In one embodiment, the crystalline form of Compound A ethanolate, i.e. Form 4, has a powder x-ray diffraction pattern comprising peaks at 7.9°±0.2° 2θ, 9.7±0.2° 2θ, 11.0°±0.2° 2θ, 11.3°±0.2° 2θ, 13.6°±0.2° 2θ, 16.1°±0.2° 2θ, 17.2°±0.2° 2θ, 17.9°±0.2° 2θ and 20.1°±0.2° 2θ.

In one aspect, this application pertains to a crystalline form of Compound A characterized by the XRPD pattern in FIG. 3A, which is also referred to herein as Form 2.

The crystalline form of Compound A, referred to as Form 2 and characterized by the XRPD pattern in FIG. 3A, has a powder x-ray diffraction pattern comprising at least one peak selected from the group consisting of 3.2°±0.2° 2θ, 7.6°±0.2° 2θ, 11.5°±0.2° 2θ, 17.6°±0.2° 2θ, 18.50°±0.2° 2θ, and 21.4°±0.2° 2θ, wherein said powder x-ray diffraction pattern is obtained using Cu Kα radiation at an x-ray wavelength of 1.5406 Å. In one embodiment, this crystalline form of Compound A, i.e. Form 2, comprises peaks at 17.5°, 7.6°, and 11.50°±0.2° 2θ, wherein said powder x-ray diffraction pattern is obtained using Cu Kα radiation at an x-ray wavelength of 1.5406 Å. In one embodiment, this crystalline form of Compound A, i.e. Form 2, has a powder x-ray diffraction pattern further comprising a peak at 18.5°±0.2° 2θ. In one embodiment, this crystalline form of Compound A, i.e. Form 2, has a powder x-ray diffraction pattern further comprising a peak at 21.4°±0.2° 2θ. In one embodiment, this crystalline form of Compound A, i.e. Form 2, has a powder x-ray diffraction pattern further comprising a peak at 3.2°±0.2° 2θ. In one embodiment, this crystalline form of Compound A, i.e. Form 2, comprises peaks at 7.6°±0.2° 2θ, 11.5°±0.2° 2θ, 17.6°±0.2° 2θ, and 18.5°±0.2° 2θ. In one embodiment, this crystalline form of Compound A, i.e. Form 2, comprises peaks at 7.6°±0.2° 2θ, 11.5°±0.2° 2θ, 17.6°±0.2° 2θ, 18.5°±0.2° 2θ, and 21.4°±0.2° 2θ. In one embodiment, this crystalline form of Compound A, i.e. Form 2, comprises peaks at 3.2°±0.2° 2θ, 7.6°±0.2° 2θ, 11.5°±0.2° 2θ, 17.6°±0.2° 2θ, 18.5°±0.2° 2θ, and 21.4°±0.2° 2θ.

In one embodiment, the crystalline form of Compound A referred to as Form 2 and characterized by the XRPD pattern in FIG. 3A, serves as a convenient storage form for the preparation of the amorphous and/or ultrapure amorphous forms of Compound A and further used in the preparation of pharmaceutical compositions of the disclosure, including, for example, tablets.

Amorphous Forms of Compound a and the Manufacturing Process of a Spray-Dried Intermediate Comprising an Amorphous Form of Compound a This application further provides an amorphous form of Compound A, or a salt or solvate thereof.

In one embodiment, the amorphous form of Compound A is ultrapure.

In one embodiment, the amorphous form of Compound A is characterized by a glass transition temperature, Tg, of about 146° C. at 25° C. and 0% relative humidity.

In one embodiment, the amorphous form of Compound A is characterized by a glass transition temperature, Tg, of about 103° C. at 40° C. and 75% relative humidity.

In one embodiment, the amorphous form of Compound A is characterized by a $D_v(10)$ particle size of about 0.1-10 μm.

In one embodiment, the amorphous form of Compound A is characterized by a $D_v(10)$ particle size of about 0.5-8 μm.

In one embodiment, the amorphous form of Compound A is characterized by a $D_v(10)$ particle size of about 0.6-7 μm.

In one embodiment, the amorphous form of Compound A is characterized by a $D_v(10)$ particle size of about 0.7-6 μm.

In one embodiment, the amorphous form of Compound A is characterized by a $D_v(10)$ particle size of about 0.8-5 μm.

In one embodiment, the amorphous form of Compound A is characterized by a $D_v(10)$ particle size of about 0.5, 1, 2, 3, 4, 5, 6, 7, or 8 μm.

In one embodiment, the amorphous form of Compound A is characterized by a $D_v(10)$ particle size of about 4 μm.

In one embodiment, the amorphous form of Compound A is characterized by a $D_v(10)$ particle size of about 5 μm.

In one embodiment, the amorphous form of Compound A is characterized by a $D_v(50)$ particle size of about 5-15 μm.

In one embodiment, the amorphous form of Compound A is characterized by a $D_v(50)$ particle size of about 6-14 μm.

In one embodiment, the amorphous form of Compound A is characterized by a $D_v(50)$ particle size of about 7-13 μm.

In one embodiment, the amorphous form of Compound A is characterized by a $D_v(50)$ particle size of about 8-12 μm.

In one embodiment, the amorphous form of Compound A is characterized by a $D_v(50)$ particle size of about 9-11 μm.

In one embodiment, the amorphous form of Compound A is characterized by a $D_v(50)$ particle size of about 5, 6, 7, 8, 9, 10, 11, 12, 13, 14, or 15 μm.

In one embodiment, the amorphous form of Compound A is characterized by a $D_v(50)$ particle size of about 9 μm.

In one embodiment, the amorphous form of Compound A is characterized by a $D_v(50)$ particle size of about 10 μm.

In one embodiment, the amorphous form of Compound A is characterized by a $D_v(50)$ particle size of about 11 μm.

In one embodiment, the amorphous form of Compound A is characterized by a $D_v(90)$ particle size of about 5-25 μm.

In one embodiment, the amorphous form of Compound A is characterized by a $D_v(90)$ particle size of about 6-24 μm.

In one embodiment, the amorphous form of Compound A is characterized by a $D_v(90)$ particle size of about 7-23 μm.

In one embodiment, the amorphous form of Compound A is characterized by a $D_v(90)$ particle size of about 8-22 μm.

In one embodiment, the amorphous form of Compound A is characterized by a $D_v(90)$ particle size of about 9-21 μm.

In one embodiment, the amorphous form of Compound A is characterized by a $D_v(90)$ particle size of about 10-20 μm.

In one embodiment, the amorphous form of Compound A is characterized by a $D_v(90)$ particle size of about 8, 9, 10, 11, 12, 13, 14, 15, 16, 17, 18, 19, 20, 21, 22, or 23 μm.

In one embodiment, the amorphous form of Compound A is characterized by a $D_v(90)$ particle size of about 18 μm.

In one embodiment, the amorphous form of Compound A is characterized by a $D_v(90)$ particle size of about 19 μm.

In one embodiment, the amorphous form of Compound A is characterized by a $D_v(90)$ particle size of about 20 μm.

In some embodiments, the particle size of the amorphous form of Compound A is determined by laser diffraction.

In one embodiment, the amorphous form of Compound A has a purity of greater than about 95%, 96%, 97%, 98%, 99%, 99.5, or 99.9%.

In one embodiment, the amorphous form of Compound A is characterized in that the amorphous form is stable for at least 1 month at 2-8° C.; for 1 month at 25° C. and 60% relative humidity; and for 1 month at 40° C. and 75% relative humidity. In one embodiment, the amorphous form of Compound A is characterized in that the amorphous form is stable for at least 6 months at 2-8° C.; for 6 months at 25° C. and 60% relative humidity, and for 6 months at 40° C. and 75% relative humidity. In one embodiment, the amorphous form of Compound A is characterized in that the amorphous form is stable for at least 12 months at 2-8° C.; for 12 months at 25° C. and 60% relative humidity; and for 12 months at 40° C. and 75% relative humidity. In one embodiment, the amorphous form of Compound A is characterized in that the amorphous form is stable for at least 24 months at 2-8° C.; for 24 months at 25° C. and 60% relative humidity; and for 24 months at 40° C. and 75% relative humidity. In one embodiment, the stability of Compound A is assessed by storing it in wire-tied low-density polyethylene bags placed in heat-induction sealed, high-density polyethylene (HDPE) bottles containing a desiccant canister, and capped with a polypropylene-lined closure.

This application also pertains to a method for manufacturing the amorphous form of Compound A, or a salt or solvate thereof. In one embodiment, the amorphous form of Compound A prepared according to the methods described herein is ultrapure.

In one embodiment, the amorphous form of Compound A is manufactured by taking an amount of Compound A, including any of the crystalline forms of Compound A, ultrapure forms of Compound A, and crystalline ultrapure forms of Compound A described herein, and dissolving in an appropriate solvent until a clear solution is obtained. This solution of Compound A is introduced into a spray dryer and the damp solid output from the spray dryer is tray-dried to produce the amorphous solid form of Compound A, i.e., "the spray-dried intermediate." The spray-dried intermediate is checked for residual solvent before using in the preparation of pharmaceutical compositions comprising Compound A (e.g., tablets).

Figure 14:
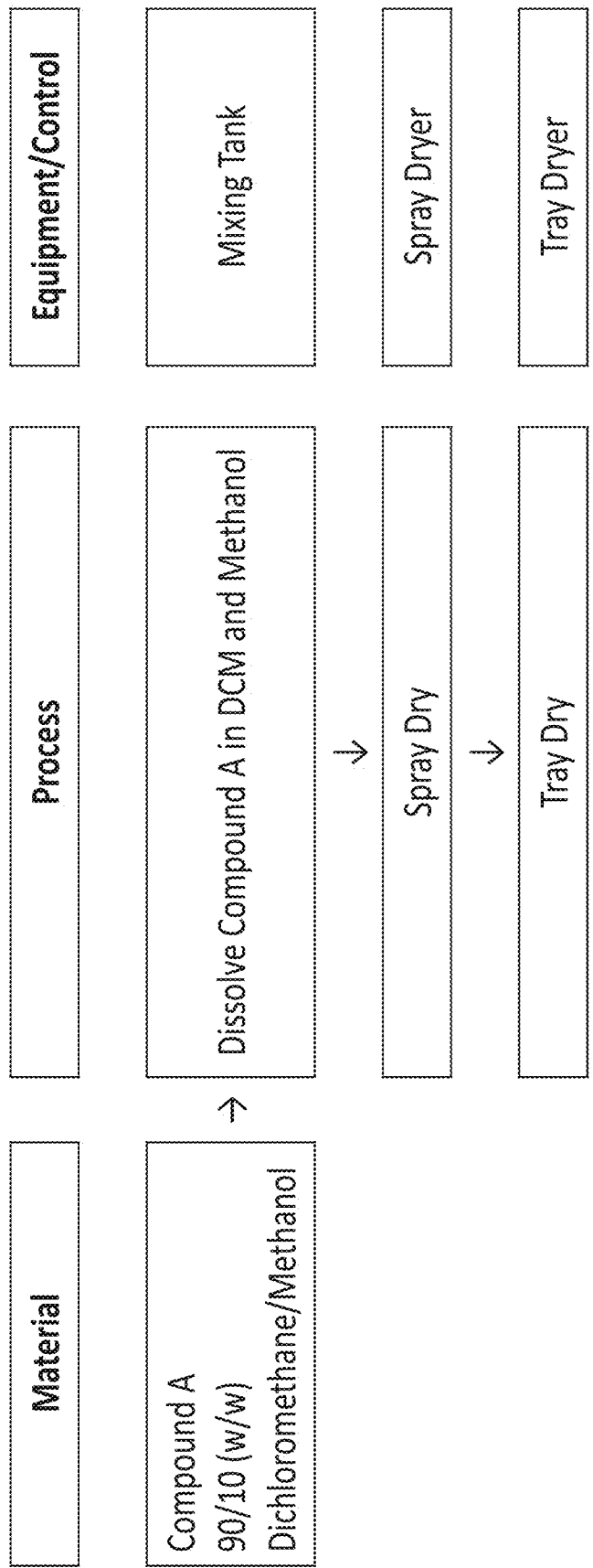
FIG. 14 is flow diagram of the manufacturing process of the amorphous Compound A spray-dried intermediate product.

In one embodiment, the manufacturing process of an amorphous form of Compound A may be accomplished according to the flow diagram in FIG. 14.

In one embodiment, the amorphous form of Compound A prepared as described above is useful in the preparation of pharmaceutical compositions, e.g., tablets, comprising Compound A.

In one embodiment, for the process of preparing the amorphous form of Compound A described herein, Compound A is dissolved in methanol, ethanol, isopropanol, 1-butanol, 2-butanol, acetone, tert-butyl methyl ether, diethyl ether, ethyl acetate, chloroform, dichloromethane, 2,2-dichlorethane, or any mixture thereof.

In one embodiment, for the process of preparing the amorphous form of Compound A described herein, Compound A is dissolved in a mixture of dichloromethane and methanol. In one embodiment, the mixture of dichloromethane and methanol is about 99/1 (w/w), about 95/5 (w/w), about 90/10 (w/w), about 85/15 (w/w), about 80/20 (w/w), about 70/30 (w/w), about 60/40 (w/w), about 50/50 (w/w), about 40/60 (w/w), about 30/70 (w/w), about 20/80 (w/w), about 10/90 (w/w), or about 1/99 (w/w). In a preferred embodiment, the mixture of dichloromethane and methanol is from about 70/30 (w/w) to about 95/5 (w/w), preferably about 90/10 (w/w), and most preferably about 93/7 (w/w).

In one embodiment, for the process of preparing the amorphous form of Compound A described herein, the concentration of Compound A in solvent to be introduced into the spray drier is from about 1 mg/mL to about 100 mg/mL.

In one embodiment, for the process of preparing the amorphous form of Compound A described herein, the concentration of Compound A in solvent to be introduced into the spray drier is from about 1 mg/mL to about 50 mg/mL. In one embodiment, for the process of preparing the amorphous form of Compound A described herein, the concentration of Compound A in solvent to be introduced into the spray drier is from about 1 mg/mL to about 25 mg/mL. In one embodiment, for the process of preparing the amorphous form of Compound A described herein, the concentration of Compound A in solvent to be introduced into the spray drier is from about 1 mg/mL to about 10 mg/mL. In one embodiment, for the process of preparing the amorphous form of Compound A described herein, the concentration of Compound A in solvent to be introduced into the spray drier is from about 1 mg/mL to about 5 mg/mL. In one embodiment, for the process of preparing the amorphous form of Compound A described herein, the concentration of Compound A in solvent to be introduced into the spray drier is from about 2 mg/mL to about 5 mg/mL. In one embodiment, for the process of preparing the amorphous form of Compound A described herein, the concentration of Compound A in solvent to be introduced into the spray drier is from about 2 mg/mL to about 4 mg/mL. In one embodiment, for the process of preparing the amorphous form of Compound A described herein, the concentration of Compound A in solvent to be introduced into the spray drier is from about 2 mg/mL to about 3 mg/mL.

In one embodiment, for the process of preparing the amorphous form of Compound A described herein, the concentration of Compound A in solvent to be introduced into the spray drier is about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL.

In one embodiment, for the process of preparing the amorphous form of Compound A described herein, the amount of Compound A in solvent that is introduced into the spray drier is about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), or about 15% (w/w). In one embodiment, for the process of preparing the amorphous form of Compound A described herein, the amount of Compound A in solvent that is introduced into the spray drier is between about 1 and about 10% (w/w), between about 3 and about 8% (w/w), between about 5 and about 7% (w/w), between about 5.5 and about 6.8% (w/w), or preferably between about 5.8 and about 6.2% (w/w).

In one embodiment, the process for manufacturing the amorphous form of Compound A comprises the following steps:
(1) dissolving crystalline and/or ultrapure Compound A in a solution of dichloromethane:methanol to afford a solution of Compound A;
(2) introducing the solution of Compound A from step (1) into a spray dryer;
(3) spraying the solution of Compound A from the spray dryer to create the amorphous form of Compound A; and
(4) drying the amorphous form of Compound A to remove residual solvent.

In one embodiment, step (1) of the process for manufacturing the amorphous form of Compound A comprises dissolving Compound A in a solution of dichloromethane and methanol of about 95:5 (w/w) to about 80:20 (w/w).

In one embodiment, step (1) of the process for manufacturing the amorphous form of Compound A comprises dissolving Compound A in an 80:20 (w/w) mixture of dichloromethane and methanol. In one embodiment, step (1) of the process for manufacturing the amorphous form of Compound A comprises dissolving Compound A in a 90:10 (w/w) mixture of dichloromethane and methanol. In one embodiment, step (1) of the process for manufacturing the amorphous form of Compound A comprises dissolving Compound A in a 93:7 (w/w) mixture of dichloromethane and methanol. In one embodiment, step (1) of the process for manufacturing the amorphous form of Compound A comprises dissolving Compound A in a 95:5 (w/w) mixture of dichloromethane and methanol.

In one embodiment, the temperature of the solution in step (1) is about 20° C. to about 40° C. prior to introducing the solution into the spray dryer. In one embodiment, the temperature of the solution in step (1) is about 25° C. to about 35° C. prior to introducing the solution into the spray dryer. In one embodiment, the temperature of the solution in step (1) is about 27.5° C. to about 32.5° C. prior to introducing the solution into the spray dryer. In one embodiment, the temperature of the solution in step (1) is about 30° C. prior to introducing the solution into the spray dryer.

The spray dryer used in the process for manufacturing the amorphous form of Compound A may be set at an appropriate temperature, gas flow rate, feed rated pressure as determined by one skilled in the art in view of this disclosure.

In one embodiment, the spray dryer used in the process for manufacturing the amorphous form of Compound A has an SK80-16 nozzle and is employed using the following conditions:
Dryer Inlet Temperature: 65-125° C.;
Dryer Outlet Temperature: 32.5-42.5° C.;
System Gas Flow: 1550-2150 g/min;
Liquid Feed Rate: 145-205 g/min; and
Liquid Feed Pressure: 300-600 psig.

In one embodiment, the spray dryer used in the process for manufacturing the amorphous form of Compound A has an SK80-16 nozzle and is employed using the following conditions:
Dryer Inlet Temperature: about 95° C.;
Dryer Outlet Temperature: about 37.5° C.;
System Gas Flow: about 1850 g/min;
Liquid Feed Rate: about 180 g/min; and
Liquid Feed Pressure: about 450 psig.

In one embodiment, the spray dryer used in the process for manufacturing the amorphous form of Compound A has an Schlick Model 121 nozzle and is employed using the following conditions:
Dryer Inlet Temperature: 46-96° C.;
Dryer Outlet Temperature: 30-40° C.;
System Gas Flow: 60-100 kg/h;
Condenser Temperature: −10-0° C.
Liquid Feed Rate: 3.5-8.5 kg/h; and
Liquid Feed Pressure: about 50 bar.

In one embodiment, the spray dryer used in the process for manufacturing the amorphous form of Compound A has an Schlick Model 121 nozzle and is employed using the following conditions:
Dryer Inlet Temperature: about 71° C.;
Dryer Outlet Temperature: about 35° C.;
System Gas Flow: about 80 kg/h;
Condenser Temperature: about −5° C.
Liquid Feed Rate: about 6.0 kg/h; and
Liquid Feed Pressure: about 50 bar.

In one non-limiting embodiment, the amorphous form of Compound A is dried in step (4) by tray drying. In one embodiment, the amorphous form of Compound A is dried in step (4) by filter drying. In one embodiment, the amorphous form of Compound A is dried in step (4) by tumble drying. In one embodiment, the amorphous form of Compound A is dried in step (4) by agitated conical drying. In one embodiment, the amorphous form of Compound A is dried in step (4) by fluid bed drying.

In one non-limiting embodiment, the amorphous form of Compound A is tray-dried in step (4) to remove any residual solvent from the spray drying process.

In one embodiment, the depth of the tray is about 2.5 cm.

In one embodiment, the tray containing the amorphous Compound A is dried in step (4) for a total of 1, 2, 3, 4, 5, 6, 7, 8, 9, 10, 11, 12, 13, 14, 15, 16, 17, 18, 19, 20, 21, 22, 23, 24, 30, 36, or 48 hours either under reduced or at ambient pressure. In one embodiment, the tray containing the amorphous Compound A is dried for about 1 to about 24 hours. In one embodiment, the tray containing the amorphous Compound A is dried for about 1 to about 10 hours. In one embodiment, the tray containing the amorphous Compound A is dried for about 5 to about 10 hours. In one embodiment, the tray containing the amorphous Compound A is dried for about 5 to about 7 hours.

In one embodiment, the temperature during the tray drying procedure in step (4) is ramped from about 20° C. up to about 30° C., up to about 40° C., up to about 50° C., up to about 60° C., up to about 70° C., or higher.

In one embodiment, the relative humidity during the tray drying procedure in step (4) is ramped up from about 15% relative humidity (RH) to about 20% RH, to about 25% RH, to about 30% RH, to about 35% RH, to about 40% RH, to about 45% RH, to about 50% RH, or higher.

In one embodiment, the tray-drying procedure in step (4) involves no ramping of either the temperature or the relative humidity, i.e., the temperature and relative humidity are held constant.

In one embodiment, the tray-drying procedure in step (4) involves heating the product of step (3) in a bed depth of about 2.5 cm at about 40° C. to about 60° C. for about 6 hours to about 18 hours at from about 5% RH to about 35% RH, under reduced or ambient pressure, where the temperature and relative humidity are both held constant.

In one non-limiting embodiment, the amorphous form of Compound A is filter-dried to remove any residual solvent from the spray drying process.

In one embodiment, the amorphous form of Compound A is filter-dried for a total of 1, 2, 3, 4, 5, 6, 7, 8, 9, 10, 11, 12, 13, 14, 15, 16, 17, 18, 19, 20, 21, 22, 23, 24, 30, 36, or 48 hours under vacuum. In one embodiment, the amorphous form of Compound A is filter-dried for a total of from about 1 to about 50 hours. In one embodiment, the amorphous form of Compound A is filter-dried for a total of from about 12 to about 50 hours. In one embodiment, the amorphous form of Compound A is filter-dried for a total of from about 12 to about 36 hours. In one embodiment, the amorphous form of Compound A is filter-dried for a total of from about 20 to about 30 hours.

In one embodiment, the pressure during the filter drying procedure is below ambient pressure. In one embodiment, the pressure during the filter drying procedure is about 0.1 bar, about 0.2 bar, about 0.3 bar, about 0.4 bar, about 0.5 bar, about 0.6 bar, about 0.7 bar, about 0.8 bar, or about 0.9 bar. In one embodiment, the pressure during the filter drying procedure is about 0.9 bar below ambient pressure.

In one embodiment, the temperature during the filter drying procedure is ramped from about 20° C. up to about 30° C., up to about 40° C., up to about 50° C., up to about 60° C., up to about 70° C., or higher.

Manufacturing Process of Tablet Comprising the Spray-Dried Intermediate (i.e., the Ultrapure and Stable Amorphous Form of Compound A)

In one aspect, this application provides tablets comprising Compound A, and processes for manufacturing the same.

In certain embodiment, the tablets of the disclosure comprise the amorphous form of Compound A, i.e., the spray-dried form disclosed herein. In one embodiment, the tablets of the disclosure comprise the amorphous form of Compound A that is also ultrapure. In one embodiment, the tablets contain about 2.5% to about 50% (w/w) of Compound A.

Tablets of the disclosure may further comprise one or more pharmaceutically acceptable excipients, including, for example, carriers, fillers, surfactants, diluents, sweeteners, disintegrants, binders, lubricants, glidants, colorants, flavors, stabilizing agents, coatings, or any mixtures thereof.

Fillers include, but are not limited to, mannitol, sorbitol, xylitol, microcrystalline cellulose, lactose, silicified microcrystalline cellulose, hydroxypropyl methylcellulose, hydroxypropyl cellulose, pullulan and fast dissolving carbohydrates such as Pharmaburst™, mixtures thereof, and the like. For examples of fast-dissolving carbohydrates, see U.S. Pat. No. 8,617,588, which is incorporated herein by reference.

Glidants include, but are not limited to, silicon dioxide, colloidal silicon dioxide, calcium silicate, magnesium silicate, magnesium trisilicate, talc, starch, mixtures thereof, and the like.

Lubricants include, but are not limited to, calcium stearate, glyceryl monostearate, glyceryl behenate, glyceryl palmitostearate, hexagonal boron nitride, hydrogenated vegetable oil, light mineral oil, magnesium stearate, mineral oil, polyethylene glycol, poloxamer, sodium benzoate, sodium lauryl sulfate, sodium stearyl fumarate, stearic acid, talc, zinc stearate, mixtures thereof, and the like.

Disintegrants include, but are not limited to, sodium starch glycolate, sodium carboxymethyl cellulose, calcium carboxymethyl cellulose, croscarmellose sodium, crospovidone, chitosan, agar, alginic acid, calcium alginate, methyl cellulose, microcrystalline cellulose, powdered cellulose, lower alkyl substituted hydroxypropyl cellulose, hydroxylpropyl starch, low-substituted hydroxypropylcellulose, polacrilin potassium, starch, pregelatinized starch, sodium alginate, magnesium aluminum silicate, polacrilin potassium, povidone, sodium starch glycolate, mixtures thereof, and the like.

In one embodiment, the tablets contain about 5% to about 95% w/w of one or more fillers, such as, e.g., about 75% to about 95% w/w, about 65% to about 85% w/w, about 55% to about 75% w/w, about 45% to about 65% w/w, about 35% to about 55% w/w, about 25% to about 45% w/w, about 15% to about 35% w/w, or about 5% to about 25% w/w of one or more fillers.

In one embodiment, the tablets contain about 80% w/w of one or more fillers.

In one embodiment, the tablets contain about 1% to about 20% w/w disintegrant, such as, e.g., about 1% to about 15% w/w, about 1% to about 10% w/w, about 2% to about 9% w/w, about 3% to about 8% w/w, about 4% to about 7% w/w, or about 5% to about 7% w/w disintegrant.

In one embodiment, the tablets contain about 0.20% to about 2.5% w/w lubricant, such as, e.g., about 0.2% to about 2.0% w/w, about 0.2% to about 1.8% w/w, about 0.2% to about 1.5% w/w, or about 0.25% to about 1.5% w/w lubricant.

In some embodiments, the tablets contain 0% to about 1% w/w glidant, such as, e.g., about 0.25% to about 0.75% w/w, or about 0.25% to about 0.50% w/w glidant.

In one aspect, this application pertains to a process for manufacturing a tablet comprising Compound A.

In one embodiment, the process for manufacturing a tablet comprising Compound A comprises dry granulation. Dry granulation is a well-known pharmaceutical manufacturing process. In general, API is combined with appropriate excipients, including lubricant, and then compacted to form a mass. This mass typically is then comminuted or milled, then sieved to obtain the desired size of particle. Extragranular excipients are then added and mixed in, and the granular product is then compressed into tablets, filled into capsules or otherwise formed into a unitary dosage form in conventional fashion. In some embodiments, high dosage tablets comprising Compound A are produced by this process. In other embodiments, the granular product comprising high dosage Compound A is filled into capsules or otherwise formed into a unitary dosage form.

In one embodiment, the process for manufacturing a tablet comprising Compound A comprises wet granulation. Wet granulation involves the formation of granules by the addition of a granulation liquid onto a powder bed of the API, which may be under the influence of an impeller, one or more screws, and/or air flow. After formation of the granules, the granulation liquid is removed by drying.

In one embodiment, the process for manufacturing a tablet comprising Compound A comprises direct compression. In essence, direct compression bypasses the formation of a granule and involves the blending of an API with one or more pharmaceutically acceptable carriers, diluents, and/or other excipients, followed by compression.

Compaction into a mass is accomplished using conventional equipment. Typically, the blended API and excipients are passed through a roller compactor or a Chilsonator® dry granulation roller/compactor apparatus for compaction. However, other means for compacting, e.g., compaction into slugs (or "slugging"), the API/excipient blend optionally are used. The compacted mass in turn is comminuted or milled, and then optionally sieved to produce the desired size granules.

A dry granulated composition comprising Compound A is defined as the product of a dry granulation process. Dry granulated compositions include the direct product of dry granulation, i.e., dry granules per se, as well as products made from such granules including tablets, capsules, suppositories and other pharmaceutical dosage forms.

In one aspect, this application pertains to a tablet comprising one or more pharmaceutically acceptable excipients and Compound A, including ultrapure forms of Compound A as described herein.

In one embodiment, the tablet comprises from about 5 to about 1000 mg of Compound A. In one embodiment, the tablet comprises from about 5 to about 500 mg of Compound A. In one embodiment, the tablet comprises from about 5 to about 250 mg of Compound A. In one embodiment, the tablet comprises from about 25 to about 250 mg of Compound A. In one embodiment, the tablet comprises from about 25 to about 200 mg of Compound A. In one embodiment, the tablet comprises from about 25 to about 150 mg of Compound A. In one embodiment, the tablet comprises from about 5 to about 50 mg of Compound A. In one embodiment, the tablet comprises from about 30 to about 40 mg of Compound A. In one embodiment, the tablet comprises from about 65 to about 70 mg of Compound A. In one embodiment, the tablet comprises from about 100 to about 110 mg of Compound A. In one embodiment, the tablet comprises from about 135 to about 145 mg of Compound A.

In one embodiment, the tablet comprises about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg of Compound A.

In one embodiment, the tablet comprises about 5 mg of Compound A.

In one embodiment, the tablet comprises about 35 mg of Compound A.

In one embodiment, the tablet comprises about 70 mg of Compound A.

In one embodiment, the tablet comprises about 105 mg of Compound A.

In one embodiment, the tablet comprises about 140 mg of Compound A.

In one embodiment, the tablet comprises about 175 mg of Compound A.

In one embodiment, the tablet comprises about 200 mg of Compound A.

In one embodiment, the tablet comprises about 210 mg of Compound A.

In one embodiment, the tablet comprises about 245 mg of Compound A.

In one embodiment, the tablet comprises about 280 mg of Compound A.

In one embodiment, the tablet comprises about 315 mg of Compound A.

In one embodiment, the tablet comprises about 350 mg of Compound A.

In one embodiment, a tablet of the disclosure comprises about 0.1, 0.2, 0.3, 0.4, 0.5, 0.6, 0.7, 0.8, 0.9, 1.0, 1.1, 1.2, 1.3, 1.4, 1.5, 1.6, 1.7. 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0% w/w of Compound A.

In one embodiment, a tablet of the disclosure comprises about 0.1, 0.2, 0.3, 0.4, 0.5, 0.6, 0.7, 0.8, 0.9, 1.0, 1.1, 1.2, 1.3, 1.4, 1.5, 1.6, 1.7. 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0% w/w of an ultrapure form of Compound A.

In one embodiment, a tablet of the disclosure comprises about 1% to about 5% w/w of Compound A, about 2.5% to about 7.5% w/w of Compound A, about 10% to about 15% w/w of Compound A, about 12.5% to about 17.5% w/w of Compound A, about 15% to about 20% w/w of Compound A, about 17.5% to about 22.5% w/w of Compound A, about 20% to about 25% w/w of Compound A, about 22.5% to about 27.5% w/w of Compound A, about 25% to about 30% w/w of Compound A, about 27.5% to about 32.5% w/w of Compound A, or about 30% to about 35% w/w of Compound A. In one embodiment, a tablet of the disclosure comprises about 1% to about 5% w/w of an ultrapure form of Compound A, about 2.5% to about 7.5% w/w of an ultrapure form of Compound A, about 10% to about 15% w/w of an ultrapure form of Compound A, about 12.5% to about 17.5% w/w of an ultrapure form of Compound A, about 15% to about 20% w/w of an ultrapure form of Compound A, about 17.5% to about 22.5% w/w of an ultrapure form of Compound A, about 20% to about 25% w/w of an ultrapure form of Compound A, about 22.5% to about 27.5% w/w of an ultrapure form of Compound A, about 25% to about 30% w/w of an ultrapure form of Compound A, about 27.5% to about 32.5% w/w of an ultrapure form of Compound A, or about 30% to about 35% w/w of an ultrapure form of Compound A.

In one embodiment, a tablet of the disclosure comprises:
about 2.5% to about 7.5% w/w of Compound A;
about 42% to about 47% w/w microcrystalline cellulose;
about 42% to about 47% w/w lactose monohydrate;
about 1% to about 5% w/w croscarmellose sodium;
about 0.1% to about 1.0% w/w silicon dioxide; and
about 0.1% to about 1.0% w/w magnesium stearate.

In one embodiment, a tablet of the disclosure comprises:
about 5% w/w of Compound A;
about 45.5% w/w microcrystalline cellulose;
about 45.5% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 10% w/w of Compound A;
about 57.3% w/w microcrystalline cellulose;
about 28.7% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 20% w/w of Compound A;
about 50.7% w/w microcrystalline cellulose;
about 25.3% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 40% w/w of Compound A;
about 37.3% w/w microcrystalline cellulose;
about 18.7% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 2.5% to about 7.5% w/w of an ultrapure form of Compound A;
about 42% to about 47% w/w microcrystalline cellulose;
about 42% to about 47% w/w lactose monohydrate;
about 1% to about 5% w/w croscarmellose sodium;
about 0.1% to about 1.0% w/w silicon dioxide; and
about 0.1% to about 1.0% w/w magnesium stearate.

In one embodiment, a tablet of the disclosure comprises:
about 5% w/w of an ultrapure form of Compound A;
about 45.5% w/w microcrystalline cellulose;
about 45.5% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 10% w/w of an ultrapure form of Compound A;
about 57.3% w/w microcrystalline cellulose;
about 28.7% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 20% w/w of an ultrapure form of Compound A;
about 50.7% w/w microcrystalline cellulose;
about 25.3% w/w lactose monohydrate;
about 3% w/w croscarmellose sodium;
about 0.5% w/w silicon dioxide; and
about 0.5% w/w magnesium stearate.

In one embodiment, a tablet of the disclosure comprises:
about 40% w/w of an ultrapure form of Compound A;
about 37.3% w/w microcrystalline cellulose;
about 18.7% w/w lactose monohydrate;
about 3% w/w croscarmellose sodium;
about 0.5% w/w silicon dioxide; and
about 0.5% w/w magnesium stearate.

In some embodiments, a tablet of the disclosure comprises an intra-granular portion and an extra-granular portion. In some embodiments, the intra-granular portion comprises:
about 10 to about 40% w/w of Compound A;
about 35 to about 60% w/w microcrystalline cellulose;
about 15 to about 30% w/w lactose monohydrate;
about 1 to about 10% w/w croscarmellose sodium;
0 to about 1% w/w silicon dioxide; and
0 to about 0.5% w/w magnesium stearate.

In some embodiments, the intra-granular portion comprises:
about 10 to about 40% w/w of an ultrapure form of Compound A;
about 35 to about 60% w/w microcrystalline cellulose;
about 15 to about 30% w/w lactose monohydrate;
about 1 to about 10% w/w croscarmellose sodium;
0 to about 1% w/w silicon dioxide; and
0 to about 0.5% w/w magnesium stearate.

In some embodiments, the extra-granular portion comprises:
about 1 to about 5% w/w croscarmellose sodium;
0 to about 1% w/w magnesium stearate; and
0 to about 2% w/w silicon dioxide.

In one embodiment, the tablet of the disclosure comprises an intra-granular portion and an extra-granular portion, wherein the intra-granular portion comprises:
about 10 to about 40% w/w of Compound A;
about 35 to about 60% w/w microcrystalline cellulose;
about 15 to about 30% w/w lactose monohydrate;
about 1 to about 10% w/w croscarmellose sodium;
0 to about 1% w/w silicon dioxide; and
0 to about 0.5% w/w magnesium stearate;
and wherein the extra-granular portion comprises:
about 1 to about 5% w/w croscarmellose sodium;
0 to about 1% w/w magnesium stearate; and
0 to about 2% w/w silicon dioxide.

In one embodiment, the tablet of the disclosure comprises an intra-granular portion and an extra-granular portion, wherein the intra-granular portion comprises:
about 10 to about 40% w/w of an ultrapure form of Compound A;
about 35 to about 60% w/w microcrystalline cellulose;
about 15 to about 30% w/w lactose monohydrate;
about 1 to about 10% w/w croscarmellose sodium;
0 to about 1% w/w silicon dioxide; and
0 to about 0.5% w/w magnesium stearate:
and wherein the extra-granular portion comprises.
about 1 to about 5% w/w croscarmellose sodium,
0 to about 1% w/w magnesium stearate; and
0 to about 2% w/w silicon dioxide.

In one embodiment, the tablet of the disclosure comprises an intra-granular portion and an extra-granular portion, wherein the intra-granular portion comprises:
About 20% w/w of Compound A;
About 48.7% w/w microcrystalline cellulose;
About 24.3% w/w lactose monohydrate;
About 3% w/w croscarmellose sodium;
About 0.5% w/w silicon dioxide; and
About 0.25% w/w magnesium stearate;
and wherein the extra-granular portion comprises:
About 2% w/w croscarmellose sodium;
About 0.5% w/w magnesium stearate; and
About 0.25% w/w silicon dioxide.

In one embodiment, the tablet of the disclosure comprises an intra-granular portion and an extra-granular portion, wherein the intra-granular portion comprises:
About 20% w/w of an ultrapure form of Compound A;
About 48.7% w/w microcrystalline cellulose;
About 24.3% w/w lactose monohydrate;
About 3% w/w croscarmellose sodium;
About 0.5% w/w silicon dioxide; and
About 0.25% w/w magnesium stearate;
and wherein the extra-granular portion comprises:
About 2% w/w croscarmellose sodium;
About 0.5% w/w magnesium stearate; and
About 0.25% w/w silicon dioxide.

In some embodiments, the silicon dioxide in the extra-granular portion comprises fumed silica. Fumed silica (also known as pyrogenic silica) can be produced from compounds such as silicon chloride ($SiCl_4$) by means of flame hydrolysis. Suppliers of fumed silica include Evonik (Aerosil®), Cabot Corporation (Cab-O-Sil®), Wacker Chemie (HDK®), Dow Corning, Heraeus (Zandosil®), Tokuyama Corporation (Reolosil®), OCI (Konasil®), Orisil (Orisil®) and Xunyuchem (XYSIL®). In some embodiments, the silicon dioxide in the extra-granular portion comprises fumed silica after treated with dimethyldichlorosilane. In some embodiments, the fumed silica comprises trimethylsilyl groups on the surface of the silica. In some embodiments, the silicon dioxide Zin the extra-granular portion comprises fumed silica chemically modified with trimethylsilyl groups on the surface of the silica.

In one embodiment, the tablets of the disclosure are prepared according to the procedures in the Examples.

In one embodiment, a dry granulation approach is used to produce Compound A tablets as follows: the spray-dried intermediate, i.e., the amorphous form of Compound A, is blended with at least one pharmaceutically acceptable excipient to create a powder. In one embodiment, Compound A is blended with one or more fillers, one or more disintegrants, and one or more glidants. In one embodiment, Compound A is blended with two fillers, one disintegrant, and one glidant. In one embodiment, at least one filler is microcrystalline cellulose. In one embodiment, at least one filler is lactose monohydrade. In one embodiment, the disintegrant is croscarmellose sodium. In one embodiment, the glidant is silicon dioxide. In one embodiment, Compound A is blended with microcrystalline cellulose, lactose monohydrate, croscarmellose sodium, and silicon dioxide in a suitable blender.

The resulting powder is delumped and a pharmaceutically acceptable excipient is added and blended. In one embodiment the pharmaceutically acceptable excipient is a lubricant. In one embodiment, the lubricant is magnesium stearate.

The blend is granulated using a suitable roller compactor and passed through a screen for appropriate sizing of granules.

In one embodiment, granules prepared according to this process are about 400 μm to about 600 μm in diameter.
In one embodiment, granules prepared according to this process are about 450 μm to about 550 μm in diameter.
In one embodiment, granules prepared according to this process are about 575 μm to about 625 μm in diameter.
In one embodiment, granules prepared according to this process are about 590 μm to about 610 μm in diameter.
In one embodiment, granules prepared according to this process are about 595 μm to about 605 μm in diameter.
In one embodiment, granules prepared according to this process are about 598 μm to about 602 μm in diameter.
In one embodiment, granules prepared according to this process are about 450 μm in diameter, about 460 μm in diameter, about 470 μm in diameter, about 480 μm in diameter, about 490 μm in diameter, about 500 μm in diameter, about 510 μm in diameter, about 520 μm in diameter, about 530 μm in diameter, about 540 μm in diameter, or about 550 μm in diameter.
In one embodiment, granules prepared according to this process are about 500 μm in diameter.

At least one pharmaceutically acceptable excipient is added and the bulk powder is blended in a suitable blender. In one embodiment, the pharmaceutically acceptable excipient is a lubricant. In one embodiment the lubricant is extragranular magnesium stearate.

The blend is compressed into tablets and the resulting tablets packaged in bulk containers. In some embodiments, the blend is compressed into tablets using a rotary press.

Figure 15:
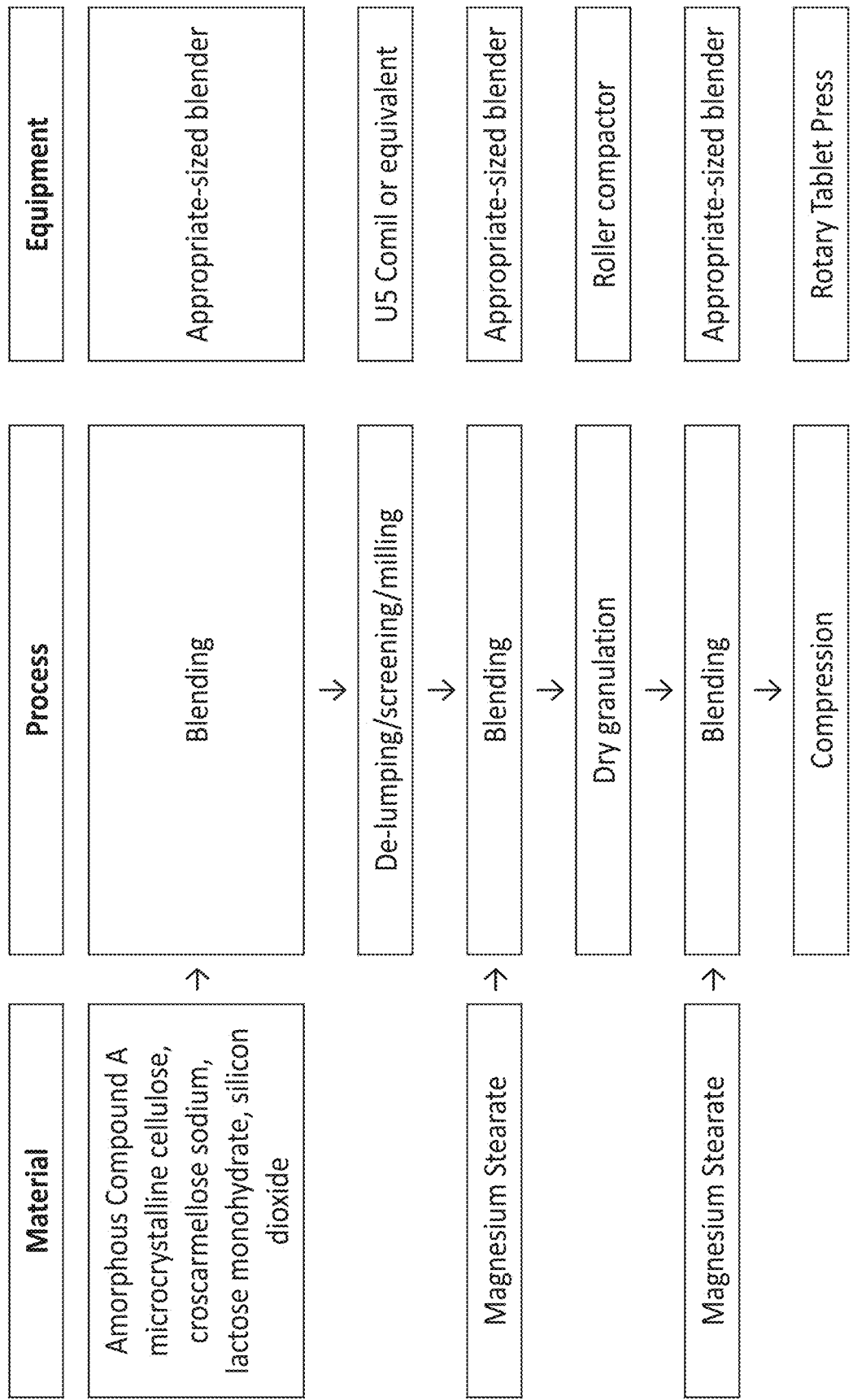
FIG. 15 is a flow diagram of the manufacturing process of Compound A tablets.

In one embodiment, the tablets of the disclosure are prepared according to the manufacturing process illustrated in the flow diagram in FIG. 15.

Methods of Ubiquitinating/Degrading a Target Protein in a Cell

The present disclosure further provides a method of ubiquitinating/degrading a target protein in a cell. The method comprises administering to a subject or patient in need thereof any of the forms of Compound A, or pharmaceutical compositions comprising any of these forms (e.g., tablets, capsules, parenteral solutions). Compound A comprises an E3 ubiquitin ligase (cereblon) binding moiety and an androgen receptor (AR) targeting moiety linked through a linker moiety, such that ubiquitination of AR will occur when the target protein is placed in proximity to the ubiquitin ligase, thereby triggering proteasomal degradation to control or reduce protein levels of AR, and inhibiting the effects of AR.

Methods of Treatment

In one embodiment, the present disclosure is directed to a method of treating a subject in need of treatment for prostate cancer modulated through AR where the ubiquitination and degradation of the AR protein results in a therapeutic effect in that subject, the method comprising administering to the subject a therapeutically effective amount of Compound A or any of the forms of Compound A disclosed herein, or compositions (e.g., tablets, capsules, parenteral solutions) of any of these forms. The disease state or condition may be causally related to the expression or overexpression of the AR protein.

In one aspect, the present application pertains to a method of treating cancer.

The methods of treating cancer described herein preferably result in a slowing or cessation of tumor growth, or more preferably a reduction in tumor size. The cancer may be metastatic cancer, and this method of treatment may include inhibition of metastatic cancer cell invasion.

In one embodiment, the cancer is prostate cancer.

In one embodiment, the cancer is metastatic prostate cancer.

In one embodiment, the cancer is castrate-resistant prostate cancer.

In one embodiment, the cancer is metastatic, castrate-resistant prostate cancer.

In one aspect, treating cancer results in a reduction in size of a tumor. A reduction in size of a tumor may also be referred to as "tumor regression." Preferably, after one or more treatments, tumor size is reduced by about 5% or greater, e.g., about 5 to about 40%, relative to its size prior to treatment; more preferably, tumor size is reduced by about 10% or greater, e.g., about 10% to about 50%; more preferably, reduced by about 20% or greater, e.g., about 20% to about 60%; more preferably, reduced by about 30% or greater, e.g., about 30% to about 70%; more preferably, reduced by about 40% or greater, e.g, about 40% to about 80%; even more preferably, reduced by about 50% or greater, e.g., about 50% to about 90%; and most preferably, reduced by greater than about 75% or greater, e.g., about 75% to about 95%. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by about 5% or greater, e.g., about 5% to about 40%, relative to its volume prior to treatment; more preferably, tumor volume is reduced by about 10% or greater, e.g., about 10% to about 50%; more preferably, reduced by about 20% or greater, e.g., about 20% to about 60%; more preferably, reduced by about 30% or greater, e.g., about 30% to about 70%; more preferably, reduced by about 40% or greater, e.g., about 40% to about 80%; even more preferably, reduced by about 50% or greater, e.g., about 50% to about 90%; and most preferably, reduced by greater than about 75% or greater, e.g., about 75% to about 95%. Tumor volume may be measured by any reproducible means of measurement.

In another aspect, treating cancer results in a decrease in number of tumors. Preferably, after treatment, tumor number is reduced by about 5% or greater, e.g., about 5% to 40%, relative to number prior to treatment; more preferably, tumor number is reduced by about 10% or greater, e.g., about 10% to about 50%; more preferably, reduced by about 20% or greater, e.g., about 20% to about 60%; more preferably, reduced by about 30% or greater, e.g., about 30% to about 70%; more preferably, reduced by about 40% or greater, e.g., about 40% to about 80%; even more preferably, reduced by about 50% or greater, e.g., about 50% to about 90%; and most preferably, reduced by greater than about 75%, e.g., about 75% to about 95%. Number of tumors may be measured by any reproducible means of measurement. In a preferred aspect, number of tumors may be measured by counting tumors visible to the naked eye or at a specified magnification. In a preferred aspect, the specified magnification is about 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by about 5% or greater, e.g., about 5% to about 40%, relative to number prior to treatment; more preferably, the number of metastatic lesions is reduced by about 10% or greater, e.g., about 10% to about 50%; more preferably, reduced by about 20% or greater, e.g., about 20 to about 60%; more preferably, reduced by about 30% or greater, e.g., about 30% to about 70%; more preferably, reduced by about 40% or greater, e.g., about 40% to about 80%; even more preferably, reduced by about 50% or greater, e.g., 50% to about 90%; and most preferably, reduced by greater than about 75%, e.g., about 75% to about 95%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is about 2×, 3×, 4×, 5×, 10×, or 50×.

In another aspect, treating cancer results in an increase in average survival time of a population of treated subjects in comparison to a population receiving carrier alone. Preferably, the average survival time is increased by more than about 30 days; more preferably, by more than about 60 days; more preferably, by more than about 90 days; and most preferably, by more than about 120 days. An increase in average survival time of a population may be measured by any reproducible means. In a preferred aspect, an increase in average survival time of a population may be measured, for example, by calculating for a population the average length of survival following initiation or completion of treatment with an active agent or compound of the disclosure. In another preferred aspect, an increase in average survival time of a population may be measured, for example, by calculating for a population the average length of survival following a first round or completion of treatment with an active agent or compound of the disclosure.

In another aspect, treating cancer results in an increase in average survival time of a population of treated subjects in comparison to a population of untreated subjects. Preferably, the average survival time is increased by more than about 30 days; more preferably, by more than about 60 days; more preferably, by more than about 90 days; and most preferably, by more than about 120 days. An increase in average survival time of a population may be measured by any reproducible means. In a preferred aspect, an increase in average survival time of a population may be measured by calculating for a population the average length of survival following initiation of treatment with an active agent or compound of the disclosure. In another preferred aspect, an increase in average survival time of a population may be measured by calculating for a population the average length of survival following completion of a first round of treatment with a compound of the disclosure.

In another aspect, treating cancer results in a decrease in tumor growth rate. Preferably, after treatment, tumor growth rate is reduced by at least about 5%, e.g., about 5% to about 40%, relative to growth rate prior to treatment; more preferably, tumor growth rate is reduced by at least about 10%, e.g., about 10% to about 50%; more preferably, reduced by at least about 20%, e.g., about 20% to about 60%; more preferably, reduced by at least about 30%, e.g., about 30% to about 70%; more preferably, reduced by at least about 40%, e.g., about 40% to about 80%; more preferably, reduced by at least about 50%, e.g., about 50% to about 90%; even more preferably, reduced by at least about 60%, e.g., about 60% to about 95%; and most preferably, reduced by at least about 75%, e.g., about 75% to about 99%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than about 5%; more preferably, tumor regrowth is less than about 10%; more preferably, less than about 20%; more preferably, less than about 30%; more preferably, less than about 40%; more preferably, less than about 50%; even more preferably, less than about 60%; and most preferably, less than about 75%. Tumor regrowth may be measured by any reproducible means of measurement. In a preferred aspect, tumor regrowth is measured by measuring an increase in the diameter of a tumor after a prior tumor shrinkage that followed treatment. In another preferred aspect, a decrease in tumor regrowth is indicated by failure of tumors to reoccur after treatment has stopped.

The dosages of the compound of the disclosure for any of the methods and uses described herein vary depending on the chemical agent, the age, weight, and clinical condition of the recipient subject, and the experience and judgment of the clinician or practitioner administering the therapy, among other factors affecting the selected dosage.

The therapeutically effective amount of the compound of the disclosure may be administered one or more times over a day for up to about 30 or more days, followed by 1 or more days of non-administration of the compound. This type of treatment schedule, i.e., administration of a the compound of the disclosure on consecutive days followed by non-administration of the compound on consecutive days may be referred to as a treatment cycle. A treatment cycle may be repeated as many times as necessary to achieve the intended affect.

In some embodiments, the method comprises administering to the subject a therapeutically effective amount of any of the forms of Compound A disclosed herein, or compositions of any of these forms in combination with at least one other bioactive agent. In some embodiments, the at least one other bioactive agent is an anti-cancer agent. In some embodiments, the anti-cancer agent is selected from a CDK inhibitor and a PARP inhibitor. In some embodiments, the anti-cancer agent is a CDK inhibitor. In some embodiments, the anti-cancer agent is a CDK 4/6 inhibitor. In some embodiments, the anti-cancer agent is a PARP inhibitor. In some embodiments, the anti-cancer agent is selected from SHR6390, trilaciclib, lerociclib, AT7519M, dinaciclib, ribociclib, abemaciclib, palbociclib, olaparib, rucaparib, talazoparib, niraparib, veliparib, pamiparib, CEP 9722, E7016, 3-aminobenzamide, mefuparib, and AZD2281. In some embodiments, the anti-cancer agent is selected from SHR6390, trilaciclib, lerociclib, AT7519M, dinaciclib, ribociclib, abemaciclib, and palbociclib. In some embodiments, the anti-cancer agent is selected from olaparib, rucaparib, talazoparib, niraparib, veliparib, pamiparib, CEP 9722, E7016, 3-aminobenzamide, mefuparib, and AZD2281. In some embodiments, the anti-cancer agent is selected from olaparib, rucaparib, talazoparib, and niraparib. In some embodiments, the anti-cancer agent is olaparib.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art in view of the present disclosure, without departing from the spirit of the present disclosure and/or scope of the appended claims.

Example 1. General Properties of Compound A

The chemical and physical characteristics of Compound A are presented in Table 1. This batch was prepared for use in the 28-day good laboratory practice (GLP) toxicology studies using the same synthetic scheme and processing employed in preparation of active pharmaceutical ingredient (API) to be used in the clinical drug product.

TABLE 1

General Properties of Compound A

Physical Parameters

Figure 2:
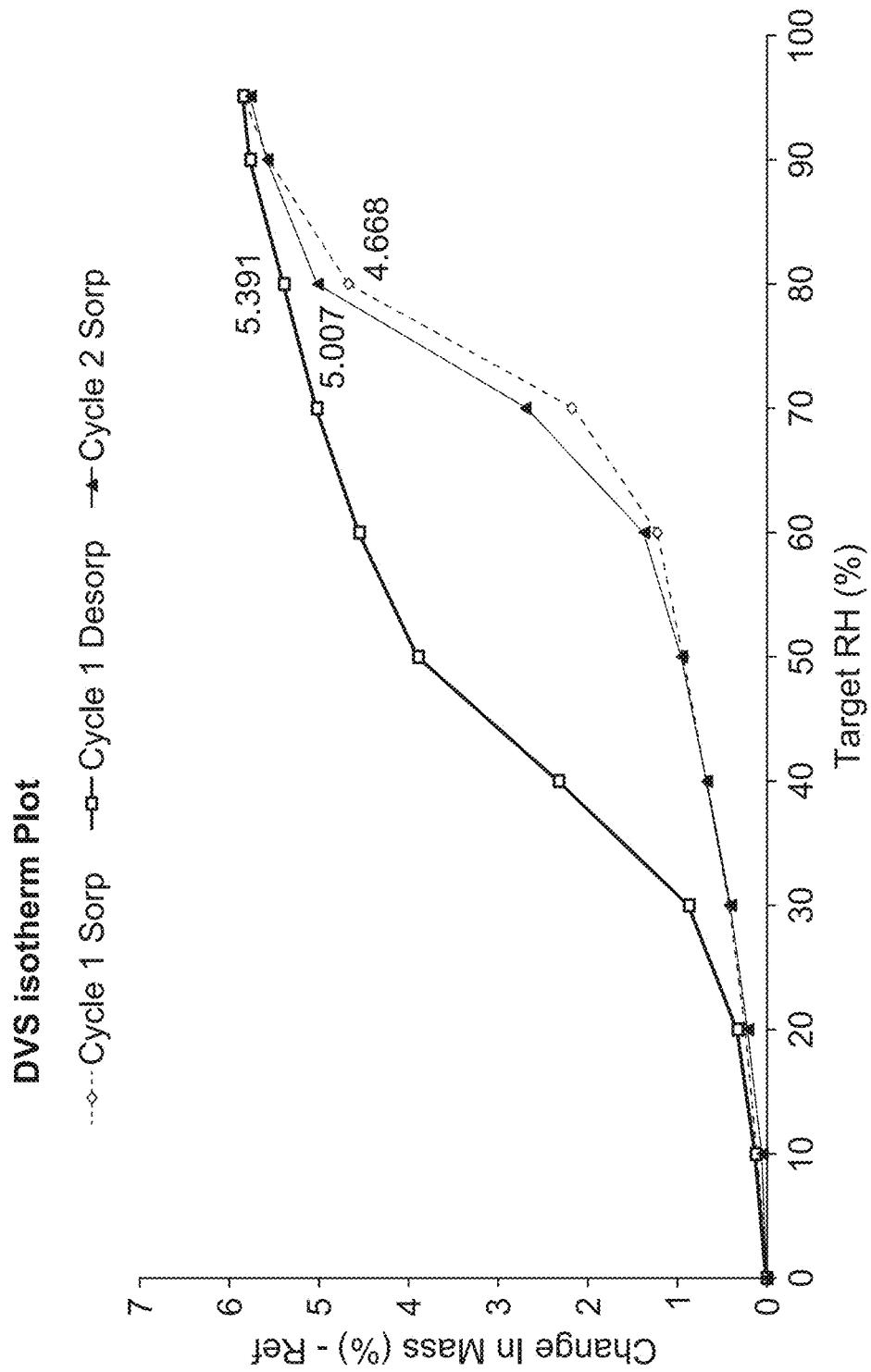
FIG. 2 is a dynamic vapor solution (DVS) isotherm plot of Compound A obtained on a laboratory batch of Compound A having the same powder x-ray diffraction pattern as in FIG. 3A.

| | |
|---|---|
| Appearance | Off-white to yellow powder |
| Differential Scanning Calorimetry | FIG. 1 (Endotherm at 289-300° C.) |
| Hygroscopicity by Dynamic Vapor Sorption (DVS)[1] | FIG. 2 |
| Powder X-ray Diffraction | FIG. 3A |
| Powder X-ray Diffraction Peak Listing | FIG. 3B |
| Optical Rotation (c = 1, DMSO) | 0° |

Solubility Parameters at 24° C. ± 3° C.

| Solvent | Conc. (mg/mL), 24 h |
|---|---|
| Methanol | 0.29 |
| Acetonitrile | 0.79 |
| Dichloromethane | 25.1 |
| Dichloromethane/methanol | 100 |
| Ethanol | 0.08 |
| Ethyl acetate | 0.20 |
| Propylene glycol | 0.75 |
| Polyethylene glycol-300 | 2.8 |
| pKa | pKa1 = 6.8 |
| | pKa2 = 2.7 | pH-Solubility Profile

| Buffer | Concentration (µg/mL) | pH of solution |
|---|---|---|
| pH 1.2 HCl (aq) | 397 | 1.2 |
| pH 3 200 mM citrate buffer | 15 | 3.0 |
| pH 5 200 mM citrate buffer | 0.5 | 5.0 |
| pH 6.5 200 mM citrate buffer | 0.3 | 6.5 |
| Fasted state simulated intestinal fluid | 1 | 6.5 |
| Fed state simulated intestinal fluid | 22 | 5.0 |

[1]The DVS was obtained on a laboratory batch having the same powder x-ray diffraction PXRD.

Example 2: First-Generation Synthesis of Compound A

Step 1: (tert-butyl N-[(1r,4r)-4-(3-chloro-4-cyanophenoxy)cyclohexyl]carbamate) (Intermediate 1). Into a 50.0-mL round-bottom flask, was placed tert-butyl N-[(1r,4r)-4-hydroxycyclohexyl]carbamate (500.0 mg, 2.32 mmol, 1.00 equiv), N,N-dimethylformamide (10.0 mL), sodium hydride (82.8 mg, 3.45 mmol, 1.50 equiv), 2-chloro-4-fluorobenzonitrile (432.6 mg, 2.78 mmol, 1.20 equiv). The resulting solution was stirred for 2 hours at 0° C. in a water/ice bath. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/2). The collected fractions were combined and concentrated under vacuum. This resulted in 470.0 mg (58%) of Intermediate 1 (tert-butyl N-[(1r,4r)-4-

(3-chloro-4-cyanophenoxy)cyclohexyl]carbamate) as yellow oil. LC-MS (ES$^+$): m/z 295.0 [MH$^+$], $t_R$=1.199 min, (1.90 minute run). Chemical formula: $C_{18}H_{23}ClN_2O_3$ [350.14].

Step 2: (4-(((1r,4r)-4-aminocyclohexyl)oxy)-2-chlorobenzonitrile) (Intermediate 7). Into a 50.0-mL round-bottom flask, was placed Intermediate 1 (tert-butyl N-[(1r,4r)-4-(3-chloro-4-cyanophenoxy)cyclohexyl]carbamate) (470.0 mg, 1.34 mmol, 1.00 equiv), methanol (5.0 mL), hydrogen chloride. The resulting solution was stirred for 2 hours at room temperature. The resulting mixture was concentrated under vacuum. This resulted in 340.0 mg (88%) of Intermediate 7 (2-chloro-4-[[(1r,4r)-4-aminocyclohexyl]oxy]benzonitrile) hydrochloride as a yellow solid. LC-MS (ES$^+$): m/z 250.90 [MH$^+$], $t_R$=0.537 min, (1.90 minute run). Chemical formula: $C_{13}H_{15}ClN_2O$ [250.09].

Step 3: (6-[4-(hydroxymethyl)piperidin-1-yl]-N-[(1r,4r)-4-(3-chloro-4-cyanophenoxy)cyclohexyl]pyridazine-3-carboxamide) (Intermediate 2). Into a 100-mL round-bottom flask, was placed 6-[4-(hydroxymethyl)piperidin-1-yl] pyridazine-3-carboxylic acid (1.0 g, 4.21 mmol, 1.00 equiv), Intermediate 7 (2-chloro-4-[(1r,4r)-4-aminocyclohexyl]oxy]benzonitrile hydrochloride) (1.2 g, 4.18 mmol, 1.00 equiv), N,N-dimethylformamide (30 mL), N,N,N',N'-Tetramethyl-O-(7-azabenzotriazol-1-yl)uronium hexafluorophosphate (2.4 g, 6.31 mmol, 1.50 equiv), N,N-diisopropylethylamine (1.6 g, 12.38 mmol, 3.00 equiv). The resulting solution was stirred for 1 hour at room temperature. The reaction was then quenched by the addition of water (50 mL) and extracted with ethyl acetate (50 mL×3). The combined organic layers were washed with brine (50 mL), dried over anhydrous sodium sulfate and concentrated under vacuum. The residue was applied onto a silica gel column with dichloromethane/methanol (v:v=12:1). This resulted in 1.1 g (56%) of Intermediate 2 (6-[4-(hydroxymethyl)piperidin-1-yl]-N-[(1r,4r)-4-(3-chloro-4-cyanophenoxy)cyclohexyl]pyridazine-3-carboxamide) as yellow oil. LC-MS (ES$^+$): m/z 470.0 [MH$^+$], $t_R$=0.90 min (1.8 minute run).

Step 4: (6-(4-formylpiperidin-1-yl)-N-[(1r,4r)-4-(3-chloro-4-cyanophenoxy) cyclohexyl] pyridazine-3-carboxamide) (Intermediate 3). Into a 100-mL round-bottom flask, was placed Intermediate 2 (700.0 mg, 1.49 mmol, 1.00 equiv), dichloromethane (20 mL), (1,1,1-Triacetoxy)-1,1-dihydro-1,2-benziodoxol-3(1H)-one (947.2 mg, 2.23 mmol, 1.50 equiv). The resulting solution was stirred for 3 hours at room temperature. The resulting mixture was concentrated under vacuum. The residue was applied onto a silica gel column with ethyl acetate/petroleum ether (v:v=1:3). This resulted in 390.0 mg (56%) of Intermediate 3 as a yellow solid. LC-MS (ES$^+$): m/z 468.2 [MH$^+$], $t_R$=1.06 min (2.0 minute run).

Figure 16A:
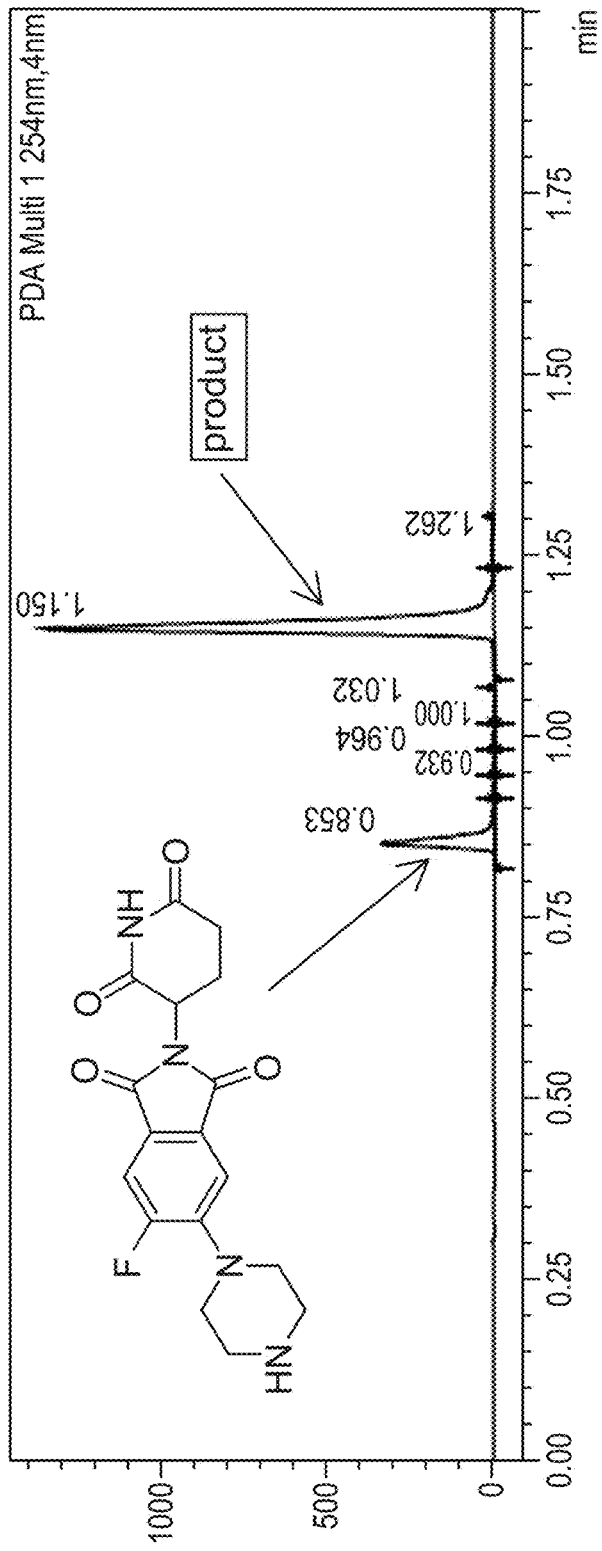
FIG. 16A is a chromatogram of crude Compound A, as produced by the First-Generation synthesis. Column: Shimpack XR-ODS, 2.2 μm 3.0×50 mm. Mobile phase A: Water/0.05% TFA. Mobile phase B: Acetonitrile/0.05% TFA. Flow rate: 1.2 mL/min. Column temperature 40° C. Detector, UV 254 nm.
Figure 16C:
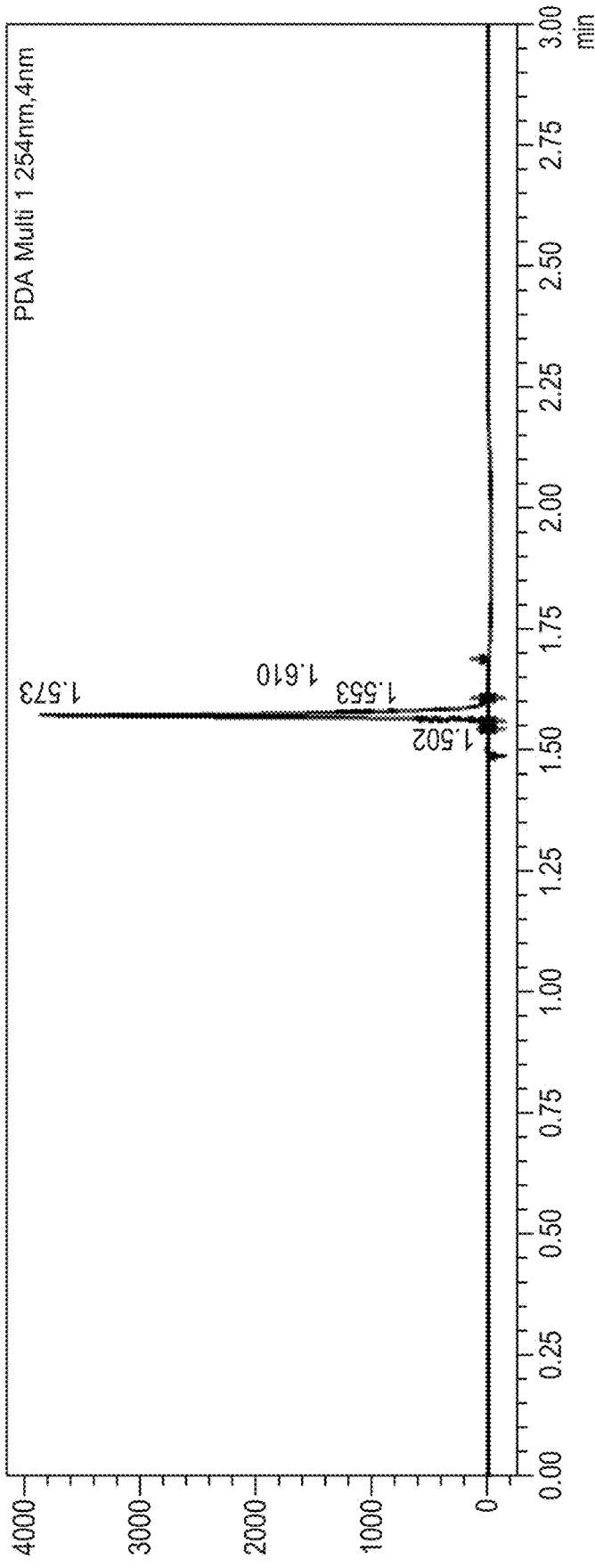
FIG. 16C is a chromatograph of Compound A following purification by prep-HPLC, as produced by the First-Generation synthesis. Column: Shimpack XR-ODS, 2.2 μm 3.0×50 mm. Mobile phase A: Water/0.05% TFA. Mobile phase B: Acetonitrile/0.05% TFA. Flow rate: 1.2 mL/min. Column temperature 40° C. Detector, UV 254 nm.
Figure 16D:
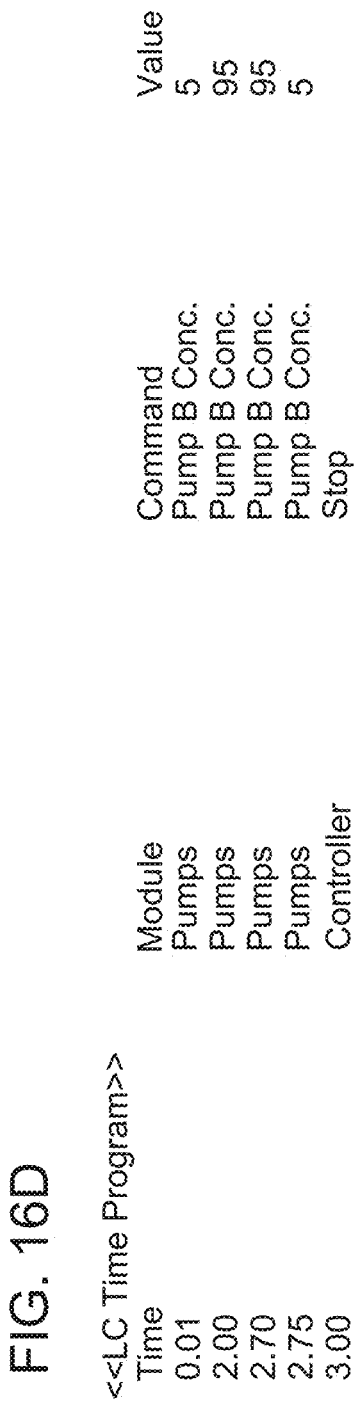
FIG. 16D is the solvent gradient used to obtain the chromatogram in FIG. 16C

Step 5: (6-[4-([4-[2-(2,6-dioxopiperidin-3-yl)-6-fluoro-1,3-dioxo-2,3-dihydro-1H-isoindol-5-yl]piperazin-1-yl] methyl)piperidin-1-yl]-N-[(1r,4r)-4-(3-chloro-4-cyanophenoxy)cyclohexyl]pyridazine-3-carboxamide) (Compound A). Into a 100-mL round-bottom flask, was placed Intermediate 3 (180.0 mg, 0.38 mmol, 1.00 equiv), dichloromethane (10 mL), Intermediate 5 (2-(2,6-dioxopiperidin-3-yl)-5-fluoro-6-(piperazin-1-yl)-2,3-dihydro-1H-isoindole-1,3-dione hydrochloride) (152.7 mg, 0.38 mmol, 1.00 equiv), sodium triacetoxyborohydride (244.6 mg, 3.00 equiv). The resulting solution was stirred for 3 hours at room temperature. The reaction was then quenched by water (30 mL), extracted with ethyl acetate (30 mL×3), washed with brine (30 mL) and concentrated under reduced pressure. The solid was filtered out. HPLC analysis revealed the crude product to be 81.5% pure by area, with 16.9% by area identified as unreacted Intermediate 5. See FIG. 16A. The crude product was purified by Prep-HPLC with the following conditions: Column, XBridge Prep C18 OBD Column, 19*150 mm 5 um; mobile phase, water (10 mmol/L ammonium bicarbonate) and acetonitrile (48.0% acetonitrile up to 73.0% in 8 min); Detector, UV 254 nm. This resulted in 146.1 mg (47%) of Compound A as a yellow solid. HPLC-UV analysis showed the purified product to be 98% pure by area, with three impurities, quantified at 0.54%, 0.74% and 0.73% respectively. See FIG. 16B $^1$H NMR (400 MHz, DMSO): δ 11.11 (s, 1H), 8.58 (d, J=8.2 Hz, 1H), 7.86 (d, J=8.8 Hz, 1H), 7.81 (d, J=9.5 Hz, 1H), 7.73 (d, J=11.4 Hz, 1H), 7.46 (d, J=7.4 Hz, 1H), 7.39 (d, J=2.4 Hz, 1H), 7.34 (d, J=9.7 Hz, 1H), 7.15-7.12 (m, 1H), 5.13-5.08 (m, 1H), 4.59-4.45 (m, 3H), 3.90-3.83 (m, 1H), 3.27 (s, 4H), 3.03 (m, 2H), 2.97-2.82 (m, 1H), 2.64-2.53 (m, 5H), 2.46 (m, 1H), 2.23 (m, 2H), 2.14-2.09 (m, 2H), 2.07-2.02 (m, 1H), 1.96-1.79 (m, 5H), 1.65 (m, 2H), 1.52 (m, 2H), 1.19-10.09 (m, 2H); LC-MS (ES$^+$): m/z 812.25 [MH$^+$], $t_R$=1.57 min (3.0 minute run). Chemical Formula: $C_{41}H_{43}ClFN_9O_6$ [811.30]. Total H count from HNMR data: 43.

Example 3: Second Generation Synthesis of Compound A

Step 1: N-((1r,4r)-4-(3-chloro-4-cyanophenoxy)cyclohexyl)-6-(4-(hydroxymethyl)piperidin-1-yl)pyridazine-3-carboxamide. To a clean, dry, 100-L jacketed, glass reactor equipped with a temperature controller, two pen chart recorder, and a nitrogen bleed was charged dimethylacetamide (24 L, 5 vol), Intermediate 4 (4800.5 g, 1 wt), piperidin-4-yl methanol (1699.9 g, 0.35 wt), and diisopropylethylamine (4759 g, 0.99 wt). The temperature of the batch was adjusted to 90° C. over 2 h, 7 min and the batch then held at 90° C. for an additional 15 h. The reaction was monitored by HPLC. The temperature of the batch was adjusted to 50° C. over 48 min then isopropyl acetate (48 L, 10 vol) added. The batch was split into two equal portions (each ≈42 L) for work-up.

Portion 1 Work-up. Portion 1 was charged to a clean, dry, 100-L, jacketed, glass reactor and heated to 50° C. Purified water (36 L, 7.5 vol) was charged and the batch stirred at 50° C. for 5 min. The layers were allowed to separate and the lower aqueous layer was discarded to waste. Isopropyl acetate (12 L, 2.5 vol) and purified water (24 L, 5 vol) were charged and the batch temperature adjusted to 50° C. The batch was stirred at 50° C. for 5 min, then the layers were allowed to separate, and the lower aqueous layer was discarded to waste. IPC: $^1$H NMR (TEST-2835)—% DMAc 8.7% relative to Intermediate 2.

Portion 2 Work-up. Portion 2 was charged to a clean, dry, 100-L, jacketed, glass reactor and heated to 50° C. Purified water (36 L, 7.5 vol) was charged and the batch stirred at 50° C. for 5 min. The layers were allowed to separate and the lower aqueous layer was discarded to waste. Isopropyl acetate (12 L, 2.5 vol) and purified water (24 L, 5 vol) were charged and the batch temperature adjusted to 50° C. The batch was stirred at 50° C. for 6 min, then the layers were allowed to separate, and the lower aqueous layer was discarded to waste. IPC: $^1$H NMR (TEST-2835)—% DMAc 2.8% relative to Intermediate 2.

The combined isopropyl acetate extracts were returned to the 100-L reactor. Intermediate 2 Seeds (48.82 g, 0.01 wt) were charged and the batch temperature adjusted to 15° C. over 2 h. The batch was distilled under vacuum (Jacket Temp. 35° C.) until 26 L (5.4 vol) remained. Isopropyl acetate (46 L, 9.6 vol) was added and the batch temperature adjusted to 50° C. over 1 h. The batch was stirred at 50° C. for 36 min then cooled to 20° C. over 28 min. The batch was distilled under vacuum (Jacket Temp. 35° C.) until 28 L (5.8 vol) remained, then the temperature adjusted to 10° C. over 18 min, and stirred at this temperature for 1 h, 18 min. The precipitated solid was isolated by vacuum filtration on a 24 inch, polyethylene filter funnel. The reactor was rinsed with isopropyl acetate (24 L, 5 vol) and the rinse used to wash the filter cake. The wet cake was further washed with isopropyl acetate (24 L, 5 vol). After conditioning on the filter under nitrogen for 46 min, the wet-cake was transferred to eight glass drying trays (wet weight 6545.8 g) and dried in a vacuum oven at 45° C. for ~22 h until a constant weight was achieved. The isolated Intermediate 2 (4597.8 g, 79.7%) was packaged into two 3 mil LDPE bags and stored inside a fiber board drum. HPLC Analysis: 99.4%.

Step 2: N-((1r,4r)-4-(3-choro-4-cyanophenoxy)cyclohexyl)-6-(4-formylpiperidin-1-yl)pyridazine-3-carboxamide. To a clean, dry, 100-L, jacketed, glass reactor equipped with a temperature controller, two pen chart recorder, and a nitrogen bleed was charged dichloromethane (36 L, 7.9 vol), Intermediate 2 (4577.1 g, 1 wt), sodium bicarbonate (1222.0 g), sodium bromide (1097.5 g, 0.24 wt), and purified water (25 L, 5.5 vol). The biphasic mixture was cooled to 0° C. over 1 h 11 min then a solution of TEMPO (15.2 g, 0.0033 wt) in dichloromethane (9 L, 2.0 vol) was added over 32 min while keeping the internal temperature at 0±5° C. Sodium hypochlorite solution (14353.4 g, 3.12 wt) was added over 45 min while maintaining the internal temperature at 0±5° C. The light yellow batch was stirred for an additional 46 min at 0±5° C. The reaction was monitored by HPLC. An additional portion of sodium hypochlorite solution (223.0 g, 0.05 wt) was added and the batch stirred for an additional 2 h at 0±5° C. Dichloromethane (9 L, 2.0 vol) was added and the batch stirred for an additional 5 min. The layers were allowed to separate and the upper aqueous layer was discarded to waste. The organic phase was washed (5 min) with a solution of sodium sulfite (1222.2 g, 0.27 wt) in purified water (19 L, 4.2 vol). The layers were allowed to separate and the upper aqueous layer was discarded to waste. The organic phase was washed (10 min) with purified water (9 L, 2.0 vol). The layers were allowed to separate and the upper aqueous layer was discarded to waste. The product rich organic phase was charged to the 100-L reactor along with acetonitrile (19 L, 4.2 vol) and vacuum distilled (Jacket Temp. 45° C.) to a final volume of 26 L. During the vacuum distillation, additional acetonitrile (37 L, 8.1 vol) was added to the reactor. Acetonitrile (54 L, 11.8 vol) was added and the batch vacuum distilled (Jacket Temp. 45° C.) to a final volume of 26 L. The distillation was monitored by $^1$H NMR. Acetonitrile (22 L, 4.8 vol) and purified water (46 L, 10 vol) was charged and the batch temperature adjusted to 20° C. The batch was stirred for 1 h 26 min then the precipitated solid was isolated by vacuum filtration on a 24-inch, polyethylene, filter funnel. The reactor was rinsed with acetonitrile/purified water 1:1 (23 L, 5 vol) and the rinse used to wash the filter cake. After conditioning on the filter under nitrogen for 31 min, the wet-cake was transferred to eight glass drying trays (wet weight 5456.9 g) and dried in a vacuum oven at 45° C. for ≈44 h until a constant weight was achieved. The isolated Intermediate 3 (4129.8 g, 90.6%) was packaged into two 3 mil LDPE bags and stored inside a fiber board drum. HPLC Analysis: 96.7%.

Step 3: N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl) pyridazine-3-carboxamide (Compound A). To a clean, dry, 50-L, jacketed, glass reactor equipped with a temperature controller, two single pen chart recorders, and a nitrogen bleed was charged dimethylacetamide (4.3 L, 2.5 vol) and sodium triacetoxyborohydride (2020.4 g, 1.17 wt). The resulting suspension was cooled to 5±5° C. over 22 min.

To a clean, dry, 22-L, jacketed, glass reactor equipped with a temperature controller, a two pen chart recorder, and a nitrogen bleed was charged dimethylacetamide (8.5 L, 4.9 vol), Intermediate 5 (1719.8 g, 1 wt), and Intermediate 3 (2134.0 g, 1.24 wt). The internal temperature was adjusted to 0±5° C. over 39 min then triethylamine (1200 mL, 0.7 vol) was added over 38 min while maintaining the internal temperature<5° C.

The contents of the reactor were transferred to a separate reactor over 1 h 25 min while maintaining an internal temperature of 5±5° C. Once the transfer was complete, the first reactor was rinsed with dimethylacetamide (1.1 L, 0.64 vol) and the rinse transferred to the second reactor. The batch was stirred for an additional 61 min at 5±5° C. Reaction was monitored by HPLC.

To a clean, dry, 100-L, jacketed, glass reactor equipped with a temperature controller, a two pen chart recorder, and a nitrogen bleed was charged ethanol (21 L, 12.4 vol) and purified water (21 L, 12.4 vol). The internal temperature was adjusted to 10±5° C. over 51 min. The contents of the reactor containing the reaction mixture were transferred to the glass reactor over 9 min while maintaining the internal temperature<20° C. Once the transfer was complete, the former reactor was rinsed with dimethylacetamide (1.1 L, 0.64 vol) and the rinse transferred to the glass reactor. The temperature of the batch was adjusted to 50° C. over 3 h and held at this temperature for an additional 33 min. The batch was cooled to 20° C. over 81 min, held at this temperature for 69 min, then the precipitated solid was isolated by vacuum filtration on a 24-inch, polyethylene, filter funnel. The reactor was rinsed with ethanol/purified water 1:1 (2×11 L, 2×6.4 vol) and the rinse used to wash the filter cake. The wet cake was further washed with ethanol (2×11 L, 2×6.4 vol). After conditioning on the filter under nitrogen for ≈13 h, the wet-cake (crude Compound A) was transferred to seven glass drying trays (wet weight 11353 g) and dried in a vacuum oven at 25° C. for ≈115 h until a constant weight (3382.4 g) was achieved. HPLC purity: 99.60 area % (see FIG. 17A).

To a clean, dry, 100-L, jacketed, glass reactor equipped with a temperature controller, a two pen chart recorder, and a nitrogen bleed was charged dichloromethane (54.7 L, 16.2 vol), methanol (6 L, 1.8 vol), and crude Compound A (3375.5 g, 1 wt). The batch was stirred until complete dissolution was observed (27 min). The batch was clarified through a 0.4-micron, in-line filter then distilled under vacuum (jacket temp. 65° C.) while adding pre-filtered ethanol (27 L, 8 vol) at such a rate that a total volume of ≈67.5 L was maintained. Compound A seed crystals (8.4 g, 0.0025 wt) slurried in pre-filtered ethanol (200 mL, C019788) were added to the batch. Distillation under vacuum (jacket temp. 65° C.) was continued while adding pre-filtered ethanol (54 L, 16 vol) at such a rate that a total volume of ≈67.5 L was maintained. Distillation was monitored by $^1$H NMR. The batch was stirred at 20±5° C. for 4 h, 30 min then the precipitated solid was isolated by vacuum filtration on a 24-inch, polyethylene, filter funnel. The reactor was rinsed with ethanol (13.5 L, 4 vol) and the rinse used to wash the filter cake. The wet cake was further washed with purified water (2×13.5 L, 2-4 vol) and ethanol (2×13.5 L, 2×4 vol). After conditioning on the filter under nitrogen for 16 h, the wet-cake was transferred to seven glass drying trays (wet weight 3336.4 g) and dried in a vacuum oven at 25° C. for ≈99.5 h until a constant weight was achieved and the dichloromethane level had dropped to an acceptable level (450 ppm). The isolated N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide (Compound A) (3052.4 g, 87%) was packaged into two 3 mil LDPE bags and stored inside an HDPE drum. HPLC Analysis: 99.6 area % (see FIG. 17B).

Example 4: Controls of Critical Steps and Intermediates in the Manufacturing Process for Compound A At this stage of development, the in-process controls consist of temperature monitoring and high performance liquid chromatography (HPLC) analysis of the reaction mixtures to determine the extent of the reaction. The transformations depicted in Scheme 4 are monitored by expected HPLC endpoints for consumption of the limiting reagent.

The critical in-process controls and target limits for the synthesis of Compound A are provided in Table 2.

TABLE 2

Critical In-Process Control Points and Acceptance Limits

| Step | In-Process Control | Acceptance Limit |
|---|---|---|
| 1 | Reaction temperature | 90° to 100° C. |
|   | Consumption of Intermediate 4 | <1.0% Intermediate 4 remaining |
| 2 | Reaction temperature | 0° to 5° C. |
|   | Consumption of Intermediate 2 | <1.0% Intermediate 2 remaining |
|   | Drying temperature | 50° to 60° C. |
| 3 | Reaction temperature | 0° to 5° C. |
|   | Consumption of Intermediate 5 | <2% Intermediate 5 remaining |
|   | Drying temperature | 45° to 65° C. |
|   | Level of residual solvent | ICHQ3C |

The process development on Compound A includes development of the synthetic route and related processes on a laboratory-scale of 10 to 100 grams and transferred into the kilo-lab for preparation of 28-day toxicology supplies at 1.5 kilogram-scale. Compound A for use in the preparation of clinical supplies was prepared at a 3-kilogram scale using the same synthetic route and processes employed for the 28-day toxicology supply.

Example 5: Second Generation Synthesis of Intermediate 4

Step 1: Tert-butyl ((1r,4r)-4-hydroxycyclohexyl)carbamate. A solution of $K_2CO_3$ (12 kg, 87 mol) in water (60 L) was added (1r, 4r)-4-aminocyclohexanol hydrochloride (12.0 kg, 79.1 mol) at 0-10° C. The mixture was stirred at 0-10° C. for 1 h. Di-tert-butyl dicarbonate (18.1 kg, 83.1 mol) was added to the mixture. The resulting mixture was stirred at ambient temperature overnight (20 h). TLC (hexane/ethyl acetate=2/1, SM: $R_f$=0; Product: $R_f$=0.4) indicated the reaction was complete. The solid was collected by filtration and dried in oven to afford the title compound tert-butyl ((1r,4r)-4-hydroxycyclohexyl)carbamate (Intermediate 6) (10.13 kg, 60% yield) as white solid. $^1$HNMR (400 MHz, DMSO-$d_6$): δ (ppm) 1.08-1.20 (m, 4H), 1.36 (s, 9H), 1.70-1.78 (m, 4H), 3.14 (s, 1H), 3.30 (s, 1H), 4.48 (s, 1H), 6.65 (d, J=4 Hz, 1H).

Step 2: Tert-butyl ((1r,4r)-4-(3-chloro-4-cyanophenoxy)cyclohexyl) carbamate. NaH (60% in mineral oil, 1110 g, 27.8 mol) was added to a solution of Intermediate 6 tert-butyl ((1r,4r)-4-hydroxycyclohexyl)carbamate (5 kg, 23 mol) in DMF (65 L) at −10° C. The mixture was stirred at −10° C. for 1 h. 2-Chloro-4-fluorobenzonitrile (3.6 kg, 23 mol) was added in portions. The resulting mixture was stirred at −10° C. for 1 h. TLC (hexane/ethyl acetate=5/1, 2-Chloro-4-fluorobenzonitrile: $R_f$=0.7; Product: $R_f$=0.4) indicated the reaction was complete. The mixture was added to ice-water (200 kg) in portions and stirred at ambient temperature for 20 h. The solid was collected by filtration and dried in oven to afford Intermediate 1 (7.8 kg, 95% yield) as white solid. $^1$HNMR (400 MHz, DMSO): δ (ppm) 1.33-1.43 (m, 13H), 1.79-1.82 (m, 2H), 2.01-2.04 (m, 2H), 4.48-4.50 (m, 1H), 6.85 (d, J=3.6 Hz, 1H), 7.11 (dd, J=8.8 Hz, J=2.4 Hz, 1H), 7.67 (d, J=1.2 Hz, 1H), 7.83 (d, J=4.4 Hz, 1H).

Step 3: 4-(((1r,4r)-4-aminocyclohexyl)oxy)-2-chlorobenzonitrile hydrochloride. Acetyl chloride (13.6 kg, 173 mol) was added dropwise to methanol (35 L) at 0-20° C. After the addition was complete, the mixture was stirred at room temperature for 1 h. Intermediate 1 (15.2 Kg) was added to the mixture and the resulting mixture was stirred at room temperature for 2 h. TLC (hexane/ethyl acetate=5/1, SM: $R_f$=0.4; Product: $R_f$=0.1) indicated the reaction was complete. The mixture was concentrated in vacuo. The residue was taken into methyl tert-butyl ether (25 L) and stirred at ambient temperature overnight (20 h). The solid was collected by filtration and dried in oven to afford 4-(((1r,4r)-4-aminocyclohexyl)oxy)-2-chlorobenzonitrile hydrochloride (Intermediate 7) (11.7 kg, 95% yield). $^1$HNMR (400 MHz, DMSO-$d_6$): δ (ppm) 1.41-1.59 (m, 4H), 2.00-2.11 (m, 4H), 3.05 (s, 1H), 4.48-4.55 (m, 1H), 7.14 (dd, J=8.8 Hz, J=2.4 Hz, 1H), 7.41 (d, J=2.4 Hz, 1H), 7.85 (d, J=8.8 Hz, 1H), 8.25 (s, 3H).

Step 4: 6-chloro-N-((1r,4r)-4-(3-chloro-4-cyanophenoxy)cyclohexyl)pyridazine-3-carboxamide. A 20-L, jacketed reactor was charged with 6-chloropyridazine-3-carboxylic acid (0.490 kg, 3.09 mol, 1.00 equiv), Intermediate 7 (0.888 kg, 3.09 mol, 1.00 equiv), and ethyl acetate (4.4 L, 9 vol). Triethylamine (1.565 kg, 15.5 mol, 5.0 equiv) was added over 47 min and the addition pump lines were rinsed with ethyl acetate (0.5 L, 1 vol). The batch temperature was adjusted to 15-25° C. and T3P (3.93 kg of 50% solution, 6.2 mol, 2.00 equiv) was dosed into the reaction over 70 min. The dosing pump was rinsed with ethyl acetate (0.5 L, 1 vol). The batch was aged at 19-20° C. for 30 min. The reaction was monitored by HPLC. The reaction was quenched by the addition of 1 N aqueous HCl (≈5 L, 1.6 equiv) over 45 min. The slurry was stirred overnight and then the batch was filtered in a Buchner funnel with filter paper. The kettle and filter cake were rinsed with water (2×2.4 L, 2×5 vol) and ethyl acetate (2 L, 4 vol). The wet cake was re-slurried in ethyl acetate (2.5 L, 5 vol) for 30 min at room temperature. The batch was filtered and was rinsed with ethyl acetate (1.5 L, 3 vol). However, in-process HPLC analysis of the wet cake showed no change to the level of N-((1r,4r)-4-(3-chloro-4-cyanophenoxy)cyclohexyl)-6-hydroxypyridazine-3-carboxamide (the hydroxyl impurity). The wet cake (1055 g) was dried in a tray drier at 40-50° C. to afford 0.96 kg of Intermediate 4 (79% yield). The water content of the batch was 0.17 wt % by KF titration. The 1H NMR spectrum was consistent with the assigned structure and the HPLC purity was 97.3 area % with 2.4 area % of the hydroxyl impurity.

Figure 20:
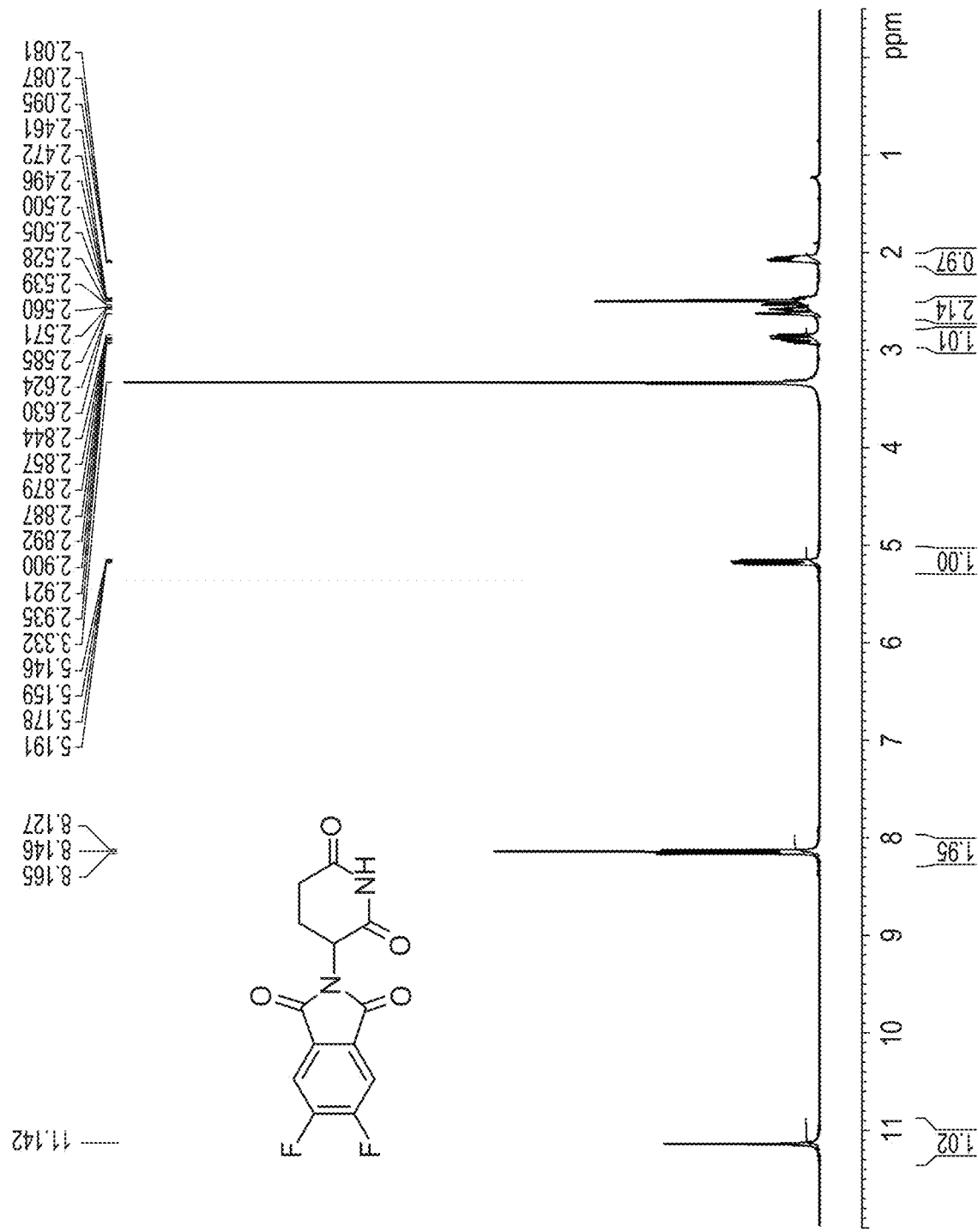
FIG. 20 is an H$^1$-NMR spectrum of Intermediate 8, produced by the second-generation synthesis, in deuterated dimethylsulfoxide (DMSO-d$_6$).

The impure Intermediate 4 (906 g) was charged to a 10-L reactor with DMAc (2.72 L, 3 vol) and the batch was warmed to 50.6° C. IPAc (2.72 L, 3 vol) was added and the batch was maintained at 50° C. for 1 h. The temperature was adjusted to 20° C. over 1.5 h and then the batch was filtered. The reactor and filter cake were rinsed with IPAc (3×1.8 L, 3×2 vol). The wet cake (1.3 kg) was dried in a tray drier at 30-35° C. to afford 0.772 kg of 6-chloro-N-((1r,4r)-4-(3-chloro-4-cyanophenoxy)cyclohexyl)pyridazine-3-carboxamide (Intermediate 4) (85% yield). The 1H NMR spectrum was consistent with the assigned structure (see FIG. 20) and the HPLC purity was 98.6 area % with 1.3 area % of the hydroxyl impurity.

Example 6: Second Generation Synthesis of Intermediate 5

Figure 19:
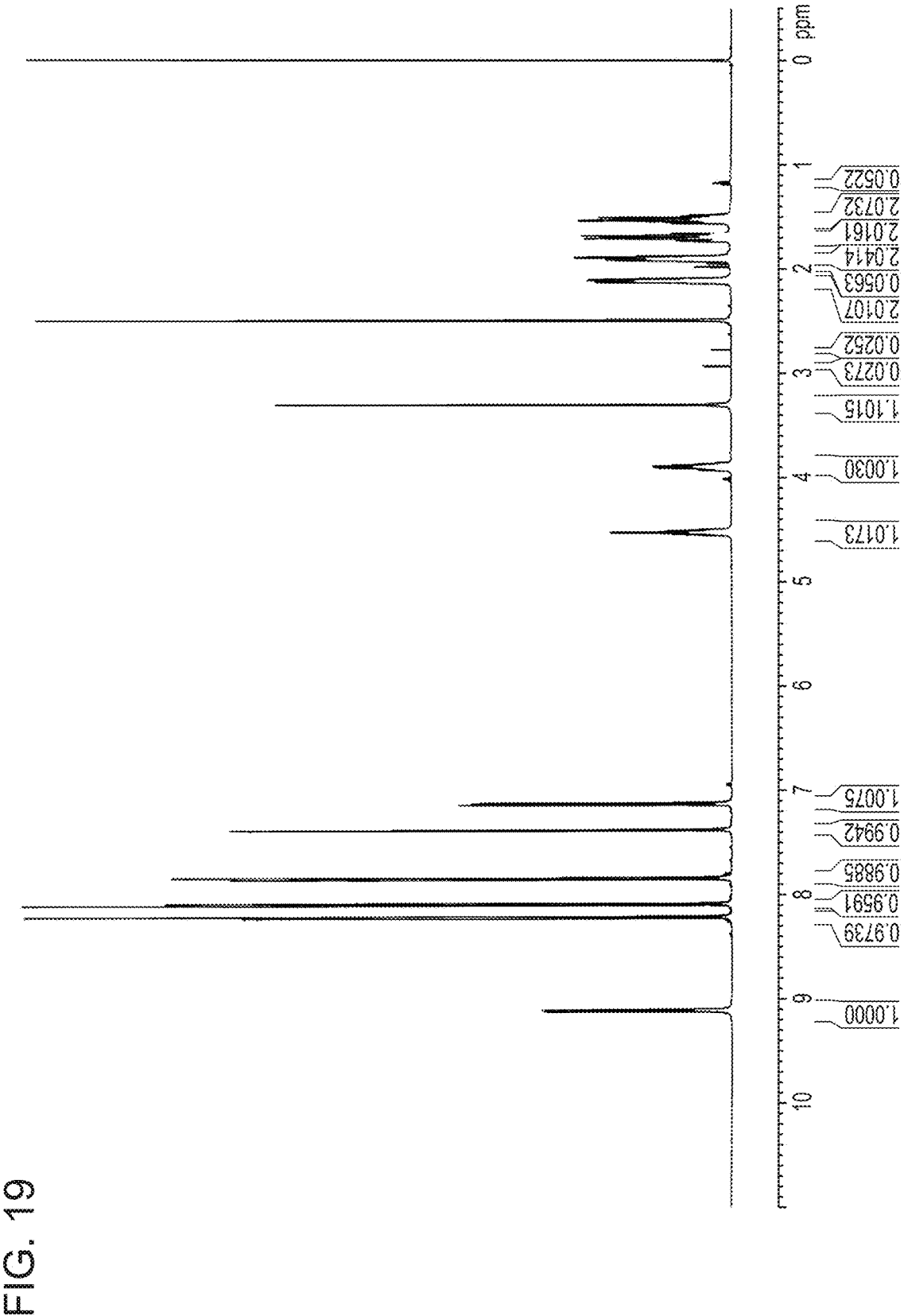
FIG. 19 is the $^1$H NMR spectrum of Intermediate 4, as produced by the second-generation synthesis, in deuterated dimethylsulfoxide (DMSO-d$_6$).

Step 1: 2-(2,6-dioxopiperidin-3-yl)-5,6-difluoroisoindoline-1,3-dione. A mixture of 4,5-difluorophthalic acid (9.81 kg, 1.0 eq.), 3-aminopiperidine-2,6-dione (10.38 kg, 1.3 eq.), $CH_3COOH$ (49 kg, 5V) was degassed by purging with nitrogen for three times. Then $CH_3COONa$ (5.375 kg, 1.35 eq) was added and degassed by purging with nitrogen for three times again. The resulting solution was stirred for 4 hrs at 117-120° C. HPLC showed the reaction was complete. Then $H_2O$ (147 L, 15V) was added to the mixture slowly at 90° C.-120° C. After cooling to 30° C., the reaction mixture was filtered and the filter cake washed with water (20 L, 2V)*2. The filter cake was collected and dried at 50° C. to get 12.6 kg 2-(2,6-dioxopiperidin-3-yl)-5,6-difluoroisoindoline-1,3-dione (Intermediate 8) as off-white solid with 88.2% yield. $H^1$-NMR conformed to reference spectrum (FIG. 19).

Figure 21:
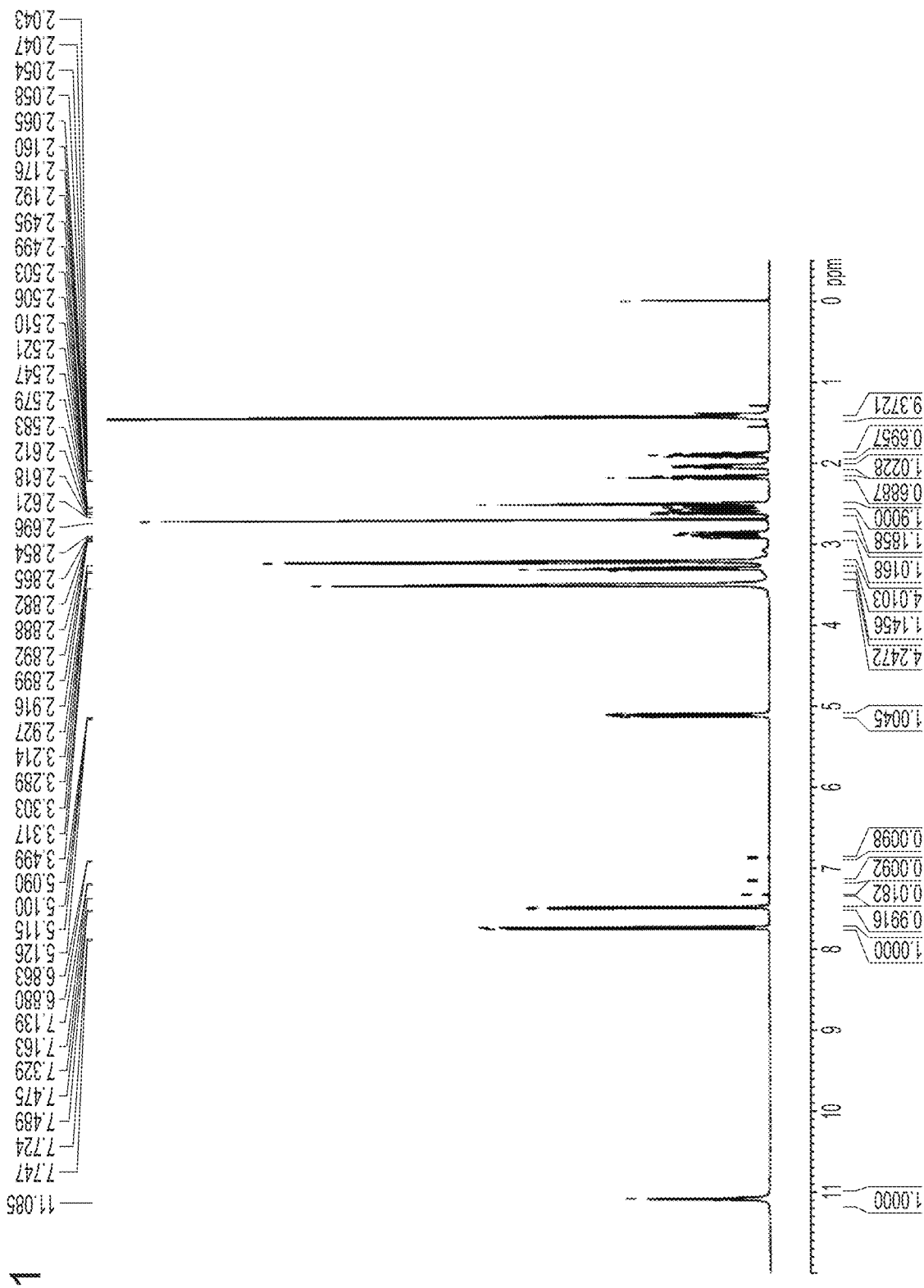
FIG. 21 is an H$^1$-NMR spectrum of Intermediate 9, produced by the second-generation synthesis, in deuterated dimethylsulfoxide (DMSO-d$_6$).

Step 2: tert-butyl 4-(2-(2,6-dioxopiperidin-3-yl)-6-fluoro-1,3-dioxoisoindolin-5-yl)piperazine-1-carboxylate. A 100-L, jacketed reactor was charged with Intermediate 8 (4.50 kg, 15.30 mol, 1.00 equiv), sodium bicarbonate (1.542 kg, 18.35 mol, 1.20 equiv), Boc-piperazine (3.134 kg, 16.82 mol, 1.10 equiv), and NMP (22.5 L, 5 vol). The batch was agitated at 125 rpm. The batch temperature was adjusted to 90° C. over 4 h. The batch was stirred at 90° C. for 16.5 h. The reaction was monitored by HPLC. The batch was cooled over approximately 2 h to 24° C. The cooled reaction mixture was removed from the reactor to a carboy, and the reactor was cleaned with methanol, acetone, and then water. The reactor was charged with water (43.2 L, 9.6 vol) and acetonitrile (1.8 L, 0.4 vol). The batch temperature was adjusted to 20° C. The product mixture in the carboy was dosed to the quench solution over 2 h maintaining the temperature at 15-25° C. The precipitated product slurry was transferred to a Nutsche filter. The reactor and filter cake were rinsed with water (2×22.5 L, 2×5 vol), and the filter cake was conditioned under nitrogen overnight. The wet cake (18.6 kg) was dried in a tray drier at 40-45° C. for 11 days to afford 7.05 kg of tert-butyl 4-(2-(2,6-dioxopiperidin-3-yl)-6-fluoro-1,3-dioxoisoindolin-5-yl)piperazine-1-carboxylate (Intermediate 9) (100% yield). The water content of the batch was 0.6 wt % by KF titration and the $^1H$ NMR potency ($d_6$-DMSO) was 84.7 wt %. The H NMR spectrum was consistent with the assigned structure (see FIG. 21) and the HPLC purity was 98.6 area %.

Step 3: 2-(2,6-dioxopiperidin-3-yl)-5-fluoro-6-(piperazin-1-yl)isoindoline-1,3-dione hydrochloride. A 30-gallon, Pfaudler reactor was equipped with a sodium hydroxide (2 M) scrubber. The reactor was charged with 3 M hydrochloric acid solution in methanol (70 L, 10 vol). The batch was agitated at 75 rpm. The batch temperature was adjusted to 31.7° C. over 30 min. Intermediate 9 (7.00 kg, 15.20 mol) and methylene chloride (28 L, 4 vol) were charged to a 40-L carboy. The slurry was stirred to dissolve the Intermediate 9. The solution of Intermediate 9 was charged to the 30-gallon reactor over 6.5 h maintaining the temperature at 30-40° C. The batch was aged at 35° C. for 21 h. The reaction was monitored by HPLC. The batch was cooled to 17.4° C. over approximately 30 min. The slurry was filtered in a Nutsche filter. The reactor and the filter cake were rinsed with a mixture of methanol (15.75 L) and methylene chloride (5.25 L). The wet cake (7.1 kg) was dried in a tray drier at 40-50° C. to afford 5.14 kg of product (85% yield). The water content of the batch was 3.4 wt % by KF titration and the $^1H$ NMR potency ($d_6$-DMSO) was 92.4 wt %. The $^1H$ NMR spectrum was consistent with the assigned structure and the HPLC purity was 97.5 area %.

Figure 22:
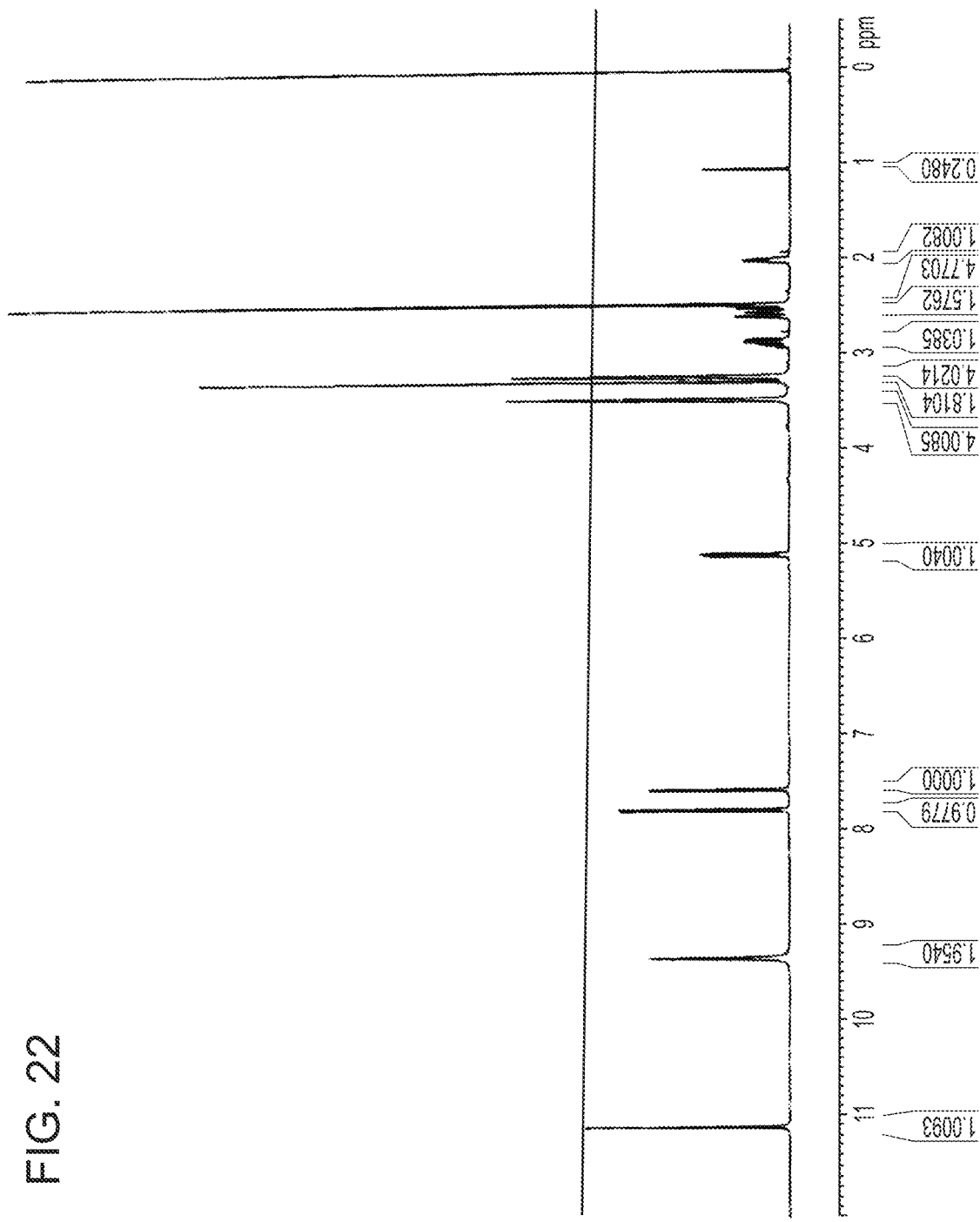
FIG. 22 is an H$^1$-NMR spectrum of Intermediate 5, produced by the second-generation synthesis, in deuterated dimethylsulfoxide (DMSO-d$_6$).

The batch was then re-purified. To a 100-L, jacketed reactor was charged the previous product (4.95 kg, 12.5 mol) and dimethylacetamide (15.0 L, 3 vol). The batch temperature was adjusted to 55° C. Water (8.4 L, 1.7 vol) was charged in one portion to the batch and the temperature was re-adjusted 55-65° C. The mixture was stirred for 44 min to obtain a clear solution. To the batch was charged 2-propanol (40 L, 8 vol) over 1 h maintaining the temperature above 45° C. The batch was seeded at 55° C. with Intermediate 5 seeds (5 g). The batch was held at 45-55° C. for 20 min and was cooled over 1 h to 25° C. The batch was aged for 17.5 h at 20-25° C. The slurry was filtered in a Nutsche filter. The reactor and filter cake was rinsed with 2-propanol (25 L, 5 vol). The filter cake was washed again with 2-propanol (25 L, 5 vol). The wet cake (5.8 kg) was dried in a tray drier at 40-50° C. to afford 3.95 kg of product (79% recovery). The water content of the batch was 2.1 wt % by KF titration and the $^1H$ NMR potency ($d_6$-DMSO) was 98.2 wt %. The $^1H$ NMR spectrum is shown in FIG. 22 and the HPLC purity was 99.8 area %.

Third Generation Synthesis

Example 7: Third Generation Synthesis of Compound A

Step 1: 6-(4-(hydroxymethyl)piperidin-1-yl)pyridazine-3-carboxylic acid (Intermediate 10). The synthetic route to Intermediate 10 is shown below in Scheme 7.

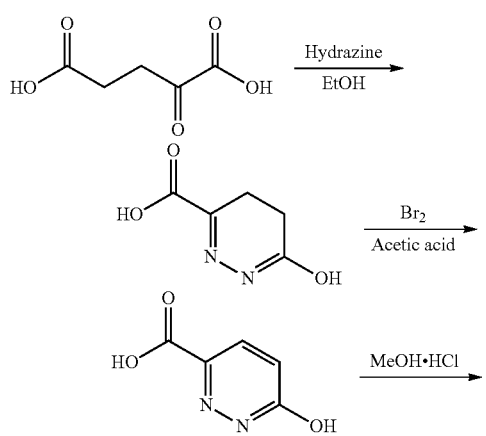

Scheme 7. Synthetic route to Intermediate 10

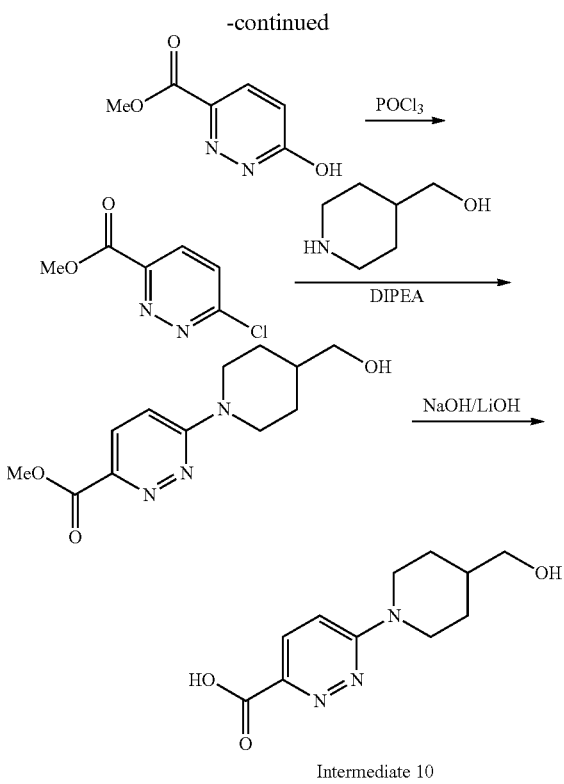

Intermediate 10

Step 2: N-((1r,4r)-4-(3-chloro-4-cyanophenoxy)cyclohexyl)-6-(4-(hydroxymethyl)piperidin-1-yl)pyridazine-3-carboxamide. In a 30-L jacketed reactor equipped with a mechanical stirrer, thermometer and nitrogen bleed was added 6-(4-(hydroxymethyl)piperidin-1-yl)pyridazine-3-carboxylic acid (Intermediate 10) (500 g, 2.11 mol, 1 eq), 4-(((1r,4r)-4-aminocyclohexyl)oxy)-2-chlorobenzonitrile hydrochloride (Intermediate 7) (654 g, 2.28 mol, 1.08 eq) and DMAc (2.5 L, 5 vol). To the mixture was added DIPEA (1.092 Kg, 8.43 mol, 4 eq) and ethyl cyanohydroxyiminoacetate (314 g, 2.21 mol, 1.05 eq). To the slurry was added 1-Ethyl-3-(3-dimethylaminopropyl)carbodiimide (EDCI) (525 g, 2.74 mol, 1.3 eq) at once. The temperature of the reaction mixture was increased to ~40° C. The reaction mixture was kept at internal temperature of ~40° C. for ~3 h. The reaction was monitored by IPC.

Figure 23:
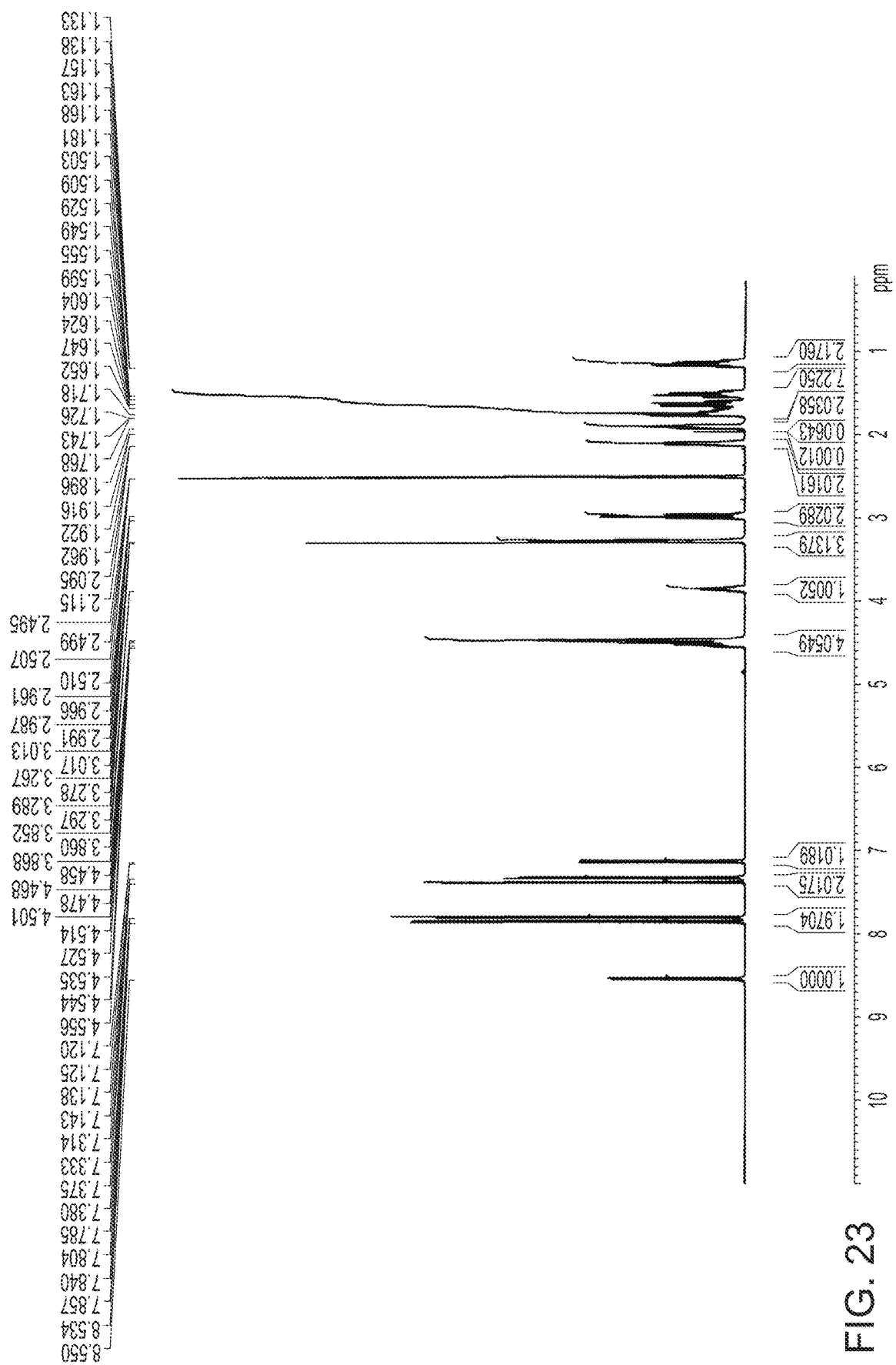
FIG. 23 is an H$^1$-NMR spectrum of Intermediate 2, produced by the third-generation synthesis, in deuterated dimethylsulfoxide (DMSO-d$_6$).

The reaction mixture was diluted with IPAc (5 L, 10 vol) and H₂O (DI, 5 L, 10 vol). The internal temperature was adjusted to 50±5° C. while the biphasic mixture was mixing vigorously. The mixture was kept at 50° C. for 15 minutes while mixing. The aqueous phase was drained and the organic phase was washed with H₂O (3×5 L, 3×10 vol) at 50° C. The organic phase was drained in to a carboy. The aqueous phase was transferred in to the reactor and washed with IPAc (2.5 L, 5 vol) at 50±5° C. All organic phases were combined and transferred in to the reactor (initial KF value: 19754 ppm). The organic phase was concentrated down to ~3 L (KF value: 4436 ppm). To the mixture was added IPAc (5 L, 10 vol) and distillation was continued to the final volume of 3 L (KF value: 1169 ppm, <3000 ppm). A thick solid residue was precipitated from the mixture. The thick slurry mixture was stirred at room temperature for the additional 18 hours. The slurry was filtered and the wet cake was rinsed with IPAc (2×5 L, 2×2.5 vol). The cake was aged under vacuum for 1.5 hours. The cake was further dried in vacuum oven at 35° C. to constant weight. N-((1r,4r)-4-(3-chloro-4-cyanophenoxy)cyclohexyl)-6-(4-(hydroxymethyl)piperidin-1-yl)pyridazine-3-carboxamide (Intermediate 2) (830 g, 84% isolated yield, 99.2% HPLC purity, RRT 1.11: ~0.13%). The ¹HNMR spectrum is shown in FIG. 23

Step 3: N-((1r,4r)-4-(3-chloro-4-cyanophenoxy)cyclohexyl)-6-(4-formylpiperidin-1-yl)pyridazine-3-carboxamide. In a 30-L jacketed reactor equipped with a mechanical stirrer, thermometer and nitrogen bleed was added Intermediate 2 (700 g, 1.49 mol, 1 eq) followed by DCM (5.6 L. 8 vol). To the clear solution was added NaHCO₃ (189 g, 2.25 mol, 0.27 wt %), NaBr (168 g, 1.63 mol, 0.24 wt %) and water (DI, 3.5 l, 5 vol) at room temperature. The biphasic mixture was cooled down to <5° C. To the reaction mixture was added solution of TEMPO (23 g, 0.015 mol, 0.0033 wt %) in DCM (1.4 L, 2 vol) at once (no exotherm was observed). To the reaction mixture was added NaOCl solution (2.18 Kg, 3.12 wt %) in portions while keeping the internal temperature<5° C. The reaction was monitored by IPC and HPLC. Extra portion of NaOCl (0.293 Kg, 0.5 wt %) was added to the reaction mixture.

Figure 24:
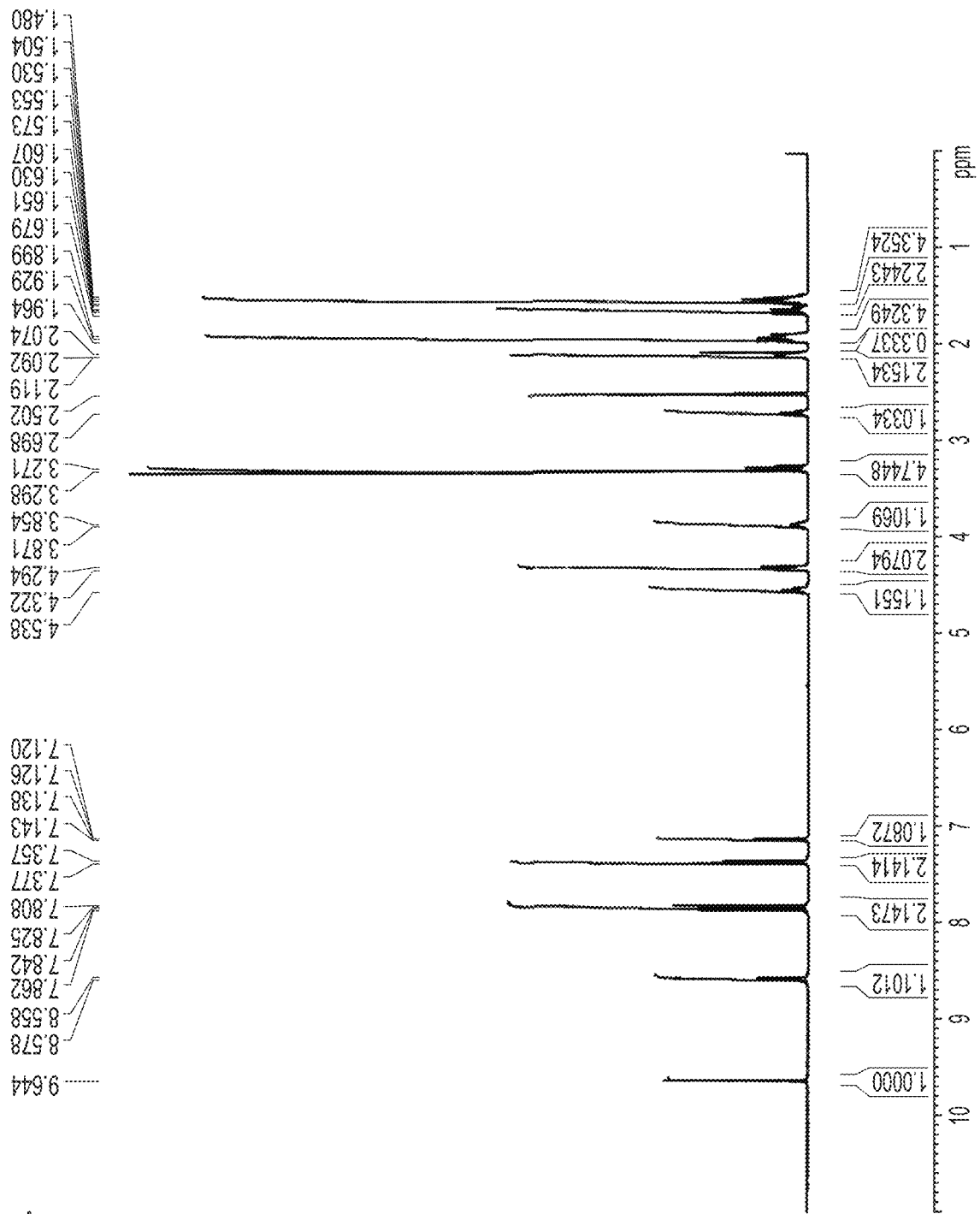
FIG. 24 is an H$^1$-NMR spectrum of Intermediate 3, produced by the third-generation synthesis, in deuterated dimethylsulfoxide (DMSO-d$_6$).

The agitation was stopped and the layers were separated. The organic phase was drained and collected in a clean carboy. The aqueous phase was back extracted using DCM (1.4 L, 2 vol) and the organic was collected. The aqueous phase was discarded. The organic phase was transferred in to the reactor and washed with Na₂SO₃ solution (0.5 M, 2.94 L, 4.2 vol). A thick emulsion was formed. To the mixture was added brine (1 L). A partial separation of the aqueous phase was observed. The clear aqueous phase was removed and to the emulsion was added THF (1.3 L, 10% with respect to the emulsion volume). The stirring was stopped after 10 min and the layers were separated. The aqueous phase was back extracted using DCM (1.4 L, 2 vol). The organic phase was collected and the aqueous phase was discarded. All organic phases were transferred into the reactor. To the reactor was added ACN (2.94 L4.2 vol) and the mixture was distilled under reduced pressure to the final volume of 4.5 L. To the reactor was charged ACN (5.7 L, 8.1 vol) and distillation was continued. An IPC of the sample showed 7 wt % of DCM with respect to Intermediate 3 remained. To the reactor was added ACN (4.2 L, 6 vol) and distillation was continued to the final volume of 4 L. Distillation was monitored by IPC. The batch temperature was adjusted to 18° C. To the batch was added ACN (3 L, 4.2 vol) total ACN volume of 7 L (10 vol). To the mixture was added water (DI, 7 L, 10 vol) and the mixture was stirred at 18° C. for 18 hours before filtration. The product was filtered on a Buckner funnel and the wet cake was aged under vacuum for 45 min. The cake was transferred into a glass tray and dried further in vacuum oven at 35±5° C. to the constant weight. N-((1r,4r)-4-(3-chloro-4-cyanophenoxy)cyclohexyl)-6-(4-formylpiperidin-1-yl)pyridazine-3-carboxamide (Intermediate 3) (676 g, 96% yield, 0.96 wt % ACN content, 94 wt % potency, 96% HPLC purity, 1.93% Intermediate 2). The ¹HNMR spectrum is shown in FIG. 24.

Step 4: N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-S-yl)piperazin-1-yl)methyl)piperidin-1-yl)pyridazine-3-carboxamide. To a clean, dry, 10-L, jacketed, glass reactor equipped with a temperature controller, thermometer, mechanical stirrer and a nitrogen bleed was charged dimethylacetamide (1.24 L, 2.75 vol) and sodium triacetoxyborohydride (528 g, 2.42 eq). The resulting suspension was cooled to 5±5° C.

To a clean, dry, 30-L, jacketed, glass reactor equipped with a temperature controller, a thermometer, mechanical stirrer and a nitrogen bleed, was charged dimethylacetamide (2.2 L, 4.9 vol), Intermediate 5 (450 g, 90.7 wt %), and Intermediate 3 (563 g, 94 wt %, 1.1 eq). The internal temperature was adjusted to 0±5° then trimethylamine (315 mL) was added over 40 min while maintaining the internal temperature<5° C. The contents of the reactor containing Intermediate 5 and Intermediate 3 were transferred to the reactor containing the sodium triacetoxyborohydride over 40 min while maintaining an internal temperature of to 5±5° C. Once the transfer was complete, the reactor was rinsed with dimethylacetamide (DMAC) (225 mL, 0.5 vol) and the rinse transferred to the other reactor. The batch was stirred for an additional 1 hour at 5±5° C. The reaction was monitored by IPC.

To a clean, dry, 30-L, jacketed, glass reactor equipped with a temperature controller, thermometer and a nitrogen bleed was charged ethanol (5.5 L, 12.1 vol) and purified water (5.6 L, 12.4 vol). The internal temperature was adjusted to 15±5° C. The contents of the reactor containing the process mixture were transferred to the new reactor over 1 hour while maintaining the internal temperature<20° C. Once the transfer was complete, the former reactor was rinsed with DMAC (200 mL, 0.5 vol) and the rinse transferred to the latter reactor. The temperature of the batch was adjusted to 50° C. and held at this temperature for an additional 1 hour. The batch was cooled to 20° C. over 81 min, held at this temperature for 1, then the precipitated solid was isolated by vacuum filtration. The reactor was rinsed with ethanol/purified water 1:1 (2×2.9 L, 2×6.4 vol) and the rinse used to wash the filter cake. The wet cake was further washed with ethanol (2×2.9 L, 2×6.4 vol). After conditioning on the filter 1 hour, the wet-cake (crude Compound A) was transferred to three glass drying trays dried in a vacuum oven at 50° C. for 3 days. Constant weight was not achieved.

Figure 25:
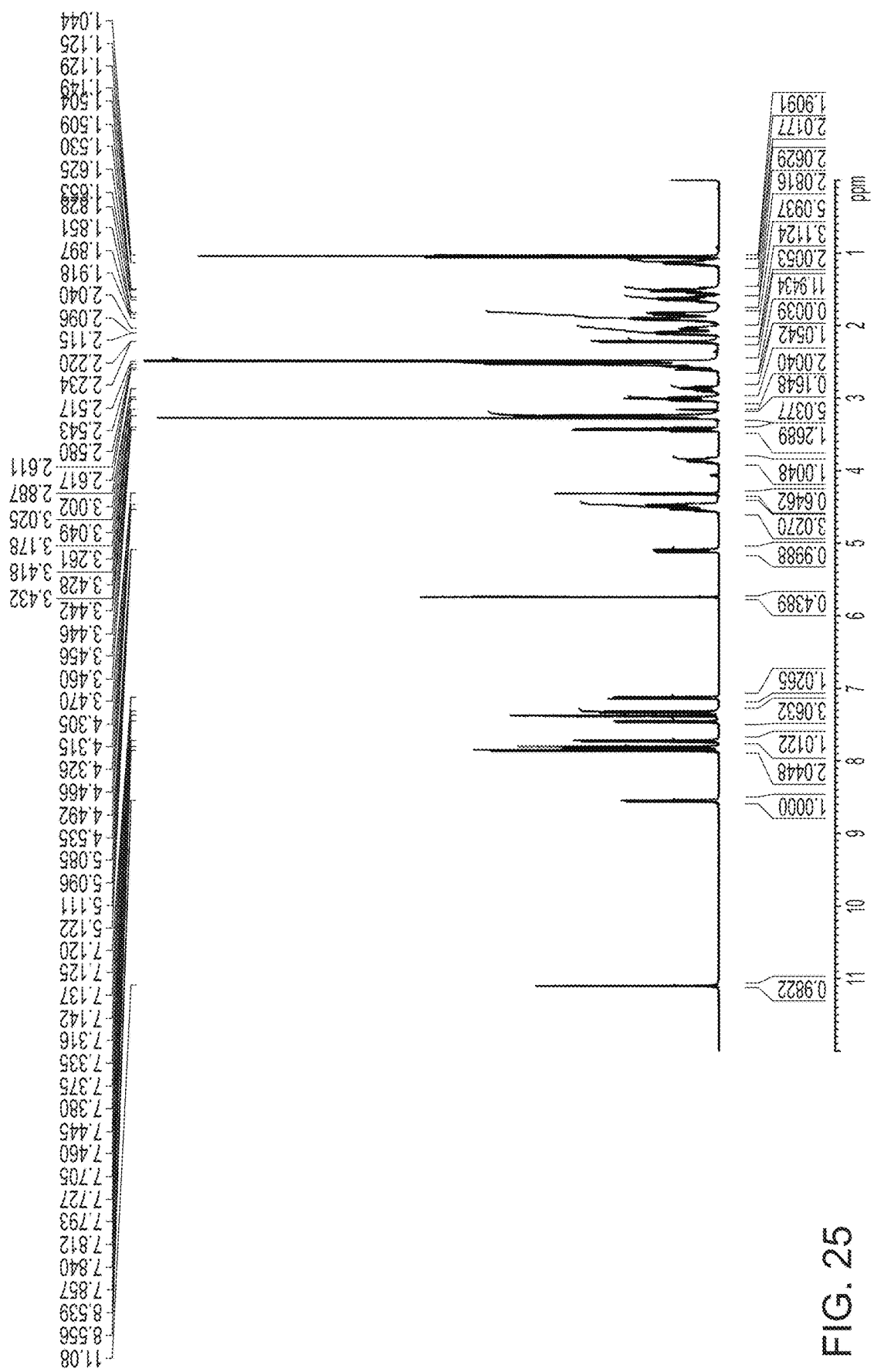
FIG. 25 is an H$^1$-NMR spectrum of Compound A, produced by the third-generation synthesis, in deuterated dimethylsulfoxide (DMSO-d$_6$).

To a clean, dry, 30-L, jacketed, glass reactor equipped with a temperature controller, a thermometer, mechanical stirrer, condenser, vacuum controller and a nitrogen bleed was charged dichloromethane (15 L, 16.2 vol), methanol (1.66 L, 1.8 vol), and crude Compound A (925 g, 1 wt). The batch was stirred until complete dissolution was observed. The batch was clarified through a 0.4 micron in-line filter then distilled under vacuum (jacket temp. 65° C.) while adding ethanol (5.6 L, 8 vol) at such a rate that a total volume of ≈18.5 L was maintained. Compound A seed crystals (1.85 g, 0.0025 wt) slurried in ethanol (120 mL) were added to the batch. Distillation under vacuum (jacket temp. 65° C.) was continued while adding ethanol (10 L, 10 vol) at such a rate that a total volume of ≈18 L was maintained. Distillation was monitored by IPC. The batch was stirred at 20±5° C. for 18 hours then the precipitated solid was isolated by vacuum filtration. The wet cake was further washed with purified water (2×2 L, 2×2 vol) and ethanol (2×2 L, 2×2 vol). The wet-cake was dried in a vacuum at 25° C. for ≈24 h until a constant weight was achieved. The isolated N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide (Compound A) (850 g, 100%) HPLC Analysis: 99.22 area % (FIG. 18). The $^1$HNMR spectrum is shown in FIG. 25.

Example 8. Elucidation of Structure and Other Physical Characteristics of Compound A Scheme 8. Numbered Carbon Atoms of Compound A.

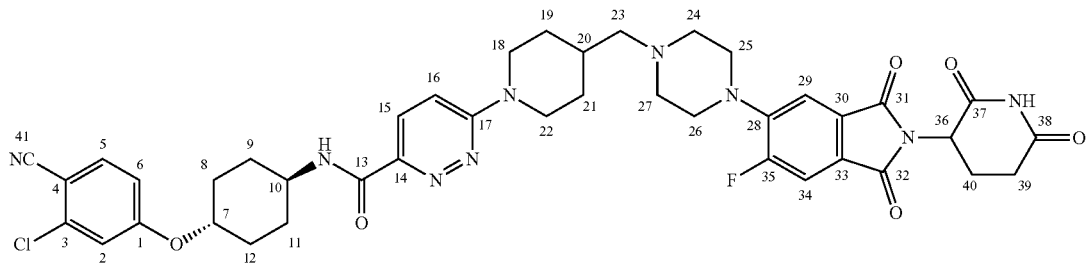

There is a single stereogenic center in the Compound A molecule at carbon 36. The starting materials for Compound A are sourced from achiral precursors, hence the molecule is racemic.

The centers carbon 10 and 7 are meso and by definition have no chirality. The 1,4-trans relationship of the amide and ether on carbons 10 and 7, respectively, is supported by $^1$H nuclear magnetic resonance (NMR) in conjunction with 2-D nOe NMR.

The drug substance has been characterized by application of various spectroscopic techniques ($^1$H NMR, $^{13}$C NMR, mass spectrometry (MS), and Infrared spectroscopy (IR)), all of which support the chemical structure.

NMR Spectroscopy

Figure 4:
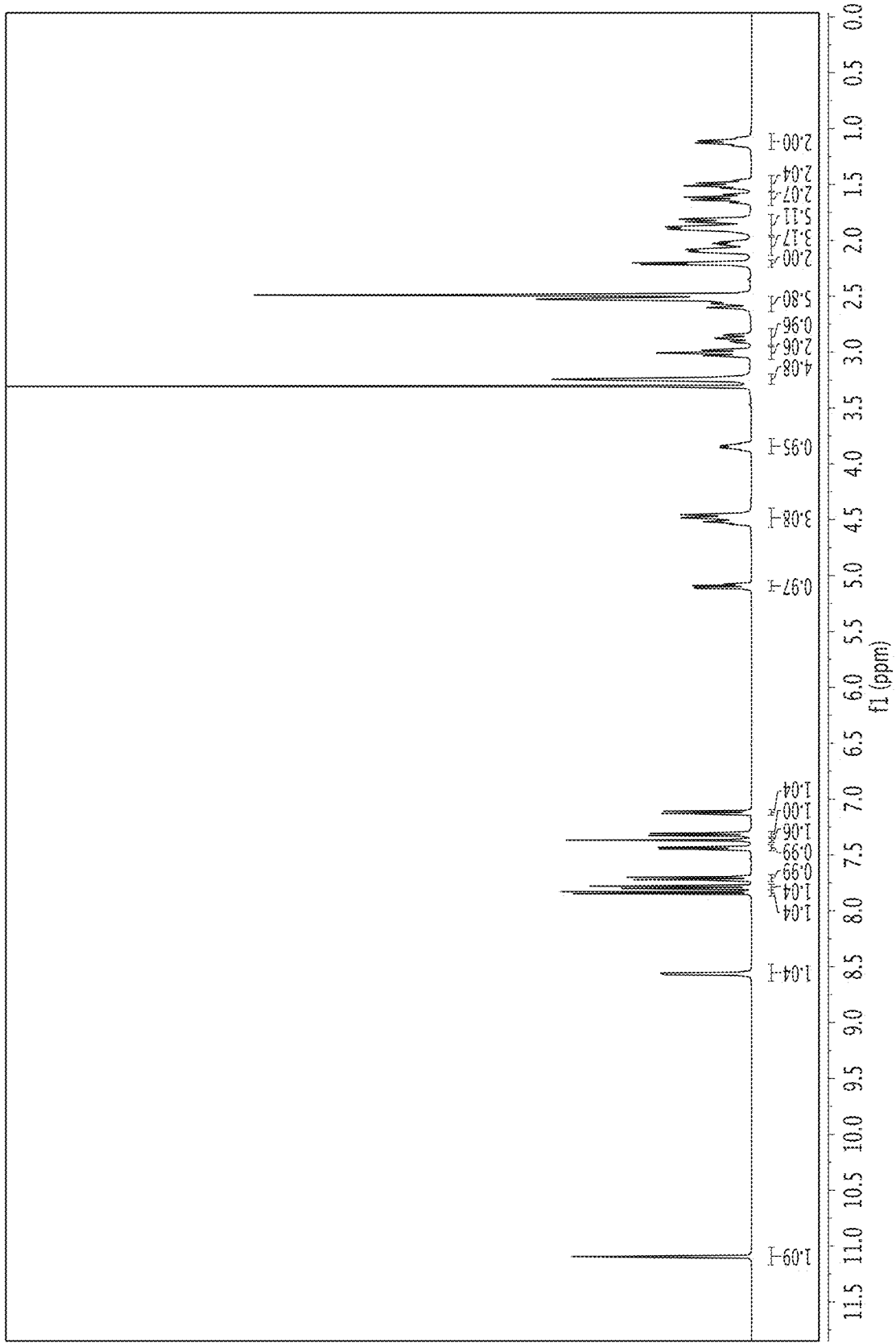
FIG. 4 is a $^1$H NMR Spectrum of Compound A in deuterated dimethylsulfoxide (DMSO-$d_6$).
Figure 5:
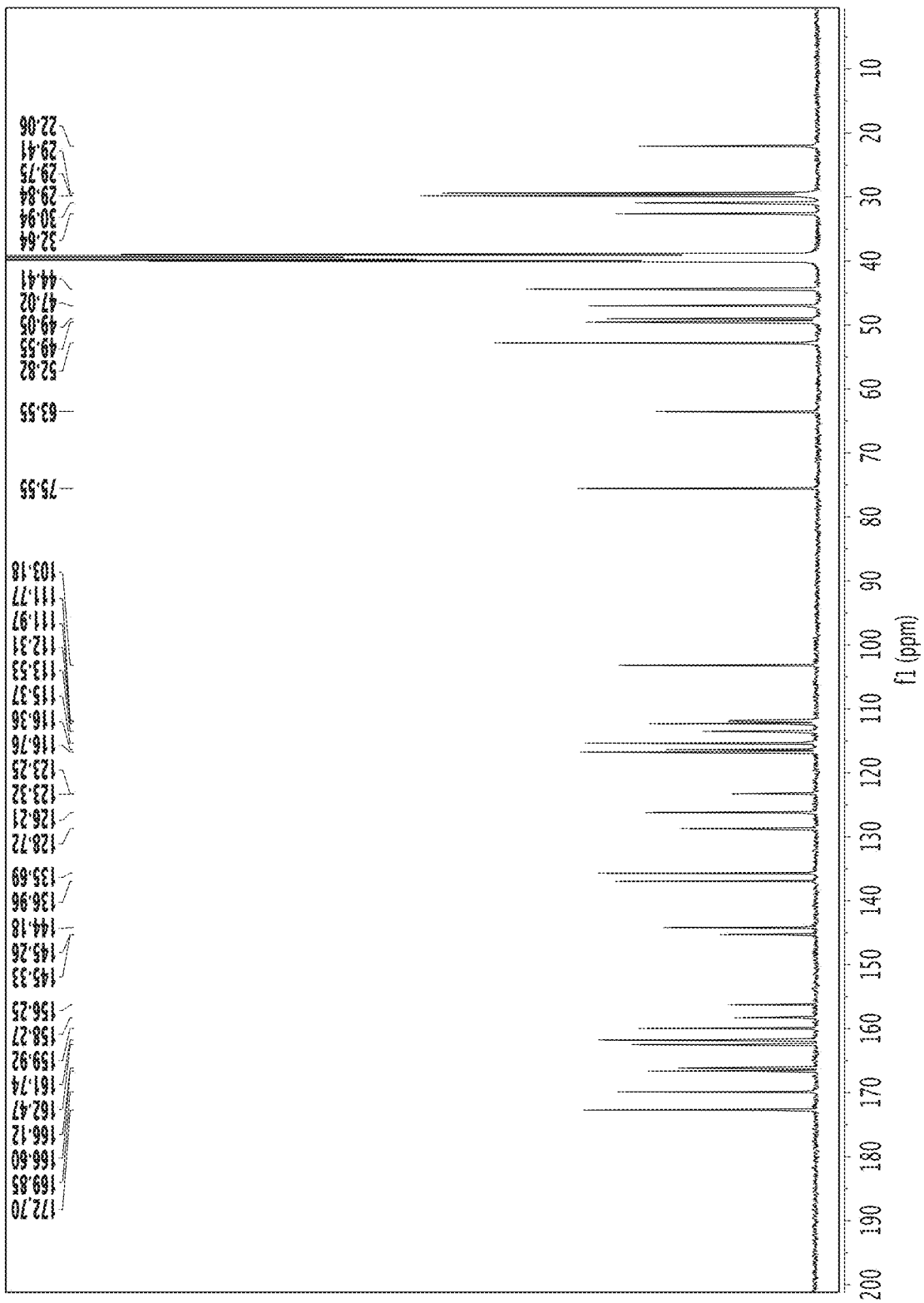
FIG. 5 is a $^{13}$C NMR Spectrum of Compound A in deuterated dimethylsulfoxide (DMSO-$d_6$).

The $^1$H and $^{13}$C NMR reference spectra of Compound A were taken in the NMR solvent deuterated dimethylsulfoxide (DMSO-d$_6$). The spectra were obtained on a Bruker 500 MHz spectrometer. The $^1$H NMR spectrum is presented in FIG. 4. The $^{13}$C NMR spectrum for Compound A is presented in FIG. 5. Chemical shift assignments for both spectra are also provided in Table 3.

The resonances in both the $^1$H and $^{13}$C spectra were assigned based on $^1$H-$^1$H COSY, $^1$H-$^{13}$C edited HSQC and $^1$H-$^{13}$C HMBC experiments. All NMR data acquired support the structure of Compound A.

TABLE 3

$^1$H and $^{13}$C NMR: Chemical Shifts of Compound A

| Position[a] | $^1$H Chemical Shift[b, c], Integ., multiplicity, J (Hz)[d] | $^{13}$C Chemical Shift[b], J (Hz) |
|---|---|---|
| 1 | — | 161.7 |
| 2 | 7.37, 1H, d (2.39) | 116.8 |
| 3 | — | 137.0 |
| 4 | — | 103.2 |
| 5 | 7.84, 1H, d(8.77) | 135.7 |
| 6 | 7.12, 1H, dd (8.80, 2.39) | 115.4 |
| 7 | 4.51, 1H, m | 75.6 |
| 8, 12 | 1.50, 2H, m; 2.09, 2H, br d (10.14) | 29.8 |
| 9, 11 | 1.63, 2H, aq; 1.88, 2H, overlapping br ad | 29.4 |
| 10 | 3.85, 1H, m | 47.0 |
| 10-NH | 8.56, 1H, d (8.21) | — |
| 13 | — | 162.5 |
| 14 | — | 144.2 |
| 15 | 7.79, 1H, d (9.55) | 126.2 |
| 16 | 7.32, 1H, d (9.71) | 112.3 |
| 17 | — | 159.9 |
| 18, 22 | 4.47, 2H, br d (12.97); 3.01, 2H, t (11.78) | 44.4 |
| 19, 21 | 1.82, 2H, br d (11.49); 1.12, 2H, m | 29.8 |
| 20 | 1.90, 1H, overlapping br ad | 32.6 |
| 23 | 2.21, 2H, d (7.04) | 63.6 |
| 24, 27 | 2.53, 4H, br s | 52.8 |
| 25, 26 | 3.24, 4H, br s | 49.6 |
| 28 | — | 145.3 ($^2J_{C-F}$ = 8.55) |
| 29 | 7.44, 1H, d ($^4J_{H-F}$ = 7.38) | 113.5 |
| 30 | — | 128.7 |
| 31 | — | 166.6 |
| 32 | — | 166.1 |
| 33 | — | 123.3 ($^3J_{C-F}$ = 9.61) |
| 34 | 7.71, 1H, d ($^3J_{H-F}$ = 11.43) | 111.9 ($^2J_{C-F}$ = 24.92) |
| 35 | — | 157.3 ($^1J_{C-F}$ = 253.69) |
| 36 | 5.10, 1H, dd (12.87, 5.41) | 49.0 |
| 37 | — | 169.9 |
| 37-NH | 11.09, 1H, s | — |
| 38 | — | 172.7 |
| 39 | 2.59, 1H, m; 2.88, 1H, m | 30.9 |
| 40 | 2.02, 1H, m; 2.51, 1H, overlapping m; | 22.1 |
| 41 | — | 116.4 |

NMR = nuclear magnetic resonance
[a]The numbering used in the structure is for convenience and may not be consistent with IUPAC nomenclature.
[b]$^1$H and $^{13}$C NMR chemical shifts were referenced to the resonances due to the NMR solvent at 2.49 and 39.5 ppm, respectively.
[c]d = doublet, dd = doublet of doublet, m = multiplet, s = singlet, t = triplet, br = broad, aq = apparent quartet, ad = apparent doublet.
[d]1H-1H coupling constants in Hertz are given in parenthesis.

Mass Spectrometry

High resolution mass spectrometry (MS) analyses of Compound A were conducted with flow injection analysis using positive ion electrospray [high-resolution electrospray ionization mass spectrometry (HR-ESI)] on a Thermo Orbitrap MS in Fourier Transform mode.

Figure 6:
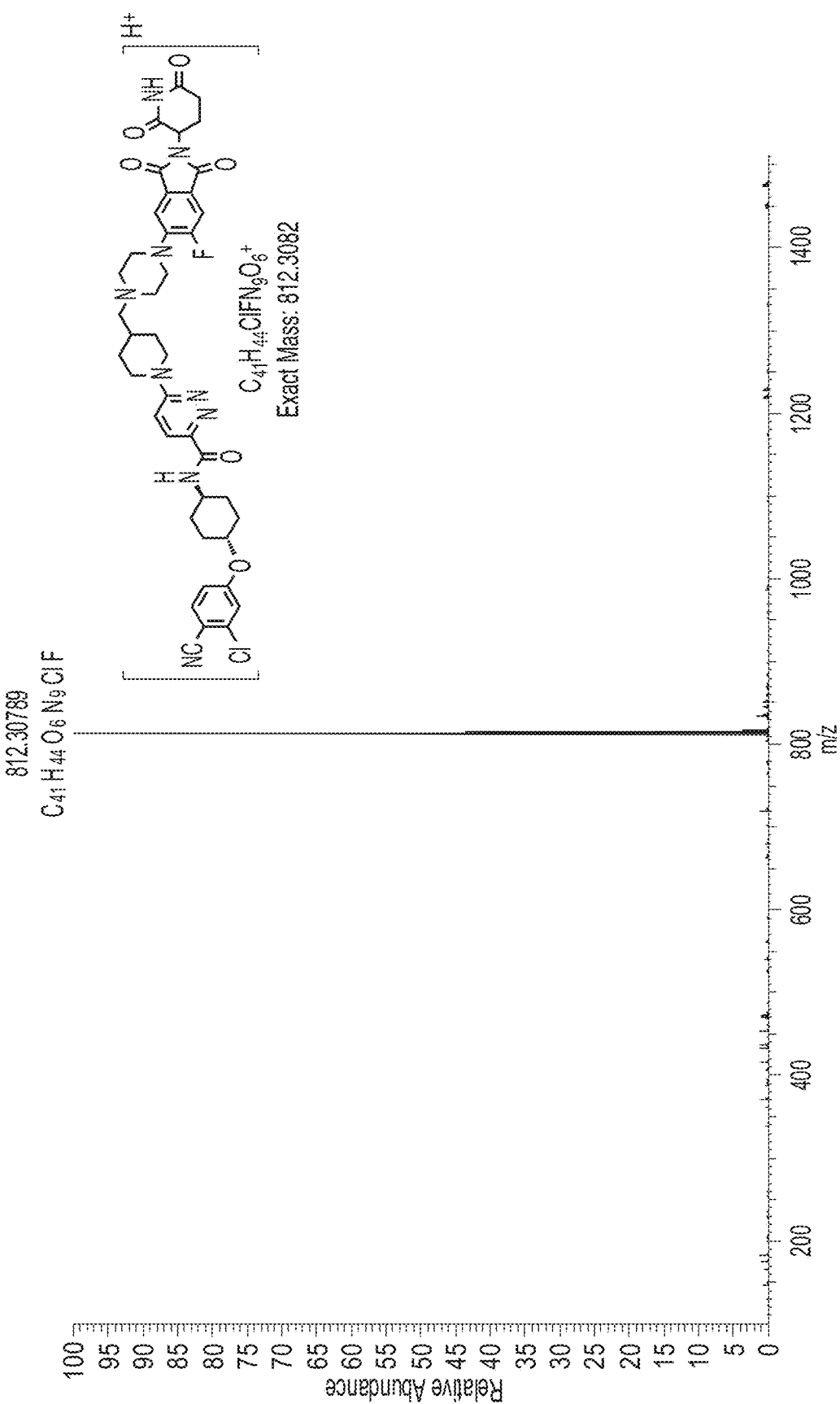
FIG. 6 is a high resolution mass spectrum of Compound A. High resolution mass spectrometry (MS) analyses of Compound A were conducted with flow injection analysis using positive ion electrospray [high-resolution electrospray ionization mass spectrometry (HR-ESI)] on a Thermo Orbitrap MS in Fourier Transform mode.
Figure 7:
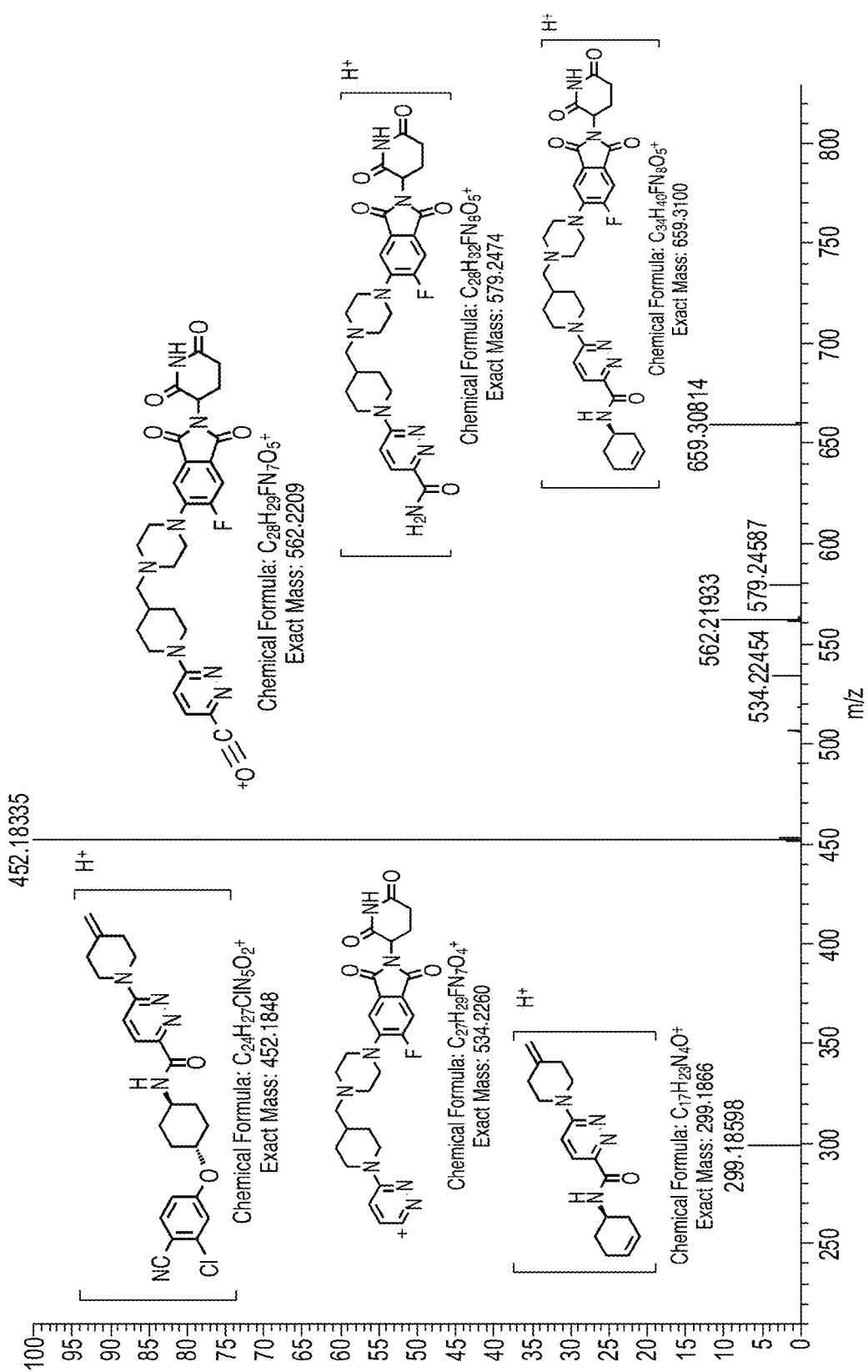
FIG. 7 shows the major peaks resulting from MS/MS fragmentation of the 812.308 parent ion from the high resolution mass spectrum of Compound A

The high resolution mass spectrum of Compound A is presented in FIG. 6, and the major peaks resulting from MS/MS fragmentation of the 812.308 parent ion are presented in FIG. 7.

Figure 8A:
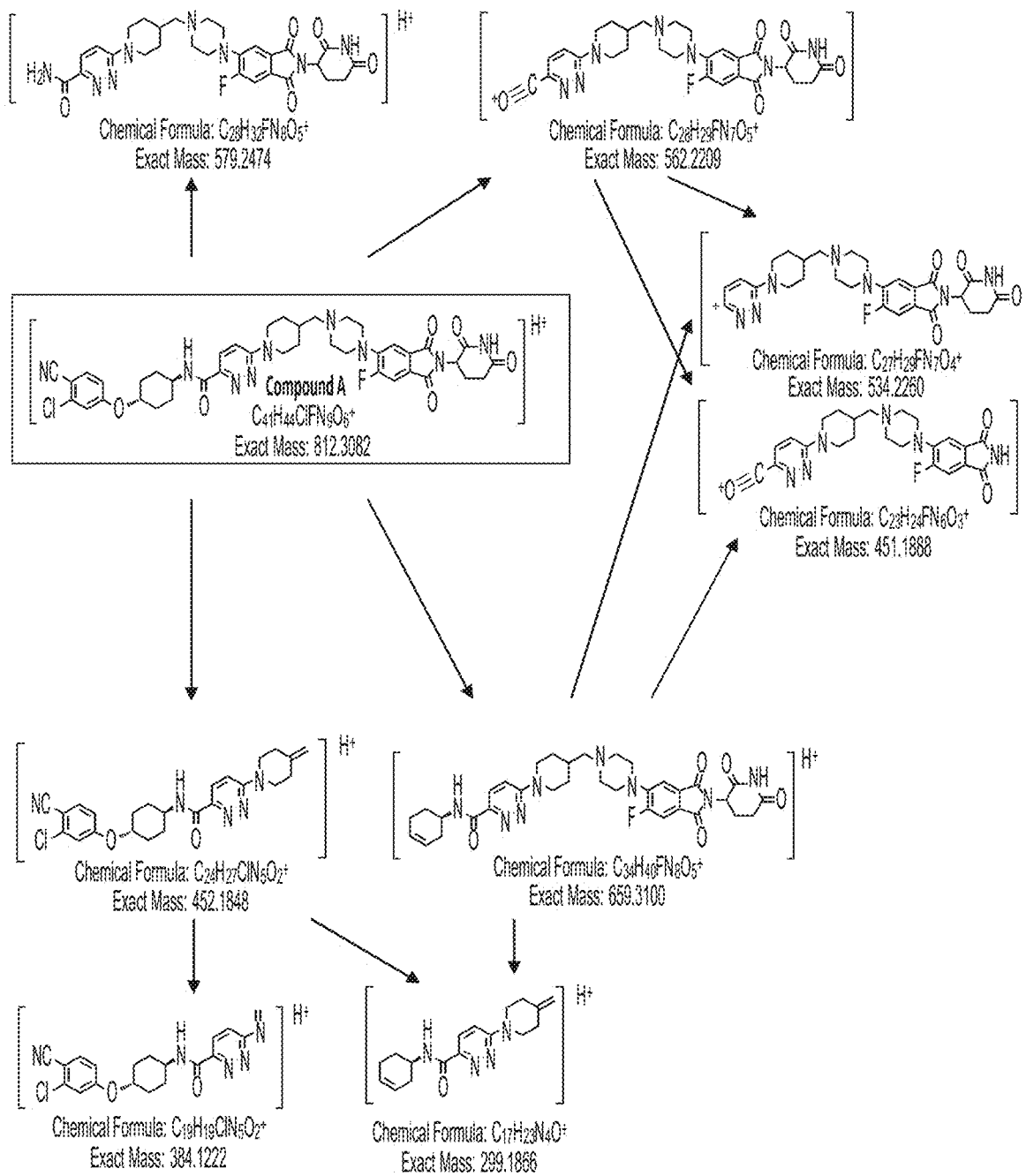

Further fragmentation of the observed MS/MS ions (MS$^3$) was carried out, yielding the ion map provided in FIG. 8. All ions observed were within 4 ppm of theory by accurate mass, and the ion map serves to further confirm the structure of Compound A.

Infrared Spectrometry

Figure 9:
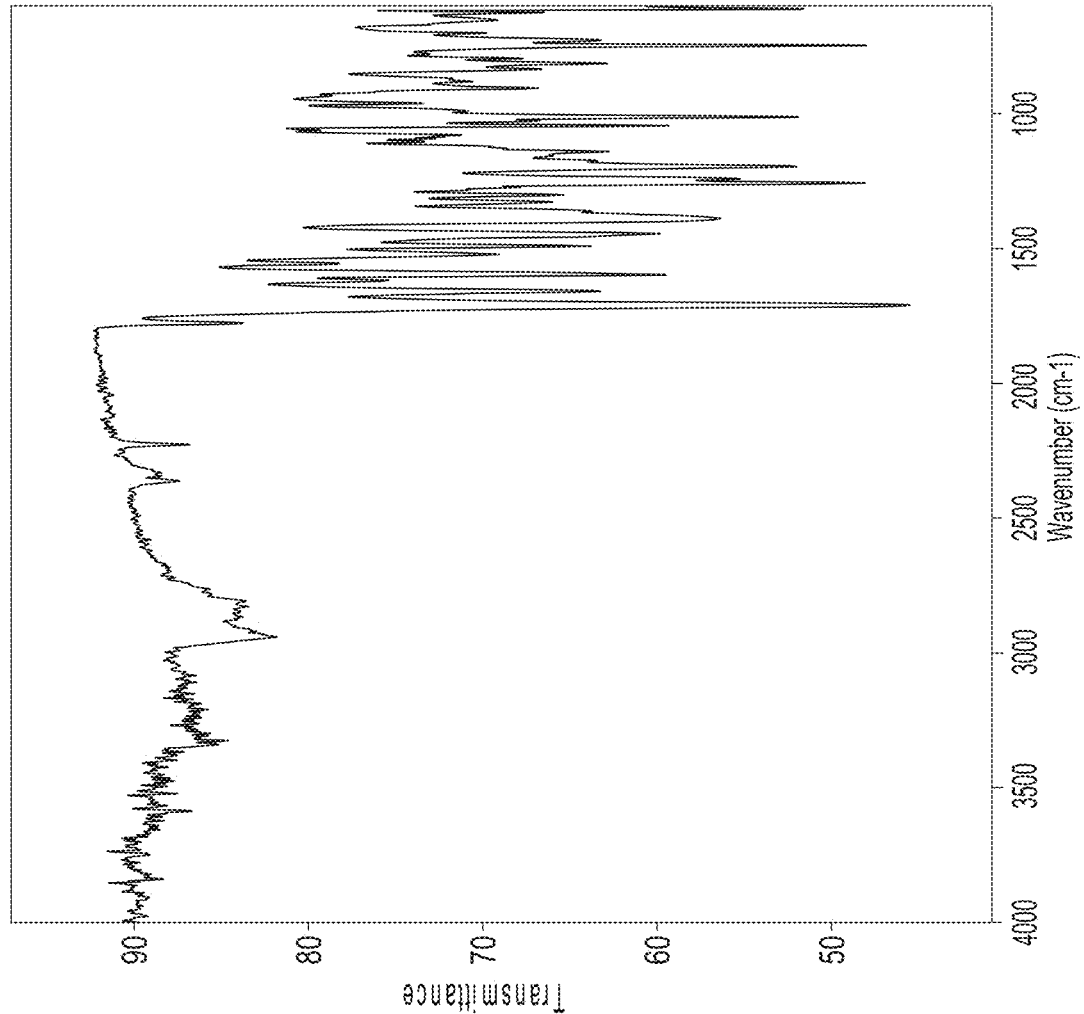
FIG. 9 is an infrared spectrum of Compound A obtained on a Bomem MB-102 FTIR spectrometer equipped with a DuraSamplIR diamond ATR probe. Key features which lend further support to the structure for Compound A are bands at 2225 cm$^{-1}$, representing a nitrile stretch vibration, and five peaks between 1774 and 1594, which represent four imide carbonyl vibrations and an amide carbonyl stretch vibration.

An infrared spectrum of Compound A was obtained on a Bomem MB-102 FTIR spectrometer equipped with a DuraSamplIR diamond ATR probe. The spectrum is shown in FIG. 9, along with a listing of peaks observed. Key features which lend further support to the structure for Compound A are bands at 2225 cm$^{-1}$, representing a nitrile stretch vibration, and five peaks between 1774 and 1594, which represent four imide carbonyl vibrations and an amide carbonyl stretch vibration. The fingerprint region from 1500-800 cm$^{-1}$ provides a distinct signature from which to identify Compound A.

Example 9: Summary of Studies to Determine the Particle Size Distribution of Compound A The particle size statistics for Batch 12070-C-01-72-01 of Compound A which will be used in preparation of drug product for use in the clinic are shown in Table 4.

TABLE 4

Particle Size Distribution of Compound A

| Batch | D (4,3) μm | D (10) μm | D (50) μm | D (90) μm |
|---|---|---|---|---|
| 12070-C-01-72-01 | 43 | 6 | 24 | 93 |

Example 10. Impurities in the Second-Generation Manufacturing Process for Compound A Batches of Compound A drug substance contain low levels of impurities. The structure and origin of each known impurity are provided in Table 5. The residual levels of solvents used in the last steps of the synthesis are within the limits as per International Conference on Harmonisation (ICH) Q3C: "Impurities: Guidelines for Residual Solvents." Residual elemental metals meet the limits as described in the United States Pharmacopeia (USP) <232/233> for drug product and follows the principles described in Food and Drug Administration (FDA) and ICH Guidelines for Elemental Impurities (ICHQ3D).

TABLE 5

Process Related Impurities in the Compound A Drug Substance

| Compound | Structure | Origin |
| --- | --- | --- |
| Intermediate 3 | 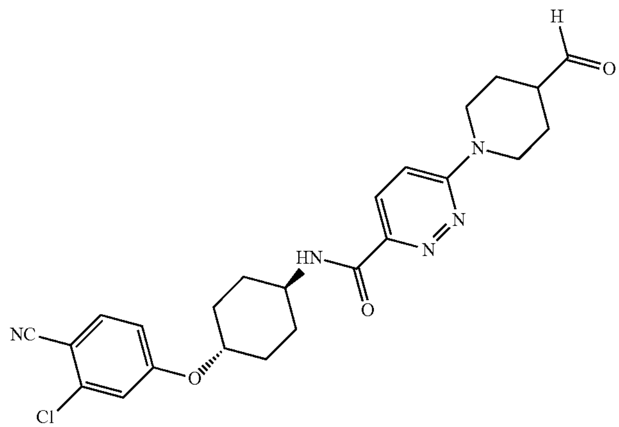 [SMILES: N#Cc1ccc(O[C@H]2CC[C@H](NC(=O)c3ccc(N4CCC(C=O)CC4)nn3)CC2)cc1Cl] | Unreacted starting material from Step 3 (reductive amination) |
| Intermediate 2 | 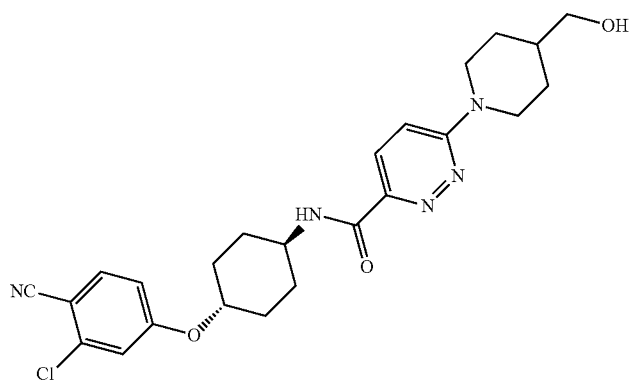 [SMILES: N#Cc1ccc(O[C@H]2CC[C@H](NC(=O)c3ccc(N4CCC(CO)CC4)nn3)CC2)cc1Cl] | A process impurity in Intermediate 3 and can be formed as a by-product of the reductive amination in Step 3. This impurity is also a metabolite in female mouse liver microsomes |
| Impurity 1 | 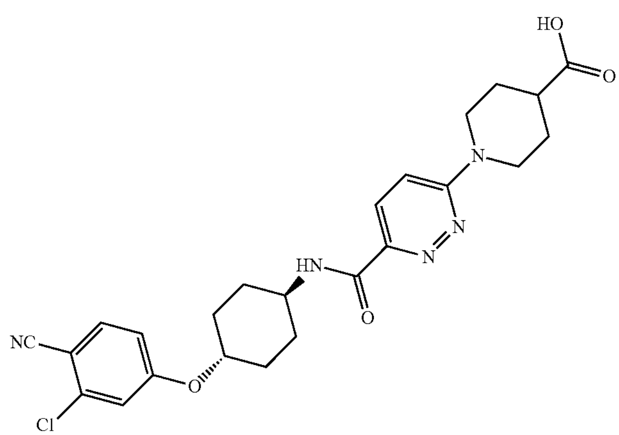 [SMILES: N#Cc1ccc(O[C@H]2CC[C@H](NC(=O)c3ccc(N4CCC(C(=O)O)CC4)nn3)CC2)cc1Cl] | A process impurity resulting from over oxidation of Intermediate 2 in Step 2. This impurity is also a metabolite in male human, monkey, dog, rat, and mouse liver microsomes and hepatocytes |
| Intermediate 5 | 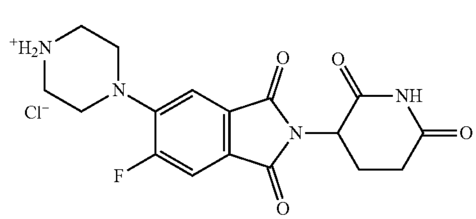 [SMILES: [Cl-] ; O=C1CCC(N2C(=O)c3cc(F)c(N4CC[NH2+]CC4)cc3C2=O)C(=O)N1] | Unreacted starting material from Step 3 (reductive amination). |

Example 11. Analytical Procedures for Compound A Manufacturing Process

Summaries of the compound specific analytical methods for Compound A are presented below.

HPLC for Identity, Assay and Impurities

This is a reverse phase high performance liquid chromatography (HPLC) method devised to determine the assay and impurity profile of Compound A for release and stability testing. The method was qualified for its intended uses. Forced degradation studies were performed and used to qualify this method as stability indicating. The HPLC parameters are listed below in Table 6.

TABLE 6

HPLC Parameters

| | |
|---|---|
| Column: | Waters Atlantis T3, 4.6 × 150 mm, 3 μm |
| Column Temperature: | 45° C. |
| Sample Temperature: | ambient |
| Detection: | 220 nm and 260 nm |
| Mobile Phase A: | 0.1% TFA in Water |
| Mobile Phase B: | 0.05% TFA in 75/25 Acetonitrile/methanol |
| Flow Rate: | 1.0 mL/minute |
| Injection Volume: | 10.0 μL |
| Data Collection Time: | 36 minutes |
| Analysis Time: | 28 minutes |

Gradient:

| Time (minutes) | % A | % B |
|---|---|---|
| 0 | 95.0 | 5.0 |
| 1.00 | 95.0 | 5.0 |
| 10.0 | 55.0 | 45.0 |
| 20.10 | 45.0 | 55.0 |
| 24.10 | 5.0 | 95.0 |
| 28.00 | 5.0 | 95.0 |
| 28.01 | 95.0 | 5.0 |
| 36.00 | 95.0 | 5.0 |

GC Method

This is a gas chromatography (GC) method used to determine the residual solvents in Compound A drug substance. The chromatographic parameters are listed in Table 7.

TABLE 7

GC Parameters for Method Number

| | | | |
|---|---|---|---|
| Column | DB-624 (60 m × 0.32 mm ID × 1.8 μm) | | |
| Carrier Gas | $N_2$ | | |
| FID Temperature | 280° C. | | |
| Makeup ($N_2$) Flow | 30 mL/min | | |
| $H_2$ Flow | 40 mL/min | | |
| Air Flow | 400 mL/min | | |
| Control Mode | Linear Velocity | | |
| Column Temperature Program | Ramp | Temp. (° C.) | Hold Time |
| | — | 45 | 5 min |
| | 10° C./min | 220 | 3 min |
| Injector Temperature | 200° C. | | |
| Split Ratio | 10:1 | | |
| Diluent | NMP | | |
| Run Time | 25.5 min | | |

FID—flame ionization detector;
GC—gas chromatography;
Temp. = temperature

The analytical procedures for the determination of assay, impurities, and residual solvents in Compound A drug substance have been qualified. The qualification criteria are provided within the methods. Qualification for high performance liquid chromatography (HPLC) Method was designed to ensure that the HPLC method is suitable for its intended use of assay and impurity determination. The method was qualified for specificity, limit of detection (LOD), limit of quantification (LOQ), linearity, precision and solution stability. Acceptance criteria were established for each studied parameter. Forced degradation studies determined that method TM05187 is stability indicating and suitable to monitor the assay and impurity determination of Compound A during stability studies. Qualification of the gas chromatographic (GC) Method was designed to ensure that the method is suitable for its intended use for residual solvent determination. The method was qualified for specificity, sensitivity, linearity, and repeatability.

Example 12. Stability Studies with Compound A

An exploratory stability study on Compound A is ongoing. The stability of Compound A will be studied at 5° C., 25° C./60% RH, and 40° C./75% RH with sampling points at 1, 2, 3, and 6 months. Samples will be analyzed using the stability indicating method TEST-05187 (high performance liquid chromatography (HPLC)).

The critical quality attributes of the drug substance Compound A that will be monitored are appearance, purity, assay (wt %), impurities, water content, and x-ray powder diffraction (XRPD). The container and closure system for the stability study consists of double plastic (PE) bags placed inside an high-density polyethylene (HDPE) container. Data from this study are shown in Tables 8, 9, and 10.

TABLE 8

Stability Data for Compound A Storage at 5° C. +/− 3° C.

| Test | At Date of Manufacture: | Initial Date[1] | Initial Date + 1 Month | Initial Date + 2 Months |
|---|---|---|---|---|
| Appearance | Yellow Solid | Yellow Solid | Yellow Solid | Yellow Solid |
| Water Content (wt %) | 0.27 | 0.86 | 0.85 | 1.0 |
| HPLC Assay (wt %) | 97.7 | 99.5 | 97.4 | 97.4 |
| HPLC Purity (%) | 98.0 | 98.4 | 98.4 | 98.4 |
| HPLC Impurities (%) | | | | |
| RRT 0.50 (Intermediate 5) | 0.06 | 0.06 | 0.05 | 0.05 |
| RRT 0.89 | 0.07 | 0.08 | 0.07 | 0.07 |
| RRT 0.90 | ND | <QL | <QL | <QL |
| RRT 0.92 | 0.07 | 0.06 | <QL | 0.06 |
| RRT 0.94 | ND | ND | ND | <QL |
| RRT 0.96 (Intermediate 2) | 0.16 | 0.18 | 0.18 | 0.17 |
| RRT 1.02 | 0.39 | 0.38 | 0.33 | 0.29 |
| RRT 1.04 (Intermediate 3) | 0.12 | 0.11 | 0.09 | <QL |
| RRT 1.05 (Impurity 1) | <QL | ND | ND | ND |
| RRT 1.07 | 0.19 | 0.15 | 0.15 | 0.15 |
| RRT 1.23 | 0.06 | 0.06 | 0.05 | <QL |
| RRT 1.32 | ND | ND | ND | 0.05 |
| RRT 1.36 | 0.05 | ND | <QL | <QL |

TABLE 8-continued

Stability Data for Compound A Storage at 5° C. +/− 3° C.

| Test | At Date of Manufacture: | Initial Date[1] | Initial Date + 1 Month | Initial Date + 2 Months |
|---|---|---|---|---|
| (Intermediate 9) | | | | |
| RRT 1.39 | 0.67 | 0.45 | 0.58 | 0.61 |
| RRT 1.54 | ND | <QL | <QL | <QL |
| Total Impurities (%) | 2.0 | 1.3 | 1.5 | 1.5 |
| XRPD | Crystalline | Crystalline | Crystalline | Crystalline |

[1]about 3 months after date of manufacture
HPLC—high performance liquid chromatography;
ND = <_0.02%;
QL = 0.05%;
XRPD—x-ray powder diffraction

TABLE 9

Stability Data for Compound A Storage at 25° C. ± 2° C./60% RH ± 5%

| Test | At Date of Manufacture: | Initial Date[1] | Initial Date + 1 Month | Initial Date + 2 Months |
|---|---|---|---|---|
| Appearance | Yellow Solid | Yellow Solid | Yellow Solid | Yellow Solid |
| Water Content | 0.27 | 0.86 | 0.93 | 1.2 |
| HPLC Assay (wt %) | 97.7 | 99.5 | 97.3 | 97.5 |
| HPLC Purity (%) | 98.0 | 98.4 | 98.3 | 98.3 |
| HPLC Impurities (%) | | | | |
| RRT 0.50 (Intermediate 5) | 0.06 | 0.06 | 0.05 | 0.05 |
| RRT 0.89 | 0.07 | 0.08 | 0.07 | 0.07 |
| RRT 0.90 | ND | <QL | <QL | <QL |
| RRT 0.92 | 0.07 | 0.06 | 0.07 | 0.06 |
| RRT 0.94 | ND | ND | ND | <QL |
| RRT 0.96 (Intermediate 2) | 0.16 | 0.18 | 0.18 | 0.17 |
| RRT 1.02 | 0.39 | 0.38 | 0.34 | 0.28 |
| RRT 1.04 (Intermediate 3) | 0.12 | 0.11 | 0.07 | QL |
| RRT 1.05 (Impurity 1) | <QL | ND | ND | ND |
| RRT 1.07 | 0.19 | 0.15 | 0.15 | 0.15 |
| RRT 1.23 | 0.06 | 0.06 | 0.05 | 0.05 |
| RRT 1.32 | ND | ND | ND | <QL |
| RRT 1.36 (Intermediate 9) | 0.05 | ND | <QL | ND |
| RRT 1.39 | 0.67 | 0.45 | 0.57 | 0.65 |
| RRT 1.54 | ND | <QL | <QL | <QL |
| Total Impurities (%) | 2.0 | 1.3 | 1.6 | 1.5 |
| XRPD | Crystalline | Crystalline | Crystalline | Crystalline |

[1]about 3 months after date of manufacture
HPLC—high performance liquid chromatography;
ND = <0.02%;
QL = 0.05%;
XRPD—x-ray powder diffraction

TABLE 10

Stability Data for Compound A Storage at 40° C. ± 2° C./75% RH ± 5%

| Test | At Date of Manufacture: | Initial Date[1] | Initial Date + 1 Month | Initial Date + 2 Months |
|---|---|---|---|---|
| Appearance | Yellow Solid | Yellow Solid | Yellow Solid | Yellow Solid |
| Water Content | 0.27 | 0.86 | 1.0 | 1.3 |
| HPLC Assay (wt %) | 97.7 | 99.5 | 97.3 | 97.2 |
| HPLC Purity (%) | 98.0 | 98.4 | 98.3 | 98.3 |
| HPLC Impurities (%) | | | | |
| RRT 0.50 (Intermediate 5) | 0.06 | 0.06 | 0.05 | 0.06 |
| RRT 0.89 | 0.07 | 0.08 | 0.06 | 0.06 |
| RRT 0.90 | ND | <QL | <QL | <QL |
| RRT 0.92 | 0.07 | 0.06 | 0.07 | 0.07 |
| RRT 0.94 | ND | ND | ND | <QL |
| RRT 0.96 (Intermediate 2) | 0.16 | 0.18 | 0.18 | 0.18 |
| RRT 1.02 | 0.39 | 0.38 | 0.34 | 0.28 |
| RRT 1.04 (Intermediate 3) | 0.12 | 0.11 | 0.08 | <QL |
| RRT 1.05 (Impurity 1) | <QL | ND | ND | ND |
| RRT 1.07 | 0.19 | 0.15 | 0.14 | 0.14 |
| RRT 1.23 | 0.06 | 0.06 | 0.05 | 0.06 |
| RRT 1.32 | ND | ND | ND | <QL |
| RRT 1.36 (Intermediate 9) | 0.05 | ND | <QL | ND |
| RRT 1.39 | 0.67 | 0.45 | 0.58 | 0.63 |
| RRT 1.54 | ND | <QL | <QL | <QL |
| Total Impurities (%) | 2.0 | 1.3 | 1.6 | 1.5 |
| XRPD | Crystalline | Crystalline | Crystalline | Crystalline |

[1]about 3 months after date of manufacture
HPLC—high performance liquid chromatography;
ND = <0.02%;
QL = 0.05%;
XRPD—x-ray powder diffraction Summary: after 2 months at all temperature stations, no increase in impurities nor change in solid properties has been observed. After 5 months from the date of manufacture, no increase in impurities or change in solid properties has been observed. A small increase in the water content has been observed.

Example 13. Description and Composition of the Compound A Tablet

Compound A tablets are intended for oral administration. Tablets containing 5 mg and 35 mg of the drug substance were manufactured with a press weight of 100 mg and 700 mg, respectively, from a common granulation. The tablet compositions are listed in Table 11.

TABLE 11

Composition of Compound A 5 Tablets (5 mg and 35 mg)

| | | Strength | | | |
|---|---|---|---|---|---|
| | | 5 mg | | 35 mg | |
| Component and Quality Standard | Function | mg per unit | % w/w | mg per unit | % w/w |
| Compound A | Active | 5 | 5 | 35 | 5 |
| Microcrystalline Cellulose NF, Ph. Eur, JP | Filler | 45.5 | 45.5 | 318.5 | 45.5 |

TABLE 11-continued

Composition of Compound A 5 Tablets (5 mg and 35 mg)

| | | Strength | | | |
|---|---|---|---|---|---|
| | | 5 mg | | 35 mg | |
| Component and Quality Standard | Function | mg per unit | % w/w | mg per unit | % w/w |
| Lactose Monohydrate NF/USP, Ph. Eur, JP | Filler | 45.5 | 45.5 | 318.5 | 45.5 |
| Croscarmellose Sodium NF, Ph. Eur, JP | Disintegrant | 3 | 5 | 21 | 3 |
| Silicon Dioxide NF/USP, Ph. Eur, JP | Glidant | 0.5 | 0.5 | 3.5 | 0.5 |
| Magnesium Stearate NF, Ph. Eur, JP | Lubricant | 0.5 | 0.5 | 3.5 | 0.5 |
| Total Weight | | 100 | 100 | 700 | 100 |

NF/USP—National Formulary/United States Pharmacopoeia;
Ph. Eur.: European Pharmacopoeia;
JP—Japanese Pharmacopoeia Example 14. Preparation of Spray-Dried Dispersion Intermediate Multiple compositions were manufactured at the small scale and evaluated both in vitro (e.g., dissolution, stability, etc.) and in vivo (e.g., bioavailability, exposure levels, etc.). There was no advantage observed with dispersions that incorporated polymers and/or surfactants compared to pure spray-dried Compound A. In order to maintain simplicity and maximize drug load, the pure API spray dried was employed.

One engineering and two clinical batches of spray-dried intermediate have been manufactured. The information shown below is taken from the GMP Manufacturing Batch Record (MBR) of the first clinical batch. Because this originates from an MBR, reference is made to specific pieces of equipment. There is no reason to expect that equivalent manufacturing equipment would not be equally effective.

The process for the preparation of a spray-dried intermediate:
1. Starting from crystalline solid Compound A, prepare a 2.5% (w/w) solution of Compound A in 90%/10% (w/w) dichloromethane/methanol;
2. Spray dry solution in PSD-1 spray dryer using SK80-16 nozzle using the following conditions:

| Parameter | Target | Target Range |
|---|---|---|
| Dryer Inlet Temperature | 95° C. | 65-125° C. |
| Dryer Outlet Temperature | 37.5 | 32.5-42.5° C. |
| System Gas Flow | 1850 g/min | 1550-2150 g/min |
| Liquid Feed Rate | 180 g/min | 145-205 g/min |
| Liquid Feed Pressure | 450 psig | 300-600 psig |

3. Collect solid in cyclones and transfer to tray dryer to remove residual dichloromethane and methanol to below ICH guideline levels using a defined temperature/humidity ramp.

Updated Preparation of Spray-Dried Dispersion
The process above was further refined. The updated process is as follows:
1. Starting from crystalline solid Compound A, prepare a 6% (w/w) solution of Compound A in 93%/7% (w/w) dichloromethane/methanol;
2. Spray dry solution in PSD-1 spray dryer using Schlick Model 121 nozzle using the following conditions:

| Parameter | Target | Target Range |
|---|---|---|
| Dryer Inlet Temperature | 95° C. | 65-125° C. |
| Dryer Outlet Temperature | 37.5 | 32.5-42.5° C. |
| System Gas Flow | 1850 g/min | 1550-2150 g/min |
| Condenser Temperature | −5° C. | −10-0° C. |
| Liquid Feed Rate | 180 g/min | 145-205 g/min |
| Liquid Feed Pressure | 450 psig | 300-600 psig |

3. Collect solid in cyclones and transfer to filter dryer to remove residual dichloromethane and methanol to below ICH guideline levels under vacuum at between 40 and 60° C.

Granulation Blends and Tablets of Pure Spray-Dried Compound A

Table 12 below shows the composition for the first clinical batch of 5 mg and 35 mg tablets as taken from the GMP MBR. The actual quantities used in the batch matched the target levels to the decimal indicated. On a percent basis, the composition of the precursor engineering batch and second clinical batch was the same, though the absolute quantities of material employed were different. Again, because it originates from an MBR, the information below references specific pieces of equipment. There is no reason to expect that equivalent manufacturing equipment would not be equally effective.

TABLE 12

Composition of First Clinical Batches of Tablets of Pure Spray-dried Compound A.

| Component ID | Item | Unit Composition (w/w %) | Target batch Quantity (g) | Purpose |
|---|---|---|---|---|
| 100% Compound A Spray-Dried Intermediate | 1 | 5.00 | 750.0 | Active Ingredient |
| Microcrystalline Cellulose (Avicel PH102) | 2 | 45.50 | 6825.0 | Filler |
| Lactose Monohydrate (Fast Flo 316) | 3 | 45.50 | 6825.0 | Filler |
| Croscarmellose Sodium (Ac-Di-Sol) | 4 | 3.00 | 450.0 | Disintegrant |
| Colloidal Silicon Dioxide (Syloid 244FP) | 5 | 0.50 | 75.0 | Glidant |
| Magnesium Stearate | 6 | 0.25 | 37.5 | Lubricant (intragranular) |
| Pregranulation Blend Totals | | 99.75 | 14962.5 | |
| Magnesium Stearate | 7 | 0.25 | 37.5 | Lubricant (extragranular) |
| Final Blend Totals | | 100.00 | 15000.0 | |

The process for preparing Tablets of Pure Spray-dried Compound A:
1. Charge Bin blender with Items 1-5
2. At 12 RPM, rotate blender 180 times
3. De-lump blend by passing through U10 Comil with an 032R screen into Bin blender
4. At 12 RPM rotate blender 180 times
5. Screen Item 6 through 20 mesh screen and add to blender 6. At 12 RPM. Rotate blender 48 times
7. Granulate blend through Gerteis Roller Compactor with knurled rolls and 1.25 mm square wire granulator screen
8. Collect granulated material in Bin blender and charge with Item 7 passed through 20 mesh screen
9. At 12 RPM rotate blender 48 times to produce final blend
10. Partition final blend into one vessel for 5 mg tablets and another for 35 mg tablets
11. With 5-station Korsch XL100 and 0.3403"×0.6807" oval tooling press 35 mg tablets with suitable compression force (~14 kN)
12. With 10-station Korsch XL100 and 0.25" SRC tooling, press 5 mg tablets with suitable compression force (~4 kN)

Figure 10:
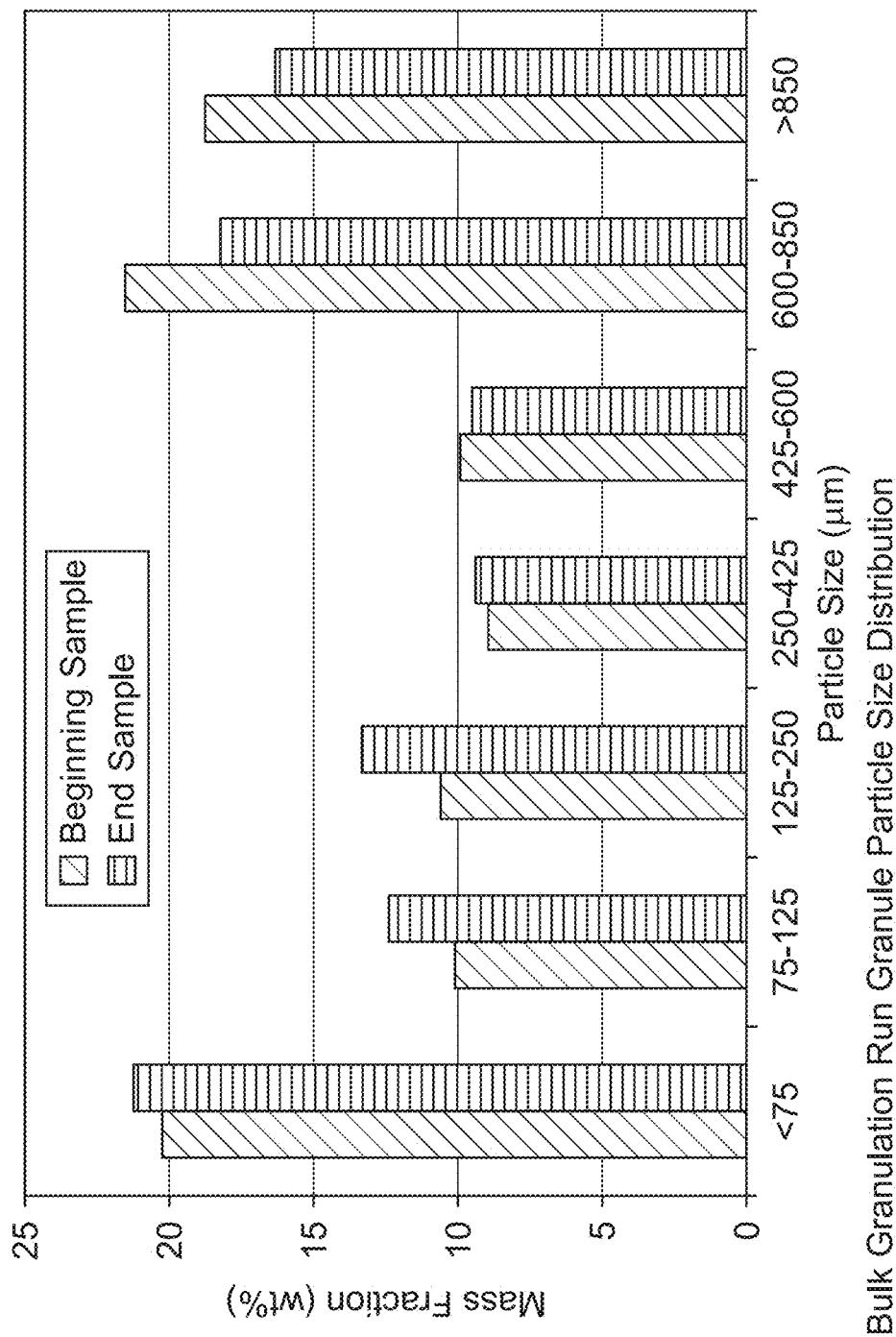
FIG. 10 shows the size distribution, as determined by a sieve analysis, of the Tablets of Pure Spray-dried Compound A.

Particle size of granulation used in preparation of clinical supplies was not measured. However, the size distribution, as determined by a sieve analysis, was measured of the engineering batch using the same percent composition and equivalent equipment and is shown FIG. 10.

Example 15. Compound A Drug Product

Compound A 5 mg and 35 mg tablets were manufactured from a common granulation of spray-dried amorphous Compound A with the following compendial excipients:

Microcrystalline Cellulose

Lactose Monohydrate

Croscarmellose Sodium

Silicon Dioxide

Magnesium Stearate

The tablets were packaged and shipped to the clinical pharmacies in heat-induction sealed high-density polyethylene bottles, that are capped with a lined, polypropylene closure. A silica desiccant canister is included to maintain a low-moisture environment.

Drug Substance Considerations

Compound A is designated as BCS IV (low solubility, low permeability). The designation is supported by the low in vitro permeability in MDCK cells, and the crystalline solid's low solubility of 1.2 µg/mL in pH 6.5 simulated intestinal fluid (SIF). This results in the modest oral bioavailability observed in the face of low hepatic clearance when colloid-forming, precipitation-resistant solutions are administered. The compound's amorphous solubility in SIF is 30 µg/mL. A membrane flux experiment was conducted in which a fixed amount of compound was introduced into the donor compartment at various concentrations of the SIF bile salts, and appearance of drug was monitored on the receiver side. The rate of compound permeation was strongly dependent on the concentration of micellar species present in the donor solution (Table 13), indicating that absorption is limited not only by low aqueous solubility, but also by diffusion of solubilized drug across the unstirred water layer adjacent to the intestinal wall. If absorption is limited entirely by solubility, the flux would not change with concentration of such species. Thus, colloid-forming excipients are not only likely to improve bioavailability through the inhibition of precipitation, but also by providing carriers that rapidly resupply the luminal surface with free drug as absorption occurs.

TABLE 13

Flux Measurements as Function of SIF Concentration

| SIF (mg/mL) | Flux ($\mu g \cdot min^{-1} \cdot cm^{-2}$) |
| --- | --- |
| 0 | 0.02 |
| 5 | 0.09 |
| 10 | 0.14 |
| 20 | 0.20 |

SIF—simulated intestinal fluid

The mechanism-based understanding of absorption limitations described above suggested the use of amorphous dispersions as a means of leveraging the higher solubility characteristic of non-crystalline solids. Compound A possesses thermal characteristics compatible with this solubilization strategy. The melting point of neat crystalline material is 290° C., consistent with a high propensity to remain in the crystalline state, and a high glass transition temperature (Tg) of 146° C. Thus, while crystals of Compound A are quite stable, there is a significant barrier to transforming to a crystalline state from an amorphous form. Indeed, a ramped temperature increase of a partially-crystalline sample does eventually lead to a recrystallization event, but not until a temperature of 200-220° C. is achieved. Hence, a very large amount of energy is required to induce the mobility and potential crystallization of amorphous Compound A even in the pure state. As discussed below, this robust resistance to crystallization is preserved even in the presence of water.

Figure 11:
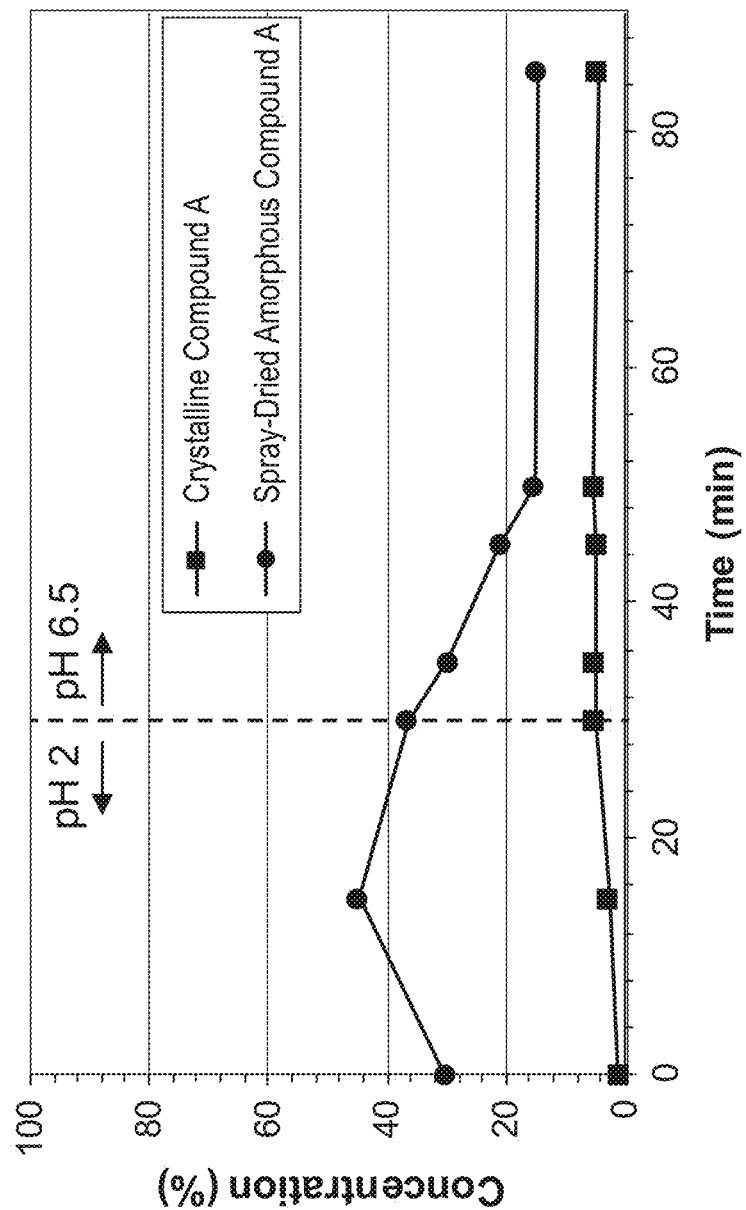
FIG. 11 is a series of line graphs showing the dissolution of crystalline vs. amorphous Compound A API. API (1 mg/mL) is present in gastric conditions (pH=2), which is 2× diluted with FaSSIF at 30 minutes to increase the pH to 6.5. (API=active pharmaceutical ingredient; FaSSIF=fasted state simulated intestinal fluid.)

A 90-minute non-sink dissolution experiment was conducted in which a Compound A suspension was introduced into pH 2 HCl at a final concentration of 1 mg/mL, which was then periodically sampled and prepared for analysis via centrifugation. A shift to pH 6.5 SIF was carried out 30 minutes into the experiment. The improved solubility of amorphous solid over the crystalline form is clearly demonstrated in FIG. 11. Higher concentrations are achieved in the gastric phase of the experiment and sustained in the intestinal phase with spray-dried amorphous Compound A.

Early Formulation Development

Due to the limited solubility of Compound A, early rat PK studies were conducted with solutions of Compound A in a variety of vehicles. Dose-linear exposure escalation in rats using solutions containing solubilizers and precipitation inhibitors demonstrated that compound can be delivered into systemic circulation if sufficient concentrations of absorbable drug can be sustained in the upper gastrointestinal (GI) tract.

Rat Studies with Spray-Dried Dispersions

Male rats were orally administered Compound A as spray-dried dispersions (SDDs) in aqueous suspension containing 0.5% Methocel A4M at 10 mL/kg. Drug loads of 10, 25, and 50% in polyvinylpyrrolidone/vinyl acetate copolymer (PVPVA) were dosed along with loads of 25% with either hydroxypropyl methylcellulose (HPMC) or L-grade hydroxypropyl methylcellulose acetate succinate (HPMCAS-L). This allowed comparison across drug loads for the lead polymer as well as with other polymers at a common drug load.

Data from the pharmacokinetic studies described in Table 14 show that use of PVPVA led to better exposures compared to the other polymers, but only at 10% drug loading, which in turn compared favorably to the solution at a similar dose. This data led to the selection of the 10:90 Compound A:PVPVA dispersion as the formulation employed in the rat good laboratory practice (GLP)-toxicology study.

While a 10% drug loaded SDD enabled the rat 28-day GLP toxicology study because of the high dosing volume permitted in preclinical species, such a value is too low to be employed in a human solid dosage form. Performance of pure spray-dried amorphous Compound A achieved the second-highest exposures of all the amorphous solids administered and would maximize strengths of the clinical solid dosage form.

TABLE 14

Formulations Tested in Rat Pharmacokinetic Studies

| Dose (mg/kg) | Composition | Dosage Form | AUC (ng × h/mL) |
|---|---|---|---|
| 125 | Cosolvent + Precipitation Inhibitor | Solution | 31,700 |
| 150 | 10:90 Compound A:PVPVA | Suspension | 34,537 |
| 150 | 25:75 Compound A:PVPVA | Suspension | 10,286 |
| 150 | 50:50 Compound A:PVPVA | Suspension | 14,337 |
| 150 | 25:75 Compound A:HPMCAS-L | Suspension | 11,293 |
| 150 | 25:75 Compound A:HPMC E3 | Suspension | 10,649 |
| 150 | 100% Spray-Dried Amorphous Compound A | Suspension | 19,362 |

DMSO—dimethylsulfoxide;
HPMC—hydroxypropyl methylcellulose;
HPMCAS-L = L-grade hydroxypropyl methylcellulose acetate succinate;
PEG400—polyethylene glycol 400;
PVPVA—polyvinylpyrrolidone/vinyl acetate copolymer Dog Studies with Spray-Dried Dispersions Data from the pharmacokinetic studies described in Table 15 show the formulations administering Compound A as 0.5% Methocel suspensions of four different polymer dispersions of the drug (10 mg/kg of active) to fasted, pentagastrin pre-treated male dogs. Suspensions in dog yielded lower exposure compared to the solution. As a consequence, the solution formulation was used in the 28-day GLP toxicology study. With respect to development of a clinical solid dosage form, however, within the variability of the area under the curve (AUC) values, there is no indication of improved exposure with low drug loaded SDDs. This data, when combined with the experimental results from the rat, suggests that 100% spray-dried amorphous Compound A will be as effective in achieving exposure as a Compound A/polymer combination. Hence, this form of the drug was chosen for incorporation into a solid oral dosage form.

TABLE 15

Formulations Tested in Dog Pharmacokinetic Studies.

| | | AUC (ng × h/mL) | |
|---|---|---|---|
| Composition | Dosage Form | Avg | SD |
| Cosolvent + Precipitation Inhibitor | Solution | 5,705 | 2,256 |
| 90:10:0 Compound A:PVPVA:TPGS | Suspension | 1,635 | 309 |
| 10:80:10 Compound A:PVPVA:TPGS | Suspension | 866 | 190 |
| 25:65:10 Compound A:PVPVA:TPGS | Suspension | 2,486 | 1,549 |
| 80:10:10 Compound A:PVPVA:TPGS | Suspension | 1,201 | 540 |

DMSO—dimethylsulfoxide;
HPMC—hydroxypropyl methylcellulose;
HPMCAS-L = L-grade hydroxypropyl methylcellulose acetate succinate;
PEG400—polyethylene glycol 400;
PVPVA—polyvinylpyrrolidone/vinyl acetate copolymer A flux experiment similar to that performed to obtain the data in Table 13 for several amorphous suspensions was conducted with results presented in Table 16. Flux remains constant regardless of polymer inclusion or drug load, thus demonstrating the ability of pure spray-dried amorphous Compound A without polymer to source free, absorbable drug in solution.

TABLE 16

Flux Measurements of Spray-Dried Amorphous and Crystalline Compound A

Table 0-1 Flux Measurements of Spray-Dried Amorphous and Crystalline Compound A

| Donor Compartment Contents | Flux ($\mu g\text{-}min^{-1}\text{-}cm^{-2}$) |
|---|---|
| Spray-Dried Amorphous Compound A | 0.15 |
| 10:90 Compound A:PVPVA | 0.15 |
| 90:10 Compound A:PVPVA | 0.11 |

PVPVA—polyvinylpyrrolidone/vinyl acetate copolymer

The amorphous form of pure Compound A is robust with a high Tg and even higher recrystallization temperature. The glass transition temperature does decrease under the plasticizing conditions of high humidity. However, the value is still well above the commonly applied 40-50° C. difference between Tg and any temperature the clinical presentation will encounter. Pure, spray-dried amorphous Compound A is predicted to be more stable under high humidity conditions than is a polymer dispersion as shown in Table 17.

TABLE 17

Glass Transition Temperatures of Spray-Dried Amorphous Compound A-Containing Solids as Function of Temperature and Relative Humidity.

| Powder | Temperature/RH (° C./%) | |
|---|---|---|
| | 25/0 | 40/75 |
| 100% Spray Dried Amorphous Compound A | 146° C. | 103° C. |
| 10% API in PVPVA | 114° C. | 25° C. |

API—active pharmaceutical ingredient;
PVPVA—polyvinylpyrrolidone/vinyl acetate copolymer;
RH—relative humidity In conclusion, in vitro and in vivo data support the use of pure, spray-dried amorphous Compound A API within the clinical formulation.

Example 16. Solvent Screen

A screen was conducted to determine the optimum solvent for use purifying Compound A and for dissolution of crystalline Compound A prior to spray drying. The results of the screen are shown in Table 18.

TABLE 18

Solvent screening preliminary data.

| Solvent system | Solids (wt %.) | Temperature | Dissolution |
|---|---|---|---|
| DCM:Acetone, 53:47% wt. | 0.82 | RT | Not dissolved |
| DCM:Ethanol, 92:8% wt. | 2.26 | RT | Dissolved |
| DCM | 0.6 | RT | Not dissolved |
| DCM:Methanol, 95:5 wt. %. | 4.2 | RT | Dissolved |
| DCM:Methanol, 90:10% wt. | 5 | RT | Dissolved |
| | 4.75 | | |
| | 6.6 | 30 | Dissolved |
| | 8.1 | 35 | Dissolved |
| DCM:Methanol, 80:20% wt. | 3.4 | RT | Dissolved |
| DCM:Methanol, 70:30% wt. | 3.2 | RT | Turbid solution |
| Methanol | 2.8 | RT | Not dissolved |
| THF | 0.7 | RT | Not dissolved |

Example 17. Manufacturing Process Development Spray-Dried Amorphous Compound A Intermediate Amorphous Compound A produced at small (laboratory) and ~0.5 kg (demonstration) scales was employed to optimize processing conditions for recovery, and study chemical stability, non-sink dissolution performance, particle size, thermal characteristics, and residual solvent levels. Crystalline Compound A was dissolved in 90:10 dichloromethane:methanol (DCM:MeOH) to afford a concentration of 2.5 wt % and was then introduced into a spray dryer to create the amorphous state. A two-stage tray-drying procedure was used to remove residual solvents.

Particle size of the dried powder was measured via laser diffraction and is shown in Table 19. As expected, the particle size obtained with a smaller scale dryer are slightly smaller than those resulting from spray drying with a larger dryer. $D_v(50)$ values of 10 μm were reproducibly obtained using the latter equipment. This same, larger dryer supplied material for all tablet development and in vivo testing carried out using spray-dried

TABLE 19

Laser Diffraction Particle Sizes of Spray-dried Intermediates.

| | | Volume-Average Diameter (μm) | | |
|---|---|---|---|---|
| Dryer | Sample | Dv(10) | Dv(50) | Dv(90) |
| BLD35 | Small Scale | 1 | 5 | 11 |
| PSD-1 | Scale-Up #1 | 3 | 9 | 18 |
| | Scale-Up #2 | 4 | 10 | 20 |
| | Demonstration | 4 | 10 | 20 |

Dv(10) = size below which 10% of the material volume is present
Dv(50) = size below which 50% of the material volume is present
Dv(90) = size below which 90% of the material volume is present Suitable chemical stability of the spray solution and the solvent-damp spray-dried intermediate (SDI) over a period of one week, have been confirmed as shown in Table 20.

TABLE 20

Chemical Stability of Solvent-damp Spray-dried Amorphous Compound A and DCM/MeOH Spray Solution at 25° C.

| Sample | Weeks @ 25° C. | Total Impurities (%) | Weight Percent of Compound A |
|---|---|---|---|
| Damp Spray-Dried Amorphous Compound A | 0 | 1.17 | 99.1 |
| | 1 | 1.20 | 97.3 |
| | 7 | 1.45 | 96.3 |
| Spray Solution | 0 | 1.18 | N/A |
| | 1 | 1.10 | |
| | 2 | 1.40 | |

DCM—dichloromethane;
MeOH = methanol

Figure 12:
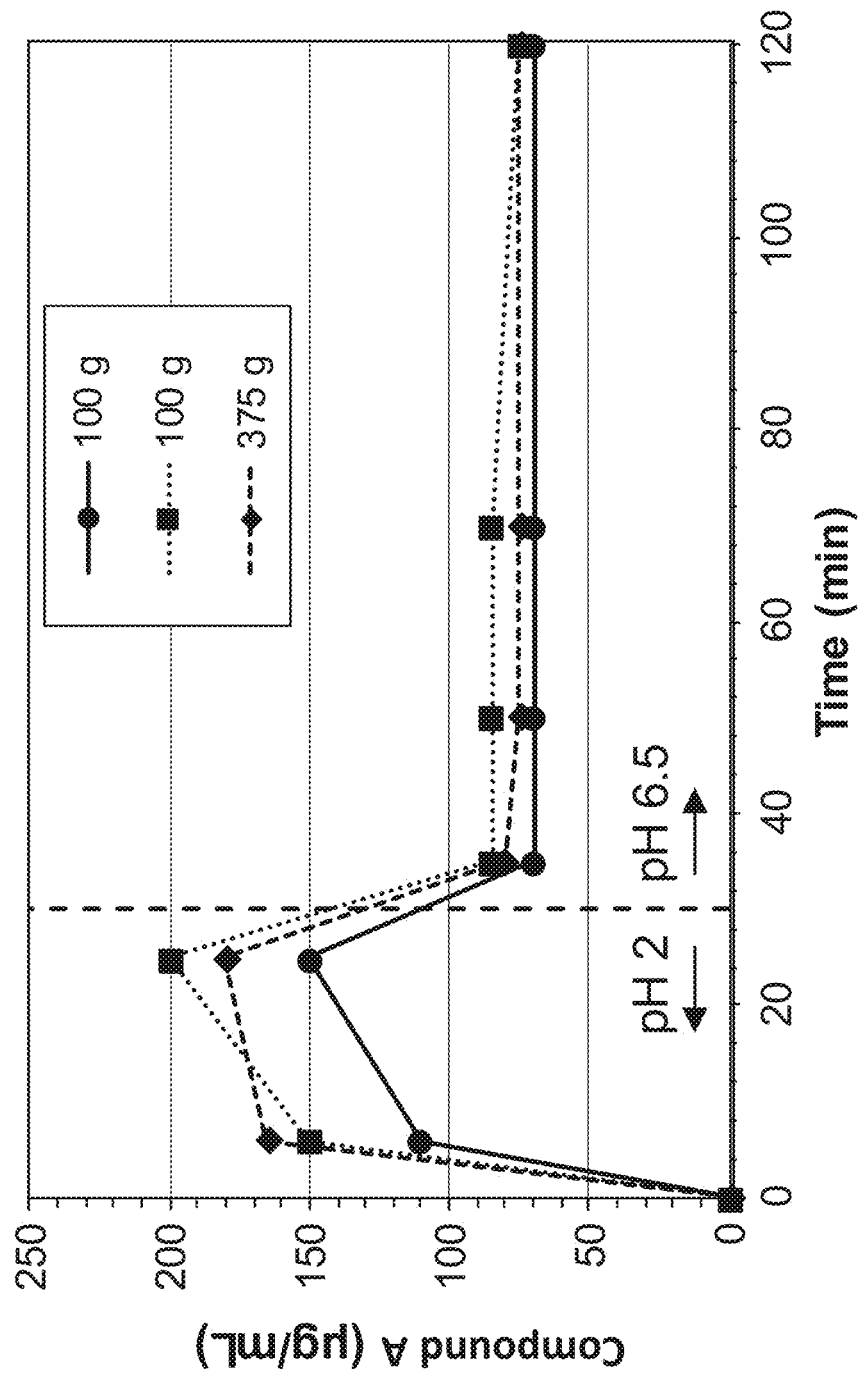
FIG. 12 is a series of line graphs showing the non-sink dissolution of spray-dried amorphous Compound A produced at multiple scales. API (500 μg/mL) is present in gastric conditions (pH=2), which is 2× Diluted with FaSSIF at 30 minutes to increase the pH to 6.5.

Finally, from a performance perspective, non-sink dissolution of several amorphous Compound A samples from different manufacturing scales, shown in FIG. 12 reconfirms the pH-shift non-sink dissolution profile observed in the initial formulation design phase.

Example 18: Compound A Tablet Development

Figure 13:
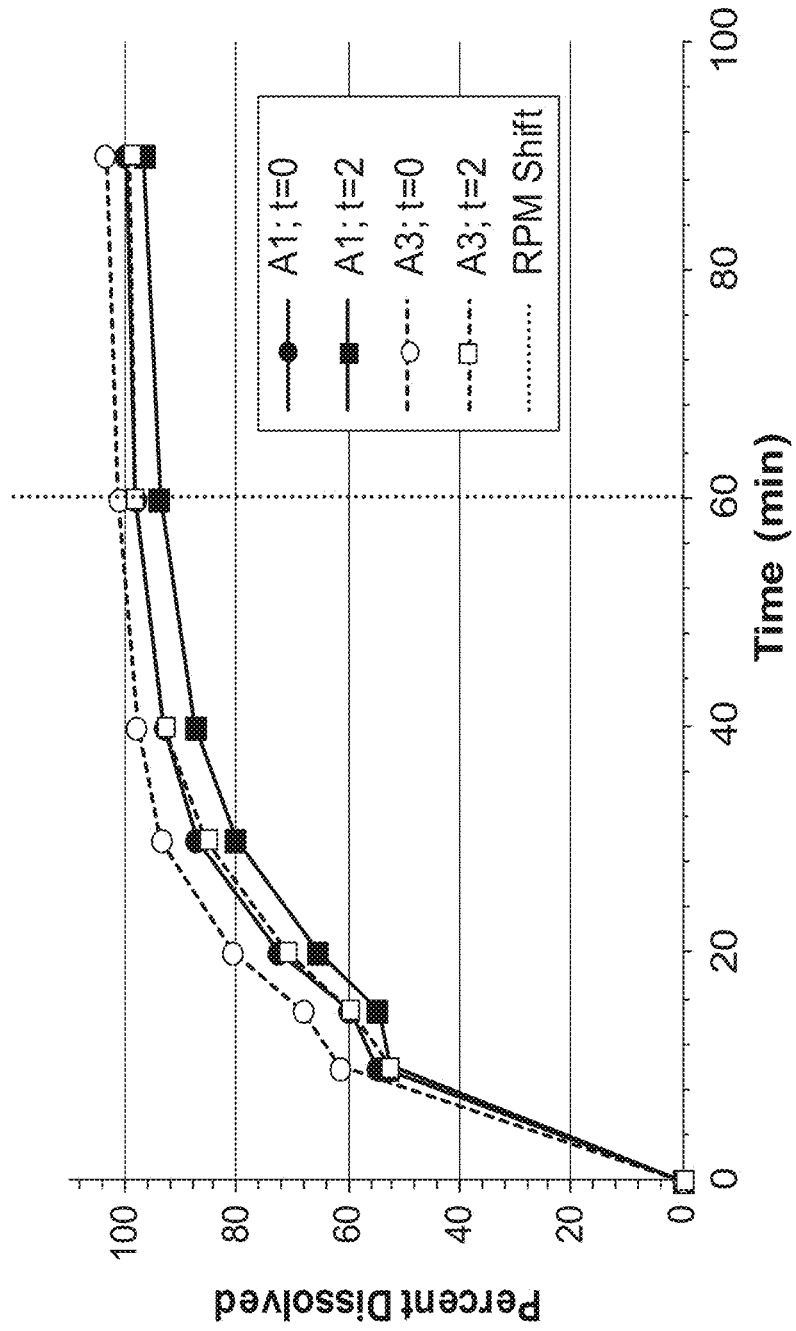
FIG. 13 is a series of line graphs showing the dissolution of prototype tablets in 900 mL of 37° C. 50 mM Na$_2$HPO$_4$ pH 6.5, 0.5% sodium lauryl sulfate both immediately after manufacture (t=0) and after 2 weeks storage at 50° C./75% RH Open. The dotted line represents accelerating the agitation from 75 to 250 RPM to simulate long-term dissolution. (N=2).

Several different compositions of 35 mg strength Compound A tablets (Table 21) were made as laboratory scale prototypes using conventional fillers, glidants, disintegrants, and lubricants for evaluation of chemical stability (Table 22) and dissolution (FIG. 13) both immediately after manufacture and after stress storage conditions (2-weeks at 50° C./75% RH open).

TABLE 21

Compositions of 35 mg Compound A Tablet Prototypes.

| | | Formulation Reference | | |
|---|---|---|---|---|
| | | A1 | A2 | A3 |
| | | Tablet Strength/Press Weight (mg/mg) | | |
| | | 35/700 | 35/700 | 35/700 |
| Function | Ingredient | % of Blend | | |
| Intra Granular | | | | |
| Active | Spray-dried amorphous Compound A | 5.00 | 5.00 | 5.00 |
| Filler | Microcrystalline cellulose | 44.50 | 44.50 | 45.50 |
| Filler | Lactose monohydrate | 44.50 | 44.50 | 45.50 |
| Disintegrant | Crospovidone | 3.00 | — | — |
| Disintegrant | Croscarmellose sodium | — | 3.00 | 3.00 |
| Glidant | Silicon dioxide | 0.50 | 0.50 | 0.50 |
| Lubricant | Magnesium stearate | 0.25 | 0.25 | 0.25 |
| Extra Granular | | | | |
| Disintegrant | Crospovidone | 2.00 | — | — |
| Disintegrant | Croscarmellose sodium | — | 2.00 | — |
| Lubricant | Magnesium stearate | 0.25 | 0.25 | 0.25 |
| Totals: | | 100.00 | 100.00 | 100.00 |

TABLE 22

Chemical Stability of Prototype Tablets After 2 Weeks at 50° C./75% RH Open

| Sample | t = (week) | Total Impurities (wt %) | Percent of Label |
|---|---|---|---|
| Formulation A1 | 0 | 1.10 | 98.7 |
| | 2 | 1.67 | 98.3 |
| Formulation A2 | 0 | 1.06 | 98.2 |
| | 2 | 1.92 | 96.8 |
| Formulation A3 | 0 | 1.15 | 99.0 |
| | 2 | 1.74 | 97.3 |

Based on the acceptable chemical stability of all compositions and the improved dissolution profile observed with formulation A3, A3 was selected for clinical development.

Example 19: Compound A Manufacturing Process Development of a Spray-Dried Amorphous Compound A Intermediate Product: Characterization and Process Assessment As demonstrated above, the maintenance of Compound A in the amorphous state is integral to achieving in vivo performance. Hence, effort was applied to assure a thorough understanding of the generation and subsequent use of the Compound A intermediate product.

The batch analysis for the spray-dried amorphous Compound A intermediate product is provided in Table 23. This data demonstrates that conversion of Compound A from a crystalline to an amorphous form via spray drying does not materially affect either the potency or impurity profile. It also confirms the amorphous nature of the spray dried intermediate.

TABLE 23

Batch Analysis Results for Spray-Dried Amorphous Compound A Intermediate Product Demonstration Batch (SDI) Contrasted to Input API

| Test | In Process Specification | API | SDI |
|---|---|---|---|
| Appearance | FIO | — | Light yellow powder |
| DCM (ppm) | <600 | 16 | 200 |
| MeOH (ppm) | <1,000 | <1.5 (LOD) | <100 (LOQ) |
| Assay (% label) | — | 98.1 | 99.1 |
| Impurities ≥0.05% | — | — | — |
| RRT = 0.50 | | Area % = 0.06 | Area % = 0.05 |
| 0.89 | | 0.07 | 0.08 |
| 0.92 | | 0.07 | 0.07 |
| 0.96 | | 0.16 | 0.16 |
| 1.02 | | 0.39 | 0.37 |
| 1.04 | | 0.12 | <0.05 (LOQ) |
| 1.07 | | 0.19 | 0.18 |
| 1.23 | | 0.06 | 0.05 |
| 1.36 | | 0.05 | <0.05 (LOQ) |
| 1.39 | | 0.67 | 0.22 |
| Total Impurities | — | 1.84 | 1.18 |
| D50 (μm) | FIO | — | 10 |
| PXRD | FIO | Crystalline | Amorphous |
| SEM Morphology | FIO | — | No crystallization or fusing |

DCM—dichloromethane;
FIO—for information only;
MeOH = methanol;
LOD—limit of detection;
LOQ—limit of quantitation;
PXRD—powder x-ray diffraction;
RRT—relative retention time;
SEM—scanning electron microscopy The difference in the low impurity levels is considered to be caused by method variability.

Example 20: Stability of the Amorphous form of Compound A ("the Spray-Dried Intermediate")

The stability of amorphous Compound A was assessed at three stability conditions: 2-8° C.; 25° C./60% RH; and 40° C./75% RH for a period of 12 months.

During stability testing, amorphous Compound A was stored in wire-tied low-density polyethylene bags placed in heat-induction sealed, high-density polyethylene (HDPE) bottles containing a desiccant canister, and capped with polypropylene-lined closures.

After 6 months of storage at 2-8° C., the purity of the amorphous form of Compound A was >95% (95.7%), with water being the major impurity (0.9%).

After 12 months of storing at 25° C./60% RH, the purity of the amorphous form of Compound A was >97% (97.7%), with water being the major impurity (1.62%).

After 12 months of storing at 40° C./75% RH, the purity of the amorphous form of Compound A was 98%, with water being the major impurity (2.16%, as measured by Karl Fischer titration).

It is noteworthy that under all three storage conditions, there was no evidence of recrystallization of the amorphous form Compound A at any time during these studies.

Example 21. Batch Manufacture of Compound A Tablets

Compound A tablets, 5 and 35 mg, were prepared from a single, common blend. Prior to blending, Compound A drug substance (DS) is dissolved, then spray-dried to form an amorphous drug product intermediate (amorphous Compound A). Formulas for each strength of the demonstration batches (5 mg and 35 mg tablets) are provided in Table 24 and Table 25, respectively.

TABLE 24

Demonstration Batch Formula for Compound A Tablets, 5 mg

| Component | Function | Quantity Per Batch (g) |
|---|---|---|
| Compound A Intermediate Product | Active Agent | 250.05 |
| Microcrystalline Cellulose Avicel ® PH102 (NF, Ph. Eur, JP) | Filler | 2275.04 |
| Lactose Monohydrate Foremost ™ 316 (NF/USP, Ph, Eur, JP) | Filler | 2275.07 |
| Croscarmellose Sodium Ac-Di-Sol ® (NF, Ph. Eur, JP) | Disintegrant | 150.04 |
| Silicon Dioxide Syloid ® 244FP (NF/USP, Ph. Eur, JP) | Glidant | 25.06 |
| Magnesium Stearate (NF, Ph. Eur, JP) | Intragranular Lubricant | 12.52 |
| Magnesium Stearate (NF, Ph. Eur, JP) | Extragranular Lubricant | 10.34$^a$ |
| Total Blend Weight | | 4998.12$^b$ |
| Tablet Press Weight | | 100 mg |
| Total Number of 5 mg Tablets | | 6930 |

$^a$Extragranular magnesium stearate amount adjusted based on granule yield.
$^b$Total weight of common blend, which was appropriately divided to make both 5 mg and 35 mg tablets.

TABLE 25

Demonstration Batch Formula for Compound A Tablets, 35 mg

| Component | Function | Quantity Per Batch (g) |
|---|---|---|
| Compound A Intermediate Product | Active Agent | 250.05 |
| Microcrystalline Cellulose Avicel ® PH102 (NF, Ph. Eur, JP) | Filler | 2275.04 |
| Lactose Monohydrate Foremost ™ 316 (NF/USP, Ph. Eur, JP) | Filler | 2275.07 |
| Croscarmellose Sodium Ac-Di-Sol ® (NF, Ph. Eur, JP) | Disintegrant | 150.04 |
| Silicon Dioxide Syloid ® 244FP (NF/USP, Ph. Eur, JP) | Glidant | 25.06 |
| Magnesium Stearate (NF, Ph. Eur, JP) | Intragranular Lubricant | 12.52 |
| Magnesium Stearate (NF, Ph. Eur, JP) | Extragranular Lubricant | 10.34$^a$ |
| Total Blend Weight | | 4998.12$^b$ |
| Tablet Press Weight | | 700 mg |
| Total Number of 35 mg Tablets | | 3500 |

$^a$Extragranular magnesium stearate amount adjusted based on granule yield.
$^b$Total weight of common blend, which was appropriately divided to make both 5 mg and 35 mg tablets.

Container Closure System for Compound A Tablets

Compound A Tablets, 5 mg and 35 mg, were packaged in heat-induction sealed, high-density polyethylene bottles, 100 cc and 500 cc in size, respectively, containing a desiccant, and closed with a child-resistant cap. The primary container closure components are in compliance with relevant United States (US) and European Union (EU) guidelines pertaining to materials that come in contact with food.

Example 22. Batch Formula for Compound A Tablets

Compound A tablets, 5 and 35 mg, were prepared from a single, common blend. Prior to blending, Compound A DS was dissolved, then spray-dried to form an amorphous drug product intermediate (amorphous Compound A). Representative formulas for each strength are provided in Table 26 and Table 27.

TABLE 26

Batch Formula for Clinical Compound A Tablets, 5 mg

| Component | Function | Batch Target Quantity (g) |
|---|---|---|
| Compound A Intermediate Product | Active Agent | 750 |
| Microcrystalline Cellulose Avicel ® PH102 (NF, Ph. Eur, JP) | Filler | 6,825 |
| Lactose Monohydrate Foremost ™ 316 (NF/USP, Ph. Eur, JP) | Filler | 6,825 |
| Croscarmellose Sodium Ac-Di-Sol ® (NF, Ph. Eur, JP) | Disintegrant | 450 |
| Silicon Dioxide Syloid ® 244FP (NF/USP, Ph. Eur, JP) | Glidant | 75 |
| Magnesium Stearate (NF, Ph. Eur, JP) | Intragranular Lubricant | 37.5 |

TABLE 26-continued

Batch Formula for Clinical Compound A Tablets, 5 mg

| Component | Function | Batch Target Quantity (g) |
|---|---|---|
| Magnesium Stearate (NF, Ph. Eur, JP) | Extragranular Lubricant | 37.5 |
| Total Blend Weight | | 15,000* |
| Tablet Press Weight | | 100 mg |
| Total Number of 5 mg Tablets | | 21,400 |

JP—Japanese Formulary;
NF—National Formulary;
Ph. Eur. = European Pharmacopoeia;
USP—United States Pharmacopeia
*Total weight of common blend, which is appropriately divided to make two batches of tablets.

TABLE 27

Batch Formula for Clinical Compound A Tablets, 35 mg

| Component | Function | Batch Target Quantity (g) |
|---|---|---|
| Compound A Intermediate Product | Active Agent | 750 |
| Microcrystalline Cellulose Avicel ® PH102 (NF, Ph. Eur, JP) | Filler | 6,825 |
| Lactose Monohydrate Foremost ™ 316 (NF/USP, Ph. Eur, JP) | Filler | 6,825 |
| Croscarmellose Sodium Ac-Di-Sol ® (NF, Ph. Eur, JP) | Disintegrant | 450 |
| Silicon Dioxide Syloid ® 244FP (NF/USP, Ph. Eur, JP) | Glidant | 76 |
| Magnesium Stearate (NF, Ph. Eur, JP) | Intragranular Lubricant | 37.5 |
| Magnesium Stearate (NF, Ph. Eur, JP) | Extragranular Lubricant | 37.5 |
| Total Blend Weight | | 15,000* |
| Tablet Press Weight | | 700 mg |
| Total Number of 35 mg Tablets | | 12,400 |

JP—Japanese Formulary;
NF—National Formulary;
Ph. Eur. European Pharmacopoeia;
USP—United States Pharmacopeia
*Total weight of common blend, which is appropriately divided to make two batches of tablets.

Example 23. Manufacturing and Process Description for the Compound A Tablets Compound A Intermediate Product: Compound A was dissolved in a 90/10 (w/w) mixture of dichloromethane (DCM) and methanol (MeOH), both of which are National Formulary (NF) grade, and stirred until a clear, yellow solution of 25 mg/mL was obtained. This solution was introduced to a spray dryer. The damp solid output was tray-dried to produce an amorphous solid (amorphous Compound A). This solid was checked for residual DCM and MeOH as an in-process test. A flow diagram of the manufacturing process of Compound A intermediate product is presented in FIG. 14.

Tableting: a common dry granulation was used to produce Compound A tablets. Amorphous Compound A was blended with microcrystalline cellulose, lactose monohydrate, croscarmellose sodium, and silicon dioxide in a suitable blender. The resulting powder was delumped and magnesium stearate added and blended. The blend was granulated using a suitable roller compactor and passed through a screen. Extragranular magnesium stearate was added and the bulk powder was blended in a suitable blender. The blend was compressed into tablets using a rotary press and the resulting tablets packaged in bulk containers. The flow diagram of the manufacturing process of Compound A tablets is presented in FIG. 15.

Controls of Critical Steps and Intermediates in the Manufacturing Process for Compound A Tablets.

A summary of controls performed at the critical steps of the manufacturing process for Compound A intermediate product and for Compound A tablets are provided in Table 28 and Table 29, respectively.

The residual solvents level in the Compound A intermediate product is a quality attribute that is carefully monitored to assure safety. Acceptance criteria are those specified in the International Council for Harmonisation (ICH) harmonized guidelines for residual solvents Q3C(R6). Tablet properties are monitored to assure consistent size and performance. Additional controls may be added or refined as drug development progresses.

TABLE 28

In-process Controls for the Manufacture of Compound A Intermediate Product.

| Critical Step | Test | Method | Acceptance Criteria |
|---|---|---|---|
| Spray drying of Compound A | Residual dichloromethane | TEST-099 | ≤600 ppm |
| Spray drying of Compound A | Residual methanol | TEST-099 | ≤3000 ppm |

TABLE 29

In-process Controls for the Manufacture of Compound A Tablets, 5 mg and 35 mg.

| Critical Step | Test | Method Type | Alert Limit (5 mg) | Alert Limit (35 mg) |
|---|---|---|---|---|
| Tableting | Individual press weight | Weighing | 100 mg ± 5% | 700 mg ± 5% |
| | Average hardness | Sotax Hardness Tester | 6.5 kp ± 2 kp | 27 kp ± 2 kp |

Control of Excipients (Compound A, Tablet)

Specifications: The excipients used in the manufacture of 5 mg and 35 mg tablets meet multi-compendial requirements: microcrystalline cellulose (National Formulary (NF), European Pharmacopoeia (Ph. Eur.), Japanese Pharmacopoeia (JP)), lactose monohydrate (NF/USP, Ph. Eur., JP), croscarmellose sodium (NF, Ph. Eur., JP), silicon dioxide (NF/USP, Ph. Eur., JP), and magnesium stearate (NF, Ph. Eur., JP). There are no non-compendial excipients used in the manufacturing process or present in the drug product.

Control of Drug Product (Compound A, Tablet)

Specifications for Compound A tablets, 5 mg and 35 mg, are outlined in Table 30 and Table 31, respectively.

TABLE 30

Specifications for Compound A Tablets, 5 mg

| Test | Analytical Procedure | Acceptance Criteria |
|---|---|---|
| Appearance | TEST-009 | Yellow to light-yellow, round tablet |
| Identity by HPLC | TEST-513 | The difference between HPLC retention time of the sample and that of the main peak in |

TABLE 30-continued

Specifications for Compound A Tablets, 5 mg

| Test | Analytical Procedure | Acceptance Criteria |
|---|---|---|
| | | the closest working standard injection is NMT 5%. |
| Assay (5 mg, % label) | TEST-513 | 90-110% of label claim |
| Related Substances (%) | TEST-513 | Report all impurities ≥0.05% |
| DP Related Substances (%) | TEST-513* | Report all impurities related to drug product manufacture or degradation ≥0.05%. Total of impurities related to drug product manufacture or degradation ≤2.5%. No single unspecified impurity ≥1%. |
| Content Uniformity | TEST-513 | Meets USP <905> |
| Dissolution | TEST-514 | Q ≥ 75% @ T = 45 min |

DP—drug product;
HPLC—high performance liquid chromatography;
NMT—not more than;
USP—United States Pharmacopoeia;
Q = amount of dissolved active ingredient as percentage of labeled content
*Value obtained by comparing chromatographic impurity peak areas of drug product with those of corresponding peaks reported in the drug substance Certificate of Analysis and taking the difference.

TABLE 31

Drug Product Specifications for Compound A Tablets, 35 mg

| Test | Analytical Procedure | Acceptance Criteria |
|---|---|---|
| Appearance | TEST-009 | Yellow to light-yellow, oval tablet |
| Identity by HPLC | TEST-513 | The difference between HPLC retention time of the sample and that of the main peak in the closest working standard injection is NMT 5%. |
| Assay (35 mg, % label) | TEST-513 | 90-110% of label claim |
| Related Substances (%) | TEST-513 | Report all impurities ≥0.05% |
| DP Related Substances (%) | TEST-513* | Report all impurities related to drug product manufacture or degradation ≥0.05%. Total of impurities related to drug product manufacture or degradation ≤2.5%. No single unspecified impurity ≥1%. |
| Content Uniformity | TEST-513 | Meets USP <905> |
| Dissolution | TEST-514 | Q ≥ 75% @ T = 45 min |

DP—drug product;
HPLC—high performance liquid chromatography;
NMT—not more than;
USP—United States Pharmacopoeia;
Q = amount of dissolved active ingredient as percentage of labeled content
*Value obtained by comparing chromatographic impurity peak areas of drug product with those of corresponding peaks reported in the drug substance Certificate of Analysis and taking the difference.

Analytical Procedures for Compound A Tablets: analytical methods for identity, assay, related substances, content uniformity, and dissolution that ensure quality of Compound A tablets, 5 mg and 35 mg, have been developed. The method summaries are described in the section below.

TABLE 32

Analytical Procedures for Compound A Tablets

| Assay | Method Number |
|---|---|
| Appearance | TEST-009 |
| Identity by HPLC | TEST-513 |
| Assay | TEST-513 |
| Related Substances | TEST-513 |
| Content Uniformity | TEST-513 |
| Dissolution | TEST-514 |

HPLC—high performance liquid chromatography

Appearance (Method TEST-009)

Using alight box for uniform illumination, material is examined for color and shape confirmation is referenced to standard color wheels and figures, respectively.

Compound A Identity, Assay, Related Substances, and Content Uniformity by High Performance Liquid Chromatography (HPLC) (TEST-513)

Samples are weighed out, dissolved in 80:20 (v/v) methanol:0.1% trifluoroacetic acid (TFA) in water, passed through a filter, and injected onto a HPLC with the conditions shown in Table 33.

TABLE 33

Chromatographic Conditions For TEST-513

| Parameter | Value |
|---|---|
| Column | Waters Atlantis T3, 4.6 × 150 mm, 3 μm |
| Column Temperature | 45° C. |
| Detection | 260 nm |
| Mobile Phase A | 0.1% Trifluoroacetic acid in Water |
| Mobile Phase B | 0.05% Trifluoroacetic acid in 75/25 acetonitrile/methanol |
| Flow Rate | 1.0 mL/minute |
| Injection Volume | 10.0 μL |
| Run Time | 36 minutes |

Identity is reported as the percent difference between HPLC retention time of the sample and that of the main peak in the closest working standard injection. Potency is determined by comparison of peak area to that of the working standard and reported as percent of label claim. All impurities with peak area≥0.05% that are not Compound A are reported. Impurities specific to drug product manufacture or degradation are obtained by comparing chromatographic impurity peak areas of drug product with those of corresponding peaks reported in the drug substance Certificate of Analysis and taking the difference. A sample of 10 tablets is analyzed to perform a content uniformity assessment, with the results reported per United States Pharmacopeia (USP) <905>.

Dissolution (Method TEST-514)

Tablets are introduced into a USP II apparatus with 1-liter vessels containing 900 mL (35 mg tablet) or 500 mL (5 mg tablet) of 50 mM $Na_2HPO_4$, pH 6.5 with 0.5 w/v % sodium lauryl sulfate at 37° C. using a paddle speed of 75 RPM. Samples are removed at 10, 15, 20, 30, 45, and 60 min, filtered through a 10 μm full-flow filter, diluted with acetonitrile, injected onto a HPLC with the conditions shown in Table 34.

TABLE 34

Chromatographic Conditions For TEST-514

| Parameter | Value |
| --- | --- |
| Column: | Agilent Zorbax SB-C18 4.6 × 150 mm, 3.5 μm |
| Column Temperature | 30° C. |
| Detection Wavelength | 260 nm |
| Mobile Phase | 60:40 Water:Acetonitrile, 0.1% TFA (v/v), 0.00025% SLS (w/v) |
| Flow Rate | 1.0 mL/minute |
| Injection Volume | 2 uL |
| Run Time | 4.0 minutes |

TFA—trifluoroacetic acid;
SLS—sodium lauryl sulfate

Six replicates of each tablet are tested, and results are reported as percent dose dissolved of label claim.

Batch Analyses (Compound A, Tablet)

The clinical batches intended for use in the proposed Phase 1 clinical trial are produced using the same formula and process as the mg and 35 mg tablet demonstration batches characterized in Table 37 and Table 38, respectively.

Batch Analyses of Compound A Tablets, 5 mg and 35 mg

A description of the demonstration batches of Compound A 5 mg and 35 mg tablets are provided in Table 35, Table 36, and Table 37.

TABLE 35

Description of Batches of Compound A Tablets, 5 and 35 mg

| Strength and Batch Number | Batch Size (number of tablets) | Date of Manufacture | Use |
| --- | --- | --- | --- |
| 5 mg | 6930 | Aug. 2018 | Demonstration, stability |
| 35 mg | 3500 | Aug. 2018 | Demonstration, stability |

TABLE 36

Batch Analysis Results for Compound A 5 mg Tablets

| Test | Acceptance Criteria | Result | |
| --- | --- | --- | --- |
| Appearance | Light yellow/yellow round tablet | Conforms | |
| Identity by HPLC | ΔRT ≤5% | Conforms | |
| Assay (% label) | 90-110% | 98.3 | |
| | | RRT | Area % |
| Related Substances (%) | Report all impurities ≥0.05% | 0.49 | 0.06 |
| | | 0.89 | 0.08 |
| | | 0.92 | 0.07 |
| | | 0.95 | 0.17 |
| | | 1.02 | 0.32 |
| | | 1.07 | 0.17 |
| | | 1.23 | 0.06 |
| | | 1.38 | 0.52 |
| Related Substances (%) | Report all impurities related to drug product manufacture or degradation ≥0.05% | NR | |
| | Total of impurities related to drug product manufacture or degradation ≤2.5%. No single unspecified impurity ≥1%. | 0.00 | |

TABLE 36-continued

Batch Analysis Results for Compound A 5 mg Tablets

| | | |
| --- | --- | --- |
| Content Uniformity | Meets USP <905> | Conforms |
| Dissolution | Q ≥ 75% T = 45 min | Conforms |

HPLC—high performance liquid chromatography;
NR—none reported;
RT—retention time;
RRT—relative retention time;
USP—United States Pharmacopeia;
Q = amount of dissolved active ingredient as percentage of labeled content

TABLE 37

Batch Analysis Results for Compound A 35 mg Tablets

| Test | Specification | Result | |
| --- | --- | --- | --- |
| Appearance | Light yellow/yellow oval tablet | Conforms | |
| Identity by HPLC | ΔRT ≤5% | Conforms | |
| Assay (% label) | 90-110% | 98.8 | |
| | | RRT | Area % |
| Related Substances (%) | Report all impurities ≥0.05% | 0.49 | 0.05 |
| | | 0.89 | 0.08 |
| | | 0.92 | 0.07 |
| | | 0.95 | 0.17 |
| | | 1.02 | 0.31 |
| | | 1.07 | 0.18 |
| | | 1.23 | 0.05 |
| | | 1.38 | 0.56 |
| Related Substances (%) | Report all impurities related to drug product manufacture or degradation ≥0.05% | NR | |
| | Total of impurities related to drug product manufacture or degradation ≤2.5%. No single unspecified impurity ≥1%. | 0.00 | |
| Content Uniformity | Meets USP <905> | Conforms | |
| Dissolution | Q ≥ 75% @ T = 45 min | Conforms | |

HPLC—high performance liquid chromatography;
NR—none reported;
RT—retention time;
RRT—relative retention time;
USP—United States Pharmacopeia;
Q = amount of dissolved active ingredient as percentage of labeled content Characterization of Impurities (Compound A, Tablet)

No additional impurities/degradants were identified as a consequence of drug product manufacture and degradation beyond those already present in the active pharmaceutical ingredient (API).

Example 24: Stability of the Compound A Tablets

The protocol used for the Compound A, 5 mg and 35 mg, is described in Table 38 During stability testing, the tablets were stored in heat-induction-sealed high-density polyethylene (H-DPE) bottles containing a desiccant canister, and capped with a polypropylene-lined closure.

TABLE 38

Stability Protocol for Demonstration Batches
of Compound A Tablets (5 mg and 35 mg)

|  | | Months | | | | |
|---|---|---|---|---|---|---|
| Condition | Initial | 1 | 3 | 6 | 9* | 12* |
| 2-8° C. | ✓ | ✓ | ✓ | ✓ | ✓ | ✓ |
| 25° C./60% RH | ✓ | ✓ | ✓ | ✓ | ✓ | ✓ |
| 40° C./75% RH | ✓ | ✓ | ✓ | ✓ | ✓ | ✓ |

✓ = Appearance, Assay/Related Substances, Sink Dissolution, Water by KF
*Optional time points;
KF = Karl Fischer titration Summary of Stability Results Phase 1 clinical trial drug product has been prepared using the same formula, process, and equipment.

No change in key quality attributes of Compound A tablets, 5 mg and 35 mg, was observed after 1 month at 40° C./75% relative humidity (RH) with the exception of the relative retention time (RRT)=1.02 chromatographic peak observed in some samples. The presence and magnitude of this peak is independent of storage conditions and is seen in both tablet strengths. It is thus potentially due to analytical variation. Likewise, real-time data for 1 month at 25° C./60% RH show no change in impurity profile.

After 6 months, all samples 40° C./75% RH are still within specification. This implies that the samples will have a shelf-life of at least 2 years.

After 24 months, all samples at 25° C./60% RH are still within specification.

Stability data to support the clinical use of 5 mg Compound A tablets, at 2-8° C., 25° C./60% RH, and 40° C./75% RH, 35 mg Compound A tablets, at 2-8° C., 25° C./60% RH, and 40° C./75% RH are presented in Tables 39-44.

TABLE 39

Stability Results at 2-8° C. Compound A Tablets, 5 mg

Batch Size: 6930 tablets    Packaging: Closed in heat-induction sealed HDPE bottle containing desiccant canister with polypropylene closure

| Test | Acceptance Criteria | Method | Initial | 1 Month | 3 Month | 6 Month |
|---|---|---|---|---|---|---|
| Appearance | Light yellow/ yellow round tablet | TEST-009 | Conforms | Conforms | Conforms | Conforms |
| Assay (% label) | 90-110% | TEST-513 | 98.3 | 98.3 | 95.8 | 98.7 |

| | | | RRT | Area % | RRT | Area % | RRT | Area % | RRT | Area % |
|---|---|---|---|---|---|---|---|---|---|---|
| Related Substances (%) | Report all impurities ≥0.05% | TEST-513 | 0.49 | 0.06 | 0.49 | 0.05 | 0.49 | 0.06 | 0.46 | 0.06 |
| | | | 0.88 | 0.08 | NR | NR | 0.88 | 0.06 | 0.87 | 0.07 |
| | | | 0.92 | 0.07 | 0.92 | 0.08 | 0.91 | 0.08 | 0.91 | 0.09 |
| | | | 0.96 | 0.17 | 0.95 | 0.16 | 0.94 | 0.14 | 0.95 | 0.20 |
| | | | 1.02 | 0.32 | 1.02 | 0.40 | 1.02 | 0.06 | 1.02 | 0.07 |
| | | | 1.07 | 0.17 | 1.07 | 0.19 | 1.07 | 0.18 | 1.07 | 0.18 |
| | | | 1.23 | 0.06 | 1.23 | 0.06 | 1.24 | 0.06 | 1.25 | 0.06 |
| | | | 1.38 | 0.52 | 1.38 | 0.27 | 1.36 | NR | 1.39 | 0.40 |
| Related Substances (%) | Report all impurities related to drug product manufacture or degradation ≥0.05% | TEST-513 | NR | | NR | | NR | | NR | |
| | Total of impurities related to drug product manufacture or degradation ≤2.5% and no single unspecified impurity ≥1% | TEST-513 | NR | | NR | | NR | | NR | |
| Dissolution | Q ≥75% @ T = 45 min | TEST-514 | Conforms | | Conforms | | Conforms | | Conforms | |
| Water by KF (%) | None | TEST-0268 | 4.7 | | 4.3 | | 4.2 | | 4.6 | |

HDPE—high-density polyethylene; NR—none reported; LOQ—limit of quantitation; RRT—relative retention time; ND—none detected; Q = amount of dissolved active ingredient as percentage of labeled content; T—Time; KF = Karl Fischer titration.

TABLE 40

Stability Results at 25° C./60% RH Compound A Tablets, 5 mg

Batch Size: 6930 tablets    Packaging: Closed in heat-induction sealed HDPE bottle containing desiccant canister with polypropylene closure

| Test | Acceptance Criteria | Method | Initial | 1 Month | 3 Month | 6 Month |
|---|---|---|---|---|---|---|
| Appearance | Light yellow/ yellow round tablet | TEST-009 | Conforms | Conforms | Conforms | Conforms |
| Assay (% label) | 90-110% | TEST-513 | 98.3 | 97.8 | 96.6 | 98.7 |

TABLE 40-continued

Stability Results at 25° C./60% RH Compound A Tablets, 5 mg

| | | | RRT | Area % | RRT | Area % | RRT | Area % | RRT | Area % |
|---|---|---|---|---|---|---|---|---|---|---|
| Related Substances (%) | Report all impurities ≥0.05% | TEST-513 | 0.49 | 0.06 | 0.49 | 0.05 | 0.49 | 0.06 | 0.46 | 0.06 |
| | | | 0.88 | 0.08 | NR | NR | 0.88 | 0.06 | 0.87 | 0.07 |
| | | | 0.92 | 0.07 | 0.92 | 0.07 | 0.91 | 0.08 | 0.91 | 0.09 |
| | | | 0.96 | 0.17 | 0.95 | 0.16 | 0.94 | 0.14 | 0.95 | 0.20 |
| | | | 1.02 | 0.32 | 1.02 | 0.38 | 1.02 | 0.06 | 1.02 | 0.07 |
| | | | 1.07 | 0.17 | 1.07 | 0.18 | 1.07 | 0.18 | 1.07 | 0.18 |
| | | | 1.23 | 0.06 | 1.23 | 0.07 | 1.24 | 0.06 | 1.25 | 0.06 |
| | | | 1.38 | 0.52 | 1.38 | 0.58 | 1.36 | 0.05 | 1.39 | 0.40 |
| Related Substances (%) | Report all impurities related to drug product manufacture or degradation ≥0.05% | TEST-513 | NR | | NR | | NR | | NR | |
| | Total of impurities related to drug product manufacture or degradation ≤2.5% and no single unspecified impurity ≥1% | TEST-513 | NR | | NR | | NR | | NR | |
| Dissolution | Q ≥75% @ T = 45 min | TEST-514 | Conforms | | Conforms | | Conforms | | Conforms | |
| Water by KF (%) | None | TEST-0268 | 4.7 | | 4.2 | | 4.6 | | 5.2 | |

HDPE—high-density polyethylene; NR—none reported; LOQ—limit of quantitation; RRT—relative retention time; ND—none detected; Q = amount of dissolved active ingredient as percentage of labeled content; T—Time; KF = Karl Fischer titration.

TABLE 41

Stability Results at 40° C./75% RH Compound A Tablets, 5 mg

Batch Size: 6930 tablets  Packaging: Closed in heat-induction sealed HDPE bottle containing desiccant canister with polypropylene closure

| Test | Acceptance Criteria | Method | Initial | 1 Month | 3 Month | 6 Month |
|---|---|---|---|---|---|---|
| Appearance | Light yellow/yellow round tablet | TEST-009 | Conforms | Conforms | Conforms | Conforms |
| Assay (% label) | 90-110% | TEST-513 | 98.3 | 98.4 | 96.1 | 97.4 |

| | | | RRT | Area % | RRT | Area % | RRT | Area % | RRT | Area % |
|---|---|---|---|---|---|---|---|---|---|---|
| Related Substances (%) | Report all impurities ≥0.05% | TEST-513 | 0.49 | 0.06 | 0.49 | 0.06 | 0.49 | 0.06 | 0.46 | 0.07 |
| | | | 0.88 | 0.08 | NR | NR | NR | NR | 0.85 | 0.05 |
| | | | NR | NR | NR | NR | 0.88 | 0.08 | 0.87 | 0.10 |
| | | | NR | NR | NR | NR | 0.89 | 0.06 | NR | NR |
| | | | 0.92 | 0.07 | 0.92 | 0.08 | 0.91 | 0.12 | 0.91 | 0.21 |
| | | | 0.96 | 0.17 | 0.95 | 0.16 | 0.94 | 0.14 | 0.95 | 0.19 |
| | | | 1.02 | 0.32 | 1.02 | 0.41 | 1.02 | 0.06 | 1.02 | 0.08 |
| | | | 1.07 | 0.17 | 1.07 | 0.18 | 1.07 | 0.19 | 1.07 | 0.17 |
| | | | NR | NR | NR | NR | NR | NR | 1.11 | 0.09 |
| | | | 1.23 | 0.06 | 1.23 | 0.06 | 1.24 | 0.06 | 1.25 | 0.06 |
| | | | 1.38 | 0.52 | 1.38 | 0.65 | 1.36 | 0.09 | 1.39 | 0.37 |
| Related Substances (%) | Report all impurities related to drug product manufacture or degradation ≥0.05% | TEST-513 | NR | | NR | | 0.89 | 0.06 | 0.85 | 0.05 |
| | | | | | | | 0.91 | 0.05 | 0.91 | 0.14 |
| | | | | | | | | | 1.11 | 0.09 |
| | Total of impurities related to drug product manufacture or degradation ≤2.5% and no single unspecified impurity ≥1% | TEST-513 | NR | | NR | | 0.11 | | 0.28 | |
| Dissolution | Q ≥75% @ T = 45 min | TEST-514 | Conforms | | Conforms | | Conforms | | Conforms | |
| Water by KF (%) | None | TEST-0268 | 4.7 | | 4.4 | | 4.9 | | 5.1 | |

HDPE—high-density polyethylene; NR—none reported; LOQ—limit of quantitation; RRT—relative retention time; ND—none detected; Q = amount of dissolved active ingredient as percentage of labeled content; T—Time; KF = Karl Fischer titration.

TABLE 42

Stability Results at 2-8° C. Compound A Tablets, 35 mg

Batch Size: 3500 tablets  Packaging: Closed in heat-induction sealed HDPE bottle containing desiccant canister with polypropylene closure

| Test | Acceptance Criteria | Method | Initial | | 1 Month | | 3 Month | | 6 Month | |
|---|---|---|---|---|---|---|---|---|---|---|
| Appearance | Light yellow/ yellow round tablet | TEST-009 | Conforms | | Conforms | | Conforms | | Conforms | |
| Assay (% label) | 90-110% | TEST-513 | 98.8 | | 100.2 | | 95.8 | | 97.1 | |
| | | | RRT | Area % | RRT | Area % | RRT | Area % | RRT | Area % |
| Related Substances (%) | Report all impurities ≥0.05% | TEST-513 | 0.49 | 0.05 | 0.49 | 0.05 | 0.48 | 0.05 | 0.46 | 0.06 |
| | | | 0.88 | 0.08 | 0.89 | 0.11 | 0.87 | 0.06 | 0.87 | 0.07 |
| | | | 0.92 | 0.07 | 0.92 | 0.07 | 0.91 | 0.07 | 0.91 | 0.08 |
| | | | 0.95 | 0.17 | 0.95 | 0.16 | 0.94 | 0.13 | 0.94 | 0.21 |
| | | | 1.02 | 0.31 | 1.02 | 0.50 | NR | NR | 1.02 | 0.08 |
| | | | 1.07 | 0.18 | 1.07 | 0.17 | 1.06 | 0.19 | 1.07 | 0.18 |
| | | | 1.23 | 0.05 | 1.23 | 0.06 | 1.23 | 0.06 | 1.25 | 0.07 |
| | | | NR | NR | 1.36 | 0.06 | NR | NR | NR | NR |
| | | | 1.37 | 0.56 | 1.38 | 0.65 | 1.35 | 0.06 | 1.39 | 0.59 |
| Related Substances (%) | Report all impurities related to drug product manufacture or degradation ≥0.05% | TEST-513 | NR | | 1.02 | 0.11 | NR | | 0.94 | 0.05 |
| | Total of impurities related to drug product manufacture or degradation ≤2.5% and no single unspecified impurity ≥1% | TEST-513 | NR | | 0.11 | | NR | | 0.05 | |
| Dissolution | Q ≥75% @ T = 45 min | TEST-514 | Conforms | | Conforms | | Conforms | | Conforms | |
| Water by KF (%) | None | TEST-0268 | 4.2 | | 4.1 | | 4.2 | | 4.3 | |

HDPE—high-density polyethylene; NR—none reported; LOQ—limit of quantitation; RRT—relative retention time; ND—none detected; Q = amount of dissolved active ingredient as percentage of labeled content; T—Time; KF = Karl Fischer titration.

TABLE 43

Stability Results at 25° C./60% RH Compound A Tablets, 35 mg

Batch Size: 3500 tablets  Packaging: Closed in heat-induction sealed HDPE bottle containing desiccant canister with polypropylene closure

| Test | Acceptance Criteria | Method | Initial | | 1 Month | | 3 Month | | 6 Month | |
|---|---|---|---|---|---|---|---|---|---|---|
| Appearance | Light yellow/ yellow round tablet | TEST-009 | Conforms | | Conforms | | Conforms | | Conforms | |
| Assay (% label) | 90-110% | TEST-513 | 98.8 | | 100.9 | | 92.4 | | 92.4 | |
| | | | RRT | Area % | RRT | Area % | RRT | Area % | RRT | Area % |
| Related Substances (%) | Report all impurities ≥0.05% | TEST-513 | 0.49 | 0.05 | 0.49 | 0.05 | 0.48 | 0.05 | 0.46 | 0.06 |
| | | | 0.88 | 0.08 | 0.89 | 0.11 | 0.87 | 0.06 | 0.87 | 0.07 |
| | | | 0.92 | 0.07 | 0.92 | 0.07 | 0.91 | 0.07 | 0.91 | 0.12 |
| | | | 0.95 | 0.17 | 0.95 | 0.16 | 0.94 | 0.13 | 0.94 | 0.20 |
| | | | 1.02 | 0.31 | 1.02 | 0.49 | 1.02 | 0.05 | 1.02 | 0.08 |
| | | | 1.07 | 0.18 | 1.07 | 0.18 | 1.06 | 0.18 | 1.07 | 0.18 |
| | | | 1.23 | 0.05 | 1.23 | 0.06 | 1.23 | 0.06 | 1.25 | 0.07 |
| | | | 1.37 | 0.56 | 1.38 | 0.56 | NR | NR | 1.39 | 0.48 |
| Related Substances (%) | Report all impurities related to drug product manufacture or degradation ≥0.05% | TEST-513 | NR | | 1.02 | 0.10 | NR | | 0.91 | 0.05 |
| | Total of impurities related to drug product manufacture or degradation ≤2.5% and no single unspecified impurity ≥1% | TEST-513 | NR | | 0.10 | | NR | | 0.11 | |

TABLE 43-continued

Stability Results at 25° C./60% RH Compound A Tablets, 35 mg

| | | | | | | |
|---|---|---|---|---|---|---|
| Dissolution | Q ≥75% @ T = 45 min | TEST-514 | Conforms | Conforms | Conforms | Conforms |
| Water by KF (%) | None | TEST-0268 | 4.2 | 4.1 | 4.3 | 4.4 |

HDPE—high-density polyethylene; NR—none reported; LOQ—limit of quantitation; RRT—relative retention time; ND—none detected; Q = amount of dissolved active ingredient as percentage of labeled content; T—Time; KF = Karl Fischer titration.

TABLE 44

Stability Results at 40° C./75% RH Compound A Tablets, 35 mg

Batch Size: 3500 tablets    Packaging: Closed in heat-induction sealed HDPE bottle containing desiccant canister with polypropylene closure

| Test | Acceptance Criteria | Method | Initial | | 1 Month | | 3 Month | | 6 Month | |
|---|---|---|---|---|---|---|---|---|---|---|
| Appearance | Light yellow/ yellow round tablet | TEST-009 | Conforms | | Conforms | | Conforms | | Conforms | |
| Assay (% label) | 90-110% | TEST-513 | 98.8 | | 99.9 | | 87.4 | | 95.4 | |

| | | | RRT | Area % | RRT | Area % | RRT | Area % | RRT | Area % |
|---|---|---|---|---|---|---|---|---|---|---|
| Related Substances (%) | Report all impurities ≥0.05% | TEST-513 | 0.49 | 0.05 | 0.49 | 0.06 | 0.48 | 0.06 | 0.46 | 0.07 |
| | | | NR | NR | NR | NR | NR | NR | 0.85 | 0.10 |
| | | | 0.88 | 0.08 | 0.89 | 0.11 | 0.87 | 0.08 | 0.87 | 0.16 |
| | | | NR | NR | NR | NR | NR | NR | 0.88 | 0.05 |
| | | | 0.92 | 0.07 | 0.92 | 0.09 | 0.91 | 0.15 | 0.91 | 0.21 |
| | | | 0.95 | 0.17 | 0.95 | 0.15 | 0.94 | 0.13 | 0.94 | 0.20 |
| | | | 1.02 | 0.31 | 1.02 | 0.51 | 1.02 | 0.05 | 1.02 | 0.08 |
| | | | 1.07 | 0.18 | 1.07 | 0.17 | 1.06 | 0.16 | 1.07 | 0.17 |
| | | | 1.23 | 0.05 | 1.23 | 0.06 | 1.23 | 0.06 | 1.11 | 0.06 |
| | | | NR | NR | NR | NR | NR | NR | 1.25 | 0.07 |
| | | | 1.37 | 0.56 | 1.38 | 0.58 | 1.35 | 0.10 | 1.39 | 0.39 |
| | | | NR | NR | 1.48 | 0.05 | NR | NR | 1.50 | 0.05 |
| Related Substances (%) | Report all impurities related to drug product manufacture or degradation ≥0.05% | TEST-513 | | | 1.02 | 0.12 | | | 0.85 | 0.10 |
| | | | | | | | | | 0.87 | 0.09 |
| | | | NR | NR | | | 0.91 | 0.08 | 0.88 | 0.05 |
| | | | | | 1.48 | 0.05 | | | 0.91 | 0.14 |
| | | | | | | | | | 1.11 | 0.06 |
| | | | | | | | | | 1.50 | 0.05 |
| | Total of impurities related to drug product manufacture or degradation ≤2.5% and no single unspecified impurity ≥1% | TEST-513 | NR | | 0.17 | | 0.08 | | 0.49 | |
| Dissolution | Q ≥75% @ T = 45 min | TEST-514 | Conforms | | Conforms | | Conforms | | Conforms | |
| Water by KF (%) | None | TEST-0268 | 4.2 | | 4.3 | | 4.8 | | 5.2 | |

HDPE—high-density polyethylene; NR—none reported; LOQ—limit of quantitation; RRT—relative retention time; ND—none detected; Q = amount of dissolved active ingredient as percentage of labeled content; T—Time; KF = Karl Fischer titration.

Fourth Generation Synthesis

Example 25: Fourth Generation Synthesis of Compound A

Step 1: N-((1r,4r)-4-(3-chloro-4-cyanophenoxy)cyclohexyl)-6-(4-(hydroxymethyl)piperidin-1-yl)pyridazine-3-carboxamide (Intermediate 2)

To a 260 L glass-lined carbon steel jacketed reactor was charged Intermediate 10 (7.00 kg), Intermediate 7 (8.89 kg), 2-pyridinol 1-oxide (HOPO) (491.4 g), and dimethylacetamide (26.32 g), under nitrogen. The reaction mixture was agitated at 110 rpm (allowed range: 70 to 150 rpm) and cooled to approximately 10° C. (allowed temperature range: 5° C. to 15° C.) over 39 minutes. To the reactor was charged N,N-Diisopropylethylamine (DIPEA) (4193.0 g) and the reaction mixture was agitated and the temperature re-adjusted back to approximately 10° C. (allowed temperature range: 5° C. to 15° C.) over 47 minutes, and the mixture held for a further 32 minutes. Agitation was halted, and the reactor was charged with 1-ethyl-3-(3-dimethylaminopropyl)carbodiimide (EDAC) (5936.0 g) and the reactor was purged for 6 minutes. The reaction mixture was agitated at 110 rpm, and dimethylacetamide (6580.0 g) was added and the temperature was adjusted to approximately 20° C. (allowed temperature range: 10° C. to 30° C.) over 1 hour and 8 minutes. Agitation was maintained and the reactor was held at approximately 20° C. for 16 hours. At the end of 16 hours, in-process control (IPC) showed 0.3% area (acceptance criterion: ≤1.0% area) of Intermediate 10, indicating completion.

To the reactor was charged tap water (35.0 kg), producing a thick slurry. The reactor was agitated at approximately 140 rpm (allowed range: 100 to 180 rpm) and heated to approximately 60° C. (allowed temperature range: between 55° C. to 65° C.) over the course of 1 hour and 15 minutes. To the reactor was charged additional tap water (35.0 kg) and isopropyl acetate (73.08 kg). The reactor temperature was adjusted to approximately 78° C. (allowed temperature range: 73° C. to 83° C.) and held for 40 minutes, during which time the slurry dissolved, and two layers formed. The contents of the reactor were allowed to settle for 3 hours at approximately 78° C. The reactor was purged with nitrogen and the bottom aqueous layer was removed.

To an 800 L glass-lined carbon steel jacketed reactor was charged isopropyl acetate (11.90 kg), followed by the organic layer from the 260 L reactor. A sodium chloride solution (77.0 kg, 9.1% w/w) was charged, followed by isopropyl acetate (60.90 kg). A biphasic solution was formed, and the mixture was heated to approximately 78° C. (allowed temperature range: 73° C. to 83° C.) over 47 minutes under agitation. The mixture was agitated for 4 hours and 5 minutes at approximately 78° C. The hot mixture was filtered through Celite 545 into the 260 L reactor. The 800 L reactor was rinsed with isopropyl acetate (23.80 g), which was filtered and added to the 260 L reactor. The 260 L reactor was heated to approximately 78° C. (between 73° C. to 83° C.) over 3 hours and 6 minutes and the contents were allowed to settle for 4 hours and 1 minute. The reactor was purged with nitrogen and the bottom aqueous layer was removed.

The reactor was agitated at approximately 110 rpm (between 90 and 110 rpm). To the reactor was charged sodium chloride solution (76.3 kg, 9.1% w/w), and a biphasic solution was formed. The reactor was heated to approximately 78° C. (allowed temperature range: 73° C. to 83° C.) over 1 hour and 54 minutes and the temperature was held for 31 minutes. Agitation was stopped and the contents were allowed to settle for 3 hours and 11 minutes. The reactor was purged with nitrogen and the bottom aqueous layer was removed.

The contents of the reactor were concentrated under vacuum distillation at 75° C. (allowed temperature range: 70° C. to 80° C.) to approximately 42 L. Isopropyl acetate (6.09 kg) was added and the reactor was heated to approximately 80° C. (allowed temperature range: 70° C. to 85° C.) under agitation. The reactor was held for 1 hour and 2 minutes at approximately 80° C. and then cooled to approximately 20° C. (allowed temperature range: 15° C. to 25° C.) over 6 hours and 28 minutes. The reactor was held at approximately 20° C. for 4 hours and 31 minutes. The resultant slurry was quickly transferred to an electrically agitated Hastelloy filter dryer with an 8 μm polypropylene filter cloth. The slurry was filtered under vacuum, and the mother liquor was used to rinse the reactor. The contents of the reactor were added to the filter dryer and filtered under vacuum. The solid cake was washed twice with isopropyl acetate (9.17 kg×2) and filtered under vacuum. The resulting cake was dried under vacuum with a jacket temperature of 60° C. (allowed temperature range: 55° C. to 65° C.) until total volatiles (by moisture analyzer) not more than 1.0% w/w (6 hours and 1 minute). The dryer was subsequently cooled, and the cake was collected to afford Intermediate 2 (10.90 kg, 79%). Release results are shown below in Table 45.

TABLE 45

Release results for Intermediate 2:

| Test Name | Specification | Result |
|---|---|---|
| Description | White to brown solid | Conforms |
| Identification (by IR) | Conforms to ref. spectrum | Conforms |
| Purity (by UPLC) | Not less than 96.0% (area) | 99.7% (area) |
| Related Substances (by HPLC) Intermediate 10 | Not more than 0.5% (area) Alert level: More than 0.15%(area) | Not detected |
| Related Substances (by HPLC) Intermediate 7 | Not more than 0.5% (area) Alert level: More than 0.15%(area) | Not detected |
| Related Substances (by HPLC) Any individual impurity | Report result by RRT in % (area) Alert level: More than 0.15%(area) | RRT 0.907: 0.07%(area) RRT 1.204: 0.20%(area) RRT 1.218 Less than 0.05% (area) |
| Related Substances (by HPLC) Total impurities | Not more than 2.0% (area) | 0.2% (area) |

Step 2: N-((1r,4r)-4-(3-chloro-4-cyanophenoxy)cyclohexyl)-6-(4-formylpiperidin-1-yl)pyridazine-3-carboxamide (Intermediate 3)

To an 800 L glass-lined carbon steel jacketed reactor, under nitrogen, Intermediate 2 (10.80 kg), sodium bromide (4.75 kg), sodium bicarbonate (3.89 kg) were added. The reactor was purged with nitrogen (×3), and deionized water (129.6 kg), and dichloromethane (186.73 kg) were subsequently added. The reactor was then allowed to agitate at 50 rpm (allowed range: 30 to 70 rpm) for 1 hour and 39 minutes.

Agitation was halted and (2,2,6,6-tetramethylpiperidin-1-yl)oxyl (TEMPO) (35.64 g) was added over 40 mins. The reactor was purged with nitrogen (×3), and the reaction subsequently charged with dichloromethane (7.18 kg). The reactor was then allowed to agitate at 50 rpm (allowed range: 30 to 70 rpm). The reactor was further charged with isopropyl alcohol (2.81 kg) and dichloromethane (7.18 kg). Agitation was increased to 110 rpm (allowed range: 105 to 115 rpm) and the reaction mixture was allowed to adjust to 20° C. (allowed temperature range: 15° C. to 25° C.), over 33 minutes. Once adjusted, ensuring all solids were dissolved, the reaction mixture, at this temperature and agitation speed, was held for 2 hours and 5 minutes.

The reaction mixture was then cooled to −2° C. (allowed temperature range: −3° C. to 0° C.) over 2 hours and 1 minute, and a sodium hypochlorite solution (34.85 kg) was then added over 40 minutes, ensuring the temperature was maintained between −3° C. and 0° C. (allowed temperature range: −3° C. and 3° C.), with agitation maintained at approximately 110 rpm (allowed range: 105 to 115 rpm). The addition rate and batch temperature are critical due to the exothermic nature of the reaction. Deionized water (5.40 kg) was then added through the transfer line used in the sodium hypochlorite transfer, ensuring the temperature was maintained between −3° C. and 0° C. The mixture was then subsequently held at −2° C. (allowed temperature range: −3° C. and 3° C.) for 1 hour and 2 minutes. After 1 hour, the in-process control (IPC) showed 0.3% area (acceptance criterion: ≤1.0% area) of Intermediate 2, indicating reaction completion.

The reaction mixture was allowed to warm to 20° C. (allowed temperature range: 15° C. and 25° C.), and agitation held at 90 rpm (allowed range: 80 to 100 rpm), and the reaction mixture was charged with acetic acid (4.104 kg), and the mixture held for 2 hours and 37 minutes, upon which a biphasic solution formed. An electrically agitated Hastelloy filter dryer with a 3-5 μm polypropylene filter cloth, was charged with Celite 545, and dichloromethane (24.6 kg) subsequently filtered through. A portion of the reaction mixture was filtered into a 260 L reactor, and the remaining mixture subsequently transferred into a 100 L reactor, and the 800 L reactor rinsed with dichloromethane (28.73 kg), which was filtered and added into the 100 L reactor. The 800 L reactor was rinsed with dichloromethane and filtered. The mixture was transferred from both the 260 L, and the 100 L reactor, back into the 800 L reactor, subsequently rinsing both with dichloromethane (5.40 kg×2).

Agitation was halted and the mixture allowed to settle into two phases for 3 hours and 25 minutes. The organic phase that separated was transferred into a 260 L reactor. The organic layer was transferred back into the 800 L, and the 260 L vessel subsequently rinsed with dichloromethane and the contents transferred into the 800 L reactor. Deionized water (108.0 kg) was added and the reactor allowed to agitate and the temperature increased to 20° C. and the content held at this agitation and temperature for 49 minutes. Agitation was halted and the mixture allowed to settle over 2 hours and 14 minutes, and two layers formed. The organic layer was transferred into the 260 L reactor, and the aqueous layer discarded appropriately.

The mixture was then concentrated by distillation, under normal atmosphere at 40° C. (allowed temperature range: 35° C. to 45° C.) maintaining the volume approximately between 38-49 L by replenishing as required with tetrahydrofuran allowing the temperature to increase to 60° C. (allowed temperature range: 55° C. to 65° C.) and the final volume approximately 46 L. The contents of the reactor were then concentrated under vacuum distillation, replenishing with tetrahydrofuran as required, at 60° C. (allowed temperature range: 55° C. to 65° C.) until ≤1.0% v/v of dichloromethane remained.

Recrystallization was undertaken by the addition of n-heptane (29.38 kg) (65° C.), and held for 1 hour and 10 minutes, maintaining a temperature of approximately 65° C., until a thick slurry was obtained. The slurry was subsequently cooled down slowly to 20° C. (allowed temperature range: 15° C. to 25° C.) by 4 hours and 34 minutes (temperature should not reach below 20° C. before 4 hours), and held at 20° C. for an additional 6 hours and 53 minutes. The resultant slurry was quickly transferred to an electrically agitated Hastelloy filter dryer with an 8 μm polypropylene filter cloth and the slurry was filtered under vacuum. The cake was washed twice with a tetrahydrofuran (4.86 kg) and n-heptane (3.67 kg) solution (×3) and filtered under vacuum. The resulting cake was dried under vacuum with a jacket temperature of 50° C. (allowed temperature range: 45° C. and 55° C.) for 8 hours and 2 minutes, and then increasing the jacket temperature of 75° C. (allowed temperature range: 70° C. and 80° C.) for 7 hours and 42 minutes, until total volatiles (by moisture analyzer) not more than 1.0% w/w. The dryer was subsequently cooled, and the cake was collected to afford Intermediate 3 (10.20 kg, 95%). Release results are shown below in Table 46.

TABLE 46

| Release results for Intermediate 3: | | |
|---|---|---|
| Test Name | Specification | Result |
| Description | White to light brown solid | Conforms |
| Loss on Drying | Not more than 1.5% w/w (2 gram at 12.0° C.) | 0.7% (w/w) |
| Identification (by HPLC) | Retention time of the main peak in the sample solution is consistent with reference standard (Not more than 5%) | Conforms |
| Purity (by HPLC) | Not less than 95.0% (area) | 99.0% (area) |
| Related Substances (by HPLC) Intermediate 2 | Not more than 1.5% (area) | 0.3% (area) |
| Related Substances (by HPLC) Impurity 1 | Not more than 3.0% (area) | 0.7% (area) |
| Related Substances (by HPLC) Major unspecified impurity | Not more than 0.50% (areal | Less than 0.05%(area) |
| Related Substances (by HPLC) at RRT 1.24 | Report results Alert limit: More than 0.35% (area) | 0.06% (area) |
| Related Substances (by HPLC) Any other unspecified Individual Impurity | Report results Alert limit: More than 0.15% (area) | RRT 1.24: Less than 0.05% (area) RRT 1.42 Less than 0.05% (area) |
| Identification (by IR) | Report result | Report test |

Step 3: N-((1r,4r)-4-(3-chloro-4-cyanophenoxy) cyclohexyl)-6-(4-((4-(2-(2,6-dioxopiperidin-3-yl)-6-fluoro-1,3-dioxoisoindolin-5-yl)piperazin-1-yl) methyl)piperidin-1-yl)pyridazine-3-carboxamide (Compound A)

To a 260 L glass-lined carbon steel jacketed reactor, under nitrogen, Intermediate 3 (8.48 kg), Intermediate 5 (7.62 kg), and dimethylacetamide (38.45 kg) were added. The reaction mixture was agitated at 110 rpm (allowed range: 80 to 130 rpm) and allowed to cool to 0° C. (allowed range: −5° C. to 5° C.) over 1 hour and 26 minutes. To this was added N-methylmorpholine (4.50 kg), and dimethylacetamide (0.751 kg), and the reaction heled at 0° C. and 110 rpm agitation for 3 h and 7 mins.

In a 100 L reactor, under nitrogen, a solution of sodium triacetoxyborohydride (STAB) (5.66 kg), in dimethylacetamide (21.60 kg) was prepared, and the solution allowed to agitate at 110 rpm (allowed range: 90 to 120 rpm), at 20° C. (allowed temperature range: 15° C. and 25° C. for 6 hours and 24 minutes. The STAB/dimethylacetamide solution was slowly added to the reaction mixture contained in the 260 L reactor over 2 hours, maintaining the temperature at 0° C. (allowed temperature range: −5° C. to 5° C.) and agitation at 110 rpm (allowed range: 80 to 130 rpm). Upon addition completion, the reactor was washed with dimethylacetamide (5.00 kg), subsequently cooled to 0° C., and its contents added to the reaction mixture in the 260 L reactor over 20 minutes, ensuring the temperature and agitation of 0° C. and 110 rpm, respectively, were maintained. The reaction mixture was held at 0° C. (allowed temperature range: −5° C. to 5° C.), 110 rpm for 6 h and 43 min. At the end of the 6 h and 43 mins, the in-process control (IPC) showed 0.7% area (acceptance criterion: ≤2.0% area) of Intermediate 3, indicating reaction completion.

Recrystallization was undertaken by charging the reactor vessel with absolute ethanol (40.78 kg), and deionized water (51.71 kg), under nitrogen, and allowing it to heat at 50° C. (allowed temperature range: 45° C. to 55° C.) over 1 hour and 14 minutes, and then further held at this temperature for 1 hour and 24 minutes. The mixture was then allowed to cool to 20° C. (allowed temperature range: 15 to 25) and held at this temperature for 4 hours and 3 minutes. The mixture was transferred to an electrically agitated Hastelloy filter dryer with 3-5 μm polypropylene filter cloth. The mixture was filtered under vacuum and the mother liquor was used to rinse the reactor, and was subsequently refiltered.

An absolute ethanol:water (deionized) wash solution was prepared by mixing absolute ethanol (11.51 kg), and deionized water (14.60 kg). The wash was used to rinse the reactor, and the filter cake was washed using this solution. The ethanol:water wash was repeated. The filter cake was agitated (×3) forming a slurry that was subsequently allowed to settle. The filter cake was further washed with absolute ethanol (23.02 kg×4), agitating the filter cake and sufficiently allowing the solid to deliquor.

The solid filter cake was dissolved in a solution of dichloromethane (155.12 kg) and methanol (9.26 kg), and the resultant solution subsequently transferred into an 800 L reactor through a 0.2 μm polytetrafluoroethylene capsule filter. The filter dryer was rinsed twice with dichloromethane/methanol, and the rinse solutions were filtered through a 0.2 μm polytetrafluoroethylene capsule filter into the 800 L reactor. The mixture was then subject to atmospheric distillation, under normal atmosphere at 45° C. (allowed temperature range: 35° C. to 50° C.) maintaining the volume by replenishing as required with absolute ethanol to the final volume of approximately 292 L, and a slurry was obtained. The temperature was then allowed to increase to 55° C., maintaining the volume by replenishing as required with absolute ethanol to the final volume of approximately 292 L. The contents of the reactor were then subject to vacuum distillation, replenishing with absolute ethanol as required, at 55° C. (allowed temperature range: 45° C. to 65° C.), to the final volume of approximately 300 L. The vacuum distillation step was repeated until ≤1.0% v/v of dichloromethane remained.

The temperature of the mixture was then adjusted to 55° C. (allowed temperature range: 50° C. and 60° C.), and agitation maintained at approximately 100 rpm (allowed range: 90 to 110 rpm) over 30 minutes, and then subsequently held at 55° C. for 34 minutes. The mixture was then allowed to slowly cool to 20° C. (allowed temperature range: 15° C. and 25° C.), over 3 hours and 59 minutes (temperature should not reach below 20° C. before 3 hours), and then held at 20° C. for an additional 4 hours and 16 minutes. The resultant slurry was quickly transferred to an electrically agitated Hastelloy filter dryer with 3-5 μm polypropylene filter cloth and the slurry was filtered under vacuum.

The cake was washed with absolute ethanol (23.02 kg, ×3) and IPC criterion required to be met. The wet cake was subsequently dried under vacuum with a jacket temperature of 65° C. (allowed temperature range: 60° C. to 70° C.) for 29 hours and 59 minutes, until total volatiles (by moisture analyzer) are not more than 1.0% w/w. The dryer was subsequently cooled, and the cake was collected to afford Compound A (13.08 kg, 89%). Release results are shown below in Table 47.

TABLE 47

Release results for Compound A:

| Test Name | Specification | Result |
| --- | --- | --- |
| Description | Light yellow to greenish yellow crystals | Conforms |
| Identification (by IR) | Conforms to ref. spectrum | Conforms |
| Identification (by HPLC) | Retention time of the main peak in the sample solution is consistent with reference standard (Not more than 5%) | Conforms |
| Purity (by HPLC) | Not less than 98.0% (area) | 99.6% (area) |
| Related Substances (by UPLC) Impurity 2 | Not more than 0.15% (area) | Not detected |
| Related Substances (by UPLC) Impurity 3 | Not more than 0.13% (area) | Less than 0.05% (area) |
| Related Substances (by UPLC) Impurity 4 | Not more than 0.15% (area) | Not detected |
| Related Substances (by UPLC) impurity at RRT ~1.64 | Not mote than 0.35% (area) | 0.12% (area) |
| Related Substances (by UPLC) Major unspecified impurity | Not more than 0.13% (area) | 0.11% (area) |
| Related Substances (by UPLC) Any individual unspecified impurity | Report result by RRT in % (area) | RRT 0.39: 0.11% (area) RRT 0.41: 0.05% (area) RRT 0.46: 0.06% (area) RRT 0.50: 0.05% (area) RRT 0.56: 0.09% (area) RRT (0.06, 0.33, 0.48, 0.64, 0.65, 0.68, 1.12 and 1.17): Less than 0.05% (area) |

TABLE 47-continued

Release results for Compound A:

| Test Name | Specification | Result |
| --- | --- | --- |
| Residual Solvents (by GC) Ethanol | Not more than 10000 ppm | 5962 ppm |
| Residual Solvents (by GC) Acetonitrile | Not more man 410 ppm | Less than 123 ppm |
| Residual Solvents (by GC) Acetone | Not more man 5000 ppm | Not detected |
| Residual Solvents (by GC) Isopropyl Alcohol | Not more man 5000 ppm | Not detected |
| Residual Solvents (by GC) Tetrahydrofuran | Not more than 720 ppm | Not detected |
| Residual Solvents (by GC) Isopropyl Acetate | Not more than 5000 ppm | Less than 1500 ppm |
| Residual Solvents (by GC) n-Heptane | Not more than 5000 ppm | Not detected |
| Residual Solvents (by GC) 4-Methylmorpholine | Not more than 1000 ppm | Not detected |
| Residual Solvents (by GC) Diisopropylethylamine | Not more than 1000 ppm | Not detected |
| Residual Solvents (by GC) N-N,Dimethylacetamide | Not more than 1090 ppm | Less than 327 ppm |
| Residual Solvents (by GC) Methanol | Report result | Less than 900 ppm |
| Residual Solvents (by GC) Dichloromethane | Report result | Less than 180 ppm |
| Water content (by KF- Oven) | Report result | Less than 0.5% (w/w) |
| Residue on ignition | Report result | 0.0% (w/w) |
| Particle size d(0.1) | Report result | 3 μm |
| Particle size d(0.5) | Report result | 12 μm |
| Particle size d(0.9) | Report result | 33 μm |
| X-ray powder diffraction | Report result | Crystalline |
| Content of (by HPLC) Acetic Acid | Report result | Not detected |
| Differential scanning calorimetry (DSC) | Report result (Onset and endotherm temperatures) | Onset temperature: 289.85° C. Endotherm temperature: 293.68° C. |

Fifth Generation Synthesis

Example 26: Fifth Generation Synthesis of Compound A

The fifth generation sequence followed the same general scheme as the fourth generation sequence. The steps of the fifth generation sequence are shown below. Material quantities are normalized to a hypothetical 1 kg starting material for each step. The quantities of starting materials are adjusted for potency according to the following formulae:

Step 1:

Reaction is performed under $N_2$.

Potency Calculations to Determine Input (Per Kg) of Intermediate 10 and Intermediate 7

Intermediate 7 potency=(100%−Loss on Drying %)×Purity=a wt. %

Intermediate 7 corrected target calculation=Intermediate 7: 1.00 kg×[1.0/(Intermediate 7(% w/w)/100)]

Intermediate 10 potency=(100%−(Loss on Drying %+Residue on Ignition %))×Purity=b wt. %

Intermediate 10 corrected target calculation=1.00 kg×[0.843/(Intermediate 10 Potency (% w/w)/100)]

1. To Reactor A, add Intermediate 7 (1.000 Kg±1.0%, corrected for potency as described above), Intermediate 10 (0.843 Kg±1.0%), HOPO (0.0580 Kg±1.0%, corrected for potency as described above).
2. To Reactor A add DMAc (2.82 Kg; or 3.0 L±5.0%) by spray ball.
3. Purge with $N_2$.
4. Cool to 10±5° C.
5. To Reactor A add DIPEA (0.495 Kg, or 0.669 L±1.0%) at 10±5° C.
   Note: slightly exothermic, control addition to maintain temperature range.
6. Rinse line with DMAc (0.09 Kg or 0.10±5.0%).
7. Adjust to 10±5° C.
8. Stir at 10±5° C. for NLT 0.5 h.
9. To Reactor A add EDAC (0.701 Kg±1.0%).
10. Chase with additional DMAc (0.66 Kg or 0.70 L±5.0%) via spray ball if necessary
11. Adjust to 20±10° C.
12. Stir at 20±5° C.
13. After NLT 20 hrs, sample for IPC-1.
    Note: IPC≤1.0 AP residual Intermediate 7;
14. To Reactor B add NaCl (1.00 Kg±5.0%).
15. To Reactor B add tap water (6.6 Kg, or 6.6 L±5.0%).
16. Stir at 25±5° C. until a solution is formed.
17. Transfer contents of Reactor B to Reactor A
18. To Reactor A add tetrahydrofuran (5.34 Kg or 6.0 L±5.0%).
19. Adjust the internal temperature to 50±5° C.
20. Stir at 50±5° C. for NLT 0.5 h.
21. Transfer the mixture from Reactor A through a Celite bed to Reactor B.
22. Wash Reactor A and the Celite bed with Tetrahydrofuran (1.34 Kg or 1.5 L±5%) and transfer to Reactor B.
23. Adjust contents of Reactor B to 50±5° C.

24. Stop agitation and hold for NLT 1 hr.
25. Separate out the bottom aqueous layer.
26. To Reactor A add Sodium Chloride (1.25 Kg±5.0%).
27. To Reactor A add tap Water (6.60 Kg or 6.6 L/Kg±5.0%).
28. Agitate Reactor A for NLT 0.5 h. at 25° C. until a solution is formed.
29. Transfer contents of Reactor A to Reactor B.
30. Adjust contents of Reactor B to 50±5° C.
31. Stop agitation and hold for NLT 1 h.
32. Separate out the bottom aqueous layer from Reactor B.
33. To Reactor A add sodium chloride (1.50 Kg±5.0%).
34. To Reactor A add tap water (6.60 Kg or 6.6 L/Kg±5.0%).
35. Agitate Reactor A for NLT 0.5 h. at 25° C. until a solution is formed
36. Transfer contents of Reactor A to Reactor B.
37. Adjust contents of Reactor B to 50±5° C.
38. Stop agitation and hold for NLT 1 h.
39. Separate out the bottom aqueous layer from Reactor B.
40. To Reactor B add tetrahydrofuran (7.57 Kg or 8.5 L±5.0%).
41. Heat contents of Reactor B to 65±5° C.
42. Distill contents of Reactor B under atmospheric pressure at 65±5° C. with slight vacuum bleed (scrubber) until the volume is 3.30 L/Kg (±0.5 L).
43. To Reactor B add tetrahydrofuran (7.57 Kg or 8.5 L±5.0%).
44. Heat contents of Reactor B to 65±5° C.
45. Distill contents of Reactor B under atmospheric pressure at 65±5° C. with slight vacuum bleed (scrubber) until the volume is 3.30 L/Kg (±0.5 L).
46. Clean Reactor A with water and Tetrahydrofuran.
47. To Reactor A add Tetrahydrofuran (4.45 Kg or 5.0 L±5.0%).
48. Heat contents of Reactor A to 65±5° C.
49. Transfer contents of Reactor A to Reactor B via spray ball
50. Transfer contents of Reactor B to Reactor A via an in-line filter.
51. Rinse contents of Reactor B with Tetrahydrofuran (1.34 Kg or 1.5 L±5.0%) via spray ball and transfer to Reactor A via in-line filter.
52. Adjust contents of Reactor A to 65±5° C.
53. Clean Reactor B with water and THF.
54. Distill contents of Reactor A under atmospheric pressure at 65±5° C. with slight vacuum bleed (scrubber) until the volume is 6.0 L/Kg (±0.5 L).
55. To Reactor B charge THF (1.34 Kg, 1.5 L±5.0%).
56. Heat contents of Reactor B to 65±5° C.
57. Transfer contents of Reactor B to Reactor A via spray ball.
58. Take sample for Water content (KF coulometric).
59. If result is 50.50 wt. % then continue to Step 62, if not continue to Step 60.
60. To Reactor A charge THF via spray ball (4.45 Kg or 5.0 L±5.0%).
61. Continue to Step 54.
62. Verify solution is present, increase agitation to help dissolve any solids on walls of reactor that are above solution.
63. To Reactor A charge n-Heptane (0.68 Kg, or 1.0 L±5%) at 65±5° C.
64. Charge a slurry of Intermediate 2 seed or Intermediate 2 (0.002 Kg) in n-Heptane (0.034 Kg or 0.05 L).
65. Stir at 65±5° C. for 1 hr (±30 minutes).
66. To Reactor A charge n-Heptane (2.72 Kg, or 4.0 L±5%) at 65±5° C. over 3 hrs (±30 minutes).
67. Stir at 65±5° C. for 1 hr (±30 minutes).
68. Cool down to 20±5° C. over 3 hrs (±60 minutes).
69. Stir at 20±5° C. for 6 hrs (±60 minutes).
70. Filter the slurry under vacuum at 20±5° C. and de-liquor the cake.
71. Verify solids from Reactor A have been transferred to filter dryer.
72. Clean Reactor B with Water and Tetrahydrofuran.
73. To a Reactor B add Tetrahydrofuran (1.34 Kg or 1.5 L/Kg).
74. To a Reactor B add n-Heptane (0.68 Kg or 1.0 L/Kg).
75. Stir contents of Reactor B for 5 minutes at 20±5° C.
76. Transfer contents of Reactor B via spray ball to Reactor A.
77. Transfer contents of Reactor A to filter dryer and then re-slurry the cake for NLT 5 minutes.
78. De-liquor the cake under vacuum and nitrogen.
79. Dry the wet cake at 580° C. (filter dryer jacket temperature) under vacuum until LOD passes (NLT 6 hrs).

LOD spec.=≤1.0%/120° C.

80. The expected yield of Intermediate 2=1.44 Kg (88 mol % yield).

Step 2:

Reaction is performed under $N_2$.

1. To Reactor A add Intermediate 2 (1.00 Kg±1.0%), NaBr (0.219 Kg±1.0%), and $NaHCO_3$ (0.3575 Kg±1.0%) and NaCl (1.80 kg±1.0%).
2. To Reactor A add TEMPO (3.325 g±1.0%).
3. To Reactor A add DCM (19.0 L±5.0%).
4. Chase TEMPO addition with DCM (0.50 L±5.0%) and add the solution to Reactor A.
5. Stir at 20° C. for 0.5 h.
6. To Reactor A add deionized $H_2O$ (7.0 L±5.0%).
7. To Reactor A add IPA (0.127 Kg±1.0%).
8. Chase IPA addition with DCM (0.50 L±5.0%) and add the solution to Reactor A.
9. Stir at 20° C. for NLT 2.0 h.
10. Cool the mixture to −12 to −10° C., preferably to −11° C.
    Note: maximum cooling control of the batch temperature is critical for this step;
11. To Reactor A add aq. NaClO (1.15 eq±1.0%) by Spray Ball in NLT 15 min but NMT 45 min, preferably in <0.5 h, while controlling the internal temperature between −12 to −3° C., preferably −12 to −8° C.
    Note: Mass of aq. NaClO (Kg)=(1.15×74.44)/(469.97× Conc of aq. NaClO (wt %))
    Note: the bleach solution is pre-cooled to 0±5° C.
12. Chase the line with additional deionized $H_2O$ (0.50 L±5.0%) by Spray Ball in NLT 5 min but NMT 0.5 h.
13. Stir at −12 to −3° C. for NLT 1.0 h.
14. Sample the organic layer for IPC-1 analysis.
15. If IPC-1 fails, kicker charge of aq NaClO (pre-cooled to 0±5° C.) by Spray Ball in NLT 15 min but NMT 45 min, preferably in <0.5 h, while controlling the internal temperature between −12 to −3° C., preferably −12 to −8° C.
16. Chase the line with additional deionized $H_2O$ (0.50 L±5.0%) by Spray ball in NLT 5 min but NMT 0.5 h.
17. Stir at −12 to −3° C. for NLT 1.0 h
18. Sample for IPC-1.
19. If IPC-1 passes, adjust to 20±5° C.

21. Separate the bottom DCM layer in Reactor A to Reactor B.
    Approximate volume of organic DCM phase (20 L/Kg) and solution is colorless to brown soln.
    Approximate volume of aqueous phase is (10 L/Kg) and solution is colorless to light brown.
22. Remove aqueous phase from Reactor A and send to waste.
23. Clean Reactor A with Water, THF.
24. To Reactor B charge H$_2$O (7.0 L/Kg±5.0%).
25. Stir Reactor B for NLT 0.5 h at 20±5° C.
26. Filter the mixture through a Celite bag to Reactor A.
27. Chase wash Reactor B with DCM (2.0 L/Kg) to Reactor A.
28. Wash Reactor B with H$_2$O and THF.
29. Stop agitation of Reactor A for NLT 2.0 h.
30. Separate the bottom organic layer to Reactor B.
    Note: Sample the DCM layer for UPLC analysis;
31. Distill the organic solution in Reactor B to volume=5.0 L/Kg (+/−0.5 vol) under normal atmosphere and batch temperature=40±5° C.
32. To Reactor B charge THF (1.0 L/Kg±5.0%) by spray ball.
33. Adjust the batch temperature to 38±2° C.
34. Add 5.0 L/Kg of n-Heptane over 0.5 h maintaining the batch temperature of 38±2° C.
35. Add Intermediate 3 seeds (5.0 g/Kg) in n-Heptane (0.10 L/Kg).
36. Stir at 38±2° C. for NLT 4.0 h.
37. Add additional 5.0 L/Kg of n-Heptane over 1.0 h.
38. Stir at 38±2° C. for NLT 2.0 h.
39. Cool down to 20±5° C. over NLT 4 h.
40. Stir at 20±5° C. for additional NLT 6 h.
41. Filter the slurry under vacuum at 20° C. and nitrogen.
42. If solids remain in the reactor, recirculate mother liquors back into reactor through spray ball and filter mixture again.
43. Wash Reactor B with 1.5 L/Kg of n-Heptane by spray ball.
44. Slurry wash the cake and remove liquors under vacuum until most of liquors are removed.
45. Remove liquors under vacuum and pull until most of liquors are removed.
46. Dry the cake at NMT 50° C.±5° C. for NLT 8 h under vacuum and nitrogen.
47. Continue drying the cake at 75±5° C. under vacuum and nitrogen flow until LOD≤1.0%/120° C.
48. Expected Intermediate 3 amount=0.95 Kg (95 mol %).

Step 3:

Potency Calculations to Determine Input (Per Kg) of Intermediate 3 and Intermediate 5

Intermediate 3 potency calculation=(100%−Loss on Drying %)×Purity=$a$ wt. %

Intermediate 3 Corrected Target Calculation:

Intermediate 5: 1.00 Kg×(1.0/(Intermediate 3 Potency (% w/w)/100))

Intermediate 5 potency calculation=(100%−(Water Content %+Residual Solvents %))×Purity=$b$ wt. %

Note: Water Content, Residual Solvents, and Purity data obtained from Intermediate 5 CofA Intermediate 5 Corrected Target Calculation:

Intermediate 5: 1.00 Kg×(0.848/(overall potency/100))

1. To Reactor A, charge NaBH(OAc)$_3$ (0.679 Kg±1.0%).
2. To Reactor A, charge DMAc-1 (2.75 vol±5%).
3. Once dissolved, hold Reactor A at 20±5° C. for NLT 1.0 h
4. To Reactor B, charge Intermediate 5 [0.848/(b wt. %/100)] Kg)±1.004), Intermediate 3 (1.000/(a wt. %/100) Kg±1.0%) and DMAc-2 (4.90 vol±5%).
5. Cool Reactor B to 0±5° C.
6. To Reactor B, charge N-Methylmorpholine (0.540 Kg±1.0%) in NLT 0.5 h while keeping the batch temperature at 0±5° C.
7. Agitate Reactor B at 0±5° C. for NLT 2.0 h but NMT 4.0 h.
8. Transfer the contents in Reactor A to Reactor B over NLT 1.0 h, while maintaining internal temperature at 0±5° C.
9. Rinse Reactor A with DMAc-4 (0.64 vol±5%) and transfer to Reactor B in NLT 15 min.
10. Agitate Reactor B at 0±5° C. for NLT 6.0 h.
11. Sample for IPC-1.
IPC-1 criteria: Intermediate 3≤2.0%;
12. If IPC-1 fails, continue agitation at 0±5° C. for an additional 6 h.
13. Sample again for IPC-1.
14. If IPC-1 fails again, check for technical advice.
15. To Reactor B, charge EtOH (6.2 vol±5%) over NLT 0.5 h while maintaining temperature at 0±5° C.
16. To Reactor B, charge H$_2$O (6.2 vol±5%) over NLT 0.5 h while maintaining temperature at 0±5° C.
17. Adjust the content in Reactor B to 50±5° C. in NMT 2.0 h.
18. Hold the content in Reactor B at 50±5° C. for NLT 1.0 h but NMT 2.0 h.
19. Cool the content in Reactor B to 20±5° C. in 3.0 h±0.5 h.
20. Hold the content in Reactor B at 20±5° C. for NLT 4.0±0.5 h.
21. Transfer the slurry in Reactor B to Filter C (filter cloth=3-5 μm) under N$_2$ blanket and filter.
22. Wash Reactor B by spray ball with EtOH (1.75 vol±5%) and H$_2$O (1.75 vol±5%) at 20±5° C.
23. Filter the content in Reactor B (re-slurry) under N$_2$ blanket.
24. Wash the wet cake (re-slurry) with EtOH/H$_2$O (1:1; 3.5 vol±5%) at 20±5° C.
25. After de-liquoring washes, continue to de-liquor the wet cake for NLT 2 hrs and until no major solvent is removed from the filter drier.
26. Perform four slurry washes of the wet cake in Filter C with EtOH (4×3.5 vol±5%).
27. De-liquor the wet cake in Filter C for NLT 1 h after each of the four slurry washes.
28. Sample the wet cake in Filter C for IPC-2 (LOD (2 g, 120° C.)) and perform the calculation:
    Correction for EtOH in Compound a crude cake (97 mol % compound A):

Intermediate 3 (Kg) input×1.684=Calculated Compound $A$ crude product (Kg)

EtOH in wet Compound $A$ crude product (Kg)=LOD %×Calculated Compound $A$ crude product (Kg)/(1−LOD %)

(EtOH in wet Compound A crude product (Kg)/
0.789)/(Intermediate 3 (Kg) input)=EtOH content (vol) to be corrected EtOH content (vol) to be corrected→Subtract from EtOH to be added in Step 38 (7 vol EtOH)

*Charges based on initial Intermediate 3 input*

29. Charge DCM (28.0 vol±5% of Intermediate 3) to Reactor A.
30. Charge MeOH (2.8 vol±5% of Intermediate 3) to Reactor A and agitate for NLT 0.5 h.
31. Transfer half of DCM/MeOH (10:1, 15.4 vol±20%) from Reactor A to Filter C.
32. Agitate Filter C at 20±5° C. for NLT 0.5 h to dissolve most of the wet crude solids.
33. Polish filter the solution in Filter C to Reactor B via an in-line capsule filter.
34. Transfer part of the remaining DCM/MeOH (10:1, 14.4 vol±5%) from Reactor A to Filter C.
35. Agitate Filter C at 20±5° C. for NLT 0.5 h to dissolve all of the remaining crude solids.
36. Polish filter the solution in Filter C to Reactor B via an in-line capsule filter.
37. Rinse Filter C with remaining DCM/MeOH (10:1; 1.0 vol±5%) and filter to Reactor B via an in-line capsule filter.
38. Distill the solution in Reactor B while maintaining a constant volume (vmax ~32 vol) under atmospheric conditions with continuous addition of EtOH (7.0 vol±5%–vol EtOH from Step 28 calculation) at an internal temperature between 35-45° C.
39. Sample for IPC-3, GC analysis for DCM content.
IPC-3 criteria: DCM≤67 vol % (relative to total volume of DCM+MeOH+EtOH peaks);
Report EtOH vol % and MeOH vol %.
40. If DCM content is passing, go directly to Step 43. If it is failing, go to Step 41
41. If IPC-3 fails, continue distillation with additional EtOH (1.0 vol±5%) and re-sample for GC analysis
IPC-3 criteria: DCM≤67% (relative to total volume of DCM+MeOH+EtOH peaks);
Report EtOH vol % and MeOH vol %.
42. If IPC-3 fails again, repeat Step 41.
43. Cool Reactor B to 35±2° C. and charge Compound A seeds (0.50 wt %±5%) in EtOH (0.075 vol±5%).
44. Agitate Reactor B at 35±2° C. for NLT 0.5 h
45. Heat Reactor B back up to reflux conditions (41±2° C.) and continue constant volume distillation (vmax –32 vol) under atmospheric conditions with the continuous addition of EtOH (7.0 vol±5%) while maintaining batch temperature between 40-50° C.
46. Continue distillation in Reactor B under constant volume (vmax –32 vol) under atmospheric conditions until the internal temperature reaches at least 50° C.
47. Perform remainder of distillation in Reactor B under vacuum maintaining a constant volume (vmax –32 vol) with addition of EtOH (28.0 vol±5%) and maintaining internal temperature at 55±10° C.
48. Sample Reactor B for IPC-4 by GC.
IPC-4 criteria: DCM/EtOH≤1.0%.
49. If IPC-4 fails, repeat the vacuum distillation with additional EtOH (4.0 vol±5%) and continue to step 50.
50. Sample Reactor B for IPC-4 by GC.
IPC-4 criteria: DCM/EtOH≤1.0%.
51. If IPC-4 passes, adjust the batch temperature to 55±5° C.
52. Agitate the slurry in Reactor B at 55±5° C. for NLT 0.5 h.
53. Cool the slurry in Reactor B down to 20±5° C. in NLT 3.0 h.
54. Agitate the slurry in Reactor B at 20±5° C. for NLT 4.0 h.
55. Filter the slurry in Reactor B to Filter C (filter cloth=8 μm).
56. Rinse Reactor B with EtOH (3.5 vol±5%).
Note: EtOH should be polish filtered.
57. Filter the rinse in Reactor B and transfer to Filter C as a slurry wash.
58. Perform two slurry washes of the wet cake in Filter C with EtOH (2×3.5 vol±5%).
Note: EtOH should be polish filtered.
59. De-liquor the cake in Filter C for NLT 1 h
60. Sample Filter C for IPC-5 for the impurity profile of the wet cake.

| IPC-5 | Specified Impurities | | | | Unspecified Individual Impurity | |
|---|---|---|---|---|---|---|
| Impurity | Impurity 2 | Impurity 3 | Impurity 4 | RRT 1.64 | Any | Compound A |
| Criteria (%) | ≤0.15 | ≤0.13 | ≤0.15 | ≤0.35 | ≤0.13 | NLT 98.0% |

61. If IPC-5 fails, go back to step 28 (Sample wet cake for LOD, perform EtOH Calculation and start the distillation).
62. If IPC-5 passes, dry the cake under vacuum with agitation at 80±5° C. Note: sample the wet cake for PDXR, DSC and KF (FIO).
63. Sample contents in Filter C for IPC-6, LOD (2 g, 120° C.)
IPC-6 criteria: LOD (2 g, 120° C.)≤1.0% after NLT 8 h.
64. If IPC-6 fails, continue drying until LOD criteria is met.
65. If IPC-6 passes, sample for IPC-7 (GC analysis).
66. IPC-7 criteria: GC residual solvents

| | ACN | Acetone | IPA | EtOH | THF | iPAc | Heptane | NMM | DIPEA | DMA |
|---|---|---|---|---|---|---|---|---|---|---|
| Solvent ppm | NMT 410 | NMT 5000 | NMT 5000 | NMT 10000 | NMT 720 | NMT 5000 | NMT 5000 | NMT 1000 | NMT 1000 | NMT 1090 |

67. If IPC-7 fails, continue drying until criteria is met.
68. Once IPC-7 passes, discharge the material from Filter C.

Figure 26:
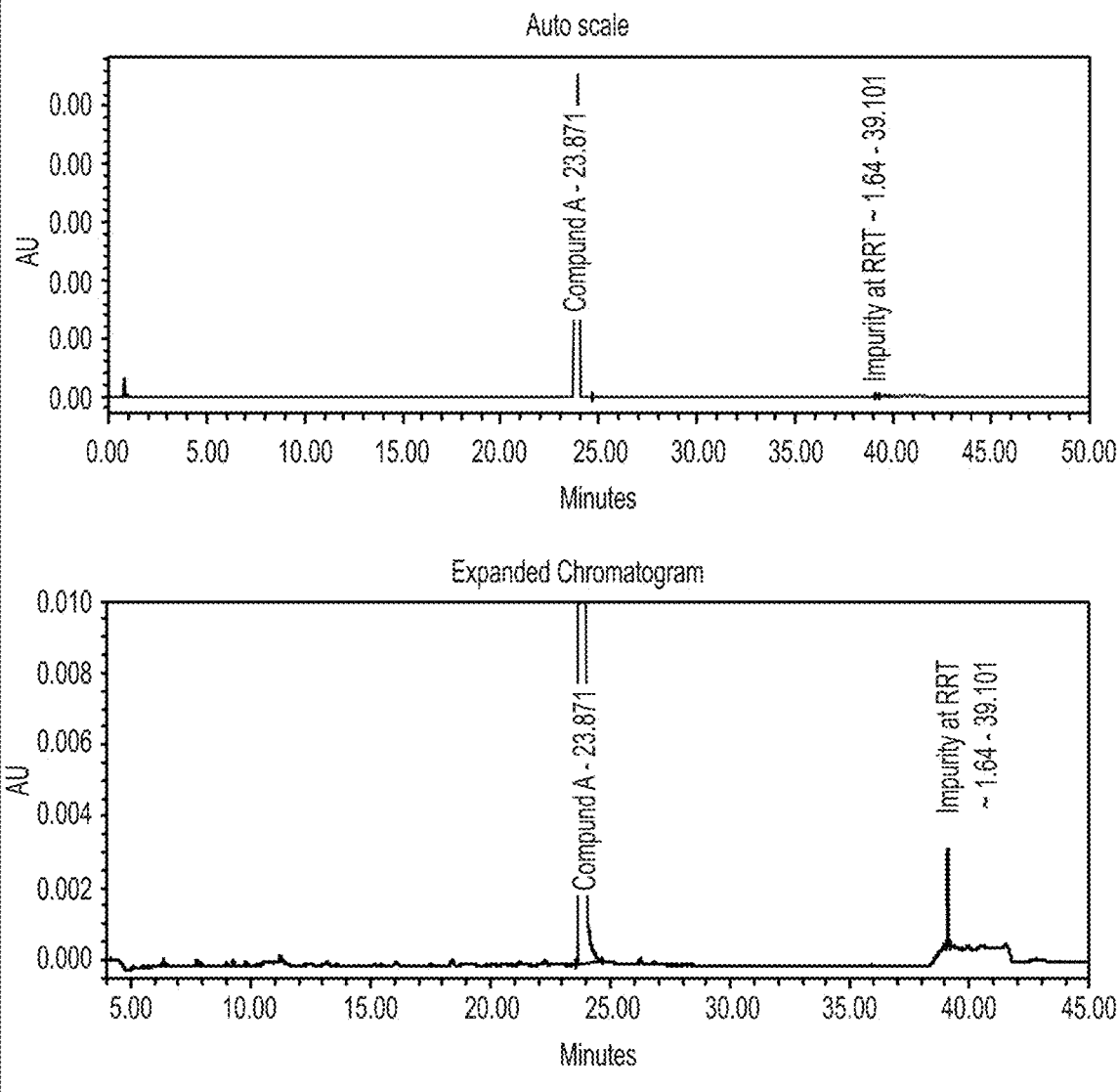
FIG. 26 is a chromatogram of purified Compound A, as produced by the fifth-generation synthesis.

The fifth generation process described above was conducted on a 1.7 kg scale (relative to Intermediate 3), to afford Compound A (2.420 kg). Purity was calculated to be 99.9% by UPLC (see FIG. 26 and Table 48).

TABLE 48

Peak Results for Chromatogram of Purified Compound A

| | Name | RT | RRT | Area | % Area | USP Resolution | USP Tailing |
|---|---|---|---|---|---|---|---|
| 1 | Intermediate 5 | 1.361 | | | | | |
| 2 | Intermediate 7 | 5.252 | | | | | |
| 3 | Impurity 1 | 6.374 | | | | | |
| 4 | Impurity at RT ~7.78 | 7.782 | | | | | |
| 5 | Impurity at RT ~7.95 | 7.949 | | | | | |
| 6 | Intermediate 3 Acetal | 8.379 | | | | | |
| 7 | Diacid Impurity | 8.594 | | | | | |
| 8 | Impurity at RT ~8.78 | 8.784 | | | | | |
| 9 | Impurity at RT ~9.72 | 9.715 | | | | | |
| 10 | Intermediate 2 | 10.169 | | | | | |
| 11 | Intermediate 3Methyl Hemiacetal | 11.239 | | | | | |
| 12 | Intermediate 3 | 13.057 | | | | | |
| 13 | Ring 2 Methanolysis Adduct-1 | 16.232 | | | | | |
| 14 | Ring 2 Methanolysis Adduct-2 | 18.381 | | | | | |
| 15 | Impurity 2 | 19.097 | | | | | |
| 16 | Impurity 3 | 20.529 | | | | | |
| 17 | Impurity at RT ~21.77 | 21.770 | | | | | |
| 18 | Impurity 4 | 22176 | | | | | |
| 19 | Compound A | 23.871 | 1.00 | 3784159 | 99.854 | | 0.9 |
| 20 | Impurity at RT ~24.18 | 24.181 | | | | | |
| 21 | Impurity at RT ~24.90 | 24.897 | | | | | |
| 22 | Carbamate Impurity | 26.735 | | | | | |
| 23 | Impurity at RRT ~1.64 | 39.10 | 1.64 | 5527 | 0.146 | 138.8 | 2.3 |
| Sum | | | | 3789585 | | | |

Example 27: Development of High-Strength Compound A Tablet

Due to a demand for a higher strength tablet for Phase 1 dose escalation trials, a higher strength tablet was developed.

The higher strength tablet formulation was accomplished in two phases. The first phase screened the loading of the 100% amorphous spray dried API (SDI) in the tablet formulation using miniaturized laboratory techniques, and the second phase optimized the selected formulation composition.

The formulation compositions during the screening phase encompassed a range of SDI loads equal to 10% to 40%, and tablet strengths equal to 70 mg, 140 mg, 280 mg (for 700 mg Tablet Press Weight), as outlined in Table 49

TABLE 49

Formulation compositions of higher strength SDI loads - 10%, 20% and 40% (700 mg Tablet Press Weight)

| | | Formulation Reference | | |
|---|---|---|---|---|
| | | C1 | C2 | C3 |
| | | Tablet Strength/Tablet Press Weight (mg/mg) | | |
| | | 70/700 | 140/700 | 280/700 |
| Function | Ingredient | % of Blend | | |
| Intra Granular | | | | |
| Active | Spray-dried amorphous Compound A | 10.00 | 20.00 | 40.00 |
| Filler | Microcrystalline cellulose | 57.33 | 50.67 | 37.33 |
| Filler | Lactose monohydrate | 28.67 | 25.33 | 18.67 |
| Disintegrant | Croscarmellose sodium | 3.00 | 3.00 | 3.00 |

TABLE 49-continued

Formulation compositions of higher strength SDI loads - 10%, 20% and 40% (700 mg Tablet Press Weight)

| | | Formulation Reference | | |
|---|---|---|---|---|
| | | C1 | C2 | C3 |
| | | Tablet Strength/Tablet Press Weight (mg/mg) | | |
| | | 70/700 | 140/700 | 280/700 |
| Function | Ingredient | % of Blend | | |
| Glidant | Silicon dioxide | 0.50 | 0.50 | 0.50 |
| Lubricant | Magnesium stearate | 0.25 | 0.25 | 0.25 |
| | Extra Granular | | | |
| Lubricant | Magnesium stearate | 0.25 | 0.25 | 0.25 |
| Totals: | | 100.00 | 100.00 | 100.00 |

Tablets were made using a miniaturized laboratory technique to simulate dry granulation and compression. The pregranulation blend was slugged on an F-press. The slugs were size reduced using a mortar/pestle, and passed through a 20-mesh sieve for proper sizing. The granules were mixed with magnesium stearate and compressed on an F-press.

After selecting a tablet tensile strength to achieve a sufficiently hard tablet with disintegration time of less than 5 minutes, the tablet in vitro performance of each tablet composition (C1, C2 and C3) was evaluated using a USP sink dissolution test. As a benchmark, the 10-40% SDI loaded tablets were compared against the original 5% SDI loaded tablets (Tablet reference A3, above).

Figure 27:
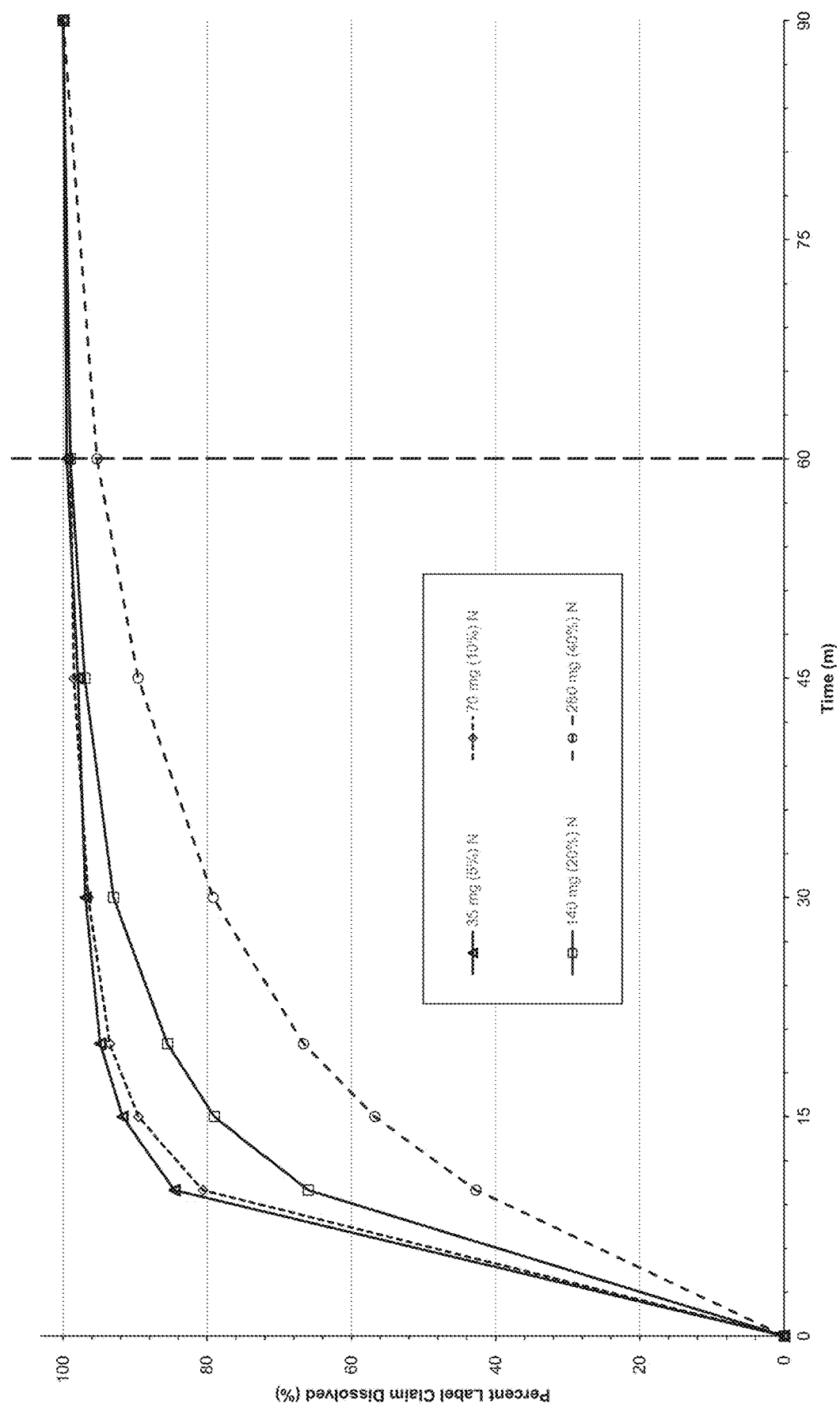
FIG. 27 shows a dissolution comparison between 5, 10, 20 and 40% SDI tablet formulations. The vertical line represents the point of an "infinity" spin, when the paddle speed increased from 75 to 250 RPM.

Dissolution method TEST-1973: To maintain equivalent sink conditions that enabled a valid comparison between formulations, the dissolution media consisted of 0.01N HCl with 0.1 wt % Tween 80. Using USP compatible vessels, the volume of the media was adjusted for each tablet strength to maintain a constant sink condition (approximately 4×). The dissolution parameters are USP II paddles, 37.0±0.5° C. media temperature, 75 RPM and sampling times equal to 10, 15, 20, 30, 45 and 60 minutes. The dissolution results are shown in FIG. 27. The data for each composition was normalized to the 90 minute time point to compensate for variability in the potency and permit a more valid comparison. The dissolution extent for all compositions was equivalent at 60 minutes. The 20% load tablet provided sufficient tablet strength for intended use.

Since the goal was to maximize the SDI loading, the 20% formulation composition was systematically modified with the aim of increasing the dissolution rate. Refer to Table 50 for a listing of the 20% SDI loaded compositions. These formulations were prepared using the miniaturized laboratory techniques described above for the 10, 20 and 40% compositions. The rationale of the modifications is a more rapid de-aggregation phase of the disintegration/dissolution mechanism. The changes are summarized below:

D1—smaller microcrystalline cellulose to enhance the association with the micron sized SDI particles and therefore enhance disintegration D2—addition of extra-granular disintegrant to reduce the time for the primary SDI particles to be exposed to the dissolution medium D3—addition of smaller size glidant to aid in the more intimate association with the SDI particles and therefore favor the physical separation of the SDI particles in the formulation D4—similar to D2, increased the total level of the disintegrant to favor a faster disintegration time

TABLE 50

Formulation compositions of 20% SDI loaded higher strength tablet compositions (700 mg Tablet Press Weight)

| | | Formulation Reference | | | |
|---|---|---|---|---|---|
| | | D1 | D2 | D3 | D4 |
| | | Tablet Strength/Tablet Press Weight (mg/mg) | | | |
| | | 140/700 | 140/700 | 140/700 | 140/700 |
| Function | Ingredient | % of Blend | | | |
| Intra Granular | | | | | |
| Active | Spray-dried amorphous Compound A | 20.00 | 20.00 | 20.00 | 20.00 |
| Filler | Microcrystalline cellulose (Avicel PH 102) | — | 49.33 | 50.33 | 46.00 |
| Filler | Macrocrystalline cellulose (Avicel PH 101) | 76.00 | — | — | — |
| Filler | Lactose monohydrate | — | 24.67 | 25.17 | 23.00 |
| Disintegrant | Croscarmellose sodium | 3.00 | 3.00 | 3.00 | 6.00 |
| Glidant | Silicon dioxide (Syloid 244 FP) | 0.50 | 0.50 | — | 0.50 |
| Glidant | Silicon dioxide (Cab-O-Sil M5P) | — | — | 1.00 | — |
| Lubricant | Magnesium stearate | 0.25 | 0.25 | 0.25 | 0.25 |
| Extra Granular | | | | | |
| Disintegrant | Croscarmellose sodium | — | 2.00 | — | 4.00 |
| Lubricant | Magnesium stearate | 0.25 | 0.25 | 0.25 | 0.25 |
| Totals: | | 100.00 | 100.00 | 100.00 | 100.00 |

Figure 28:
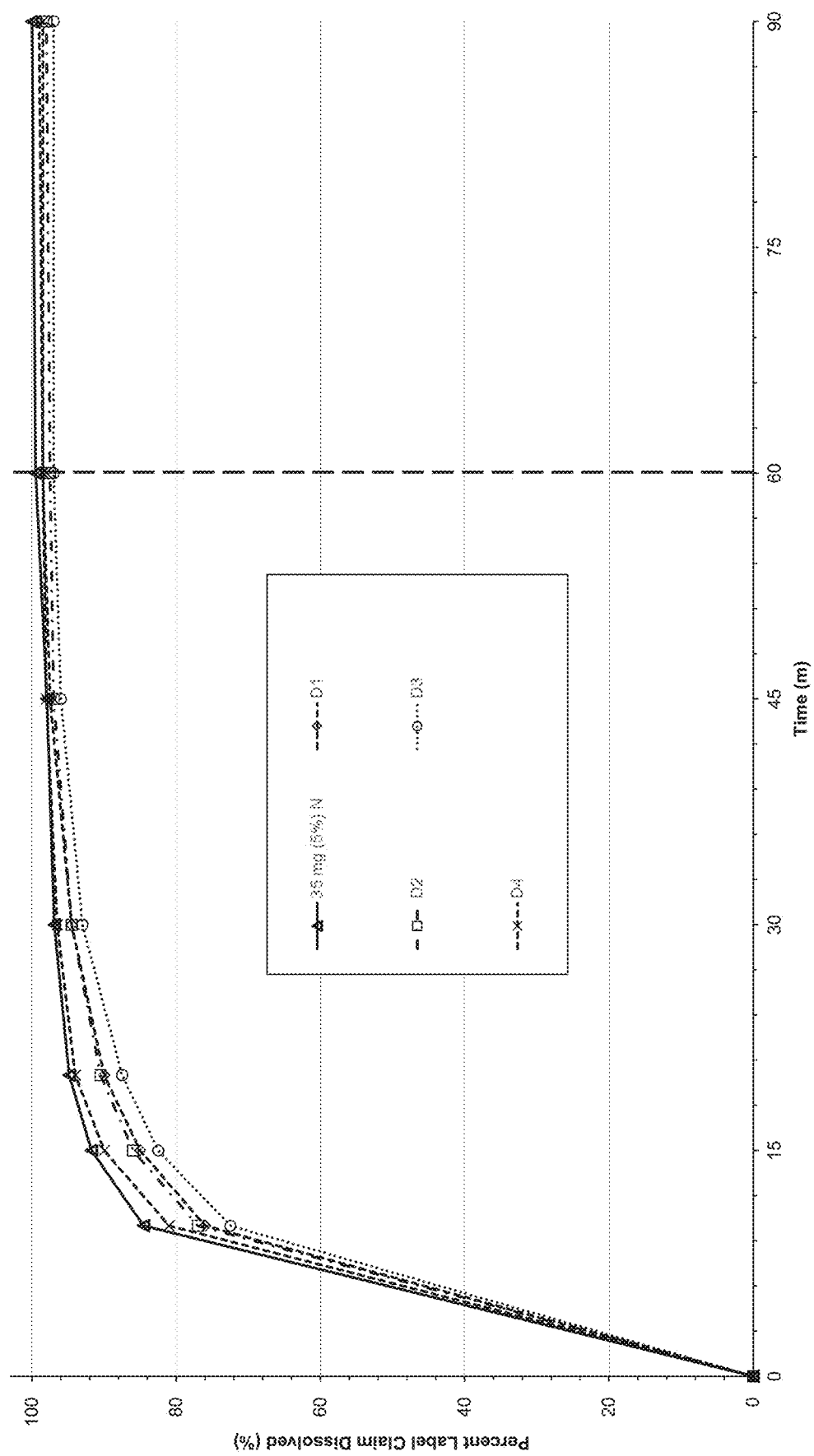
FIG. 28 shows a dissolution comparison between 5% and 20% SDI loaded tablet formulations (D1, D2, D3 and D4). The vertical line represents the point of an "infinity" spin, when the paddle speed increased from 75 to 250 RPM.

Overall, the formulations processed similarly except for flowability of D1 and all of them exhibited disintegration times in 0.01 N HCl of less than 1 minute; therefore, a major selection criterion for further evaluation was the dissolution characteristics. Dissolution profiles using the 0.01 N HCl media method (TEST-1973) for D1, D2, D3, D4 and 35 mg (5%) are illustrated in FIG. 28.

The scale up and process evaluation of the D2 formulation was conducted to identify the processing conditions to be used for the planned clinical manufacture. The batch size was approximately 3 kg and consisted of the following major steps:

- Pre-granulation blend using the 100% spray-dried intermediate of Compound A
- Roller compaction (Gerteis Minipactor machine)
- Final blend (addition of extra-granular disintegrant and lubrication)
- Compression (Korsch XM12)

The flow properties of the pre-granulation blend and final blend were determined using laboratory techniques (Carr Index, shear cell flow function/cohesion coefficient and FloDex measurements), roller compaction parameters determined and a compression evaluation (compressibility, tabletabilty and compactability) was conducted.

During the compression of the final blend on the Korsch XM-12 equipped with 2 tool stations to accommodate the batch size, the granulation exhibited insufficient flow. The material rat-holed and bridged in the feed hopper, starving the feed frame, and thus, resulted in poor weight control.

Due to the flow challenges, it was determined that the D2 formulation and process were not suitable and therefore, not transferrable for clinical manufacture. As a result, another round of formulations was evaluated in the laboratory to improve flowability characteristics.

The modification strategy for the D2 formulation hinged on evaluation of the glidant system being used and optimized its functionality. Two new formulations F7 and F11 are shown in Table 51.

TABLE 51

D2, F7 and F11 Formulation compositions of 20% SDI loaded tablet (525 mg Tablet Press Weight)

| Function | Ingredient | D2 | F7 | F11 |
|---|---|---|---|---|
| | | Tablet Strength/Tablet Press Weight (mg/mg) | | |
| | | 105/525 | 105/525 | 105/525 |
| | | % of Blend | | |
| Intra Granular | | | | |
| Active | Spray-dried amorphous Compound A | 20.00 | 20.00 | 20.00 |
| Filler | Microcrystalline cellulose (Avicel PH 102) | 49.33 | 48.17 | 49.00 |

TABLE 51-continued

D2, F7 and F11 Formulation compositions of 20% SDI loaded tablet (525 mg Tablet Press Weight)

| Function | Ingredient | D2 | F7 | F11 |
|---|---|---|---|---|
| | | Tablet Strength/Tablet Press Weight (mg/mg) | | |
| | | 105/525 | 105/525 | 105/525 |
| | | % of Blend | | |
| Filler | Lactose monohydrate | 24.67 | 24.33 | 24.50 |
| Disintegrant | Croscarmellose sodium | 3.00 | 3.00 | 3.00 |
| Glidant | Silicon dioxide (Syloid 244 FP) | 0.50 | — | — |
| Glidant | Silicon dioxide (Cab-O-Sil M5P) | — | 1.00 | 0.50 |
| Lubricant | Magnesium stearate | 0.25 | 0.25 | 0.25 |
| | Extra Granular | | | |
| Glidant | Silicon dioxide (Cab-O-Sil M5P) | — | 1.00 | 0.25 |
| Disintegrant | Croscarmellose sodium | 2.00 | 2.00 | 2.00 |
| Lubricant | Magnesium stearate | 0.25 | 0.25 | 0.50 |
| Totals: | | 100.00 | 100.00 | 100.00 |

The F7 and F11 compositions were manufactured at bench scale (50 g per blend) at a Tablet Press Weight of 105 mg using the miniaturization techniques described above for formulations C1-C3. The lower Tablet Press Weight was chosen to represent the midpoint of a range of Tablet Press Weights that may be needed for further dose escalation. Both formulations implemented an initial SDI/glidant blend-mill-blend process as part of the pre-granulation blend manufacture in an attempt to adhere to the SDI particles and reduce their cohesivity. Formulation F7 increased the overall glidant levels (intra- and extra-granular) and formulation F11 added glidant extra-granular and also increased extra-granular lubricant to assess if increased extra-granular glidant and lubricant had a synergistic effect on blend flow.

The flowability of F7 and F11 was compared to D2. Table 52 shows a modest improvement in the flowability (FloDex, FFc and Cohesion Coefficient) for the final blend for both F7 and F11 compositions however, Carr Index remained at an unacceptable value.

Scanning electron microscopic analysis showed minimal adherence of Cab-O-Sil to SDI particles, and miniscule to no surface coverage of SDI particles with Cab-O-Sil.

TABLE 52

Compound A Formulation D2, F7 and F11 Pre-granulation and Final Blend Flow Properties

| Parameter | Formulation D2[A] | | Formulation F7 | | Formulation F11 | |
|---|---|---|---|---|---|---|
| | Pre-granulation Blend | Final Blend | Pre-granulation Blend | Final Blend | Pre-granulation Blend | Final Blend |
| Bulk Density (g/mL) | 0.42 | 0.50 | 0.36[B] | 0.44[B] | 0.39[B] | 0.48[B] |
| Tapped Density (g/mL) | 0.63 | 0.70 | 0.59[B] | 0.63[B] | 0.63[B] | 0.69[B] |
| Carr Index (%) | 34 | 28 | 39 | 30 | 38 | 31 |
| FloDex (mm) | 24 | 30 | 26 | 20 | 24 | 22 |
| FFc[C] | 4.9 | 5.1 | 5.9 | 7.6 | 4.7 | 6.1 |

TABLE 52-continued

Compound A Formulation D2, F7 and F11 Pre-granulation and Final Blend Flow Properties

| Parameter | Formulation D2[A] | | Formulation F7 | | Formulation F11 | |
|---|---|---|---|---|---|---|
| | Pre-granulation Blend | Final Blend | Pre-granulation Blend | Final Blend | Pre-granulation Blend | Final Blend |
| Cohesion Coefficient[D] | 103 | 103 | 84 | 64 | 107 | 83 |

[A]Values from scale up manufacture. Blend not remanufactured at bench scale.
[B]Generated using 10 mL cylinder due to limited material. Results less reliable than those generated using 100 mL cylinder.
[C]FFc is the shear cell flow function
[D]Cohesion coefficient was derived from the shear cell data Tablet compression evaluation of F7 and F11 showed similar results with D2 and confirmed no significant adverse impact of changing the glidant system. The formulations formed acceptable tablets at relatively low range compression stress (75 to 100 MPa), and both formulations exhibited disintegration times of less than 1 minute.

Dissolution characteristics of F7 and F11 were similar to D2 demonstrating no adverse effect of new glidant system on the dissolution properties.

In conclusion, the modest improvement in flowability of F7 and F11 compared to D2 was not sufficient to nominate either one of them as the clinical formulation candidate, therefore, further formulation optimization was undertaken.

Since the additional step of pre-mixing glidant with SDI did not produce a desirable outcome, this approach was abandoned. However, the unexpected result of almost no adhesion of the glidant to the SDI formed the basis of evaluating a chemically modified formed of colloidal silicon dioxide to increase its hydrophobicity and lower its surface free energy.

A direct comparison of Cab-O-Sil M5P and Aerosil R972 was carried out. As mentioned above, Aerosil R972 is colloidal silicon dioxide chemically modified to produce trimethylsilyl groups on the surface. It complies with USP/NF monograph for colloidal silicon dioxide. In this comparison, each of these glidants was added to the D2 blend from the scale up batch to directly study their impact on flowability compared to D2. The formulation compositions are listed in Table 53.

TABLE 53

Compound A - G1* and G2* formulation compositions

| | | Formulation Reference | |
|---|---|---|---|
| | | G1* | G2* |
| | | Dose/Tablet Press Weight (mg/mg) | |
| | | 105/530.3 | |
| Function | Ingredient | % of Blend | |
| Active | 200 mg/g Compound A Formulation D2 Final Blend | 99.00% | 99.00% |
| Glidant | Silicon Dioxide (Cab-O-Sil M5P) | 1.00% | — |
| Glidant | Silicon Dioxide (Aerosil R972) | — | 1.00% |
| Total | | 100.00% | 100.00% |

The flow metrics are listed in Table 55. G2* exhibited the best flow properties compared to D2 and G1*.

TABLE 54

Compound A Formulations D2, G1* and G2* Final Blend Flow Properties

| | Formulation D2[A] | | Formulation G1* | Formulation G2* |
|---|---|---|---|---|
| Parameter | Pre-granulation Blend | Final Blend | Final Blend | Final Blend |
| Bulk Density (g/mL) | 0.42 | 0.50 | 0.49 | 0.54 |
| Tapped Density (g/mL) | 0.63 | 0.70 | 0.65 | 0.69 |
| Carr Index (%) | 34 | 28 | 25 | 22 |
| FloDex (mm) | 24[B] | 30[B] | 26 | 14 |
| FFc[C] | 4.9 | 5.1 | 6.2 | 8.0 |
| Cohesion Coefficient[D] | 103 | 103 | 81 | 64 |

[A]Values from scale up manufacture. Blend not remanufactured at bench scale.
[B]Scale-up blend samples retested using the same fill levels as used for formulation G1* and G2* blends.
[C]FFc is the shear cell flow function
[D]Cohesion coefficient was derived from the shear cell data The compressibility (solid vs compression stress), tabletability (tablet tensile strength vs compression stress) and compactability (tablet tensile strength vs tablet solid fraction) i.e. CTC profiles, for G1 and G2 were compared. Formulation G1 had similar CTC properties to formulation D2 suggesting Cab-O-Sil had minimal impact on the final blend material properties. Formulation G2 showed an improvement in compressibility but a reduction in both tabletability and compactability properties compared to both formulations G1 and D2. The significance of this finding was eventually assessed at larger scale and rotary press. The compressive stress regime for both G formulations was well within the typical range observed for optimal tooling wear performance and tablet porosity (100 to 300 MPa).

Figure 29:
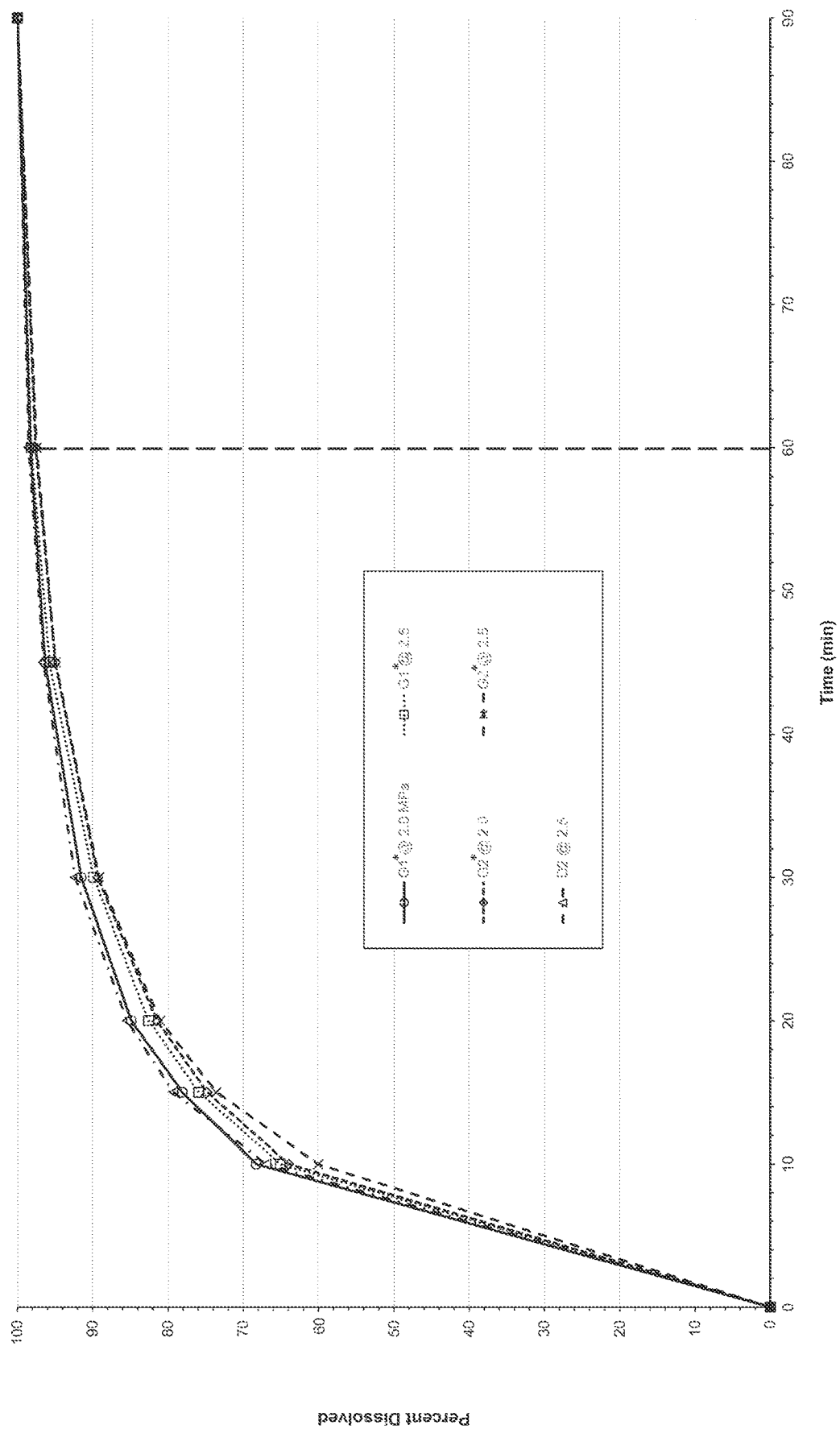
FIG. 29 shows dissolution comparison between D2, G1* and G2* tablet compositions (525 mg tablet). Normalized for variable assay to the 90 minute time point. The vertical line represents the point of an "infinity" spin when the paddle speed increased from 75 to 250 RPM.

A dissolution comparison of the bench-scale tablets of G1 and G2 demonstrated comparable dissolution profile, as shown in FIG. 29.

Given G2 exhibited the best flowability, acceptable compression/tablet properties, and similar dissolution profile to D2, it was selected for further evaluation for a pre-demonstration processability assessment.

A processability pre-demonstration assessment was conducted on a Gerteis Minipactor using bench scale batch size equal to 100 gram to determine target Gerteis settings for the demonstration batch. The Gerteis was set up with a feed funnel system designed to feed material quantities that are too small to use the auger feed and tamping systems. Ribbons were collected and then manually fed through the oscillating granulator to size them.

The main purpose was to evaluate the effect of ribbon solid fraction on granule size.

The G2 formulation composition is listed in Table 55. The composition differs slightly from the composition of G2* but was not expected to significantly impact granule or tablet properties. The tablet press weight was adjusted to 525 mg (vs 530 mg for G2*) and the Aerosil R972 quantity is exactly 1% of the composition.

TABLE 55

G2 formulation composition (20% SDI loaded tablet - 525 mg Tablet Press Weight)

| Function | Ingredient | Formulation Reference G2 Tablet Strength/Tablet Press Weight (mg/mg) 105/525 % of Blend |
|---|---|---|
| Intra Granular | | |
| Active | Spray-dried amorphous Compound A | 20.00 |
| Filler | Microcrystalline cellulose (Avicel PH 102) | 48.67 |
| Filler | Lactose monohydrate | 24.33 |
| Disintegrant | Croscarmellose sodium | 3.00 |
| Glidant | Silicon dioxide (Syloid 244 FP) | 0.50 |
| Lubricant | Magnesium stearate | 0.25 |
| Extra Granular | | |
| Glidant | Silicon dioxide (Aerosil R972) | 1.00 |
| Disintegrant | Croscarmellose sodium | 2.00 |
| Lubricant | Magnesium stearate | 0.25 |
| Totals: | | 100.00 |

Figure 30A:
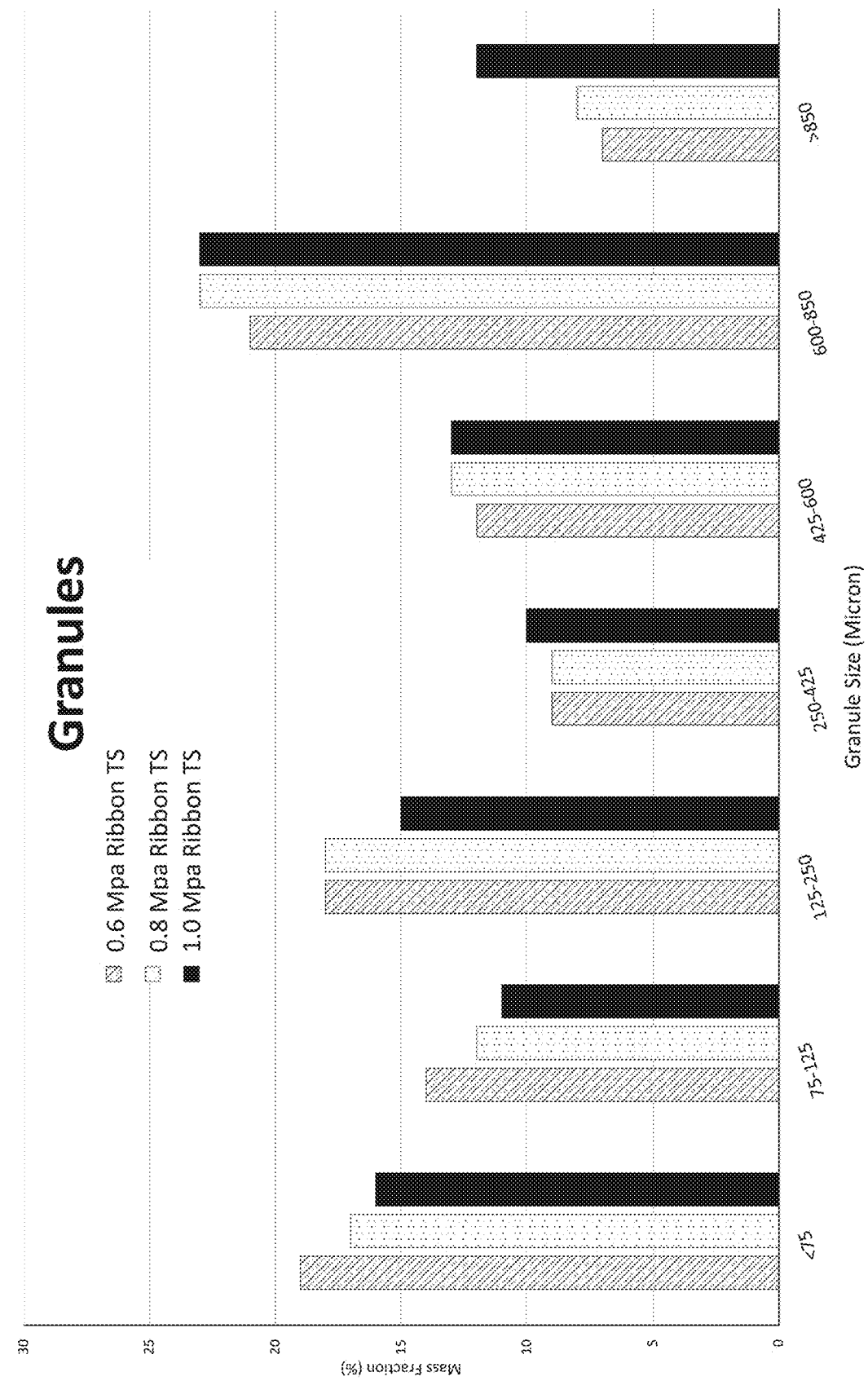

The effect of adjusting the ribbon tensile strength on the granule size distribution and the effect of final blending on the granule size distribution is shown in FIGS. 30A and 30B. Granule size decreased as the ribbon tensile strength increased.

The effect of ribbon tensile strength (granulator screen constant=1.00 mm) on flow properties was also assessed and shown in Table 57. The flow metrics are better compared to the bench-scale trials, Carr Index=21-23; FloDex=16, and FFc=7.1-8.5 are indicative of a free-flowing granulation.

TABLE 56

Pre-demo G2 composition final blend flow characteristics

| Parameter | 1 | 2 | 3 |
|---|---|---|---|
| Ribbon Tensile Strength (MPa) | 1.10 | 0.60 | 0.77 |
| Flow Characteristics | | | |
| Bulk Density (g/mL) | 0.60 | 0.55 | 0.51 |
| Tapped Density (g/mL) | 0.76 | 0.71 | 0.66 |
| Carr Index (%) | 21 | 23 | 22 |
| FloDex (mm) | 16 | 16 | 16 |
| Flow Function, FFc | 7.1 | 8.1 | 8.5 |
| Cohesion Coefficient (Pa) | 73 | 65 | 58 |

CTC scans of tablets made on the F-press using G2 pre-demo batches are consistent with what was observed for the tablets manufactured using bench-scale equipment. The granulation is highly compressible and compactible and produces a tablet with acceptable tensile strength at compressive stresses in the range of 100 MPa. Noteworthy is a steep tensile strength vs. solid fraction, as noted previously. Higher solid fraction means lower tablet porosity. Tablet porosity is a known factor that can affect dissolution, therefore, the effect of tensile strength of tablets on dissolution rate and extent was also evaluated.

Figure 31:
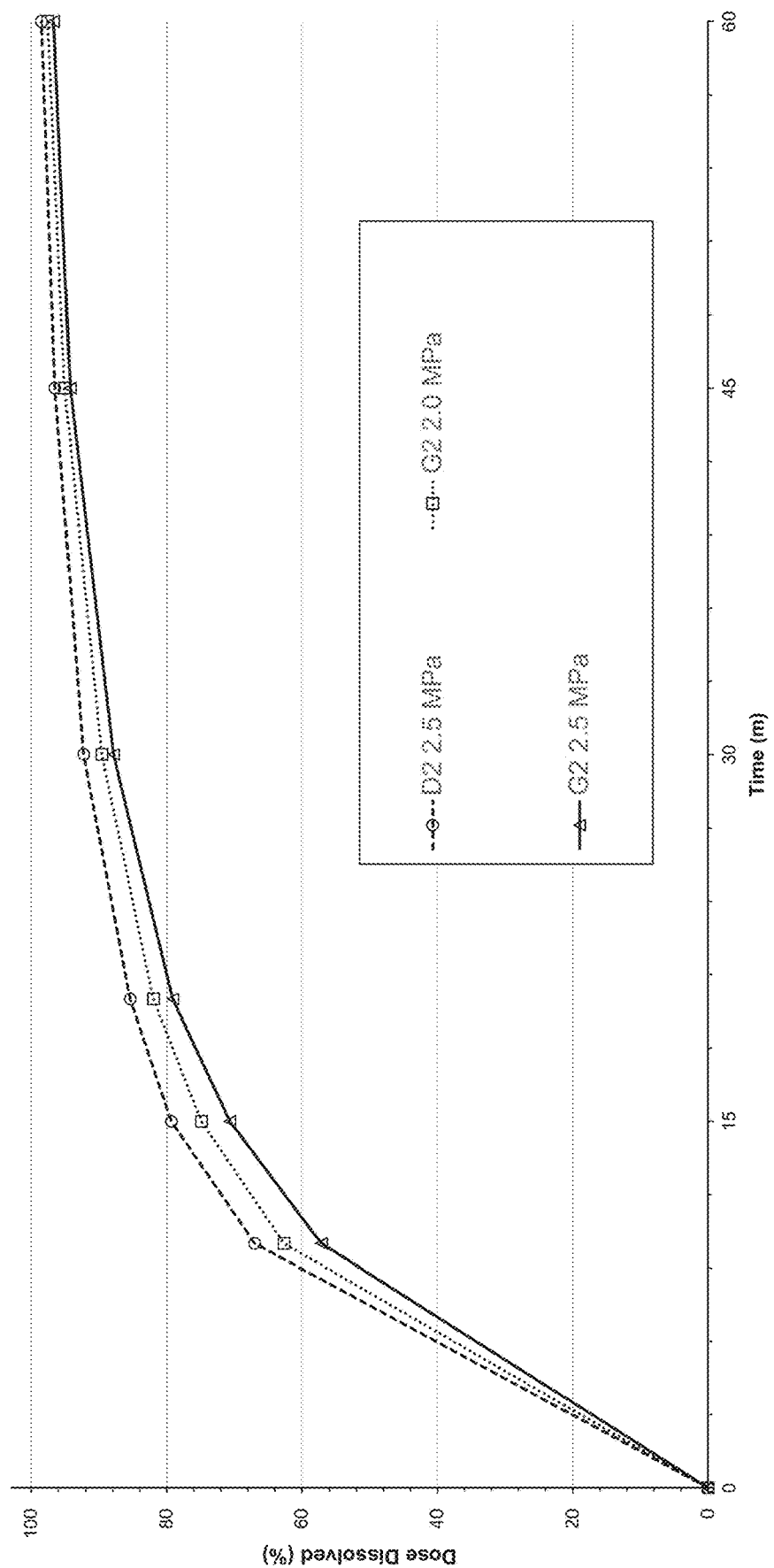
FIG. 31 shows a dissolution comparison between D2, and G2 pre-demo tablets compressed at 2.0 and 2.5 MPa tensile strength (525 mg tablet). Normalized for variable assay to the 90 minute time point.

The dissolution profiles of G2 pre-demo tablets compressed at 2.0 and 2.5 MPa are compared to the D2 tablets compressed at 2.5 MPa, as shown in FIG. 31. The dissolution profiles are similar, showing no discernable difference in dissolution profile as function of tablet porosity.

In conclusion, based on improved flow behavior, acceptable tablet properties and acceptable tablet dissolution, the G2 tablet composition using Gerteis settings determined during the pre-demo laboratory-sized batches was selected for manufacture of a demonstration batch.

Biopharmaceutical performance of 5% (A3) and 20% (G2) drug loaded tablets was assessed by orally dosing the corresponding tablets and comparing the plasma levels thereby obtained. 24 dogs were divided into two groups. Each group was fasted overnight and then fed regular chow 30 minutes before tablet administration followed by 30 mL of water. Otherwise, water was withheld from 1 hour before to 1 hour after dosing. 50 minutes before tablet dosing all subjected were pretreated with a 6 μg/mL intramuscular pentagastrin solution. Blood samples were collected at 0, 0.5, 1, 2, 3, 4, 6, 8, 10, 12, 16, 20, 24, 36, 48, 72, 96, 120, 144, and 168 hours post-dose. One group was administered 2 of the 35 mg tablets containing a 5% load of Compound A and the other group was given 1 of the 70 mg tablets containing a 20% of Compound A.

As shown in Table 57, similar exposure in pentagastrin pretreated, fed state dogs was observed when orally administered two of the 35 mg (5%) or one of the 70 mg (20%) tablets.

TABLE 57

Comparison of Oral Exposure Derived From Dosing Two 35 mg (5% Drug Load) orOne 70 mg (20% Drug Load) Tablet to Dogs

| Tablets Administered | AUC$_{0-last}$ (ng × h/mL) | |
|---|---|---|
| | Avg | SD |
| 2 × 35 mg | 5,489 | 3,511 |
| 1 × 70 mg | 5,481 | 4,404 |

Example 28. Late Phase 1 Tablet Demonstration Batch Formulas

A common granulation/bracketing strategy was applied for manufacturing the demonstration batch for the 20% SDI drug load formulation composition. The manufacture of tablets with a tablet press weight bracketed between 35 mg and 140 mg tablet strength (i.e. 175 mg to 700 mg tablet press weight) was implemented in the following manner. A portion of a demonstration common granulation final blend was aliquoted to compress 35 mg, 70 mg and 140 mg tablets using a single-station compression machine. The remainder of the common granulation was used to compress a batch at 105 mg strength (525 mg tablet press weight) on a rotary tablet press, representative of the clinical manufacturing tablet machine. The 35 mg, 70 mg, 105 mg and 140 mg demonstration batches were used in the stability studies described in Example 29 below.

The formulation compositions, granulation batch quantities and number of tablets are listed in Table 58.

TABLE 58

Demonstration Batch Formulae for Compound A Tablets, 35 mg, 70 mg, 105 mg and 140 mg Strengths Using 20% SDI Load.

| | Theoretical Quantity per Batch (g) | | | | |
|---|---|---|---|---|---|
| Ingredient | Common Granulation | 35 mg strength/ 175 mg Tablet Press Weight | 70 mg strength/ 350 mg Tablet Press Weight | 105 mg strength/ 525 mg Tablet Press Weight | 140 mg strength/ 700 mg Tablet Press Weight |
| Intra-granular | | | | | |
| 100% Compound A SDI | 398.61 | 10.50 | 9.80 | 278.62 | 41.40 |
| Microcrystalline cellulose (Avicel pH102) | 970.06 | 25.55 | 23.85 | 678.06 | 100.74 |
| Lactose monohydrate (FastFlo 316) | 485.01 | 12.77 | 11.92 | 339.02 | 50.37 |
| Croscarmellose sodium (Ac-Di-Sol) | 59.78 | 1.57 | 1.47 | 41.79 | 6.21 |
| Silicon Dioxide (Syloid-244) | 10.03 | 0.26 | 0.25 | 7.01 | 1.04 |
| Magnesium stearate | 5.01 | 0.13 | 0.12 | 3.50 | 0.52 |
| Total Intra-granular | 1928.5 | 50.79 | 47.41 | 1348.00 | 200.27 |
| Extra-granular | | | | | |
| Croscarmellose sodium (Ac-Di-Sol) | 39.87 | 1.05 | 0.98 | 27.87 | 4.14 |
| Silicon Dioxide (Aerosil R972) | 19.93 | 0.53 | 0.49 | 13.93 | 2.07 |
| Magnesium stearate | 4.98 | 0.13 | 0.12 | 3.48 | 0.52 |
| Total granulation | 1993.28 | 53 | 49 | 1393.28 | 207 |
| Total number of tablets | — | 300 | 140 | 2654 | 296 |

Theoretical quantity per batch for the 105 mg tablet was calculated after samples taken for testing and manufacture of the 35 mg, 70 mg, and 140 mg tablet strengths
Common granulation was divided to manufacture the 35 mg, 70 mg, 105 mg and 140 mg tablet strengths Prior to blending, Compound A drug substance is dissolved, then spray-dried to form an amorphous drug product intermediate as described above.

The common granulation ribbons were manufactured to achieve an actual ribbon solid fraction=0.60 that equates to an estimated tensile strength of 0.8 MPa.

Figure 32:
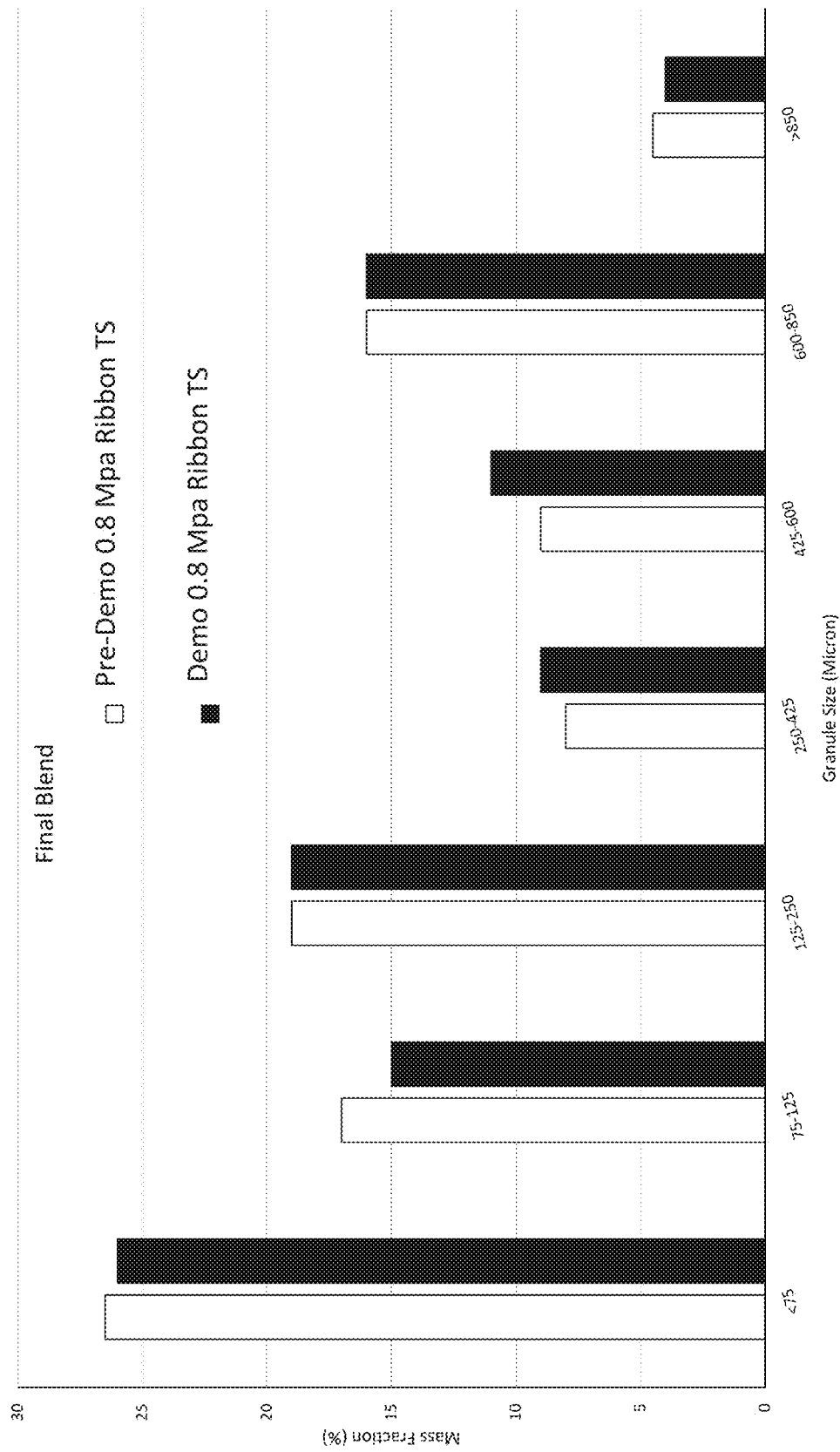
FIG. 32 shows a comparison of granule size between Compound A final blend demonstration batch for 20% API and pre-demo batch.

The final blend granule size distribution was reproducible, comparing favorably to the pre-demo batch, as depicted in FIG. 32.

The final blend flow metrics were also reproducible, comparing favorably to the pre-demo batch, shown in Table 59.

TABLE 59

Comparison of flow metrics between the pre-demonstration and demonstration final blend batches of G2 composition, granulated to a ribbon tensile strength of 0.8 MPa.

| Parameter | Final Blend- Pre-demo Batch | Final Blend - Demo Batch |
|---|---|---|
| Bulk Density (g/mL) | 0.51 | 0.55 |
| Tapped Density (g/mL) | 0.66 | 0.69 |
| Carr Index (%) | 22 | 20 |
| FloDex (mm) | 16 | 14 |
| Flow Function, FFc | 8.5 | 13.8 |
| Cohesion Coefficient (Pa) | 58 | 34 |

The final blend was divided into 4 portions. Three portions of 100 gram each were used to manufacture the 35 mg, 70 mg and 140 mg tablets on the single-station machine, and the remainder (approximately 2 kg) was used to manufacture the 105 mg batch on a rotary tablet machine.

The 35 mg, 70 mg and 140 mg tablet strengths were compressed to 2.0 MPa tensile strength round tablets. The tablet disintegration times were 2.3 to ~3.0 minutes for the 140 mg, 1.5 to 2.0 minutes for the 70 mg and ~1 to 1.3 minutes for the 35 mg tablet.

The 105 mg demonstration batch exhibited good flow as evidenced by the excellent weight and hardness control and excellent uniformity of dosage units. Tablet press weights were easily maintained at the in-process limit for individual tablets of ±5%. Uniformity of dosage units UPS <905> AV=3.5, mean=97.2% label claim.

Figure 33:
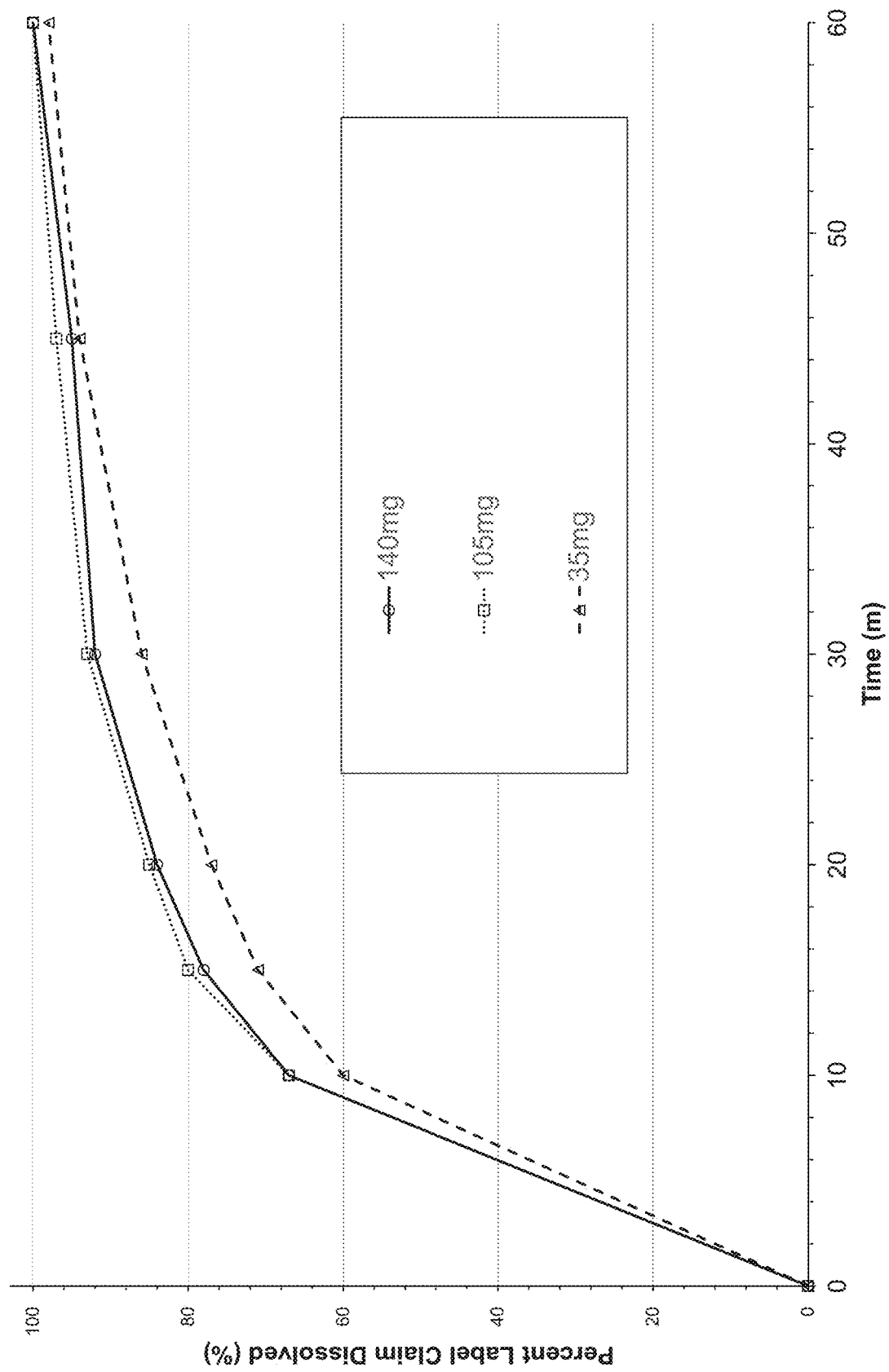
FIG. 33 shows a dissolution comparison between 35 mg, 105 mg, and 140 mg demonstration batch tablets.

Comparison of the dissolution for 35 mg, 105 mg and 140 mg are shown in FIG. 33. The dissolution was performed for the tablet strengths that were used in stability studies, which bracketed the highest, lowest and mid-range strengths. The dissolution profiles are comparable, demonstrating no tablet strength effect on the dissolution rate and extent.

In conclusion, based on acceptable processability and final product performance, the G2 composition was nominated for manufacture of clinical tablets that can be bracketed between 35 mg and 140 mg strengths Example 29: Stability of Formulation G2 Tablets Tablets of formulation G2 with strengths of 35 mg, 105 mg, and 140 mg Compound A were subjected to a stability study (Table 61).

Protocol (Tablet Packaging)
Packaging Supplies:
White 500 cc HDPE Pharma Round Bottles with HIS lids
1 g Sorb-It desiccant canisters
Tablet Packaging Protocol:
1. Add (22) tablets to a 500 cc HDPE bottle.
2. Add (1) 1 g Sorb-it desiccant canister to the HDPE bottle.
3. Place a HIS lid on the HDPE bottle and seal the bottle using an Enercon Super Seal Jr. cap sealer at 60% sealing power for one second.
4. Remove the bottle lid to ensure the foil seal is properly adhered to the bottle. Screw the cap back on the bottle before placing the bottle in the appropriate stability chamber.

TABLE 60

Tablet Stability Conditions, Time Points and Testing

| Condition | 1 Month (1) | 3 Month (2) | 6 Month (3) | 12 Month (4) |
|---|---|---|---|---|
| (a) 5° C., dosed with desiccant | A | A | A | A, B, C |
| (b) 25° C./60% RH, closed with desiccant | A, B, C | A, B, C | A, B, C | A, B, C |
| (c) 40° C./75% RH, closed with desiccant | A, B, C | A, B. C | A. B, C | |

A—105 mg Formulation G2
B—140 mg Formulation G2
C—35 mg Formulation G2

The tablets were analyzed for appearance, assay and related substances by UPLC, dissolution by USPII, and water content by volumetric KF. Based upon the characterization below, all of the tablet doses were as expected for appearance, assay, dissolution performance, and water content. The purity was slightly increased when compared with the SDI used for manufacture and should be monitored closely in subsequent stability pulls.

The tablets were visually evaluated for appearance. All of the tablets were yellow, smooth surfaced tablets.
Tablet assay values were consistent for each dose and met the current specification of 90%-110% LC (Table 62).

TABLE 61

Tabulated Composite Assay Data for Compound A Stability Tablets

| Sample | % LC | Range (n = 2, 5 tablet composite) |
|---|---|---|
| 140 mg Tablet | 95 | 0.2 |
| 105 mg Tablet | 97 | 0.2 |
| 35 mg Tablet | 95 | 0.3 |

Protocol (Blister Packaging)
Tablets were Blister Packaged by Fisher
5 tablets per strip (1×5), with 1 tab/cavity
ALU/ALU—blisters (Cold form foil)
At each time point below, 5 strips (25 total tablets) were pulled at each time point for each stability condition for analysis.

TABLE 62

Blister Stability Conditions, Time Points and Testing

| Condition | 1 Month (1) | 3 Month (2) | 6 Month (3) | 12 Month (4) |
|---|---|---|---|---|
| (a) 5° C., closed with desiccant | A | A | A | A |
| (b) 25° C./60% RH, closed with desiccant | A | A | A | A |
| (c) 40° C./75% RH, dosed with desiccant | A | A | A | |

Stability stud results are shown below in Tables 63-66.

TABLE 63

Summary of the 140 mg Dose Compound Tablet Bottle Stability Results

| 140 mg, Formulation G2 | Condition | Initial | 1 Month | 3 Month | 6 Month |
|---|---|---|---|---|---|
| Appearance | 25° C./60% RH | Light Yellow | Light Yellow | Light Yellow | Light Yellow |
| | 40° C./75% RH | | Light Yellow | Light Yellow | Light Yellow |
| Assay | 25° C./60% RH | 95 | 96 | 96 | 96 |
| | 40° C./75% RH | | 95 | 95 | 95 |
| Total Related Substances | 25° C./60% RH | 0.28 | 0.35 | 0.24 | 0.36 |
| | 40° C./75% RH | | 0.33 | 0.27 | 0.55* |
| Water Content | 25° C./60% RH | 4.06 | 3.64 | 3.71 | 3.90 |
| | 40° C./75% RH | | 3.70 | 4.57 | 5.06 |
| % LC at 45 minutes | 25° C./60% RH | 95 | 92 | 94 | 95 |
| | 40° C./75% RH | | 93 | 93 | 92 |
| Tablet Hardness | 25° C./60% RH | 21.8 | 21.2 | 21.3 | 21.8 |
| | 40° C./75% RH | | 21.8 | 21.0 | 19.4 |

*Increase appears to be related to an increase in peak at RRT 0.43

TABLE 64

Summary of the 105 mg Dose Compound Tablet Bottle Stability Results

| 140 mg, Formulation G2 | Condition | Initial | 1 Month | 3 Month | 6 Month |
|---|---|---|---|---|---|
| Appearance | 5° C. | Light Yellow | Light Yellow | Light Yellow | Light Yellow |
| | 25° C./60% RH | | Light Yellow | Light Yellow | Light Yellow |
| | 40° C./75% RH | | Light Yellow | Light Yellow | Light Yellow |

TABLE 64-continued

Summary of the 105 mg Dose Compound Tablet Bottle Stability Results

| 140 mg, Formulation G2 | Condition | Initial | 1 Month | 3 Month | 6 Month |
|---|---|---|---|---|---|
| Assay | 5° C. | 97 | 96 | 95 | 97 |
| | 25° C./60% RH | | 99 | 98 | 100 |
| | 40° C./75% RH | | 97 | 98 | 97 |
| Total Related Substances | 5° C. | 0.25 | 0.31 | 0.24 | .044 |
| | 25° C./60% RH | | 0.34 | 0.25 | 0.47 |
| | 40° C./75% RH | | 0.32 | 0.27 | 0.52* |
| Water Content | 5° C. | 3.40 | 3.04 | 2.78 | 3.11 |
| | 25° C./60% RH | | 3.23 | 3.46 | 3.55 |
| | 40° C./75% RH | | 3.32 | 4.31 | 5.12 |
| % LC at 45 minutes | 5° C. | 97 | 92 | 95 | 95 |
| | 25° C./60% RH | | 91 | 95 | 97 |
| | 40° C./75% RH | | 93 | 93 | 96 |
| Tablet Hardness | 5° C. | 20.4 | 19.9 | 20.4 | 18.2 |
| | 25° C./60% RH | | 18.9 | 21.5 | 19.9 |
| | 40° C./75% RH | | 20.2 | 18.0 | 18.2 |

*Increase appears to be related to an increase in peak at RRT 0.43

TABLE 65

Summary of the 105 mg Dose Compound Tablet Blister Stability Results

| 140 mg, Formulation G2 | Condition | Initial | 1 Month | 3 Month |
|---|---|---|---|---|
| Appearance | 5° C. | Light Yellow | Light Yellow | Light Yellow |
| | 25° C./60% RH | | Light Yellow | Light Yellow |
| | 40° C./75% RH | | Light Yellow | Light Yellow |
| Assay | 5° C. | 97 | 99 | 98 |
| | 25° C./60% RH | | 99 | 99 |
| | 40° C./75% RH | | 99 | 97 |
| Total Related Substances | 5° C. | 0.25 | 0.46 | 0.44 |
| | 25° C./60% RH | | 0.46 | 0.45 |
| | 40° C./75% RH | | 0.41 | 0.39 |
| Water Content | 5° C. | 3.4 | 3.55 | 3.56 |
| | 25° C./60% RH | | 3.56 | 3.61 |
| | 40° C./75% RH | | 3.55 | 3.58 |
| % LC at 45 minutes | 5° C. | 97 | 97 | 95 |
| | 25° C./60% RH | | 97 | 95 |
| | 40° C./75% RH | | 95 | 94 |
| Tablet Hardness | 5° C. | 20.4 | 20.4 | 18.1 |
| | 25° C./60% RH | | 19.6 | 18.9 |
| | 40° C./75% RH | | 19.6 | 19.5 |

TABLE 66

Summary of the 35 mg Dose Compound Tablet Bottle Stability Results

| 140 mg, Formulation G2 | Condition | Initial | 1 Month | 3 Month | 6 Month |
|---|---|---|---|---|---|
| Appearance | 25° C./60% RH | Light Yellow | Light Yellow | Light Yellow | Light Yellow |
| | 40° C./75% RH | | Light Yellow | Light Yellow | Light Yellow |
| Assay | 25° C./60% RH | 95 | 93 | 97 | 96 |
| | 40° C./75% RH | | 95 | 95 | 94 |
| Total Related Substances | 25° C./60% RH | 0.26 | 0.35 | 0.19 | 0.47 |
| | 40° C./75% RH | | 0.32 | 0.27 | 0.50* |
| Water Content | 25° C./60% RH | 5.05 | 3.65 | 3.38 | 4.16 |
| | 40° C./75% RH | | 3.72 | 4.95 | 5.97 |
| % LC at 45 minutes | 25° C./60% RH | 94 | 91 | 94 | 94 |
| | 40° C./75% RH | | 91 | 92 | 89 |
| Tablet Hardness | 25° C./60% RH | 8.0 | 8.3 | 7.7 | 7.8 |
| | 40° C./75% RH | | 8.1 | 8.0 | 6.6 |

*Increase appears to be related to an increase in peak at RRT 0.43

Embodiments

The aspects of the present disclosure are further described with reference to the following numbered embodiments:
1. A crystalline form of Compound A

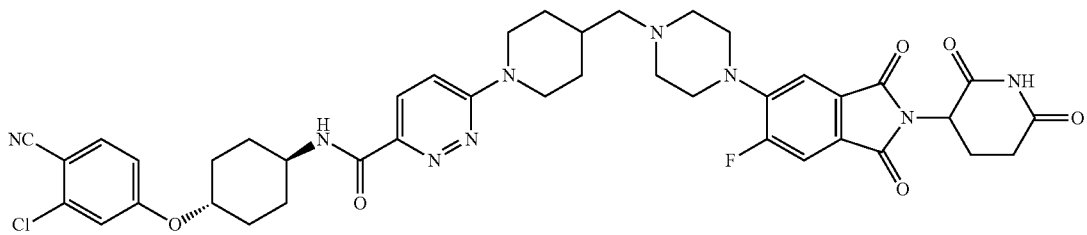 [SMILES: N#Cc1ccc(O[C@H]2CC[C@H](NC(=O)c3ccc(N4CCC(CN5CCN(c6cc7c(cc6F)C(=O)N(C6CCC(=O)NC6=O)C7=O)CC5)CC4)nn3)CC2)cc1Cl]

(Compound A)

having a powder x-ray diffraction pattern comprising peaks at 7.6±0.2° 2θ, 11.5°±0.2° 2θ, and 17.6°±0.2° 2θ, wherein said powder x-ray diffraction pattern is obtained using Cu Kα radiation at an x-ray wavelength of 1.5406 Å.
2. The crystalline form of Compound A of Embodiment 1, further comprising a peak at 18.5°±0.2° 2θ.
3. The crystalline form of Compound A of Embodiment 1 or 2, further comprising a peak at 21.4°±0.2° 2θ.
4. The crystalline form of Compound A of any one of Embodiments 1-3, further comprising a peak at 3.10°±0.2° 2θ.
5. A crystalline form of Compound A having a powder x-ray diffraction pattern as shown in FIG. 3A.
6. A crystalline form of Compound A having a powder x-ray diffraction pattern comprising peaks at 11.0°±0.2° 2θ, 16.10°±0.2° 2θ, and 17.9°±0.2° 2θ, wherein said powder x-ray diffraction pattern is obtained using Cu Kα radiation at an x-ray wavelength of 1.5406 Å.
7. The crystalline form of Compound A of Embodiment 6, further comprising a peak at 11.3°±0.2° 2θ.
8. The crystalline form of Compound A of Embodiment 6 or 7, further comprising a peak at 17.2±0.2° 2θ.
9. The crystalline form of Compound A of any one of Embodiments 6-8, further comprising a peak at 7.9°±0.2° 2θ.
10. A crystalline form of Compound A having a powder x-ray diffraction pattern as shown in FIG. 3C.
11. A process for manufacturing Compound A, wherein the process comprises the reductive amination of N-((1r,4r)-4-(3-chloro-4-cyanophenoxy)cyclohexyl)-6-(4-formylpiperidin-1-yl)pyridazine-3-carboxamide (Intermediate 3) with 2-(2,6-dioxopiperidin-3-yl)-5-fluoro-6-(piperazin-1-yl)isoindoline-1,3-dione hydrochloride (Intermediate 5) and a reducing agent to provide Compound A:

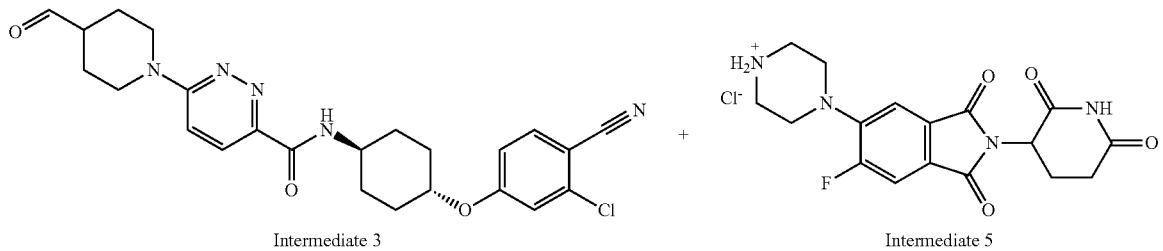

Intermediate 3    Intermediate 5

↓

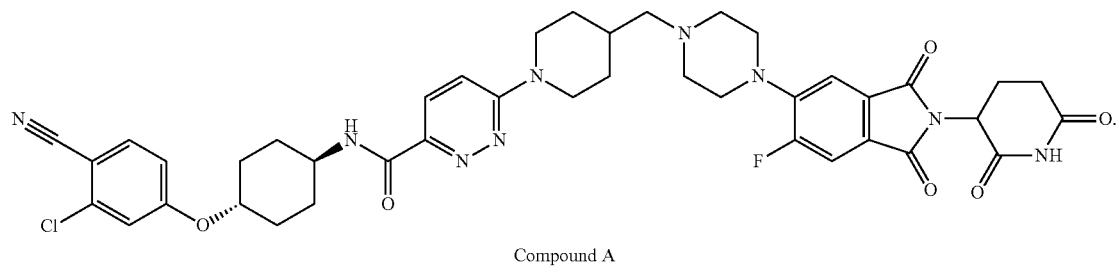

Compound A

12. The process of Embodiment 11, wherein the reductive amination is conducted in a polar solvent.

13. The process of Embodiment 12, wherein the polar solvent for the reductive amination is dimethylacetamide (DMA).

14. The process of any one of Embodiments 11-13, wherein the reducing agent for the reductive amination is sodium triacetoxyborohydride.

15. The process of any one of Embodiments 11-14, wherein the reductive amination is conducted at a temperature range of about −15 to about 30° C., about −10 to about 25° C., about −5 to about 20° C., about 0 to about 15° C., or about 5 to about 10° C.

16. The process of any one of Embodiments 11-15, wherein once the reductive amination reaction is complete, a mixture of ethanol and water is added to the crude reaction mixture to precipitate Compound A.

17. The process of Embodiment 16, wherein the mixture of ethanol to water has an ethanol:water ratio of about 1:1 (v/v).

18. The process of any one of Embodiments 11-17, wherein the reductive amination is conducted in the presence of a base 19. The process of Embodiment 18, wherein the base for the reductive amination is triethylamine or N-methyl morpholine.

20. The process of Embodiment 19, wherein the ratio of Intermediate 5 to base is about 1:0.7 (w/v).

21. The process of Embodiment 19, wherein the ratio of Intermediate 5 to base is about 1.7:1 (w/w).

22. The process of Embodiment 19, wherein the ratio of Intermediate 5 to base is about 1.9:1 (w/w).

23. The process of any one of Embodiments 11-22, wherein the molar ratio of Intermediate 3 to Intermediate 5 is about 1.1:1.

24. The process of any one of Embodiments 11-22, wherein the molar ratio of Intermediate 3 to Intermediate 5 is about 1.05:1.

25. The process of any one of Embodiments 11-22, wherein the molar ratio of Intermediate 3 to Intermediate 5 is between about 1:1 and about 1.1:1.

26. The process of any one of Embodiments 11-22, wherein the molar ratio of Intermediate 3 to Intermediate 5 is about 1.0:1.0.

27. The process of any one of Embodiments 11-26, further comprising a step for the purification of Compound A.

28. The process of Embodiment 27, wherein the purification of Compound A comprises:
(A1) dissolving Compound A in about a mixture of dichloromethane and methanol;
(A2) filtering the solution comprising Compound A;
(A3) distillatively exchanging the solvent of the solution comprising Compound A with ethanol;
(A4) crystallizing Compound A from the ethanol solution; and
(A5) drying the purified crystalline solid form of Compound A.

29. The process of Embodiment 28, wherein the ratio of dichloromethane to methanol in (A1) is about 9:1 (w/w).

30. The process of Embodiment 28, wherein the ratio of dichloromethane to methanol in (A1) is about 10:1 (v/v).

31. The process of Embodiment 28, wherein the volume of ethanol in step (A3) is approximately 7 volumes relative to the amount of Intermediate 3 provided in the reductive amination step.

32. The process of Embodiment 31, wherein the amount of ethanol in step (A3) is corrected for the ethanol content in the crude Compound A.

33. The process of one of Embodiments 28-32, wherein the drying in step (A5) of the purified crystalline form of Compound A is conducted in vacuo.

34. The process of Embodiment 33, wherein the in vacuo drying occurs at about 15 to about 30° C., about 20 to about 30° C., about 30 to about 40° C., or about 35 to about 45° C.

35. The process of Embodiment 33, wherein the in vacuo drying occurs at greater than about 50° C., greater than about 60° C., greater than about 70° C., or greater than about 80° C.

36. The process of Embodiment 33, wherein the in vacuo drying occurs at between about 60° C. and about 70° C.

37. The process of Embodiment 33, wherein the in vacuo drying occurs at about 65° C.

38. The process of Embodiment 33, wherein the in vacuo drying occurs at between about 75° C. and about 85° C.

39. The process of Embodiment 33, wherein the in vacuo drying occurs at about 80° C.

40. The process of any one of Embodiments 11-39, further comprising the oxidation of N-((1r,4r)-4-(3-chloro-4-cyanophenoxy)cyclohexyl)-6-(4-(hydroxymethyl)piperidin-1-yl)pyridazine-3-carboxamide (Intermediate 2) to form N-((1r,4r)-4-(3-chloro-4-cyanophenoxy)cyclohexyl)-6-(4-formylpiperidin-1-yl)pyridazine-3-carboxamide (Intermediate 3):

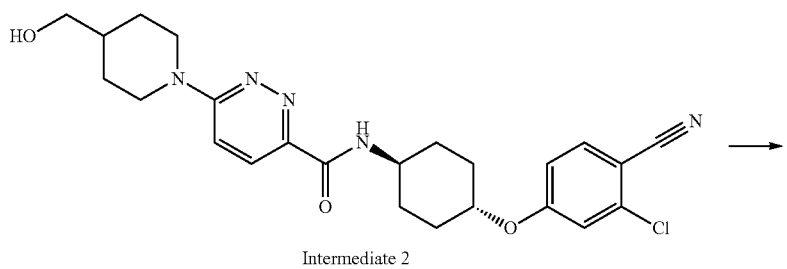

Intermediate 2

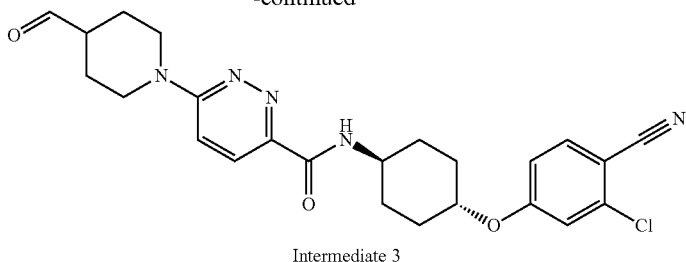

Intermediate 3

41. The process of Embodiment 40, wherein the oxidation is performed using about 0.01 equivalents of (2,2,6,6-tetramethylpiperidin-1-yl)oxyl (TEMPO) and about 1 equivalents of sodium hypochlorite.

42. The process of Embodiment 40, wherein the oxidation is performed using about 0.01 equivalents of TEMPO and about 1.15 equivalent of sodium hypochlorite.

43. The process of any one of Embodiments 41 or 42, wherein the oxidation is performed in a solvent comprising dichloromethane.

44. The process of any one of Embodiments 41-43, wherein the oxidation occurs in the presence of a secondary alcohol.

45. The process of Embodiment 44, where in the secondary alcohol is isopropanol.

46. The process of any one of Embodiments 43-45, wherein the solvent for the oxidation further comprises aqueous sodium chloride.

47. The process of any one of Embodiments 40-46, wherein the oxidation is performed at a temperature less than about 25° C., less than about 20° C., less than about 15° C., less than about 10° C., less than about 5° C., less than about 0° C., less than about −5° C., or less than about −11° C.

48. The process of any one of Embodiments 40-46, wherein the oxidation is performed at a temperature of about −11° C.

49. The process of any one of Embodiments 41-46, wherein the sodium hypochlorite is added over the course of less than 60 minutes, less than 45 minutes less than 30 minutes, or less than 20 minutes.

50. The process of any one of Embodiments 41-46, wherein the sodium hypochlorite is added over the course of between about 15 and about 45 minutes.

51. The process of any one of Embodiments 41-46, wherein the sodium hypochlorite is added over the course of about 30 minutes.

52. The process of any one of Embodiments 41-51, further comprising the step of exchanging the solvent comprising dichloromethane for a second solvent.

53. The process of Embodiment 52 wherein the second solvent comprises acetonitrile.

54. The process of Embodiment 52 wherein the second solvent comprises tetrahydrofuran.

55. The process of Embodiment 52, wherein the exchange of solvents is accomplished by distillation.

56. The process of any one of Embodiments 40-55 further comprising the step of purifying Intermediate 3 by recrystallization.

57. The process of Embodiment 56, wherein the purification of Intermediate 3 by recrystallization occurs in the presence of a solvent and an anti-solvent.

58. The process of Embodiment 56, wherein the recrystallization comprises the following steps:
   Bi) combining crude Intermediate 3 with a mixture of solvent and anti-solvent;
   Bii) stirring the mixture of crude Intermediate 3, solvent, and anti-solvent; and
   Biii) filtering the mixture of crude Intermediate 3, solvent, and anti-solvent to obtain Intermediate 3.

59. The process of Embodiment 58, wherein the recrystallization solvent is a polar aprotic organic solvent and the anti-solvent is an aqueous solvent.

60. The process of Embodiment 59, wherein the recrystallization solvent for Intermediate 3 comprises acetonitrile.

61. The process of Embodiment 59, wherein the recrystallization solvent for Intermediate 3 comprises dichloromethane.

62. The process of Embodiment 59, wherein the recrystallization solvent for Intermediate 3 comprises tetrahydrofuran.

63. The process of Embodiment 59, wherein the recrystallization solvent for Intermediate 3 comprises dichloromethane and tetrahydrofuran.

64. The process of any one of Embodiments 59-63, wherein the recrystallization anti-solvent is water.

65. The process of any one of Embodiments 59-63, wherein the recrystallization anti-solvent comprises n-heptane.

66. The process of any one of Embodiments 59-65, wherein the ratio of recrystallization solvent to anti-solvent is about 1:1 (v/v).

67. The process of any one of Embodiments 59-65, wherein the ratio of recrystallization solvent to anti-solvent is about 1.04:1 (v/v).

68. The process of any one of Embodiments 59-65, wherein the ratio of recrystallization solvent to anti-solvent is about 0.6:1 (v/v).

69. The process of any one of Embodiments 59-68, wherein step Bii) is performed at a temperature between 15° C. and 25° C.

70. The process of Embodiment 69, wherein step Bii) is performed at a temperature of about 18° C.

71. The process of Embodiment 69, wherein step Bii) is performed at a temperature of about 20° C.

72. The process of any one of Embodiments 59-71, wherein the stirring of step Bii) is performed for at least 5 hours, at least 12 hours, at least 14 hours, at least 16 hours, or at least 18 hours.

73. The process of Embodiment 72, wherein the stirring of step Bii) is performed for at least 16 hours.

74. The process of Embodiment 72, wherein the stirring of step Bii) is performed for about 18 hours.

75. The process of any one of Embodiments 11-74, further comprising a nucleophilic aromatic substitution reaction of 6-chloro-N-((1r,4r)-4-(3-chloro-4-cyanophenoxy)cyclohexyl)pyridazine-3-carboxamide (Intermediate 4) and piperidin-4-yl methanol in the presence of a base to provide N-((1r,4r)-4-(3-chloro-4-cyanophenoxy)cyclohexyl)-6-(4-(hydroxymethyl)piperidin-1-yl)pyridazine-3-carboxamide (Intermediate 2):

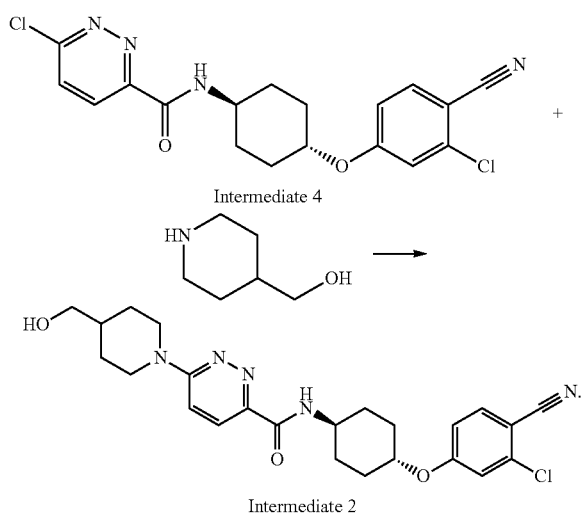

Intermediate 4

Intermediate 2

76. The process of Embodiment 75, wherein the nucleophilic aromatic substitution reaction is conducted in a polar solvent.
77. The process of Embodiment 76, wherein the polar solvent for the nucleophilic aromatic substitution is dimethylacetamide (DMA).
78. The process of any one of Embodiments 75-77, wherein the base for the nucleophilic aromatic substitution is N,N-diisopropylethylamine.
79. The process of any one of Embodiments 75-78, wherein the nucleophilic aromatic substitution reaction is conducted at a temperature of about 60° C. to about 130° C., about 75° C. to about 115° C., or about 90° C. to about 100° C.
80. The process of any one of Embodiments 75-79, further comprising the step of purifying Intermediate 2 by recrystallization in an organic solvent.
81. The process of any one of Embodiments 75-80, wherein the recrystallization of Intermediate 2 further comprises the following steps:
   Ci) combining crude Intermediate 2 in an organic solvent with an agent that promotes crystallization;
   Cii) reducing the volume of organic solvent;
   Ciii) adding additional amounts of the organic solvent;
   Civ) stirring the mixture from part iii) at a temperature above 30° C.;
   Cv) cooling the mixture from part iii) to a temperature below 25° C.;
   Cvi) reducing the volume of organic solvent;
   Cvii) stirring the mixture from part vi) at a temperature below 25° C.; and
   Cvii) filtering the mixture to obtain Intermediate 2.
82. The process of Embodiment 81, wherein the organic solvent in step Cii) is isopropyl acetate.
83. The process of Embodiment 81 or 82, wherein the agent that promotes crystallization in Ci) is a seed crystal of Intermediate 2.
84. The process of any one of Embodiments 81-83, wherein the reducing of the volume of organic solvent in step Ciii) is performed by vacuum distillation.
85. The process of any one of Embodiments 81-84, wherein the reducing of the volume of organic solvent in step Cvi) is performed by vacuum distillation.
86. The process of any one of Embodiments 81-85, wherein the temperature of step Civ) is about 50° C.
87. The process of any one of Embodiments 81-86, wherein the temperature of step Cv) is about 20° C.
88. The process of any one of Embodiments 81-87, wherein the temperature of step Cvii) is about 10° C.
89. The process of any one of Embodiments 11-88, further comprising an amide coupling of 4-(((1r,4r)-4-aminocyclohexyl)oxy)-2-chlorobenzonitrile hydrochloride (Intermediate 7) and 6-(4-(hydroxymethyl)piperidin-1-yl)pyridazine-3-carboxylic acid (Intermediate 10), facilitated by a coupling agent, to provide N-((1r,4r)-4-(3-chloro-4-cyanophenoxy)cyclohexyl)-6-(4-(hydroxymethyl)piperidin-1-yl)pyridazine-3-carboxamide (Intermediate 2):

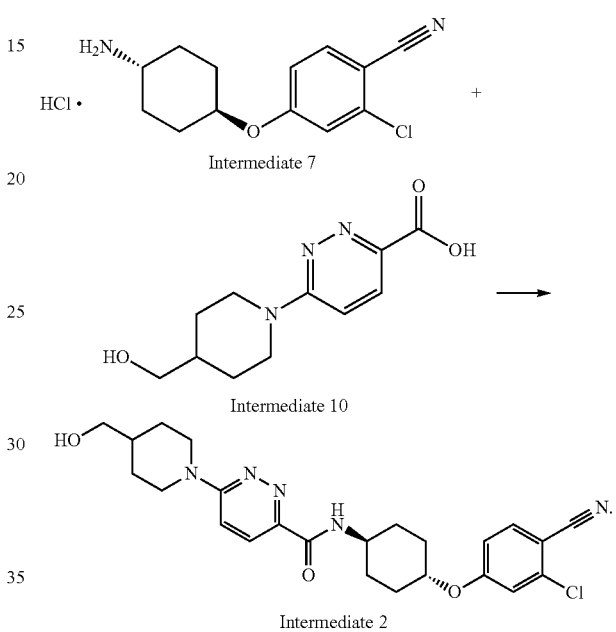

Intermediate 7

Intermediate 10

Intermediate 2

90. The process of Embodiment 89, wherein the amide coupling is conducted in a polar solvent.
91. The process of Embodiment 90, wherein the polar solvent for the amide coupling is dimethylacetamide (DMA).
92. The process of any one of Embodiments 89-91, wherein the coupling agent for the amide coupling is a carbodiimide.
93. The process of Embodiment 92, wherein the carbodiimide is 1-ethyl-3-(3-dimethylaminopropyl)carbodiimide.
94. The process of Embodiments 89-93, wherein the amide coupling reaction is conducted at a temperature of about 5° C. to about 15° C., about 10° C. to about 20° C., about 20° C. to about 40° C., about 30° C. to about 50° C., or about 35° C. to about 45° C.
95. The process of any one of Embodiments 89-94, wherein the ratio of molar ratio of Intermediate 7 to Intermediate 10 is about 1.05:1.
96. The process of any one of Embodiments 89-94, wherein the ratio of molar ratio of Intermediate 7 to Intermediate 10 is about 1.02:1.
97. The process of any one of Embodiments 89-96, further comprising the step of purifying Intermediate 2 by recrystallization in an organic solvent.
98. The process of Embodiment 97, wherein the organic solvent for the recrystallization of Intermediate 2 is isopropyl acetate.
99. The process of Embodiment 97, wherein the organic solvent for the recrystallization of Intermediate 2 comprises tetrahydrofuran and n-heptane.

100. The process of any one of Embodiments 97-99, wherein the organic solvent for the recrystallization of Intermediate 2 is seeded with crystals of pure Intermediate 2.

101. The process of any one of Embodiments 97-100, wherein the recrystallization of Intermediate 2 is performed by reduction of the volume of the organic solvent for the recrystallization of Intermediate 2.

102. The process of Embodiment 101, wherein the reduction of the volume of the organic solvent for the recrystallization of Intermediate 2 is performed by vacuum distillation.

103. The process of any one of Embodiments 97-102 wherein the recrystallization of Intermediate 2 is performed by cooling the organic solvent for the recrystallization of Intermediate 2.

104. The process of Embodiment 103, wherein organic solvent for the recrystallization of Intermediate 2 is cooled to a temperature between about 15° C. and about 25° C.

105. The process of Embodiment 103, wherein organic solvent for the recrystallization of Intermediate 2 is cooled to a temperature of about 20° C.

106. The process of any one of Embodiments 11-105, wherein the purified form of Compound A has a crystalline form with a powder x-ray diffraction pattern comprising peaks at 7.6°±0.2° 2θ, 11.5°±0.2° 2θ, and 17.6°±0.2° 2θ, wherein said powder x-ray diffraction pattern is obtained using Cu Kα radiation at an x-ray wavelength of 1.5406 Å.

107. A compound which is:
6-chloro-N-((1r,4r)-4-(3-chloro-4-cyanophenoxy)cyclohexyl)pyridazine-3-carboxamide, Intermediate 4

108. An ultrapure form of Compound A having a purity greater than about 98%.

109. An ultrapure form of Compound A having a purity greater than about 98%, and comprising less than about 1% of impurity Intermediate 2:

Intermediate 2

110. The ultrapure form of Compound A of Embodiment 109, comprising less than about 0.5% of impurity Intermediate 2.

111. The ultrapure form of Compound A of Embodiment 109, comprising less than about 0.2% of impurity Intermediate 2.

112. An ultrapure form of Compound A having a purity greater than about 98%, and comprising less than about 1% of impurity Intermediate 3:

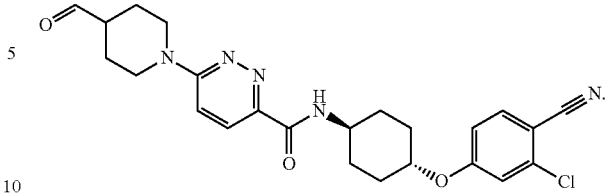

Intermediate 3

113. The ultrapure form of Compound A of Embodiment 112, comprising less than about 0.5% of impurity Intermediate 3.

114. The ultrapure form of Compound A of Embodiment 112, comprising less than about 0.1% of impurity Intermediate 3.

115. An ultrapure form of Compound A having a purity greater than about 98%, and comprising less than about 1% of impurity Intermediate 5:

Intermediate 5

116. The ultrapure form of Compound A of Embodiment 115, comprising less than about 0.5% of impurity Intermediate 5.

117. The ultrapure form of Compound A of Embodiment 115, comprising less than about 0.1% of impurity Intermediate 5.

118. The ultrapure form of Compound A of Embodiment 115, comprising less than about 0.05% of impurity Intermediate 5.

119. An ultrapure form of Compound A having a purity greater than about 98%, and comprising less than about 1% of Impurity 1:

Impurity 1

120. The ultrapure form of Compound A of Embodiment 119, comprising less than about 0.5% of Impurity 1.

121. The ultrapure form of Compound A of Embodiment 119, comprising less than about 0.1% of Impurity 1.

122. The ultrapure form of Compound A of Embodiment 119, comprising than about 0.05% of Impurity 1.

123. An ultrapure form of Compound A having a purity greater than about 95%, and comprising less than about 1% of Impurity 2:

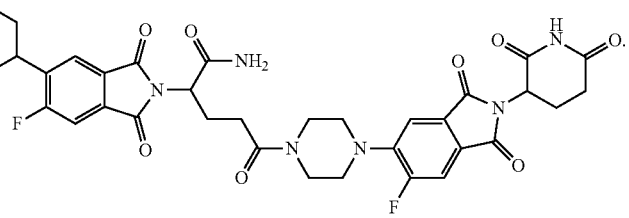

Impurity 2

124. The ultrapure form of Compound A of Embodiment 123, comprising less than about 0.5% of Impurity 2.
125. The ultrapure form of Compound A of Embodiment 123, comprising less than about 0.2% of Impurity 2.
126. The ultrapure form of Compound A of Embodiment 123, comprising less than about 0.15% of Impurity 2.
127. An ultrapure form of Compound A having a purity greater than about 95%, and comprising less than about 1% of Impurity 3:

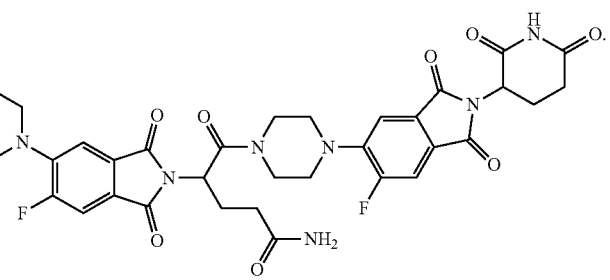

Impurity 3

128. The ultrapure form of Compound A of Embodiment 127, comprising less than about 0.5% of Impurity 3.
129. The ultrapure form of Compound A of Embodiment 128, comprising less than about 0.2% of Impurity 3.
130. The ultrapure form of Compound A of Embodiment 129, comprising less than about 0.15% of Impurity 3.
131. An ultrapure form of Compound A having a purity greater than about 95%, and comprising less than about 1% of Impurity 4:

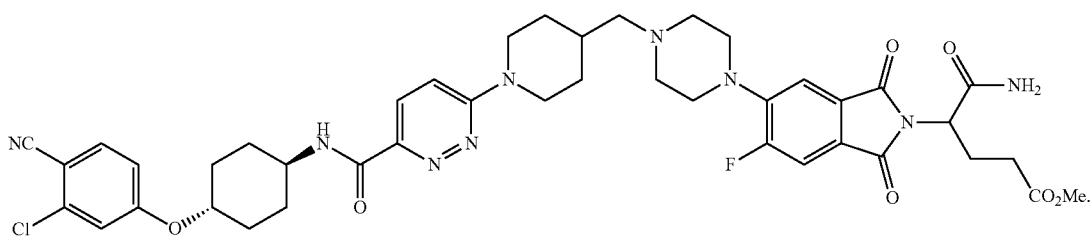

Impurity 4

132. The ultrapure form of Compound A of Claim 131, comprising less than about 0.5% of Impurity 4.
133. The ultrapure form of Compound A of Embodiment 131, comprising less than about 0.2% of Impurity 4.
134. The ultrapure form of Compound A of Embodiment 131, comprising less than about 0.15% of Impurity 4.

135A. The ultrapure form of Compound A of any one of Embodiments 108-134, wherein the purity of Compound A is determined by HPLC.
135B. The ultrapure form of Compound A of any one of Embodiments 109-135A, wherein the amount of the Intermediate or Impurity is determined by HPLC.
136. The ultrapure form of Compound A of any one of Embodiments 108-135A, wherein the purity of Compound A is greater than about 99%, about 99.5%, or about 99.9%.

137. The ultrapure form of Compound A of any one of Embodiments 108-135, wherein the purity of Compound A is greater than about 99.5%.
138. An ultrapure form of Compound A having a purity greater than about 98%, and comprising less than about 1% of at least two of the following impurities: Intermediate 2, Intermediate 3, Intermediate 5, Impurity 1, Impurity 2, Impurity 3, and Impurity 4.

139. The ultrapure form of Compound A of embodiment 138, wherein the purity of Compound A is greater than about 99%.
140. The ultrapure form of Compound A of any one of Embodiments 108-135, comprising less than about 0.9%, about 0.8%, about 0.7%, about 0.6%, or about 0.5% of at least two of the following impurities: Intermediate 2, Intermediate 3, Intermediate 5, Impurity 1, Impurity 2, Impurity 3, and Impurity 4.

141. The ultrapure form of Compound A of any one of Embodiments 108-135, wherein the Compound A has a purity of about 99.9%.

142. The ultrapure form of Compound A of any one of Embodiments 108-141, wherein Compound A is in amorphous form.

143. The ultrapure form of Compound A of any one of Embodiments 108-141, characterized by a glass transition temperature, Tg, of 146° C. at 25° C. and 0% relative humidity.

144. The ultrapure form of Compound A of any one of Embodiments 108-141, further characterized by a glass transition temperature, Tg, of 103° C. at 40° C. and 75% relative humidity.

145. The ultrapure form of Compound A of any one of Embodiments 108-144, further characterized by a $D_V(50)$ particle size of about 5 to about 20 µm.

146. The ultrapure form of Compound A of any one of Embodiments 108-145, further characterized by a $D_V(50)$ particle size of about 5 to about 15 µm.

147. The ultrapure form of Compound A of any one of Embodiments 108-146, characterized by a $D_V(50)$ particle size of about 5, 6, 7, 8, 9, 10, 11, 12, 13, 14, 15, 16, 17, 18, 19, or 20 µm.

148. The ultrapure form of Compound A of any one of Embodiments 145-147, wherein particle size is measured by laser diffraction.

149. The ultrapure form of Compound A according to any one of Embodiments 108-148, characterized in that the amorphous form is stable for at least 1 month at 2-8° C.; for at least 1 month at 25° C. and 60% relative humidity; and for at least 1 month at 40° C. and 75% relative humidity.

150. A process for manufacturing the amorphous form of Compound A of any one of Embodiments 108-149, wherein the process comprises the following steps:
 (D1) dissolving crystalline Compound A in solvent to afford a solution of Compound A;
 (D2) introducing the Compound A solution from step (1) into a spray dryer;
 (D3) spraying the Compound A solution from the spray dryer to form the amorphous form of the Compound A; and
 (D4) Removing the residual solvent from the amorphous form of Compound A.

151. The process of Embodiment 150, wherein, the solvent of step (D1) is a mixture of dichloromethane and methanol.

152. The process of Embodiment 151, wherein the solvent of step (D1) is a mixture of about 95:5 (w/w) to about 80:20 (w/w) dichloromethane:methanol.

153. The process of any one of Embodiments 150-152, wherein the solvent of step (D1) is about a 90:10 (w/w) mixture of dichloromethane:methanol.

154. The process of any one of Embodiments 150-152, wherein the solvent of step (D1) is about a 95:5 (w/w) mixture of dichloromethane:methanol.

155. The process of any one of Embodiments 150-152, wherein the solvent of step (D1) is about a 93:7 (w/w) mixture of dichloromethane:methanol.

156. The process of any one of Embodiments 150-152, wherein removal of residual solvent in step (D4) is accomplished by tray-drying.

157. The process of any one of Embodiments 150-156, wherein removal of residual solvent in step (D4) is accomplished by filter-drying.

158. The process of any one of Embodiments 150-156, wherein the removal of residual solvent in step (D4) is accomplished by tumble drying.

159. The process of any one of Embodiments 150-156, wherein the removal of residual solvent in step (D4) is accomplished by agitated conical drying.

160. The process of any one of Embodiments 150-156, wherein the removal of residual solvent in step (D4) is accomplished by fluid bed drying.

161. An oral dosage form comprising one or more pharmaceutically acceptable excipients and Compound A of any one of Embodiments 108-160, wherein the oral dosage form is selected from the group consisting of a tablet, a sachet, or a capsule.

162. The oral dosage form of Embodiment 161, wherein the Compound A is the ultrapure form of Compound A of any one of Embodiments 108-149.

163. The oral dosage form of Embodiment 161 or 162, wherein the oral dosage form is a tablet.

164. The oral dosage form of Embodiment 161 or 162, wherein the oral dosage form is a sachet.

165. The oral dosage form of Embodiment 161 or 162, wherein the oral dosage form is a capsule.

166. The tablet of Embodiment 163, wherein the amount of Compound A in the tablet is between about 5 mg and 1000 mg.

167. The tablet of Embodiment 166, wherein the amount of Compound A in the tablet is about 35 mg to about 280 mg.

168. The tablet of Embodiment 167, wherein the amount of Compound A in the tablet is about 35 mg.

169. The tablet of Embodiment 167, wherein the amount of Compound A in the tablet is about 70 mg.

170. The tablet of Embodiment 167, wherein the amount of Compound A in the tablet is about 105 mg.

171. The tablet of Embodiment 167, wherein the amount of Compound A in the tablet is about 140 mg.

172. The tablet of Embodiment 167, wherein the amount of Compound A in the tablet is about 175 mg.

173. The tablet of Embodiment 167, wherein the amount of Compound A in the tablet is about 210 mg.

174. The tablet of Embodiment 167, wherein the amount of Compound A in the tablet is about 245 mg.

175. The tablet of Embodiment 167, wherein the amount of Compound A in the tablet is about 280 mg.

176. The tablet of any one of Embodiments 163 or 166-175, wherein the pharmaceutically acceptable excipients are selected from the group consisting of fillers, disintegrants, glidants, and lubricants.

177. The tablet of Embodiment 176, wherein the filler is microcrystalline cellulose, silicified microcrystalline cellulose, lactose monohydrate, mannitol, sorbitol, xylitol, hydroxypropyl methylcellulose, hydroxypropyl cellulose, pullulan, fast-dissolving carbohydrates such as Pharmaburst™, or any mixture thereof.

178. The tablet of Embodiment 176, wherein the disintegrant is sodium starch glycolate, sodium carboxymethyl cellulose, calcium carboxymethyl cellulose, croscarmellose sodium, crospovidone, chitosan, agar, alginic acid, calcium alginate, methyl cellulose, microcrystalline cellulose, powdered cellulose, lower alkyl substituted hydroxypropyl cellulose, hydroxylpropyl starch, low-substituted hydroxypropylcellulose, polacrilin potassium, starch, pregelatinized starch, sodium alginate, magnesium aluminum silicate, polacrilin potassium, povidone, or any mixture thereof.

179. The tablet of Embodiment 176, wherein the glidant is silicon dioxide, colloidal silicon dioxide, calcium silicate, magnesium silicate, magnesium trisilicate, talc, starch, or any mixture thereof.

180. The tablet of Embodiment 176, wherein the lubricant is magnesium stearate, calcium stearate, glyceryl monostearate, glyceryl behenate, glyceryl palmitostearate, hexagonal boron nitride, hydrogenated vegetable oil, light mineral oil, mineral oil, polyethylene glycol, poloxamer, sodium benzoate, sodium lauryl sulfate, sodium stearyl fumarate, stearic acid, talc, zinc stearate, or any mixture thereof.

181. The tablet of any one of Embodiments 163 or 166-175, comprising:
   About 1 to about 50% w/w of Compound A;
   About 35 to about 60% w/w microcrystalline cellulose;
   About 15 to about 50% w/w lactose monohydrate;
   About 1 to about 5% w/w croscarmellose sodium;
   0 to about 1% w/w silicon dioxide; and
   0 to about 1% w/w magnesium stearate.

182. The tablet of any one of Embodiments 163 or 166-175, comprising:
   About 5% w/w of Compound A;
   About 45.5% w/w microcrystalline cellulose;
   About 45.5% w/w lactose monohydrate;
   About 3% w/w croscarmellose sodium;
   About 0.5% w/w silicon dioxide; and
   About 0.5% w/w magnesium stearate.

183. The tablet of any one of Embodiments 163 or 166-175, comprising an intra-granular portion and an extra-granular portion, wherein the intra-granular portion comprises
   About 10 to about 40% w/w of Compound A;
   About 35 to about 60% w/w microcrystalline cellulose;
   About 15 to about 30% w/w lactose monohydrate;
   About 1 to about 10% w/w croscarmellose sodium;
   0 to about 1% w/w silicon dioxide; and
   0 to about 0.5% w/w magnesium stearate;
   and wherein the extra-granular portion comprises
   About 1 to about 5% w/w croscarmellose sodium;
   0 to about 1% w/w magnesium stearate; and
   0 to about 2% w/w silicon dioxide.

184. The tablet of any one of Embodiments 163 or 166-175, comprising an intra-granular portion and an extra-granular portion, wherein the intra-granular portion comprises:
   About 20% w/w of Compound A;
   About 48.7% w/w microcrystalline cellulose;
   About 24.3% w/w lactose monohydrate;
   About 3% w/w croscarmellose sodium;
   About 0.5% w/w silicon dioxide; and
   About 0.25% w/w magnesium stearate;
   and wherein the extra-granular portion comprises:
   About 2% w/w croscarmellose sodium;
   About 0.5% w/w magnesium stearate; and
   About 0.25% w/w silicon dioxide.

185. The tablet of Embodiment 183 or 184, wherein the silicon dioxide in the extra-granular portion comprises fumed silica.

186. The tablet of any one of Embodiments 183-185, wherein the silicon dioxide in the extra-granular portion comprises fumed silica after treated with dimethyldichlorosilane.

187. The tablet of any one of Embodiments 183-186, wherein the silicon dioxide in the extra-granular portion comprises fumed silica chemically modified with trimethylsilyl groups on the surface of the silica.

188. The tablet of any one of Embodiments 163 or 166-187, wherein the Compound A is an ultrapure form of Compound A.

189. The tablet of any one of Embodiments 163 or 166-187, wherein the Compound A is prepared according to the process of any one of Embodiments 150-160.

190. A method of manufacturing the tablet of any one of Embodiments 163 or 166-187 comprising the following steps:
   (E1) blending a form of Compound A with at least one pharmaceutically acceptable excipient to create a powder;
   (E2) delumping the powder from step (E1), adding at least one pharmaceutically acceptable excipient, and blending to create a first blend;
   (E3) granulating the blend from step (E2) and passing the resultant powder through a screen to produce a plurality of granules;
   (E4) adding at least one pharmaceutically acceptable excipient to plurality of granules from step (E3) and blending to produce a second blend; and
   (E5) compressing the second blend from step (E4) into one or more tablets.

191. The method of Embodiment 190, wherein the form of Compound A in step (E1) is the amorphous form of Compound A.

192. The method of Embodiment 190 or 191, wherein, in step (E1), Compound A is blended with at least one filler, at least one disintegrant, and at least one glidant.

193. The method of Embodiment 192, wherein, in step (E1), Compound A is blended with two fillers, one disintegrant, and one glidant.

194. The method of Embodiment 192, wherein, in step (E1), Compound A is blended with two fillers, one disintegrant, one glidant, and one lubricant.

195. The method of Embodiment 193 or 194, wherein at least one filler is microcrystalline cellulose.

196. The method of Embodiments 193-195, wherein at least one filler is lactose monohydrate.

197. The method of any one of Embodiments 190-196, wherein at least one disintegrant is croscarmellose sodium.

198. The method of any one of Embodiments 190-197, wherein at least one glidant is silicon dioxide.

199. The method of any one of Embodiments 190-198, wherein at least one lubricant is magnesium stearate.

200. The method of any one of Embodiments 190-199, wherein at least one pharmaceutically acceptable excipient of step (E2) is a lubricant.

201. The method of Embodiment 200, wherein at least one lubricant is magnesium stearate.

202. The method of any one of Embodiments 190-201, wherein the at least one pharmaceutically acceptable excipient of step (E4) comprises at least one lubricant.

203. The method of Embodiment 202, wherein the at least one lubricant is extragranular magnesium stearate.

204. The method of any one of Embodiments 190-203, wherein at least one glidant, at least one disintegrant, and at least one lubricant are added to the plurality of granules in step (E4).

205. The method of Embodiment 204, wherein at least one glidant added in step (E4) is silicon dioxide.

206. The method of any one of Embodiment 204 or 205, wherein at least one disintegrant added in step (E4) is croscarmellose sodium.

207. The method of any one of Embodiments 204-206, wherein at least one lubricant added in step (4) is magnesium stearate.

208. The method of any one of Embodiments 190-207, wherein the blend from step (E4) is compressed in step (E5) using a rotary press.

209. A method of treating cancer in a subject comprising administering to a subject in need of said treatment one or oral dosage forms of any one of Embodiments 161-189.
210. The method of Embodiment 209, wherein the cancer is prostate cancer.
211. The method of Embodiment 210, wherein the prostate cancer is metastatic castration resistant prostate cancer.
212. The method of any one of Embodiments 209-211, wherein the one or more tablets are administered to the subject once a day, twice a day, three times a day, or four times a day.
213. The method of any one of Embodiments 209-212, wherein the one or more tablets are administered to the subject all at once or subdivided in two, three, four, or more sub-portions.
214. The method of any one of Embodiments 209-213, wherein the subject is in a fed state.
215. The method of any one of Embodiments 209-213, wherein the subject is in a fasted state.
216. The method of any one of Embodiments 209-215, wherein the subject is also taking or being administered an antacid medication.
217. The method of any one of Embodiments 209-216, further comprising administering an additional anti-cancer agent.
218. The method of Embodiment 217, wherein the additional anti-cancer agent is a PARP inhibitor.

The invention claimed is:

1. A crystalline form of Compound A:

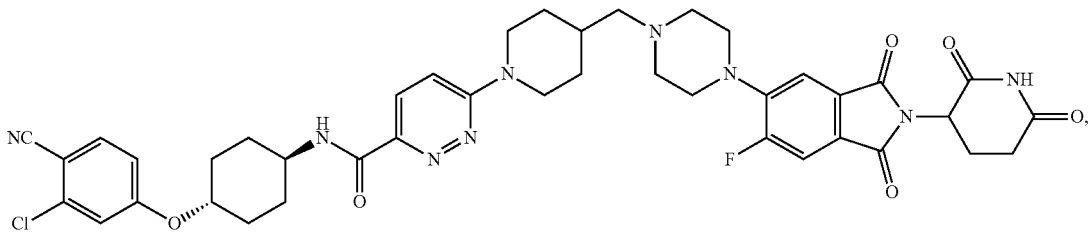 [SMILES: N#Cc1ccc(O[C@H]2CC[C@H](NC(=O)c3ccc(N4CCC(CN5CCN(c6cc7c(cc6F)C(=O)N(C6CCC(=O)NC6=O)C7=O)CC5)CC4)nn3)CC2)cc1Cl]

that is Form 4 having a powder x-ray diffraction pattern comprising peaks at 11.0°±0.2° 2θ, 16.10°±0.2° 2θ, and 17.9°±0.2° 2θ, wherein said powder x-ray diffraction pattern is obtained using Cu Kα radiation at an x-ray wavelength of 1.5406 Å.

2. The crystalline form of Compound A of claim 1, further comprising a peak at 11.30±0.2° 2θ.

3. The crystalline form of Compound A of claim 2, further comprising a peak at 17.2°±0.2° 2θ.

4. The crystalline form of Compound A of claim 3, further comprising a peak at 7.9°±0.2° 2θ.

5. A crystalline form of Compound A:

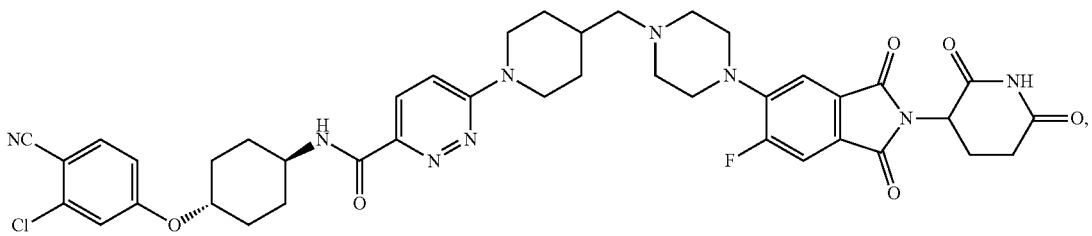

that is Form 2, having a powder x-ray diffraction pattern comprising peaks at 7.6°±0.2° 2θ, 11.5°±0.2° 2θ, and 17.6°±0.2° 2θ, wherein said powder x-ray diffraction pattern is obtained using Cu Kα radiation at an x-ray wavelength of 1.5406 Å.

6. The crystalline form of Compound A that is Form 2 of claim 5, further comprising a peak at 18.5°±0.2° 2θ.

7. The crystalline form of Compound A that is Form 2 of claim 5, further comprising a peak at 21.4°±0.2° 2θ.

8. The crystalline form of Compound A that is Form 2 of claim 6, further comprising a peak at 21.4°±0.2° 2θ.

9. The crystalline form of Compound A that is Form 2 of claim 5, further comprising a peak at 3.2°±0.2° 2θ.

10. The crystalline form of Compound A that is Form 2 of claim 6, further comprising a peak at 3.2°±0.2° 2θ.

11. The crystalline form of Compound A that is Form 2 of claim 7, further comprising a peak at 3.2°±0.2° 2θ.

12. The crystalline form of Compound A that is Form 2 of claim 8, further comprising a peak at 3.2°±0.2° 2θ.

* * * * *